US007132551B2

(12) United States Patent
Aquila et al.

(10) Patent No.: US 7,132,551 B2
(45) Date of Patent: Nov. 7, 2006

(54) LIGANDS FOR MONOAMINE RECEPTORS AND TRANSPORTERS, AND METHODS OF USE THEREOF

(75) Inventors: Brian M. Aquila, Marlborough, MA (US); Thomas D. Bannister, Northborough, MA (US); Gregory D. Cuny, Hudson, MA (US); James R. Hauske, Concord, MA (US); Joanne M. Holland, Brookline, MA (US); Paul E. Persons, Westborough, MA (US); Heike S. Radeke, South Grafton, MA (US); Fengjiang Wang, Northborough, MA (US); Liming Shao, Lincoln, MA (US)

(73) Assignee: Sepracor Inc., Marlborough, MA (US)

( * ) Notice: Subject to any disclaimer, the term of this patent is extended or adjusted under 35 U.S.C. 154(b) by 315 days.

(21) Appl. No.: 10/607,457

(22) Filed: Jun. 26, 2003

(65) Prior Publication Data

US 2004/0077706 A1 Apr. 22, 2004

Related U.S. Application Data

(62) Division of application No. 09/951,130, filed on Sep. 12, 2001.

(60) Provisional application No. 60/231,667, filed on Sep. 11, 2000, provisional application No. 60/273,530, filed on Mar. 5, 2001, provisional application No. 60/298,057, filed on Jun. 13, 2001.

(51) Int. Cl.
*C07D 207/00* (2006.01)

(52) U.S. Cl. ............ 548/530; 548/539; 548/531; 548/570

(58) Field of Classification Search ............ 548/530, 548/539, 531, 570; 514/423, 428
See application file for complete search history.

(56) References Cited

U.S. PATENT DOCUMENTS

| | | | | |
|---|---|---|---|---|
| 3,806,595 | A | 4/1974 | Jaggers et al. ............ | 424/248 |
| 3,876,769 | A | 4/1975 | Mallion et al. ............ | 424/248 |
| 3,959,273 | A | 5/1976 | Mallion et al. ............ | 260/247.7 |
| 4,033,951 | A | 7/1977 | Maiser ...................... | 260/243 R |
| 4,241,059 | A | 12/1980 | Hauck et al. ............ | 424/248.58 |
| 4,593,036 | A | 6/1986 | Lassen et al. | |
| 4,605,654 | A | 8/1986 | Cousse et al. ............ | 514/237 |
| 5,328,917 | A | 7/1994 | Jakobsen et al. | |
| 5,521,180 | A | 5/1996 | Fujii et al. ................ | 514/239 |
| 6,110,937 | A | 8/2000 | Loughhead et al. ....... | 514/317 |
| 6,124,317 | A | 9/2000 | Bigge et al. ............. | 514/317 |
| 6,124,323 | A | 9/2000 | Bigge et al. ............. | 514/327 |
| 6,653,478 | B1 * | 11/2003 | Urbanski et al. ......... | 546/199 |
| 6,703,508 | B1 * | 3/2004 | Aquila et al. ............ | 546/248 |

FOREIGN PATENT DOCUMENTS

| | | |
|---|---|---|
| EP | 0 000 693 | 2/1979 |
| EP | 0 076 089 | 4/1983 |
| EP | 0 080 940 | 6/1983 |
| EP | 0 138 716 | 4/1985 |
| EP | 0 229 623 | 7/1987 |
| EP | 0 266 574 A2 | 5/1988 |
| EP | 0 290 958 | 11/1988 |
| EP | 0 639 568 A1 | 2/1995 |
| FR | 1.221.294 | 6/1960 |
| FR | 2 248 049 | 5/1975 |
| FR | 2 471 378 | 6/1981 |
| FR | 2 534 915 | 4/1984 |
| FR | 2 553 411 | 4/1985 |
| FR | 2 564 462 | 11/1985 |
| GB | 1138405 | 1/1969 |
| GB | 1184023 | 3/1970 |
| GB | 1 260 886 | 1/1972 |
| GB | 1 382 526 | 2/1975 |
| GB | 1 382 965 | 2/1975 |
| GB | 1 452 701 | 10/1976 |
| GB | 1 501 321 | 2/1978 |
| NR | 111542 | 6/1965 |
| WO | WO 91/09032 | 6/1991 |
| WO | WO 92/01672 | 2/1992 |
| WO | WO 92/02502 | 2/1992 |
| WO | WO 93/15052 | 8/1993 |
| WO | WO 94/13291 | 6/1994 |
| WO | WO 95/03302 | 2/1995 |
| WO | WO 95/25732 | 9/1995 |
| WO | WO 95/33722 | 12/1995 |
| WO | WO 95/33723 | 12/1995 |
| WO | WO 98/51668 | 11/1998 |

(Continued)

OTHER PUBLICATIONS

Nagahara et al., 1994, CAS: 120:323168.*

(Continued)

*Primary Examiner*—Kamal A. Saeed
*Assistant Examiner*—Robert Shiao
(74) *Attorney, Agent, or Firm*—Dana M. Gordon; Foley Hoag LLP

(57) ABSTRACT

One aspect of the present invention relates to heterocyclic compounds. A second aspect of the present invention relates to the use of the heterocyclic compounds as ligands for various mammalian cellular receptors, including dopamine, serotonin, or norepinephrine transporters. The compounds of the present invention will find use in the treatment of numerous ailments, conditions and diseases which afflict mammals, including but not limited to addiction, anxiety, depression, sexual dysfunction, hypertension, migraine, Alzheimer's disease, obesity, emesis, psychosis, schizophrenia, Parkinson's disease, inflammatory pain, neuropathic pain, Lesche-Nyhane disease, Wilson's disease, and Tourette's syndrome. An additional aspect of the present invention relates to the synthesis of combinatorial libraries of the heterocyclic compounds, and the screening of those libraries for biological activity, e.g., in assays based on dopamine transporters.

17 Claims, 1 Drawing Sheet

FOREIGN PATENT DOCUMENTS

| | | |
|---|---|---|
| WO | WO 99/65487 | 12/1999 |
| WO | WO 00/09491 | 2/2000 |
| WO | WO 0071518 A2 | 11/2000 |
| WO | WO 01/32178 A1 | 5/2001 |
| WO | WO 01/68604 A2 | 9/2001 |
| WO | WO 01/92226 A1 | 12/2001 |

OTHER PUBLICATIONS

Kutsuki et al., 1990, CAS: 112: 7363.*
Andersson et al., 2001, CAS: 135:242140.*
Brown et al., 1990, CAS:112:35578.*
Engelstoft and Hansen; "Synthesis and 5HT Modulating Activity of Stereoisomers of 3-Phenoxymethyl-4-Phenylpiperidines" Acta Chemica Scandinavica 50:164-169, (1996).
O'Neill et al.; "Effect of Ca2+ and Na+ Channel Inhibitors in Vitro and In Global Cerebral Ischaemia in Vivo", European Journal of Pharmocology 332: 121-131, (1997).
Balsamo et al., "3-[(2-Ethoxyphenoxy)methyl]piperidine Derivatives. Synthesis and Antidepressant Activity," J. Med. Chem., 30:222-225 (1987).
Jones et al., "The Medical Benefit of 5-HT Research," Pharmacology, Biochemistry and Behavior 71:555-568 (2002).

* cited by examiner

Compound 124

LIGANDS FOR MONOAMINE RECEPTORS AND TRANSPORTERS, AND METHODS OF USE THEREOF

RELATED APPLICATIONS

This application is a division of U.S. patent application Ser. No. 09/951,130, filed Sep. 12, 2001; which claims the benefit of priority to: U.S. Provisional Patent Application Ser. No. 60/231,667, filed Sep. 11, 2000; U.S. Provisional Patent Application Ser. No. 60/273,530, filed Mar. 5, 2001; and U.S. Provisional Patent Application Ser. No. 60/298,057, filed Jun. 13, 2001.

BACKGROUND OF THE INVENTION

Dopamine, norepinephrine and serotonin are mammalian monoamine neurotransmitters that play important roles in a wide variety of physiological processes. Therefore, compounds that selectively modulate the activity of these three neurotransmitters, either individually, in pairs, or as a group, promise to serve as agents effective in the treatment of a wide range of maladies, conditions and diseases that afflict mammals due to atypical activities of these neurotransmitters.

For example, depression is believed to result from dysfunction in the noradrenergic, dopaminergic, or serotonergic systems. Furthermore, the noradrenergic system appears to be associated with increased drive, whereas the serotonergic system relates more to changes in mood. Therefore, it is possible that the different symptoms of depression may benefit from drugs acting mainly on one or the other of these neurotransmitter systems. On the other hand, a single compound that selectively affects both the noradrenergic and serotonergic systems should prove effective in the treatment of depression comprising symptoms related to dysfunction in both systems.

Dopamine plays a major role in addiction. Many of the concepts that apply to dopamine apply to other neurotransmitters as well. As a chemical messenger, dopamine is similar to adrenaline. Dopamine affects brain processes that control movement, emotional response, and ability to experience pleasure and pain. Regulation of dopamine plays a crucial role in our mental and physical health. Neurons containing the neurotransmitter dopamine are clustered in the midbrain in an area called the substantia nigra. In Parkinson's disease, the dopamine-transmitting neurons in this area die. As a result, the brains of people with Parkinson's disease contain almost no dopamine. To help relieve their symptoms, these patients are given L-DOPA, a drug that can be converted in the brain to dopamine.

Certain drugs are known as dopamine agonists. These drugs bind to dopamine receptors in place of dopamine and directly stimulate those receptors. Some dopamine agonists are currently used to treat Parkinson's disease. These drugs can stimulate dopamine receptors even in someone without dopamine-secreting neurons. In contrast to dopamine agonists, dopamine antagonists are drugs that bind but don't stimulate dopamine receptors. Antagonists can prevent or reverse the actions of dopamine by keeping dopamine from activating receptors.

Dopamine antagonists are traditionally used to treat schizophrenia and related mental disorders. A person with schizophrenia may have an overactive dopamine system. Dopamine antagonists can help regulate this system by "turning down" dopamine activity.

Cocaine and other drugs of abuse can alter dopamine function. Such drugs may have very different actions. The specific action depends on which dopamine receptors and brain regions the drugs stimulate or block, and how well the compounds mimic dopamine. Drugs such as cocaine and amphetamine produce their effects by changing the flow of neurotransmitters. These drugs are defined as indirect acting because they depend on the activity of neurons. In contrast, some drugs bypass neurotransmitters altogether and act directly on receptors.

Use of these two types of drugs can lead to very different results in treating the same disease. As mentioned earlier, people with Parkinson's disease lose neurons that contain dopamine. To compensate for this loss, the body produces more dopamine receptors on other neurons. Indirect agonists are not very effective in treating the disease since they depend on the presence of dopamine neurons. In contrast, direct agonists are more effective because they stimulate dopamine receptors even when dopamine neurons are missing.

Certain drugs increase dopamine concentrations by preventing dopamine reuptake, leaving more dopamine in the synapse. An example is the widely abused stimulant drug, cocaine. Another example is methylphenidate, used therapeutically to treat childhood hyperkinesis and symptoms of narcolepsy.

Sensitization or desensitization normally occurs with drug exposure. However, addiction or mental illness can tamper with the reuptake system. This disrupts the normal levels of neurotransmitters in the brain and can lead to faulty desensitization or sensitization. If this happens in a region of the brain that serves emotion or motivation, the individual can suffer severe consequences. For example, cocaine prevents dopamine reuptake by binding to proteins that normally transport dopamine. Not only does cocaine "bully" dopamine out of the way, it also hangs on to the transport proteins much longer than dopamine does. As a result, more dopamine remains to stimulate neurons, which causes a prolonged feelings of pleasure and excitement. Amphetamine also increases dopamine levels. Again, the result is over-stimulation of these pleasure-pathway nerves in the brain.

Dopamine activity is implicated in the reinforcing effects of cocaine, amphetamine and natural rewards. However, dopamine abnormalities are also believed to underlie some of the core attention deficits seen in acute schizophrenics.

Norepinephrine, also called noradrenaline, is a neurotransmitter that also acts as a hormone. As a neurotransmitter, norepinephrine helps to regulate arousal, dreaming, and moods. As a hormone, it acts to increase blood pressure, constrict blood vessels and increase heart rate—responses that occur when we feel stress.

Serotonin (5-hydroxytryptamine, 5-HT) is widely distributed in animals and plants, occurring in vertebrates, fruits, nuts, and venoms. A number of congeners of serotonin are also found in nature and have been shown to possess a variety of peripheral and central nervous system activities. Serotonin may be obtained from a variety of dietary sources; however, endogenous 5-HT is synthesized in situ from tryptophan through the actions of the enzymes tryptophan hydroxylase and aromatic L-amino acid decarboxylase. Both dietary and endogenous 5-HT are rapidly metabolized and inactivated by monoamine oxidase and aldehyde dehydrogenase to the major metabolite, 5-hydroxyindoleacetic acid (5-HIAA).

Serotonin is implicated in the etiology or treatment of various disorders, particularly those of the central nervous system, including anxiety, depression, obsessive-compulsive disorder, schizophrenia, stroke, obesity, pain, hypertension, vascular disorders, migraine, and nausea. Recently, understanding of the role of 5-HT in these and other disorders has advanced rapidly due to increasing understanding of the physiological role of various serotonin receptor subtypes.

It is currently estimated that up to 30% of clinically diagnosed cases of depression are resistant to all forms of drug therapy. To achieve an effective therapy for such patients, it is logical to develop drugs that possess reuptake inhibition profiles different from those of drugs currently available on the market. For example, the exact role of dopamine in depressive illness is far from clear; however, intervention in the dopamine system may hold promise for the treatment of a subset of major depression.

SUMMARY OF THE INVENTION

One aspect of the present invention relates to heterocyclic compounds. A second aspect of the present invention relates to the use of the heterocyclic compounds as ligands for various mammalian cellular receptors, including dopamine, serotonin, or norepinephrine transporters. The compounds of the present invention will find use in the treatment of numerous ailments, conditions and diseases which afflict mammals, including but not limited to addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, and Tourette's syndrome. An additional aspect of the present invention relates to the synthesis of combinatorial libraries of the heterocyclic compounds, and the screening of those libraries for biological activity, e.g., in assays based on dopamine transporters.

DETAILED DESCRIPTION OF THE INVENTION

Figure 1:
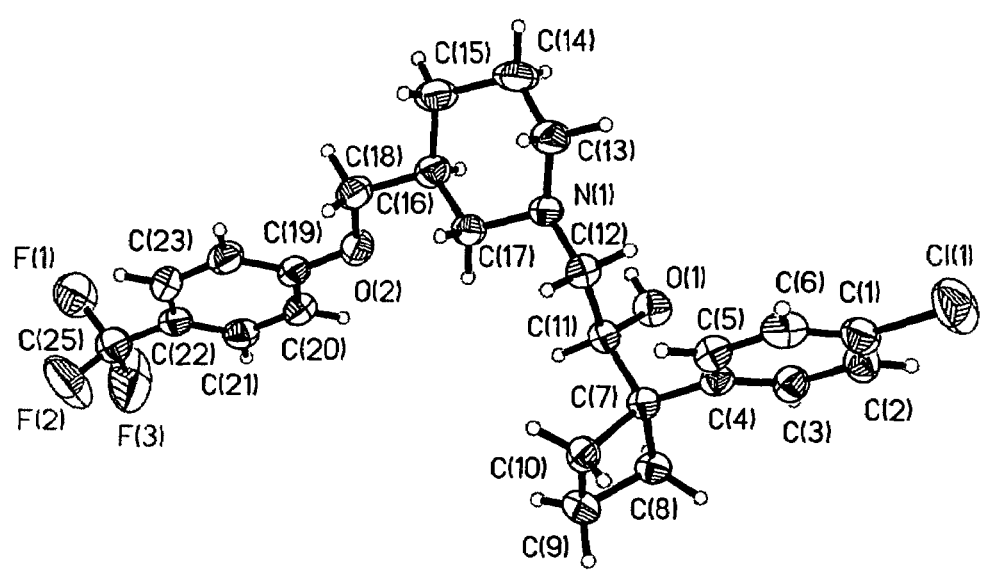
FIG. 1 depicts an ORTEP drawing of compound 124, which was the basis for the assignment of its absolute stereochemistry.

The present invention provides heterocyclic compounds, and combinatorial libraries thereof. Furthermore, the present invention provides heterocyclic compounds that are ligands for dopamine, serotonin, or norepinephrine receptors or transporters, and methods of use thereof for the treatment of numerous ailments, conditions and diseases which afflict mammals, including but not limited to addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, and Tourette's syndrome. The present invention also relates to pharmaceutical formulations of the heterocyclic compounds.

In certain embodiments, compounds of the present invention are ligands for mammalian receptors for dopamine, norepinephrine, serotonin, any two of these three neurotransmitters or all of them. In certain embodiments, compounds of the present invention are ligands for mammalian transporters of dopamine, norepinephrine, serotonin, any two of these three neurotransmitters or all of them. In certain embodiments, compounds of the present invention are agonists of mammalian receptors for dopamine, norepinephrine, serotonin, any two of these three neurotransmitters or all of them. In certain embodiments, compounds of the present invention are antagonists or inverse agonists of mammalian receptors for dopamine, norepinephrine, serotonin, any two of these three neurotransmitters or all of them. In certain embodiments, compounds of the present invention are agonists of mammalian transporters of dopamine, norepinephrine, serotonin, any two of these three neurotransmitters or all of them. In certain embodiments, compounds of the present invention are antagonists or inverse agonists of mammalian transporters of dopamine, norepinephrine, serotonin, any two of these three neurotransmitters or all of them.

In certain embodiments, compounds of the present invention are ligands for mammalian dopamine receptors. In certain embodiments, compounds of the present invention are ligands for mammalian dopamine transporters. In certain embodiments, compounds of the present invention are agonists of mammalian dopamine receptors. In certain embodiments, compounds of the present invention are antagonists or inverse agonists of mammalian dopamine receptors. In certain embodiments, compounds of the present invention are agonists of mammalian dopamine transporters. In certain embodiments, compounds of the present invention are antagonists or inverse agonists of mammalian dopamine transporters.

The mammalian dopamine receptor and transporter are members of a family of cell surface proteins that permit intracellular transduction of extracellular signals. Cell surface proteins provide eukaryotic and prokaryotic cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as growth hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. For example, neuron gene expression is modulated by numerous extracellular signals, including neurotransmitters and membrane electrical activity. Transsynaptic signals cause rapid responses in neurons that occur over a period of time ranging from milleseconds, such as the opening of ligand-gated channels, to seconds and minutes, such as second messenger-mediated events. Genes in neural cells that are responsive to transsynaptic stimulation and membrane electrical activity, include genes, called immediate early genes, whose transcription is activated rapidly, within minutes, and transiently (see, e.g., Sheng et al. (1990) Neuron 4: 477–485), and genes whose expression requires protein synthesis and whose expression is induced or altered over the course of hours.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as neurotransmitters, growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

The G protein transmembrane signaling pathways consist of three proteins: receptors, G proteins and effectors. G proteins, which are the intermediaries in transmembrane signaling pathways, are heterodimers and consist of alpha, beta and gamma subunits. Among the members of a family of G proteins the alpha subunits differ. Functions of G proteins are regulated by the cyclic association of GTP with the alpha subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors, which are glycoproteins, are known to share certain structural similarities and homologies (see, e-g., Gilman, A. G., Ann. Rev. Biochem. 56: 615–649 (1987), Strader, C. D. et al. The FASEB Journal 3: 1825–1832 (1989), Kobilka, B. K., et al. Nature 329:75–79 (1985) and Young et al. Cell 45: 711–719 (1986)). Among the G protein-coupled receptors that have been identified and cloned are the substance P receptor, the angiotensin receptor, the alpha- and beta-adrenergic receptors and the serotonin receptors. G protein-coupled receptors share a conserved structural motif. The general and common structural features of the G protein-coupled receptors are the existence of seven hydrophobic stretches of about 20–25 amino acids each surrounded by eight hydrophilic regions of variable length. It has been postulated that each of the seven hydrophobic regions forms a transmembrane alpha helix and the intervening hydrophilic regions form alternately intracellularly and extracellularly exposed loops. The third cytosolic loop between transmembrane domains five and six is the intracellular domain responsible for the interaction with G proteins.

G protein-coupled receptors are known to be inducible. This inducibility was originally described in lower eukaryotes. For example, the cAMP receptor of the cellular slime mold, *Dictyostelium*, is induced during differentiation (Klein et al., Science 241: 1467–1472 (1988). During the *Dictyostelium discoideum* differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R. A., et al. Cell 58: 235–239 (1989) and Devreotes, P., Science 245: 1054–1058 (1989)).

Definitions

For convenience, certain terms employed in the specification, examples, and appended claims are collected here.

The term "cell surface proteins" includes molecules that occur on the surface of cells, interact with the extracellular environment, and transmit or transduce information regarding the environment intracellularly.

The term "extracellular signals" includes a molecule or a change in the environment that is transduced intracellularly via cell surface proteins that interact, directly or indirectly, with the signal. An extracellular signal is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. Extracellular signals also includes as yet unidentified substances that modulate the activity of a cell surface protein and thereby affect intracellular functions and that are potential pharmacological agents that may be used to treat specific diseases by modulating the activity of specific cell surface receptors.

The term "$Ed_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

The term "agonist" refers to a compound that mimics the action of natural transmitter or, when the natural transmitter is not known, causes changes at the receptor complex in the absence of other receptor ligands.

The term "antagonist" refers to a compound that binds to a receptor site, but does not cause any physiological changes unless another receptor ligand is present.

The term "inverse agonist" refers to a compound that binds to a constitutively active receptor site and reduces its physiological function.

The term "competitive antagonist" refers to an antagonist, the effects of which can be overcome by increased concentration of an agonist.

The term "partial agonist" refers to a compound that binds to a receptor site but does not produce the maximal effect regardless of its concentration.

The term "ligand" refers to a compound that binds at the receptor site.

The term "heteroatom" as used herein means an atom of any element other than carbon or hydrogen. Preferred heteroatoms are boron, nitrogen, oxygen, phosphorus, sulfur and selenium.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 3–10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, $-CF_3$, $-CN$, or the like.

As used herein, the term "nitro" means $-NO_2$; the term "halogen" designates $-F$, $-Cl$, $-Br$ or $-I$; the term "sulfhydryl" means $-SH$; the term "hydroxyl" means $-OH$; and the term "sulfonyl" means $-SO_2-$.

The terms "amine" and "amino" are art-recognized and refer to both unsubstituted and substituted amines, e.g., a moiety that can be represented by the general formula:

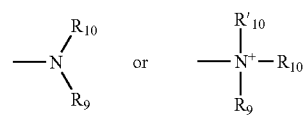

wherein $R_9$, $R_{10}$ and $R'_{10}$ each independently represent a group permitted by the rules of valence.

The term "acylamino" is art-recognized and refers to a moiety that can be represented by the general formula:

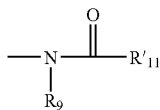

wherein $R_9$ represents a group permitted by the rules of valence, and $R'_{11}$ represents hydrogen, alkyl, cycloalkyl, alkenyl, aryl, heteroaryl, aralkyl, or heteroaralkyl.

The term "amido" is art recognized as an amino-substituted carbonyl and includes a moiety that can be represented by the general formula:

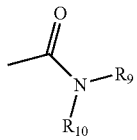

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m is an integer less than or equal to ten, and $R_8$ is alkyl, cycloalkyl, alkenyl, aryl, or heteroaryl. Representative alkylthio groups include methylthio, ethyl thio, and the like.

The term "carbonyl" is art recognized and includes such moieties as can be represented by the general formula:

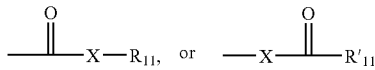

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

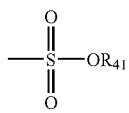

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations*. The abbreviations contained in said list, and all abbreviations utilized by organic chemists of ordinary skill in the art are hereby incorporated by reference.

The term "sulfate" is art recognized and includes a moiety that can be represented by the general formula:

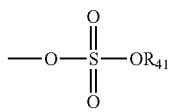

in which $R_{41}$ is as defined above.

The term "sulfonylamino" is art recognized and includes a moiety that can be represented by the general formula:

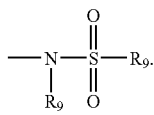

The term "sulfamoyl" is art-recognized and includes a moiety that can be represented by the general formula:

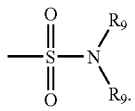

The term "sulfonyl", as used herein, refers to a moiety that can be represented by the general formula:

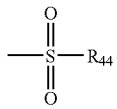

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

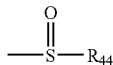

in which $R_{44}$ is selected from the group consisting of hydrogen, alkyl, alkenyl, alkynyl, cycloalkyl, heterocyclyl, aralkyl, or aryl.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_8$, m and $R_8$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers. Further, mixtures of stereoisomers may be resolved using chiral chromatographic means.

Contemplated equivalents of the compounds described above include compounds which otherwise correspond thereto, and which have the same general properties thereof, wherein one or more simple variations of substituents are made which do not adversely affect the efficacy of the compound in binding to monoamine transporters. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

Compounds of the Invention

In certain embodiments, a compound of the present invention is represented by A:

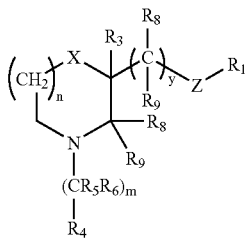

wherein
X represents $C(R_3)_2$, O, S, SO, $SO_2$, $NR_2$, $NC(O)R_7$, $NC(O)OR_2$, $NS(O)_2R_7$, or C=O;

Z represents $C(R_3)_2$, C(O), O, NR, NC(O)OR, S, SO, or $SO_2$;

m is 1, 2, 3, 4 or 5;
n is 1 or 2;
p is 0, 1, 2, or 3;
y is 0, 1, or 2;

R represents H, alkyl, cycloalkyl, aryl, heteroaryl, aralkyl, or heteroaralkyl;

$R_1$ represents H, alkyl, aryl, heteroaryl, aralkyl, or heteroaralkyl;

R and $R_1$ may be connected through a covalent bond;

$R_2$ represents independently for each occurrence H, alkyl, fluoroalkyl, aryl, heteroaryl, or cycloalkyl;

$R_3$ represents independently for each occurrence H, alkyl, aryl, $OR_2$, $OC(O)R_2$, $CH_2OR_2$, or $CO_2R_2$; wherein any two instances of $R_3$ may be connected by a covalent tether whose backbone consists of 1, 2, 3, or 4 carbon atoms;

$R_4$ represents independently for each occurrence H, alkyl, cycloalkyl, aryl, heteroaryl, alkenyl, or OR;

$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);

$R_7$ represents alkyl, cycloalkyl, aryl, heteroaryl, aralkyl, or heteroaralkyl;

$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is C(O);

Y represents independently for each occurrence $OR_2$, $N(R_2)_2$, $SR_2$, $S(O)R_2$, $S(O)_2R_2$, or $P(O)(OR_2)_2$;

any two instances of $R_2$ may be connected through a covalent bond;

a covalent bond may connect $R_4$ and an instance of $R_5$ or $R_6$;

any two instances of $R_5$ and $R_6$ may be connected through a covalent bond;

any two geminal or vicinal instances of $R_8$ and $R_9$ may be connected through a covalent bond; and the stereochemical configuration at any stereocenter of a compound represented by A is R, S, or a mixture of these configurations.

In certain embodiments, the compounds of the present invention are represented by A and the attendant definitions, wherein X is $C(R_3)_2$, O, or $NR_2$.

In certain embodiments, the compounds of the present invention are represented by A and the attendant definitions, wherein X is $C(R_3)_2$.

In certain embodiments, the compounds of the present invention are represented by A and the attendant definitions, wherein Z is O or NR.

In certain embodiments, the compounds of the present invention are represented by A and the attendant definitions, wherein m is 2 or 3.

In certain embodiments, the compounds of the present invention are represented by A and the attendant definitions, wherein n is 1.

In certain embodiments, the compounds of the present invention are represented by A and the attendant definitions, wherein y is 1.

In certain embodiments, the compounds of the present invention are represented by A and the attendant definitions, wherein $R_1$ represents aryl.

In certain embodiments, the compounds of the present invention are represented by A and the attendant definitions, wherein $R_3$ represents independently for each occurrence H or alkyl.

In certain embodiments, the compounds of the present invention are represented by A and the attendant definitions, wherein $R_4$ represents cycloalkyl, aryl, or heteroaryl.

In certain embodiments, the compounds of the present invention are represented by A and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by A and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by A and the attendant definitions, wherein X is $C(R_3)_2$, O, or $NR_2$; and Z is O or NR.

In certain embodiments, the compounds of the present invention are represented by A and the attendant definitions, wherein X is $C(R_3)_2$, O, or $NR_2$; Z is O or NR; and m is 2 or 3.

In certain embodiments, the compounds of the present invention are represented by A and the attendant definitions, wherein X is $C(R_3)_2$, O, or $NR_2$; Z is O or NR; and n is 1.

In certain embodiments, the compounds of the present invention are represented by A and the attendant definitions, wherein X is $C(R_3)_2$, O, or $NR_2$; Z is O or NR; and y is 1.

In certain embodiments, the compounds of the present invention are represented by A and the attendant definitions, wherein X is $C(R_3)_2$, O, or $NR_2$; Z is O or NR; m is 2 or 3; n is 1; and y is 1.

In certain embodiments, the compounds of the present invention are represented by A and the attendant definitions, wherein X is $C(R_3)_2$, O, or $NR_2$; Z is O or NR; m is 2 or 3; n is 1; y is 1; and $R_1$ is aryl.

In certain embodiments, the compounds of the present invention are represented by A and the attendant definitions, wherein X is $C(R_3)_2$, O, or $NR_2$; Z is O or NR; m is 2 or 3; n is 1; y is 1; $R_1$ is aryl; and $R_3$ is H or alkyl.

In certain embodiments, the compounds of the present invention are represented by A and the attendant definitions, wherein X is $C(R_3)_2$, O, or $NR_2$; Z is O or NR; m is 2 or 3; n is 1; y is 1; $R_1$ is aryl; $R_3$ is H or alkyl; and $R_4$ is cycloalkyl, aryl, or heteroaryl.

In certain embodiments, the compounds of the present invention are represented by A and the attendant definitions, wherein X is $C(R_3)_2$, O, or $NR_2$; Z is O or NR; m is 2 or 3; n is 1; y is 1; $R_1$ is aryl; $R_3$ is H or alkyl; $R_4$ is cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by A and the attendant definitions, wherein X is $C(R_3)_2$, O, or $NR_2$; Z is O or NR; m is 2 or 3; n is 1; y is 1; $R_1$ is aryl; $R_3$ is H or alkyl; $R_4$ is cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In certain embodiments, the compounds of the present invention are represented by A and the attendant definitions, wherein X is $CH_2$; Z is O; m is 2; n is 1; y is 1; $R_1$ is 4-trifluoromethylphenyl or 3,4-methylenedioxyphenyl; $R_3$ is H; $R_4$ is 4-chlorophenyl; $R_5$ and $R_6$ are selected independently for each occurrence from the group consisting of H and alkyl; and $R_8$ and $R_9$ are H.

In certain embodiments, the compounds of the present invention are represented by A and the attendant definitions, wherein X is $CH_2$; Z is O; m is 3; n is 1; y is 1; $R_1$ is 4-trifluoromethylphenyl; $R_3$ is H; $R_4$ is 4-chlorophenyl; $R_5$ and $R_6$ are selected independently for each occurrence from the group consisting of H, OH, and alkyl; and $R_8$ and $R_9$ are H.

In assays based on mammalian dopamine, serotonin, or norepinephrine receptors or transporters, certain compounds according to structure A have $EC_{50}$ values less than 1 µM, more preferably less than 100 nM, and most preferably less than 10 nM.

In assays based on mammalian dopamine receptors or transporters, certain compounds according to structure A have $EC_{50}$ values less than 1 µM, more preferably less than 100 nM, and most preferably less than 10 nM.

In assays based on mammalian dopamine, serotonin, or norepinephrine receptors or transporters, certain compounds according to structure A have $IC_{50}$ values less than 1 µM, more preferably less than 100 nM, and most preferably less than 10 nM.

In assays based on mammalian dopamine receptors or transporters, certain compounds according to structure A have $IC_{50}$ values less than 1 µM, more preferably less than 100 nM, and most preferably less than 10 nM.

In certain embodiments, compounds according to structure A are effective in the treatment of mammals suffering from addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, or Tourette's syndrome.

In certain embodiments, a compound of the present invention is represented by B:

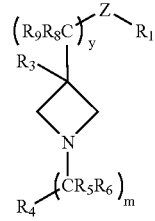

B wherein

Z represents $C(R_3)_2$, C(O), O, NR, NC(O)OR, S, SO, or $SO_2$;

m is 1, 2, 3, 4 or 5;

p is 0, 1, 2, or 3;

y is 0, 1 or 2;

R represents H, alkyl, cycloalkyl, aryl, heteroaryl, aralkyl, or heteroaralkyl;

$R_1$ represents H, alkyl, aryl, heteroaryl, aralkyl, or heteroaralkyl;

R and $R_1$ may be connected through a covalent bond;

$R_2$ represents independently for each occurrence H, alkyl, fluoroalkyl, aryl, heteroaryl, or cycloalkyl;

$R_3$ represents independently for each occurrence H, alkyl, aryl, $OR_2$, $OC(O)R_2$, $CH_2OR_2$, or $CO_2R_2$;

$R_4$ represents independently for each occurrence H, alkyl, cycloalkyl, aryl, heteroaryl, alkenyl, or OR;

$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);

$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is C(O);

Y represents independently for each occurrence $OR_2$, $N(R_2)_2$, $SR_2$, $S(O)R_2$, $S(O)_2R_2$, or $P(O)(OR_2)_2$;

any two instances of $R_2$ may be connected through a covalent bond;

a covalent bond may connect $R_4$ and an instance of $R_5$ or $R_6$;

any two instances of $R_5$ and $R_6$ may be connected through a covalent bond;

any two geminal or vicinal instances of $R_8$ and $R_9$ may be connected through a covalent bond; and the stereochemical configuration at any stereocenter of a compound represented by B is R, S, or a mixture of these configurations.

In certain embodiments, the compounds of the present invention are represented by B and the attendant definitions, wherein Z is O or NR.

In certain embodiments, the compounds of the present invention are represented by B and the attendant definitions, wherein m is 3.

In certain embodiments, the compounds of the present invention are represented by B and the attendant definitions, wherein y is 1.

In certain embodiments, the compounds of the present invention are represented by B and the attendant definitions, wherein $R_1$ represents aryl.

In certain embodiments, the compounds of the present invention are represented by B and the attendant definitions, wherein $R_3$ represents independently for each occurrence H or alkyl.

In certain embodiments, the compounds of the present invention are represented by B and the attendant definitions, wherein $R_4$ represents cycloalkyl, aryl, or heteroaryl.

In certain embodiments, the compounds of the present invention are represented by B and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by B and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by B and the attendant definitions, wherein Z is O or NR; and m is 3.

In certain embodiments, the compounds of the present invention are represented by B and the attendant definitions, wherein Z is O or NR; and y is 1.

In certain embodiments, the compounds of the present invention are represented by B and the attendant definitions, wherein Z is O or NR; m is 3; and y is 1.

In certain embodiments, the compounds of the present invention are represented by B and the attendant definitions, wherein Z is O or NR; m is 3; y is 1; and $R_1$ is aryl.

In certain embodiments, the compounds of the present invention are represented by B and the attendant definitions, wherein Z is O or NR; m is 3; y is 1; $R_1$ is aryl; and $R_3$ is H or alkyl.

In certain embodiments, the compounds of the present invention are represented by B and the attendant definitions, wherein Z is O or NR; m is 3; y is 1; $R_1$ is aryl; $R_3$ is H or alkyl; and $R_4$ is cycloalkyl, aryl, or heteroaryl.

In certain embodiments, the compounds of the present invention are represented by B and the attendant definitions, wherein Z is O or NR; m is 3; y is 1; $R_1$ is aryl; $R_3$ is H or alkyl; $R_4$ is cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by B and the attendant definitions, wherein Z is O or NR; m is 3; y is 1; $R_1$ is aryl; $R_3$ is H or alkyl; $R_4$ is cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In assays based on mammalian dopamine, serotonin, or norepinephrine receptors or transporters, certain compounds according to structure B have $EC_{50}$ values less than 1 μM, more preferably less than 100 nM, and most preferably less than 10 nM.

In assays based on mammalian dopamine receptors or transporters, certain compounds according to structure B have $EC_{50}$ values less than 1 μM, more preferably less than 100 nM, and most preferably less than 10 nM.

In assays based on mammalian dopamine, serotonin, or norepinephrine receptors or transporters, certain compounds according to structure B have $IC_{50}$ values less than 1 μM, more preferably less than 100 nM, and most preferably less than 10 nM.

In assays based on mammalian dopamine receptors or transporters, certain compounds according to structure B have $IC_{50}$ values less than 1 μM, more preferably less than 100 nM, and most preferably less than 10 nM.

In certain embodiments, compounds according to structure B are effective in the treatment of mammals suffering from addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, or Tourette's syndrome.

In certain embodiments, a compound of the present invention is represented by C:

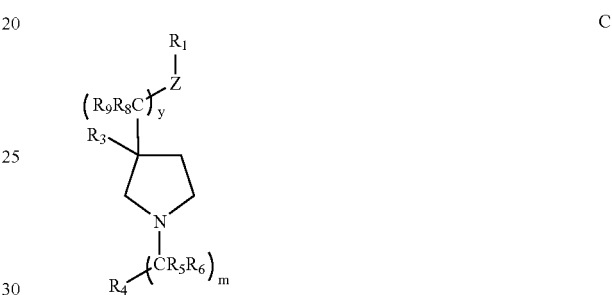

wherein
Z represents $C(R_3)_2$, C(O), O, NR, NC(O)OR, S, SO, or $SO_2$;
m is 1, 2, 3, 4 or 5;
p is 0, 1, 2, or 3;
y is 0, 1 or 2;
R represents H, alkyl, cycloalkyl, aryl, heteroaryl, aralkyl, or heteroaralkyl;
$R_1$ represents H, alkyl, aryl, heteroaryl, aralkyl, or heteroaralkyl;
R and $R_1$ may be connected through a covalent bond;
$R_2$ represents independently for each occurrence H, alkyl, fluoroalkyl, aryl, heteroaryl, or cycloalkyl;
$R_3$ represents independently for each occurrence H, alkyl, aryl, $OR_2$, $OC(O)R_2$, $CH_2OR_2$, or $CO_2R_2$;
$R_4$ represents independently for each occurrence H, alkyl, cycloalkyl, aryl, heteroaryl, alkenyl, or OR;
$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);
$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is C(O);
Y represents independently for each occurrence $OR_2$, $N(R_2)_2$, $SR_2$, $S(O)R_2$, $S(O)_2R_2$, or $P(O)(OR_2)_2$;
any two instances of $R_2$ may be connected through a covalent bond;
a covalent bond may connect $R_4$ and an instance of $R_5$ or $R_6$;
any two instances of $R_5$ and $R_6$ may be connected through a covalent bond;
any two geminal or vicinal instances of $R_8$ and $R_9$ may be connected through a covalent bond; and the stereochemical configuration at any stereocenter of a compound represented by C is R or S, or a mixture of these configurations.

In certain embodiments, the compounds of the present invention are represented by C and the attendant definitions, wherein Z is O or NR.

In certain embodiments, the compounds of the present invention are represented by C and the attendant definitions, wherein m is 3.

In certain embodiments, the compounds of the present invention are represented by C and the attendant definitions, wherein y is 1.

In certain embodiments, the compounds of the present invention are represented by C and the attendant definitions, wherein $R_1$ represents aryl.

In certain embodiments, the compounds of the present invention are represented by C and the attendant definitions, wherein $R_3$ represents independently for each occurrence H or alkyl.

In certain embodiments, the compounds of the present invention are represented by C and the attendant definitions, wherein $R_4$ represents cycloalkyl, aryl, or heteroaryl.

In certain embodiments, the compounds of the present invention are represented by C and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by C and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by C and the attendant definitions, wherein Z is O or NR; and m is 3.

In certain embodiments, the compounds of the present invention are represented by C and the attendant definitions, wherein Z is O or NR; and y is 1.

In certain embodiments, the compounds of the present invention are represented by C and the attendant definitions, wherein Z is O or NR; m is 3; and y is 1.

In certain embodiments, the compounds of the present invention are represented by C and the attendant definitions, wherein Z is O or NR; m is 3; y is 1; and $R_1$ is aryl.

In certain embodiments, the compounds of the present invention are represented by C and the attendant definitions, wherein Z is O or NR; m is 3; y is 1; $R_1$ is aryl; and $R_3$ is H or alkyl.

In certain embodiments, the compounds of the present invention are represented by C and the attendant definitions, wherein Z is O or NR; m is 3; y is 1; $R_1$ is aryl; $R_3$ is H or alkyl; and $R_4$ is cycloalkyl, aryl, or heteroaryl.

In certain embodiments, the compounds of the present invention are represented by C and the attendant definitions, wherein Z is O or NR; m is 3; y is 1; $R_1$ is aryl; $R_3$ is H or alkyl; $R_4$ is cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by C and the attendant definitions, wherein Z is O or NR; m is 3; y is 1; $R_1$ is aryl; $R_3$ is H or alkyl; $R_4$ is cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In assays based on mammalian dopamine, serotonin, or norepinephrine receptors or transporters, certain compounds according to structure C have $EC_{50}$ values less than 1 µM, more preferably less than 100 nM, and most preferably less than 10 nM.

In assays based on mammalian dopamine receptors or transporters, certain compounds according to structure C have $EC_{50}$ values less than 1 µM, more preferably less than 100 nM, and most preferably less than 10 nM.

In assays based on mammalian dopamine, serotonin, or norepinephrine receptors or transporters, certain compounds according to structure C have $IC_{50}$ values less than 1 µM, more preferably less than 100 nM, and most preferably less than 10 nM.

In assays based on mammalian dopamine receptors or transporters, certain compounds according to structure C have $IC_{50}$ values less than 1 µM, more preferably less than 100 nM, and most preferably less than 10 nM.

In certain embodiments, compounds according to structure C are effective in the treatment of mammals suffering from addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, or Tourette's syndrome.

In certain embodiments, a compound of the present invention is represented by D:

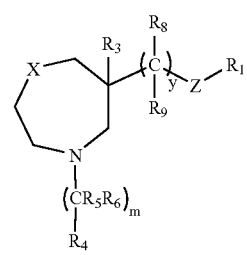

D wherein

X represents O, S, SO, $SO_2$, $NR_2$, $NC(O)R_7$, $NC(O)OR_2$, $NS(O)_2R_7$, or C=O;

Z represents $C(R_3)_2$, C(O), O, NR, NC(O)OR, S, SO, or $SO_2$;

m is 1, 2, 3, 4 or 5;

p is 0, 1, 2, or 3;

y is 0, 1, or 2;

R represents H, alkyl, cycloalkyl, aryl, heteroaryl, aralkyl, or heteroaralkyl;

$R_1$ represents H, alkyl, aryl, heteroaryl, aralkyl, or heteroaralkyl;

R and $R_1$ may be connected through a covalent bond;

$R_2$ represents independently for each occurrence H, alkyl, fluoroalkyl, aryl, heteroaryl, or cycloalkyl;

$R_3$ represents independently for each occurrence H, alkyl, aryl, $OR_2$, $OC(O)R_2$, $CH_2OR_2$, or $CO_2R_2$;

R represents independently for each occurrence H, alkyl, cycloalkyl, aryl, heteroaryl, alkenyl, or OR;

$R_5$ and $R_6$ are selected independently for each occurrence from the group consisting of H, alkyl, $(CH_2)_pY$, aryl, heteroaryl, F, $OR_2$, and $OC(O)R_2$; or an instance of $CR_5R_6$ taken together is C(O);

$R_7$ represents alkyl, cycloalkyl, aryl, heteroaryl, aralkyl, or heteroaralkyl;

$R_8$ and $R_9$ are selected independently for each occurrence from the group consisting of H, alkyl, $(CH_2)_pY$, aryl, heteroaryl, F, $OR_2$, and $OC(O)R_2$; or an instance of $CR_8R_9$ taken together is C(O);

Y represents independently for each occurrence $OR_2$, $N(R_2)_2$, $SR_2$, $S(O)R_2$, $S(O)_2R_2$, or $P(O)(OR_2)_2$;

any two instances of $R_2$ may be connected through a covalent bond;

a covalent bond may connect $R_4$ and an instance of $R_5$ or $R_6$;

any two instances of $R_5$ and $R_6$ may be connected through a covalent bond;

any two geminal or vicinal instances of $R_8$ and $R_9$ may be connected through a covalent bond; and the stereochemical configuration at any stereocenter of a compound represented by D is R, S, or a mixture of these configurations.

In certain embodiments, the compounds of the present invention are represented by D and the attendant definitions, wherein X is O or $NR_2$.

In certain embodiments, the compounds of the present invention are represented by D and the attendant definitions, wherein Z is O or NR.

In certain embodiments, the compounds of the present invention are represented by D and the attendant definitions, wherein m is 3.

In certain embodiments, the compounds of the present invention are represented by D and the attendant definitions, wherein y is 1.

In certain embodiments, the compounds of the present invention are represented by D and the attendant definitions, wherein $R_1$ represents aryl.

In certain embodiments, the compounds of the present invention are represented by D and the attendant definitions, wherein $R_3$ represents independently for each occurrence H or alkyl.

In certain embodiments, the compounds of the present invention are represented by D and the attendant definitions, wherein $R_4$ represents cycloalkyl, aryl, or heteroaryl.

In certain embodiments, the compounds of the present invention are represented by D and the attendant definitions, wherein $R_5$ and $R_6$ are selected independently for each occurrence from the group consisting of H, alkyl, $OR_2$, aryl, heteroaryl, and F.

In certain embodiments, the compounds of the present invention are represented by D and the attendant definitions, wherein $R_8$ and $R_9$ are selected independently for each occurrence from the group consisting of H, alkyl, $OR_2$, aryl, heteroaryl, and F.

In certain embodiments, the compounds of the present invention are represented by D and the attendant definitions, wherein X is O or $NR_2$; and Z is O or NR.

In certain embodiments, the compounds of the present invention are represented by D and the attendant definitions, wherein X is O or $NR_2$; Z is O or NR; and m is 3.

In certain embodiments, the compounds of the present invention are represented by D and the attendant definitions, wherein X is O or $NR_2$; Z is O or NR; and y is 1.

In certain embodiments, the compounds of the present invention are represented by D and the attendant definitions, wherein X is O or $NR_2$; Z is O or NR; m is 3; and y is 1.

In certain embodiments, the compounds of the present invention are represented by D and the attendant definitions, wherein X is O or $NR_2$; Z is O or NR; m is 3; y is 1; and $R_1$ is aryl.

In certain embodiments, the compounds of the present invention are represented by D and the attendant definitions, wherein X is O or $NR_2$; Z is O or NR; m is 3; y is 1; $R_1$ is aryl; and $R_3$ is H or alkyl.

In certain embodiments, the compounds of the present invention are represented by D and the attendant definitions, wherein X is O or $NR_2$; Z is O or NR; m is 3; y is 1; $R_1$ is aryl; $R_3$ is H or alkyl; and $R_4$ is cycloalkyl, aryl, or heteroaryl.

In certain embodiments, the compounds of the present invention are represented by D and the attendant definitions, wherein X is O or $NR_2$; Z is O or NR; m is 3; y is 1; $R_1$ is aryl; $R_3$ is H or alkyl; $R_4$ is cycloalkyl, aryl, or heteroaryl; and $R_5$ and $R_6$ are selected independently for each occurrence from the group consisting of H, alkyl, $OR_2$, aryl, heteroaryl, and F.

In certain embodiments, the compounds of the present invention are represented by D and the attendant definitions, wherein X is O or $NR_2$; Z is O or NR; m is 3; y is 1; $R_1$ is aryl; $R_3$ is H or alkyl; $R_4$ is cycloalkyl, aryl, or heteroaryl; $R_5$ and $R_6$ are selected independently for each occurrence from the group consisting of H, alkyl, $OR_2$, aryl, heteroaryl, and F; and $R_8$ and $R_9$ are selected independently for each occurrence from the group consisting of H, alkyl, $OR_2$, aryl, heteroaryl, and F.

In assays based on mammalian dopamine, serotonin, or norepinephrine receptors or transporters, certain compounds according to structure D have $EC_{50}$ values less than 1 µM, more preferably less than 100 nM, and most preferably less than 10 nM.

In assays based on mammalian dopamine receptors or transporters, certain compounds according to structure D have $EC_{50}$ values less than 1 µM, more preferably less than 100 nM, and most preferably less than 10 nM.

In assays based on mammalian dopamine, serotonin, or norepinephrine receptors or transporters, certain compounds according to structure D have $IC_{50}$ values less than 1 µM, more preferably less than 100 nM, and most preferably less than 10 nM.

In assays based on mammalian dopamine receptors or transporters, certain compounds according to structure D have $IC_{50}$ values less than 1 µM, more preferably less than 100 nM, and most preferably less than 10 nM.

In certain embodiments, compounds according to structure D are effective in the treatment of mammals suffering from addiction, anxiety, depression, sexual dysfunction, hypertension, migraine, Alzheimer's disease, obesity, emesis, psychosis, analgesia, schizophrenia, Parkinson's disease, restless leg syndrome, sleeping disorders, attention deficit hyperactivity disorder, irritable bowel syndrome, premature ejaculation, menstrual dysphoria syndrome, urinary incontinence, inflammatory pain, neuropathic pain, Lesche-Nyhane disease, Wilson's disease, or Tourette's syndrome.

In certain embodiments, the present invention relates to a compound represented by any of the structures outlined above, wherein said compound is a single stereoisomer.

In certain embodiments, the present invention relates to a formulation, comprising a compound represented by any of the structures outlined above; and a pharmaceutically acceptable excipient.

In certain embodiments, the present invention relates to ligands for receptors or transporters of dopamine, serotonin, or norepinephrine, wherein the ligands are represented by any of the structures outlined above, and any of the sets of definitions associated with one of those structures. In certain embodiments, the ligands of the present invention are antagonists or agonists of receptors or transporters of dopamine, serotonin, or norepinephrine. In any event, the ligands of the present invention preferably exert their effect on the dopamine, serotonin, or norepinephrine receptors or transporters at a concentration less than about 1 micromolar, more preferably at a concentration less than about 100 nanomolar, and most preferably at a concentration less than 10 nanomolar.

In certain embodiments, the selectivity of a ligand for dopamine receptors or transporters renders that ligand an effective therapeutic agent for an acute or chronic ailment, disease or malady. In certain embodiments, the selectivity of a ligand for dopamine receptors or transporters consists of a binding affinity for dopamine receptors or transporters at least a factor of ten greater than its binding affinity for receptors or transporters of other neurotransmitters. In certain embodiments, the selectivity of a ligand for dopamine receptors or transporters consists of a binding affinity for dopamine receptors or transporters at least a factor of one hundred greater than its binding affinity for receptors or transporters of other neurotransmitters. In certain embodiments, the selectivity of a ligand for dopamine receptors or transporters consists of a binding affinity for dopamine receptors or transporters at least a factor of one thousand greater than its binding affinity for receptors or transporters of other neurotransmitters.

The present invention contemplates pharmaceutical formulations of the ligands of the present invention. In certain embodiments, the pharmaceutical formulations will comprise ligands of the present invention that selectively effect dopamine receptors or transporters, and thereby have a therapeutic effect on an acute or chronic ailment, disease or malady that is at least in part due to biochemical or physiological processes associated with dopamine receptors or transporters. The Background of the Invention (see above) teaches examples of acute or chronic ailments, diseases or maladies that are caused or exacerbated by biochemical or physiological processes associated with dopamine receptors or transporters. One of ordinary skill in the art will be able to accumulate, by reference to the scientific literature, a more comprehensive list of acute or chronic ailments, diseases or maladies that are caused or exacerbated by biochemical or physiological processes associated with dopamine receptors or transporters. The present invention contemplates pharmaceutical formulations of ligands of the present invention that will be of medicinal value against the aforementioned acute or chronic ailments, diseases or maladies.

Biochemical Activity at Cellular Receptors, and Assays to Detect That Activity

Assaying processes are well known in the art in which a reagent is added to a sample, and measurements of the sample and reagent are made to identify sample attributes stimulated by the reagent. For example, one such assay process concerns determining in a chromogenic assay the amount of an enzyme present in a biological sample or solution. Such assays are based on the development of a colored product in the reaction solution. The reaction develops as the enzyme catalyzes the conversion of a colorless chromogenic substrate to a colored product.

Another assay useful in the present invention concerns determining the ability of a ligand to bind to a biological receptor utilizing a technique well known in the art referred to as a radioligand binding assay. This assay accurately determines the specific binding of a radioligand to a targeted receptor through the delineation of its total and nonspecific binding components. Total binding is defined as the amount of radioligand that remains following the rapid separation of the radioligand bound in a receptor preparation (cell homogenates or recombinate receptors) from that which is unbound. The nonspecific binding component is defined as the amount of radioligand that remains following separation of the reaction mixture consisting of receptor, radioligand and an excess of unlabeled ligand. Under this condition, the only radioligand that remains represents that which is bound to components other that receptor. The specific radioligand bound is determined by subtracting the nonspecific from total radioactivity bound. For a specific example of radioligand binding assay for µ-opioid receptor, see Wang, J. B. et al. *FEBS Letters* 1994, 338, 217.

Assays useful in the present invention concern determining the activity of receptors the activation of which initiates subsequent intracellular events in which intracellular stores of calcium ions are released for use as a second messenger. Activation of some G-protein-coupled receptors stimulates the formation of inositol triphosphate (IP3, a G-protein-coupled receptor second messenger) through phospholipase C-mediated hydrolysis of phosphatidylinositol, Berridge and Irvine (1984). Nature 312:315–21. IP3 in turn stimulates the release of intracellular calcium ion stores.

A change in cytoplasmic calcium ion levels caused by release of calcium ions from intracellular stores is used to determine G-protein-coupled receptor function. This is another type of indirect assay. Among G-protein-coupled receptors are muscarinic acetylcholine receptors (mAChR), adrenergic receptors, sigma receptors, serotonin receptors, dopamine receptors, angiotensin receptors, adenosine receptors, bradykinin receptors, metabotropic excitatory amino acid receptors and the like. Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores. Another type of indirect assay involves determining the activity of receptors which, when activated, result in a change in the level of intracellular cyclic nucleotides, e.g., cAMP, cGMP. For example, activation of some dopamine, serotonin, metabotropic glutamate receptors and muscarinic acetylcholine receptors results in a decrease in the cAMP or cGMP levels of the cytoplasm.

Furthermore, there are cyclic nucleotide-gated ion channels, e.g., rod photoreceptor cell channels and olfactory neuron channels [see, Altenhofen, W. et al. (1991) Proc. Natl. Acad. Sci U.S.A. 88:9868–9872 and Dhallan et al. (1990) Nature 347:184–187] that are permeable to cations upon activation by binding of cAMP or cGMP. A change in cytoplasmic ion levels caused by a change in the amount of cyclic nucleotide activation of photo-receptor or olfactory neuron channels is used to determine function of receptors that cause a change in cAMP or cGMP levels when activated. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cell for this type of assay can be made by co-transfection of a host cell with DNA encoding a cyclic nucleotide-gated ion channel and a DNA encoding a receptor (e.g., certain metabotropic glutamate receptors, muscarinic acetylcholine receptors, dopamine receptors, serotonin receptors and the like, which, when activated, causes a change in cyclic nucleotide levels in the cytoplasm.

Any cell expressing a receptor protein which is capable, upon activation, of directly increasing the intracellular concentration of calcium, such as by opening gated calcium channels, or indirectly affecting the concentration of intracellular calcium as by causing initiation of a reaction which utilizes Ca<2+> as a second messenger (e.g., G-protein-coupled receptors), may form the basis of an assay. Cells endogenously expressing such receptors or ion channels and cells which may be transfected with a suitable vector encoding one or more such cell surface proteins are known to those of skill in the art or may be identified by those of skill in the art. Although essentially any cell which expresses endogenous ion channel and/or receptor activity may be used, it is preferred to use cells transformed or transfected with heterologous DNAs encoding such ion channels and/or receptors so as to express predominantly a single type of ion channel or receptor. Many cells that may be genetically engineered to express a heterologous cell surface protein are known. Such cells include, but are not limited to, baby hamster kidney (BHK) cells (ATCC No. CCL10), mouse L cells (ATCC No. CCLI.3), DG44 cells [see, Chasin (1986) Cell. Molec. Genet. 12:555] human embryonic kidney (HEK) cells (ATCC No. CRL1573), Chinese hamster ovary (CHO) cells (ATCC Nos. CRL9618, CCL61, CRL9096), PC12 cells (ATCC No. CRL1721) and COS-7 cells (ATCC No. CRL1651). Preferred cells for heterologous cell surface protein expression are those that can be readily and efficiently transfected. Preferred cells include HEK 293 cells, such as those described in U.S. Pat. No. 5,024,939.

Any compound which is known to activate ion channels or receptors of interest may be used to initiate an assay. Choosing an appropriate ion channel- or receptor-activating reagent depending on the ion channel or receptor of interest is within the skill of the art. Direct depolarization of the cell membrane to determine calcium channel activity may be accomplished by adding a potassium salt solution having a concentration of potassium ions such that the final concentration of potassium ions in the cell-containing well is in the range of about 50–150 mM (e.g., 50 mM KCl). With respect to ligand-gated receptors and ligand-gated ion channels, ligands are known which have affinity for and activate such receptors. For example, nicotinic acetyloholine receptors are known to be activated by nicotine or acetylcholine; similarly, muscarinic and acetylcholine receptors may be activated by addition of muscarine or carbamylcholine.

Agonist assays may be carried out on cells known to possess ion channels and/or receptors to determine what effect, if any, a compound has on activation or potentiation of ion channels or receptors of interest. Agonist assays also may be carried out using a reagent known to possess ion channel- or receptor-activating capacity to determine whether a cell expresses the respective functional ion channel or receptor of interest.

Contacting a functional receptor or ion channel with agonist typically activates a transient reaction; and prolonged exposure to an agonist may desensitize the receptor or ion channel to subsequent activation. Thus, in general, assays for determining ion channel or receptor function should be initiated by addition of agonist (i.e., in a reagent solution used to initiate the reaction). The potency of a compound having agonist activity is determined by the detected change in some observable in the cells (typically an increase, although activation of certain receptors causes a decrease) as compared to the level of the observable in either the same cell, or substantially identical cell, which is treated substantially identically except that reagent lacking the agonist (i.e., control) is added to the well. Where an agonist assay is performed to test whether or not a cell expresses the functional receptor or ion channel of interest, known agonist is added to test-cell-containing wells and to wells containing control cells (substantially identical cell that lacks the specific receptors or ion channels) and the levels of observable are compared. Depending on the assay, cells lacking the ion channel and/or receptor of interest should exhibit substantially no increase in observable in response to the known agonist. A substantially identical cell may be derived from the same cells from which recombinant cells are prepared but which have not been modified by introduction of heterologous DNA. Alternatively, it may be a cell in which the specific receptors or ion channels are removed. Any statistically or otherwise significant difference in the level of observable indicates that the test compound has in some manner altered the activity of the specific receptor or ion channel or that the test cell possesses the specific functional receptor or ion channel.

In an example of drug screening assays for identifying compounds which have the ability to modulate ion channels or receptors of interest, individual wells (or duplicate wells, etc.) contain a distinct cell type, or distinct recombinant cell line expressing a homogeneous population of a receptor or ion channel of interest, so that the compound having unidentified activity may be screened to determine whether it possesses modulatory activity with respect to one or more of a variety of functional ion channels or receptors. It is also contemplated that each of the individual wells may contain the same cell type so that multiple compounds (obtained from different reagent sources in the apparatus or contained within different wells) can be screened and compared for modulating activity with respect to one particular receptor or ion channel type.

Antagonist assays, including drug screening assays, may be carried out by incubating cells having functional ion channels and/or receptors in the presence and absence of one or more compounds, added to the solution bathing the cells in the respective wells of the microtiter plate for an amount of time sufficient (to the extent that the compound has affinity for the ion channel and/or receptor of interest) for the compound(s) to bind to the receptors and/or ion channels, then activating the ion channels or receptors by addition of known agonist, and measuring the level of observable in the cells as compared to the level of observable in either the same cell, or substantially identical cell, in the absence of the putative antagonist.

The assays are thus useful for rapidly screening compounds to identify those that modulate any receptor or ion channel in a cell. In particular, assays can be used to test functional ligand-receptor or ligand-ion channel interactions for cell receptors including ligand-gated ion channels, voltage-gated ion channels, G-protein-coupled receptors and growth factor receptors.

Those of ordinary skill in the art will recognize that assays may encompass measuring a detectable change of a solution as a consequence of a cellular event which allows a compound, capable of differential characteristics, to change its characteristics in response to the cellular event. By selecting a particular compound which is capable of differential characteristics upon the occurrence of a cellular event, various assays may be performed. For example, assays for determining the capacity of a compound to induce cell injury or cell death may be carried out by loading the cells with a pH-sensitive fluorescent indicator such as BCECF (Molecular Probes, Inc., Eugene, Oreg. 97402, Catalog #B1150) and measuring cell injury or cell death as a function of changing fluorescence over time.

In a further example of useful assays, the function of receptors whose activation results in a change in the cyclic nucleotide levels of the cytoplasm may be directly determined in assays of cells that express such receptors and that have been injected with a fluorescent compound that changes fluorescence upon binding cAMP. The fluorescent compound comprises cAMP-dependent-protein kinase in which the catalytic and regulatory subunits are each labelled with a different fluorescent-dye [Adams et al. (1991) Nature 349:694–697]. When cAMP binds to the regulatory subunits, the fluorescence emission spectrum changes; this change can be used as an indication of a change in cAMP concentration.

The function of certain neurotransmitter transporters which are present at the synaptic cleft at the junction between two neurons may be determined by the development of fluorescence in the cytoplasm of such neurons when conjugates of an amine acid and fluorescent indicator (wherein the fluorescent indicator of the conjugate is an acetoxymethyl ester derivative e.g., 5-(aminoacetamido) fluorescein; Molecular Probes, Catalog #A1363) are transported by the neurotransmitter transporter into the cytoplasm of the cell where the ester group is cleaved by esterase activity and the conjugate becomes fluorescent.

In practicing an assay of this type, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art. After contacting the recombinant cell for a sufficient time to effect any interactions, the level of gene expression is measured. The amount of time to effect such interactions may be empirically determined, such as by running a time course and measuring the level of transcription as a function of time. The amount of transcription may be measured using any method known to those of skill in the art to be suitable. For example, specific mRNA expression may be detected using Northern blots or specific protein product may be identified by a characteristic stain. The amount of transcription is then compared to the amount of transcription in either the same cell in the absence of the test compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for a number of categories of cell surface-localized receptors, including: ligand-gated ion channels and voltage-gated ion channels, and G protein-coupled receptors.

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk<–> cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk<–> and COS-7 cell lines, which express the Type I human muscarinic (HM1) receptor and which are transformed with either a c-fos promoter-CAT reporter gene expression construct or a c-fos promoter-luciferase reporter gene expression construct.

Any cell surface protein that is known to those of skill in the art or that may be identified by those of skill in the art may used in the assay. The cell surface protein may endogenously expressed on the selected cell or it may be expressed from cloned DNA. Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403–410); and the like); neuronal nicotinic acetylcholine receptors (e.g., the alpha 2, alpha 3 and beta 2 subtypes disclosed in U.S. Ser. No. 504,455 (filed Apr. 3, 1990), hereby expressly incorporated by reference herein in its entirety); the rat alpha 2 subunit (Wada et al. (1988) Science 240:330–334); the rat alpha 3 subunit (Boulter et al. (1986) Nature 319:368–374); the rat alpha 4 subunit (Goldman et al. (1987) cell 48:965–973); the rat alpha 5 subunit (Boulter et al. (1990) J. Biol. Chem. 265:4472–4482); the rat beta 2 subunit (Deneris et al. (1988) Neuron 1:45–54); the rat beta 3 subunit (Deneris et al. (1989) J. Biol. Chem. 264: 6268–6272); the rat beta 4 subunit (Duvoisin et al. (1989) Neuron 3:487–496); combinations of the rat alpha subunits, beta subunits and alpha and beta subunits; GABA receptors (e.g., the bovine alpha 1 and beta 1 subunits (Schofield et al. (1987) Nature 328:221–227); the bovine alpha 2 and alpha 3 subunits (Levitan et al. (1988) Nature 335:76–79); the gamma-subunit (Pritchett et al. (1989) Nature 338:582–585); the beta 2 and beta 3 subunits (Ymer et alo (1989) EMBO J. 8:1665–1670); the delta subunit (Shivers, B. D. (1989) Neuron 3:327–337); and the like); glutamate receptors (e.g., receptor isolated from rat brain (Hollmann et al. (1989) Nature 342:643–648); and the like); adrenergic receptors (e.g., human beta 1 (Frielle et al. (1987) Proc. Natl. Acad. Sci. 84.:7920–7924); human alpha 2 (Kobilka et al. (1987) Science 238:650–656); hamster beta 2 (Dixon et al. (1986) Nature 321:75–79); and the like); dopamine receptors (e.g., human D2 (Stormann et al. (1990) Molec. Pharm. 37:1–6); rat (Bunzow et al. (1988) Nature 336:783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Reporter gene constructs are prepared by operatively linking a reporter gene with at least one transcriptional regulatory element. If only one transcriptional regulatory element is included, it must be a regulatable promoter. At least one of the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Pharmaceutical Compositions/Formulations

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue, hard gelatin capsules, soft gelatin capsules, mouth sprays, syrups, emulsions, micro-emulsions; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or stearic acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11)

polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, besylate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1–19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, benzenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, corn starch, certain silicates, and sodium carbonate; (5) solution retarding agents, such as paraffin; (6) absorption accelerators, such as quaternary ammonium compounds, and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, zinc stearate, sodium stearate, stearic acid and mixtures thereof; (10) coloring agents; and (11) controlled release agents, such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, vaginal tablets, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The compounds according to the invention may be formulated for administration in any convenient way for use in human or veterinary medicine, by analogy with other pharmaceuticals.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and CO., San Francisco, U.S.A., 1969 or "Livestock Feeds and Feeding" O and B books, Corvallis, Oreg., U.S.A., 1977).

Combinatorial Libraries

The subject reactions readily lend themselves to the creation of combinatorial libraries of compounds for the screening of pharmaceutical, agrochemical or other biological or medically-related activity or material-related qualities. A combinatorial library for the purposes of the present invention is a mixture of chemically related compounds which may be screened together for a desired property; said libraries may be in solution or covalently linked to a solid support. The preparation of many related compounds in a single reaction greatly reduces and simplifies the number of screening processes which need to be carried out. Screening for the appropriate biological, pharmaceutical, agrochemical or physical property may be done by conventional methods.

Diversity in a library can be created at a variety of different levels. For instance, the substrate aryl groups used in a combinatorial approach can be diverse in terms of the core aryl moiety, e.g., a variegation in terms of the ring structure, and/or can be varied with respect to the other substituents.

A variety of techniques are available in the art for generating combinatorial libraries of small organic molecules. See, for example, Blondelle et al. (1995) Trends Anal. Chem. 14:83; the Affymax U.S. Pat. Nos. 5,359,115 and 5,362,899: the Ellman U.S. Pat. No. 5,288,514: the Still et al. PCT publication WO 94/08051; Chen et al. (1994) JACS 116: 2661: Kerr et al. (1993) JACS 115:252; PCT publications WO92/10092, WO93/09668 and WO91/07087; and the Lerner et al. PCT publication WO93/20242). Accordingly, a variety of libraries on the order of about 16 to 1,000,000 or more diversomers can be synthesized and screened for a particular activity or property.

In an exemplary embodiment, a library of substituted diversomers can be synthesized using the subject reactions adapted to the techniques described in the Still et al. PCT publication WO 94/08051, e.g., being linked to a polymer bead by a hydrolyzable or photolyzable group, e.g., located at one of the positions of substrate. According to the Still et al. technique, the library is synthesized on a set of beads, each bead including a set of tags identifying the particular diversomer on that bead. In one embodiment, which is particularly suitable for discovering enzyme inhibitors, the beads can be dispersed on the surface of a permeable membrane, and the diversomers released from the beads by lysis of the bead linker. The diversomer from each bead will diffuse across the membrane to an assay zone, where it will interact with an enzyme assay. Detailed descriptions of a number of combinatorial methodologies are provided below.

A) Direct Characterization

A growing trend in the field of combinatorial chemistry is to exploit the sensitivity of techniques such as mass spectrometry (MS), e.g., which can be used to characterize sub-femtomolar amounts of a compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from a library can be irradiated in a MALDI step in order to release the diversomer from the matrix, and ionize the diversomer for MS analysis.

B) Multipin Synthesis

The libraries of the subject method can take the multipin library format. Briefly, Geysen and co-workers (Geysen et al. (1984) PNAS 81:3998–4002) introduced a method for generating compound libraries by a parallel synthesis on polyacrylic acid-grated polyethylene pins arrayed in the microtitre plate format. The Geysen technique can be used to synthesize and screen thousands of compounds per week using the multipin method, and the tethered compounds may be reused in many assays. Appropriate linker moieties can also been appended to the pins so that the compounds may be cleaved from the supports after synthesis for assessment of purity and further evaluation (c.f., Bray et al. (1990) Tetrahedron Lett 31:5811–5814; Valerio et al. (1991) Anal Biochem 197:168–177; Bray et al. (1991) Tetrahedron Lett 32:6163–6166).

C) Divide-Couple-Recombine

In yet another embodiment, a variegated library of compounds can be provided on a set of beads utilizing the strategy of divide-couple-recombine (see, e.g., Houghten (1985) PNAS 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where compound synthesis occurs on resin sealed inside porous polypropylene bags (Houghten et al. (1986) *PNAS* 82:5131–5135). Substituents are coupled to the compound-bearing resins by placing the bags in appropriate reaction solutions, while all common steps such as resin washing and deprotection are performed simultaneously in one reaction vessel. At the end of the synthesis, each bag contains a single compound.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use of protection/deprotection reactions with photolabile protecting groups.

The key points of this technology are illustrated in Gallop et al. (1994) *J Med Chem* 37:1233–1251. A synthesis substrate is prepared for coupling through the covalent attachment of photolabile nitroveratryloxycarbonyl (NVOC) protected amino linkers or other photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each compound is precisely known; hence, its interactions with other molecules can be directly assessed.

In a light-directed chemical synthesis, the products depend on the pattern of illumination and on the order of addition of reactants. By varying the lithographic patterns, many different sets of test compounds can be synthesized simultaneously; this characteristic leads to the generation of many different masking strategies.

E) Encoded Combinatorial Libraries

In yet another embodiment, the subject method utilizes a compound library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with Sequenceable Bio-oligomers

The principle of using oligonucleotides to encode combinatorial synthetic libraries was described in 1992 (Brenner et al. (1992) PNAS 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, compound libraries can be derived for use in the subject method, where the oligonucleotide sequence of the tag identifies the sequential combinatorial reactions that a particular bead underwent, and therefore provides the identity of the compound on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test compound library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr J M et al. (1993) *J Am Chem Soc* 115:2529–2531), orthogonality in synthesis is achieved by employing acid-labile protection for the coding strand and base-labile protection for the compound strand.

In an alternative approach (Nikolaiev et al. (1993) *Pept Res* 6:161–170), branched linkers are employed so that the coding unit and the test compound can both be attached to the same functional group on the resin. In one embodiment, a cleavable linker can be placed between the branch point and the bead so that cleavage releases a molecule containing both code and the compound (Ptek et al. (1991) *Tetrahedron Lett* 32:3891–3894). In another embodiment, the cleavable linker can be placed so that the test compound can be selectively separated from the bead, leaving the code behind. This last construct is particularly valuable because it permits screening of the test compound without potential interference of the coding groups. Examples in the art of independent cleavage and sequencing of peptide library members and their corresponding tags has confirmed that the tags can accurately predict the peptide structure.

2) Non-sequenceable Tagging: Binary Encoding

An alternative form of encoding the test compound library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the compound would be attached to the solid support via the photocleavable linker and the tag is attached through a catechol ether linker via carbene insertion into the bead matrix (Nestler et al. (1994) *J Org Chem* 59:4723–4724). This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) *PNAS* 92:6027–6031) and provide guidance for generating the subject compound library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, compounds are partially detached and transferred to assay plates; third, a metal binding assay identifies the active wells; fourth, the corresponding beads are rearrayed singly into new microtiter plates; fifth, single active compounds are identified; and sixth, the structures are decoded.

EXEMPLIFICATION

The invention now being generally described, it will be more readily understood by reference to the following examples, which are included merely for purposes of illustration of certain aspects and embodiments of the present invention, and are not intended to limit the invention.

Example 1

Synthesis of [1-(4-chloro-phenyl)-cyclobutyl]-(3-hydroxymethyl piperidin-1yl)-methadone

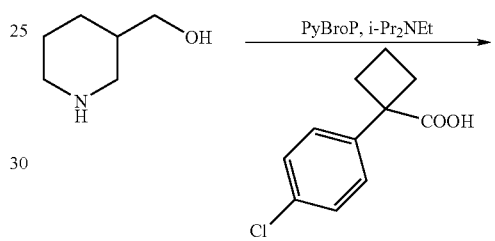

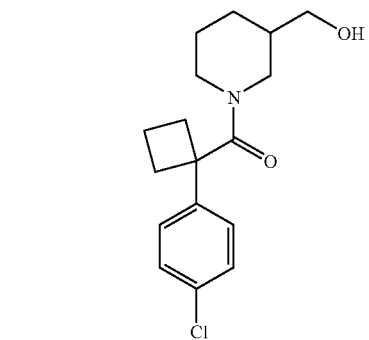

1

To a stirred solution of piperdin-3-yl methanol (5.0 g, 0.043 moles) and 1-(4-chloro-phenyl)-cyclobutane carboxylic acid (13.58 g, 0.065 moles) in anhydrous dichloromethane (100 mL) was added di-isopropyl ethyl amine (22.47 mL, 0.219 moles) dropwise. After completion of addition solid PyBroP (30.07 g, 0.065 moles) was added to the stirring reaction mixture. The reaction mixture continued stirring at RT for 10 h and was quenched with 10% KOH (aq.). The aqueous layer was extracted with EtOAc (3×200 mL). The combined organic layers were dried over $Na_2SO_4$ and concentrated to yield an oil. This crude material was purified using silica gel chromatography (4:1 hexane:

EtOAc-1:1 hexane EtOAc) to yield 1 as a brown oil (7 g, 0.028 moles, 53%). $^1$H (CDCl$_3$) δ 7.26 (4H, s), 4.45 (2H, d, J=12.3 Hz), 3.93 (4H, m), 3.4–1.03 (11H, m). LRMS: M+ 308.

Example 2

Synthesis of [1-(4-chloro-phenyl)-cyclobutyl]-(3-hydroxymethyl piperidin-1yl)-methanol

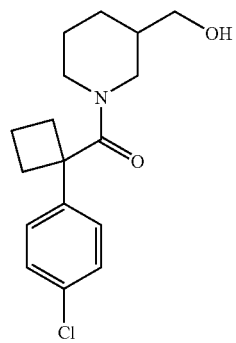

1

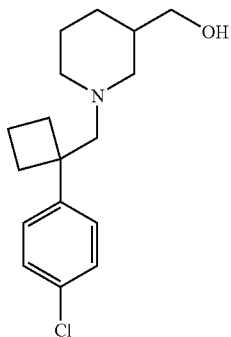

2

Example 3

Synthesis of [1-(4-chloro-phenyl)-cyclobutyl]-(3-phenoxymethyl piperidin-1yl)-methadone

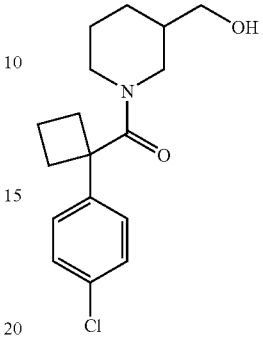

1

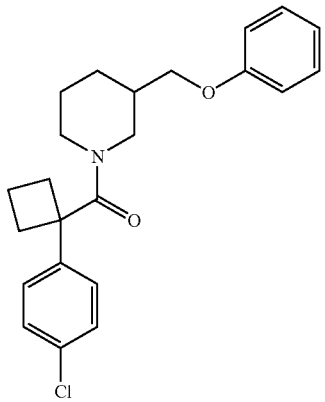

3

A solution of amide 1 (300 mg, 0.977 mmoles) dissolved in anhydrous toluene (10 mL) was cooled to 0° C. RedAl (691 mg, 3.4 mmoles) was added dropwise to the cooled stirring reaction mixture. After completion of addition the reaction continued stirring at RT. After 12 h, 10% KOH was added to the reaction mixture. The aqueous layer was extracted with EtOAc (3×5 mL). The combined organic layers were dried over Na$_2$SO$_4$ and concentrated to yield an oil. The crude material was purified using silica gel chromatography (4:1 hexanes:EtOAc-4:1 EtOAc:hexanes) to yield 2 (230 mg, 0.785 mmole, 80%). $^1$H (CDCl$_3$) δ 7.32–7.12 (4H, m), 3.66–3.47 (2H, m), 2.80–1.28 (17H, m). LRMS: M+ 293.

A solution of 1 (2.07 g, 6.72 mmoles), triphenylphosphine (2.64 g, 10.08 mmole), and phenol (1.27 g, 13.44 mmoles) dissolved in anhydrous ether (50 mL) was cooled in a brine bath to −5° C. DEAD (1.60 mL, 10.08 mmoles) dissolved in ether (10 mL) was added to the cooled stirring reaction mixture. After completion of addition, the reaction mixture continued stirring at −5° C. After 4 h, the reaction mixture was concentrated and crude material was dissolved in a hexane/ethyl acetate mixture (70% hexanes:30% ethyl acetate, 30 mL). Phosphine by-products precipitated and were filtered off. The filtrate was concentrated to yield an oil. This oil was purified using silica gel chromatography (100% hexanes-1:1 hexanes:EtOAc) to yield the amine 3 (840 mg, 2.19 mmole, 32%). LRMS: M+ 384.

Example 4

Synthesis of [1-(4-chloro-phenyl)-cyclobutyl]-3-phenoxymethyl-piperidine

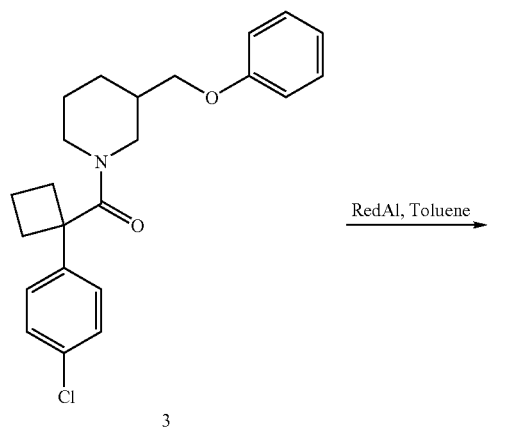

3

RedAl, Toluene →

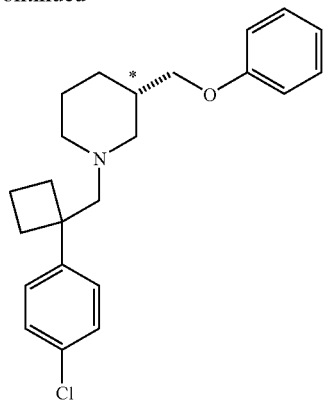

6

*stereochemistry randomly assigned

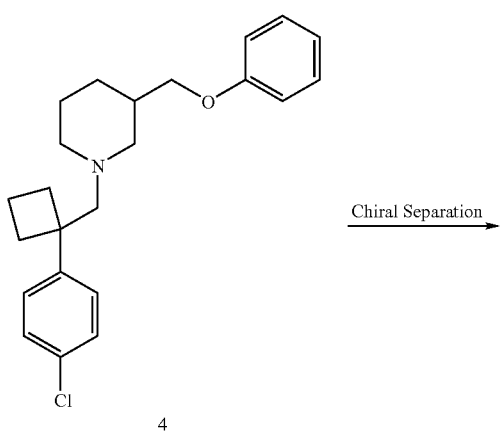

4

Chiral Separation →

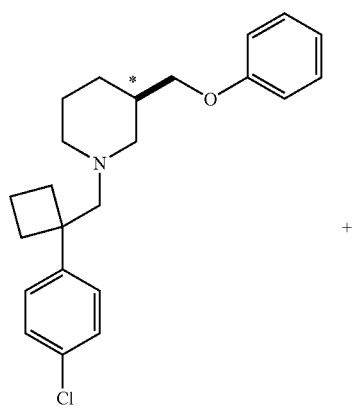

5

+

A solution of amide 3 (0.5 g, 1.3 mmole) dissolved in anhydrous toluene (15 mL) was cooled to 0° C. RedAl (920 mg, 4.55 mmole) was added dropwise to the cooled stirring reaction mixture. After completion of addition, the reaction continued stirring at RT. After 12 h, 10% KOH was added to the reaction mixture. The aqueous layer was extracted with EtOAc (3×20 mL). The combined organic layers were dried over $Na_2SO_4$ and concentrated to yield an oil. The crude material was purified using silica gel chromatography (100% hexanes-9:1 hexanes:EtOAc) to yield 4 (300 mg, 0.811 mmoles, 62%). Enantiomers 5 and 6 were isolated on a chiral AD column (100% MeOH). $^1H$ (CDCl$_3$) δ 7.35–6.86 (9H, m), 3.80–3.64 (2H, m), 2.65–1.15 (15H, m). $^{13}C$ (CDCl$_3$) δ 159.3, 148.6, 131.0, 129.7, 128.0, 127.8, 120.7, 114.7, 70.7, 69.0, 59.2, 56.6, 47.3, 36.4, 31.9, 31.8, 27.0, 45.0, 16.3. LRMS: M+ 370.

Example 5

Synthesis of [1-(4-chloro-phenyl)-cyclobutylmethyl]-3-(4-trifluoromethyl-phenoxymethyl)-piperidine

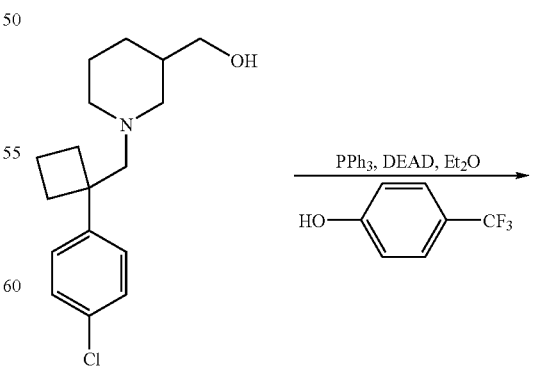

2

PPh$_3$, DEAD, Et$_2$O →

-continued

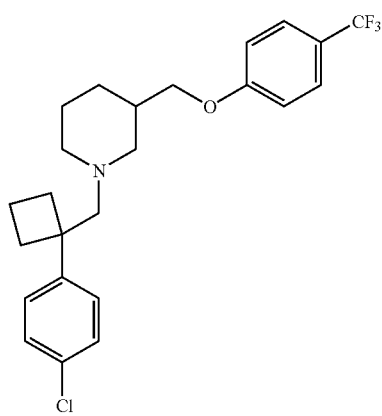

7

A solution of 2 (50 mg, 0.170 mmoles), triphenylphosphine (66.88 g, 0.340 mmoles), and phenol (55.12 mg, 0.340 mmoles) dissolved in anhydrous ether (1.0 mL) was cooled in a brine bath to −5° C. DEAD (40.14 µL, 0.255 mmoles) dissolved in ether (0.5 mL) was added to the cooled stirring reaction mixture. After completion of addition, the reaction mixture continued stirring at −5° C. After 4 h, the reaction mixture was concentrated and crude material was dissolved in a hexane/ethyl acetate mixture (70% hexanes:30% ethyl acetate, 30 mL). Phosphine by-products precipitated and were filtered off. Filtrate was concentrated to yield an oil. This oil was purified using silica gel chromatography (4:1 hexanes:EtOAc) to yield 7 (42 mg, 0.096 mmoles, 56%). LRMS: M+ 438.

Example 6

Synthesis of 1-[2-(4-Chloro-phenyl)-ethyl]-3-(4-trifluoromethyl-phenoxymethyl)-piperidine

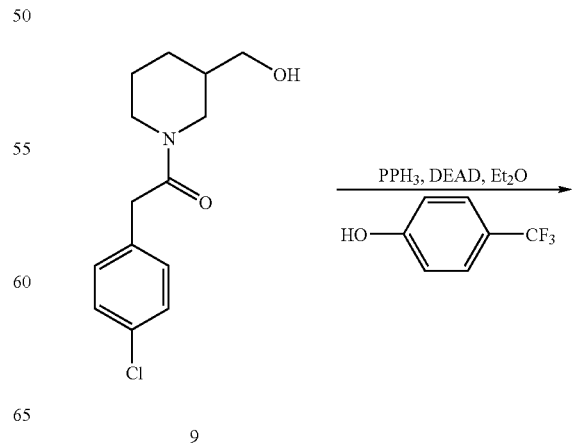

8

Synthesis of [1-(4-chloro-phenyl)-1-(3-hydroxymethyl piperidin-1yl)-ethanone

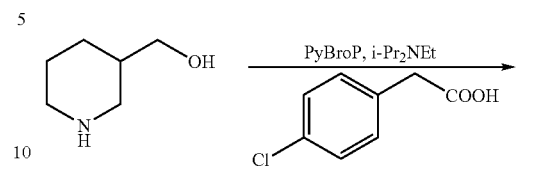

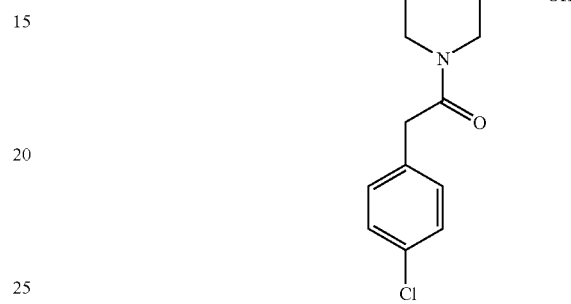

9

To a stirred solution of piperidin-3-yl methanol (1.0 g, 8.7 mmoles) and 4-chloro-phenyl)-acetic acid (2.22 g, 13.0 mmoles) in anhydrous dichloromethane (20 mL) was added di-isopropyl ethyl amine (4.55 mL, 26.0 mmoles) dropwise. After completion of addition, solid PyBroP (6.06 g, 13.0 moles) was added to the stirring reaction mixture. The reaction mixture continued stirring at RT for 10 h and was quenched with 10% KOH (aq.). The aqueous layer was extracted with EtOAc (3×20 mL). The combined organic layers were dried over $Na_2SO_4$ and concentrated to yield an oil. This crude material was purified using silica gel chromatography (4:1 hexane:EtOAc-95:5 hexane EtOAc) to yield 9 as an oil (2.47 g, 0.028 moles, 9.25 mmole, 93%). LRMS: M+ 267.

Synthesis of 2-(4-Chloro-phenyl)-1-[3-(4-trifluoromethyl-phenoxymethyl)-piperidi-1-yl]-ethanone

9

-continued

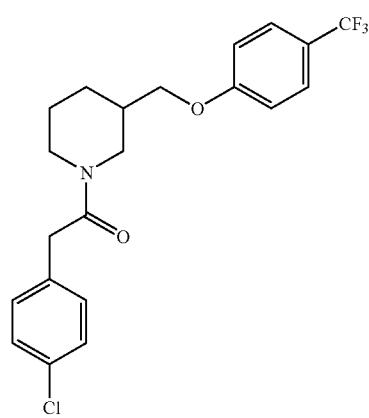

10

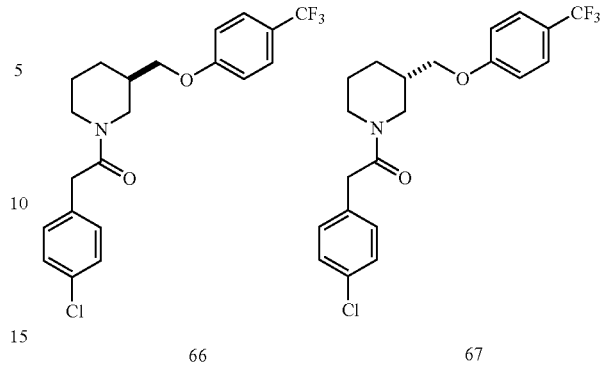

66  67 absolute configurations were assigned arbitrarily

A solution of 9 (333 mg, 1.24 mmoles), triphenylphosphine (483 mg, 1.86 mmoles), and phenol (403 mg, 2.49 mmoles) dissolved in anhydrous ether (4.5 mL) was cooled in a brine bath to −5° C. DEAD (325 mg, 1.86 mmoles) dissolved in ether (0.5 mL) was added to the cooled stirring reaction mixture. After completion of addition, the reaction mixture continued stirring at −5° C. After 4 h, the reaction mixture was concentrated and crude material was dissolved in a hexane/ethyl acetate mixture (70% hexanes:30% ethyl acetate, 30 mL). Phosphine by-products precipitated and were filtered off. Filtrate was concentrated to yield an oil. This crude material was purified using silica gel chromatography (100% hexanes-100% EtOAc) to yield 10 as an oil (249 mg, 0.606 mmoles, 49%). LRMS: M+ 411.

Compound 10 could be separated into enantiomers 66 and 67 using a chiral AD column (75:25 MeOH: acetonitrile).

Synthesis of 1-[2-(4-chloro-phenyl)-ethyl]-3-(4-trifluoromethyl-phenoxymethyl)-piperidine

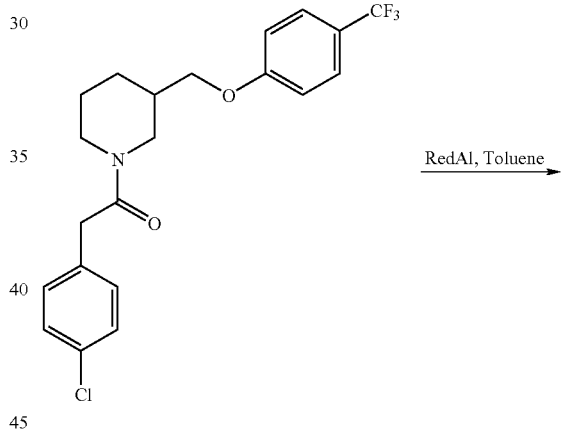

10

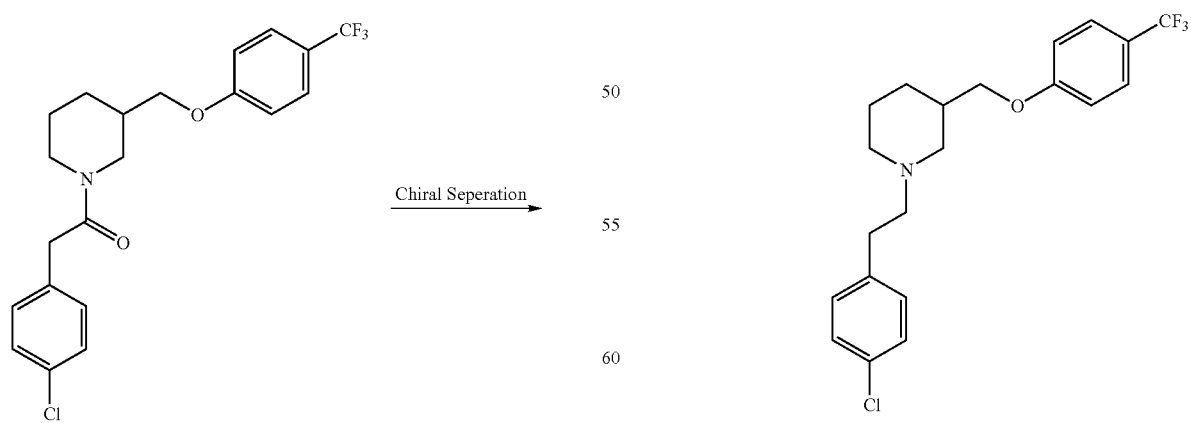

10  8

A solution of amide 10 (100 mg, 0.243 mmole) dissolved in anhydrous toluene (5 mL) was cooled to 0° C. RedAl (172 mg, 0.852 mmole) was added dropwise to the cooled stirring reaction mixture. After completion of addition, the reaction continued stirring at RT. After 12 h, 10% KOH was added to the reaction mixture. The aqueous layer was extracted with EtOAc (3×2 mL). The combined organic layers were dried over $Na_2SO_4$ and concentrated to yield an oil. The crude material was purified using a silica gel prep plate (100% hexanes-9:1 hexanes:EtOAc) to yield 8 (42 mg, 0.106 mmole, 43%). LRMS: M+ 396.

Example 7

Synthesis of 4-[1-(4-Chloro-phenyl)-cyclobutylmethyl]-[2-(4-trifluoromethyl-phenoxymethyl)-[1,4]oxazepane

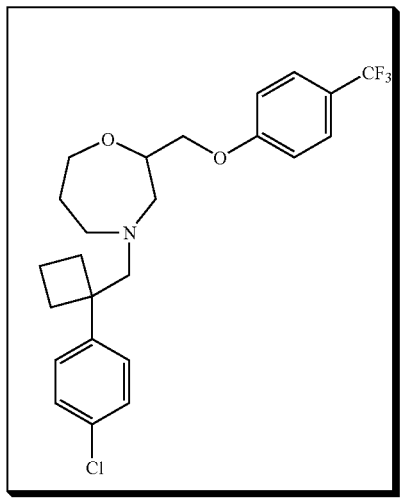

Synthesis of 3-benzylamino-propan-1-ol

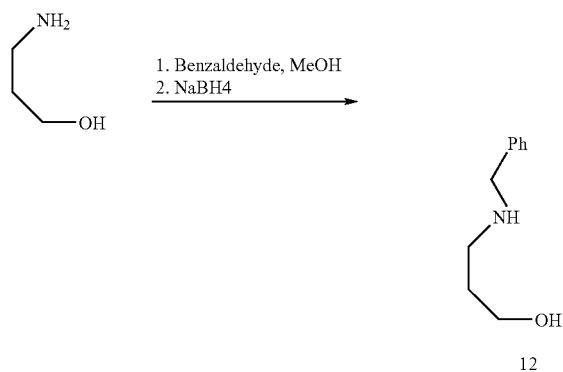

To a stirring solution of benzaldehyde (19.15 mL, 188.3 mmole) dissolved in anhydrous MeOH (375 mL) was added 3-amino-1-propanol (15.13 mL, 197.8 mmole) dropwise. After completion of addition, the reaction mixture was heated to 75° C. After 1 h, the reaction mixture was cooled down to RT and placed in an ice bath. Solid $NaBH_4$ was added over 20 min. After completion of addition, the reaction mixture continued stirring at RT. After 10 h, the reaction mixture was concentrated and the white crude material was taken up in dichloromethane (300 mL). The organic layer was extracted with water (200 mL). The aqueous layer was acidified with 10% HCl and then extracted with dichloromethane (3×200 mL). The combined organic layers were dried over $Na_2SO_4$ and concentrated to yield 12 as a yellow oil (23 g, 0.14 moles, 70%). $^1$H ($CD_3OD$) δ 7.40–7.20 (5H, m), 4.98 (2H, s), 3.75 (2H, s), 3.64 (1H, t, J=6.2 Hz), 2.70 (2H, t, J=7.1 Hz), 1.77 (2H, m). LRMS: M+ 165.

Synthesis of 4-benzyl-2-chloromethyl-[1,4]oxazepane

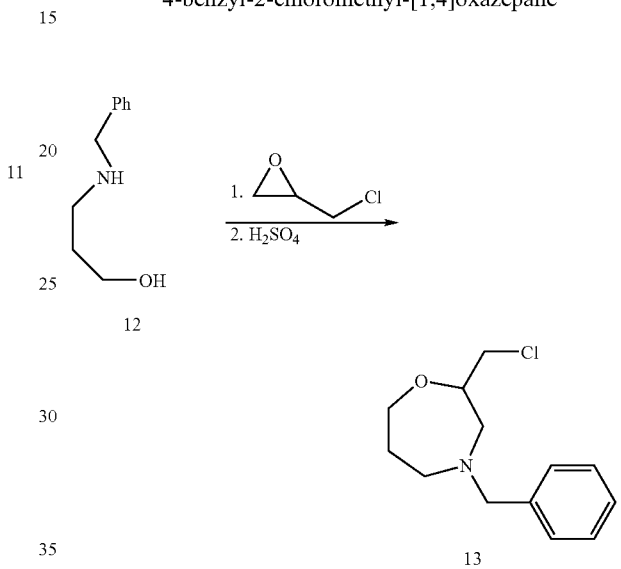

A solution of alcohol 12 (3.0 g, 18.18 mmoles) and epichlorohydrin (14.22 mL, 181.8 mmoles) was heated to 40° C. After 2.5 h, the reaction was cooled down to RT and the excess epichlorohydrin was evaporated in vacuo. Sulfuric acid (5.52 mL) was added slowly to the crude mixture. After completion of addition, the reaction flask was placed in a preheated oil bath (150° C.). The reaction mixture was heated for 30 minutes, cooled down to RT, and quenched with ice. The aqueous layer was basified with 10% KOH and extracted with EtOAc (3×300 mL). The combined organic layers were dried over $Na_2SO_4$ and concentrated to yield a crude oil. This oil was purified using silica gel chromatography (70:28:2 hexanes: DCM:2M $NH_3$ in EtOH) to obtain the oxazepine 13 (1.47 g, 6.13 mmole, 34%). LRMS: 239.

Synthesis of 4-benzyl-2-(4-trifluoromethyl-phenoxymethyl)-[1,4]oxazepane

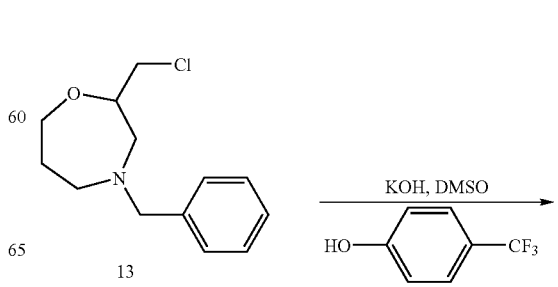

-continued

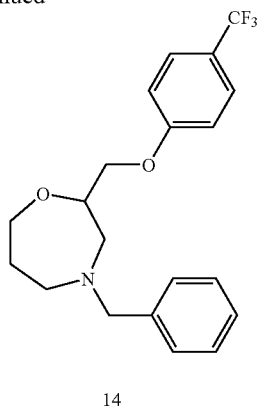

14

To a solution of KOH (131 mg, 2.3 mmoles) in DMSO (2 mL) was added 4-trifluoromethylphenol (189 mg, 1.17 mmoles) followed by the halide 13 (280 mg, 1.17 mmoles). After completion of addition, the reaction mixture was heated to 55° C. After 12 h, the reaction mixture was cooled to RT and quenched with water. The aqueous layer was extracted with EtOAc (3×2 mL) and the combined organic layers were dried over $Na_2SO_4$ and concentrated to yield a crude oil. The crude material was purified using silica gel chromatography (9:1 hexane:EtOAc-85:15 hexanes:EtOAc) to yield 14 (113.5 mg, 0.31 mmole, 26%). LRMS: M+ 366.

Synthesis of 2-(4-trifluoromethyl-phenoxymethyl)-[1,4]oxazepane

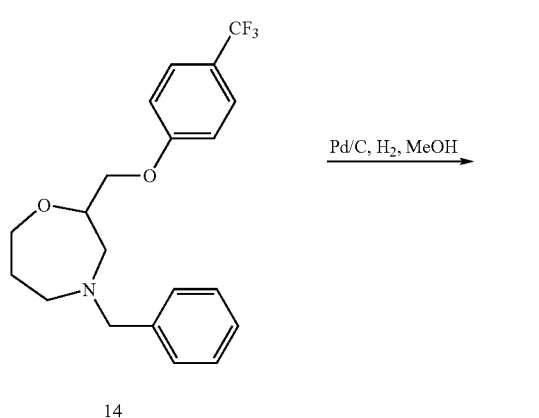

14

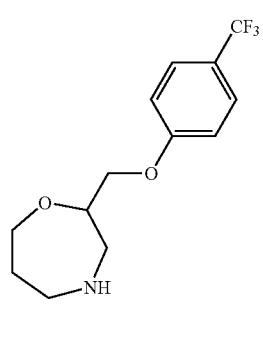

15

Benzyl-protected amine 14 (92.5 mg, 0.253 mmole) was dissolved in MeOH (8.0 mL). To this solution 10% Pd/C (78 mg) was added. The system was alternately evacuated and filled with hydrogen from a balloon. The reaction mixture was stirred vigorously under hydrogen for 5 h. The system was purged with nitrogen and the reaction mixture was filtered. The filtrate was concentrated to yield 15 was a yellow oil (43.6 mg, 0.159 mmole, 63%). LRMS: M+ 275.

Synthesis of [1-(4-Chloro-phenyl)-cyclobutyl]-[2-(4-trifluoromethyl-phenoxymethyl)-[1,4]oxazepan-4-yl]-methanone

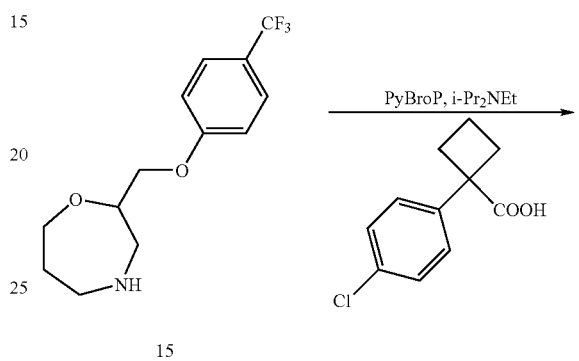

15

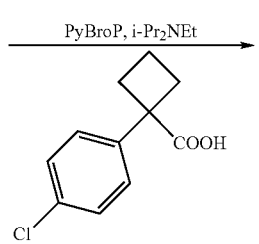

16

To a stirred solution of 15 (43 mg, 0.158 mmole) and 1-(4-chloro-phenyl)-cyclobutane carboxylic acid (50 mg, 0.237 mmole) in anhydrous dichloromethane (4 mL) was added di-isopropyl ethyl amine (82.6 µL, 0.474 mmoles) dropwise. After completion of addition, solid PyBroP (110.5 g, 0.237 moles) was added to the stirring reaction mixture. The reaction mixture continued stirring at RT for 10 h, and was quenched with 10% KOH (aq.). The aqueous layer was extracted with EtOAc (3×8 mL). The combined organic layers were dried over $Na_2SO_4$ and concentrated to yield an oil. This crude material was purified using silica gel chromatography (4:1 hexane:EtOAc-1:1 hexane EtOAc) to yield 16 as a brown oil (53.3 mg, 0.113 mmole, 72%). LRMS: M+ 468.

Synthesis of 4-[1-(4-Chloro-phenyl)-cyclobutylmethyl]-2-(4-trifluoromethyl-phenoxymethyl)-[1,4]oxazepane

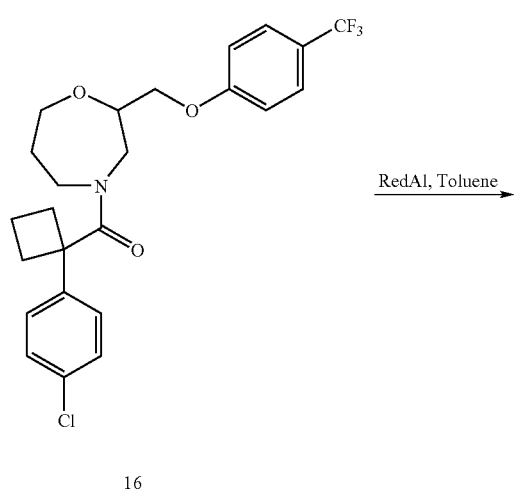

A solution of amide 16 (53.3 mg, 0.114 mmole) in anhydrous toluene (1.5 mL) was cooled to 0° C. RedAl (80.54 mg, 0.399 mmole) was added dropwise to the cooled stirring reaction mixture. After completion of addition, the reaction continued stirring at RT. After 12 h, 10% KOH was added to the reaction mixture. The aqueous layer was extracted with EtOAc (3×2 mL). The combined organic layers were dried over $Na_2SO_4$ and concentrated to yield an oil. The crude material was purified using silica gel chromatography (85:15 hexanes:EtOAc) to yield 11 (30 mg, 0.066 mmole, 59%) LRMS: M+ 453.

Example 8

Synthesis of 1-[1-(4-Chlorophenyl)cyclobutyl]-2-(3-phenoxymethylpiperidin-1-yl)ethanone

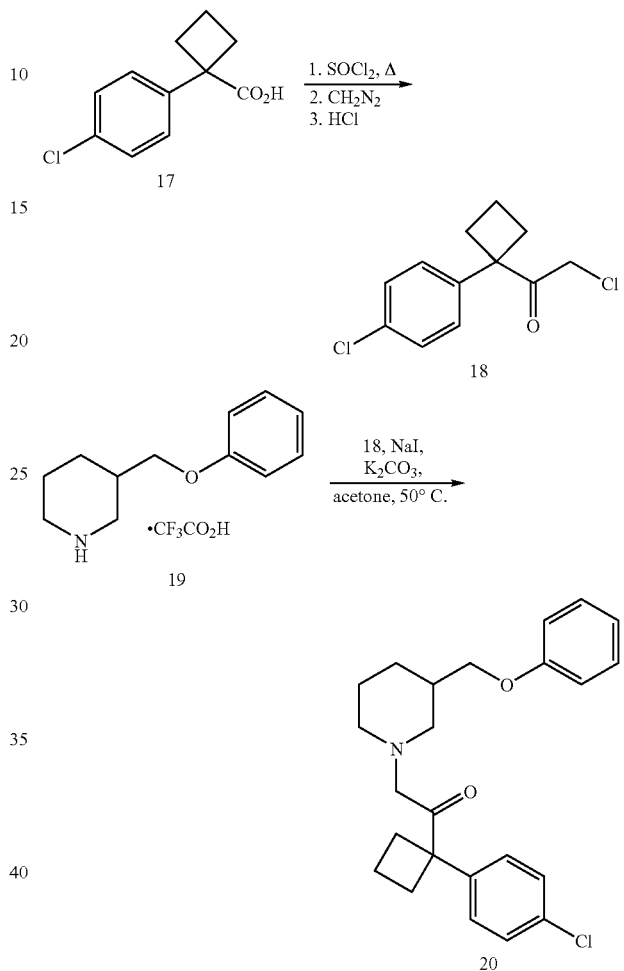

A mixture of 17 (0.942 g, 4.48 mmol) and thionyl chloride (2 mL) were heated at reflux for 3 h. The reaction mixture was concentrated, diluted with THF (2 mL), and concentrated in vacuo to give a brownish-yellow oil. The oil was dissolved in THF (15 mL) and then cooled to 0° C. Next, diazomethane (generated at 0° C. from 2 g 1-methyl-3-nitro-1-nitrososguanidine in 15 mL diethyl ether and 1.36 g sodium hydroxide in 15 mL water) was added. The resulting solution was maintained at 0° C. overnight. Hydrochloric acid (5 mL; 4 M) was carefully added. The reaction mixture was maintained at 0° C. for 1 h, and then concentrated to a yellow oil. The oil was purified by column chromatography on silica gel eluting with hexane/ethyl acetate (90:10) to give 18 as a colorless oil.

To a solution of 18 (96 mg, 0.393 mmol) in acetone (0.5 mL) was added sodium iodide (59 mg, 0.393 mmol). After 5 min at room temperature, the mixture was added to a mixture of 19 (100 mg, 0.328 mmol) and potassium carbonate (226 mg) in acetone (0.5 mL). The resulting mixture was heated at 50° C. for 18 h. The reaction mixture was poured into water (20 mL) and extracted with ethyl acetate (2×20 mL). The organic extracts were combined, washed with brine (15 mL), dried over anhydrous sodium sulfate, filtered, and concentrated to a yellow oil. The oil was purified by column chromatography on silica gel eluting with hexane/ethyl acetate/2 N ammonia in ethanol (80:16:4) to give 20 as a colorless oil.

Example 9

Synthesis of 1-[1-(4-Chloro-phenyl)cyclobutyl]-2-(3-phenoxymethylpiperidin-1-yl)ethanol

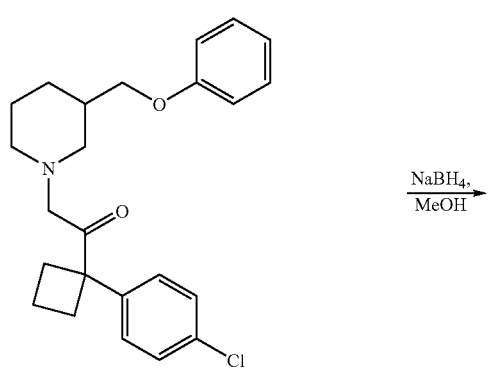

20

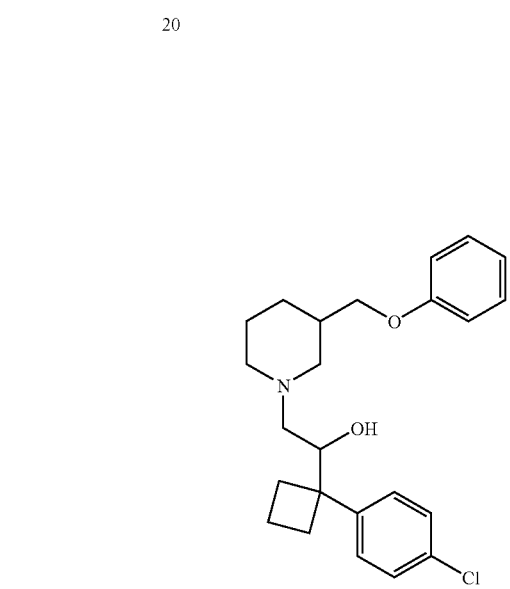

21

To a solution of 20 (56 mg, 0.141 mmol) in methanol (1 mL) at 0° C. was added sodium borohydride (11 mg, 0.282 mmol). The reaction mixture was maintained at room temperature for 2 h. The reaction mixture was poured into water (10 mL) and extracted with ethyl acetate (2×15 mL). The organic extracts were combined, washed with brine (10 mL), dried over anhydrous sodium sulfate, filtered, and concentrated to give a colorless oil. The oil was purified by column chromatography on silica gel eluting with hexane:ethyl acetate:2 N ammonia in ethanol (80:16:4) to give 21 as a colorless oil.

Example 10

Synthesis of 1-[1-(4-Chlorophenyl)cyclobutyl]-2-[3-(4-trifluoromethyl-phenoxymethyl)piperidin-1-yl]ethanone

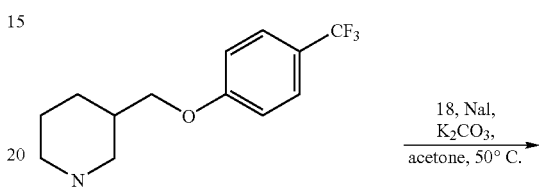

22

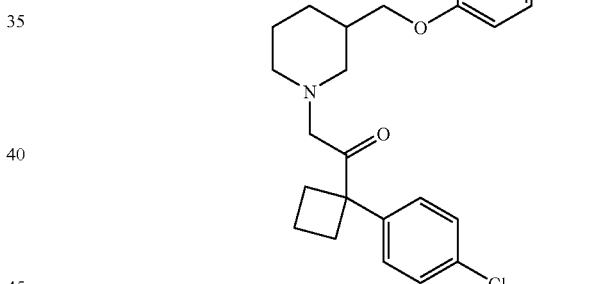

23

To a solution of 18 (96 mg, 0.396 mmol) in acetone (1.0 mL) was added sodium iodide (59 mg, 0.393 mmol). After 5 min at room temperature, the mixture was added to a mixture of 22 (123 mg, 0.330 mmol) and potassium carbonate (228 mg) in 0.5 mL acetone. The resulting mixture was heated at 50° C. for 18 h. The reaction mixture was poured into water (20 mL) and extracted with ethyl acetate (2×20 mL). The organic extracts were combined, washed with brine (15 mL), dried over anhydrous sodium sulfate, filtered, and concentrated to give a yellow oil. The oil was purified by column chromatography on silica gel eluting with hexane:ethyl acetate:2 N ammonia in ethanol (80:16:4) to give 23 as a colorless oil.

Example 11

Synthesis of 1-[1-(4-Chlorophenyl)cyclobutyl]-2-[3-(4-trifluoromethyl-phenoxymethyl)piperidin-1-yl]ethanol

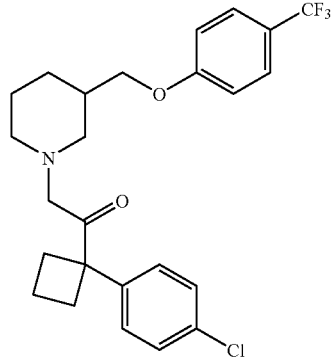

23

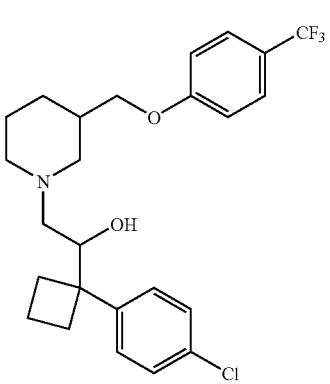

24

To a solution of 23 (121 mg, 0.26 mmol) in 2 mL methanol at room temperature was added sodium borohydride (20 mg, 0.52 mmol). The reaction mixture was maintained at room temperature for 2 h. The reaction mixture was poured into water (20 mL), and extracted with ethyl acetate (2×20 mL). The organic extracts were combined, washed with brine (15 mL), dried over anhydrous sodium sulfate, filtered, and concentrated to a colorless oil. The oil was purified by column chromatography on silica gel eluting with hexane:ethyl acetate:2 N ammonia in ethanol (80:16:4) to give 24 as a colorless oil.

Example 12

Synthesis of N-1-Carbobenzyloxy[3-R-(2'-anilino)carboxy]piperidine

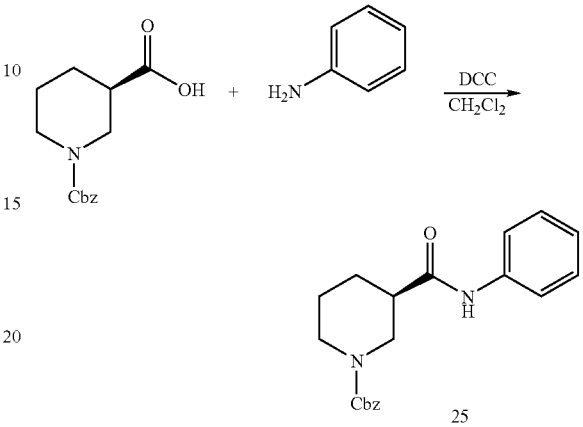

25

A solution of R-Cbz-nipecotic acid (0.038 mol, 10.0 g) and aniline (4.0 equiv, 0.15 mmol, 14 mL) in $CH_2Cl_2$ at 0° C. was treated with DCC (1.5 equiv, 0.057 mol, 12.0 g) under Ar. The reaction mixture was allowed to warm to 25° C. and stirred for 12 h. The reaction mixture was then filtered to remove the dicyclohexyl urea, and the solvent was removed in vacuo. Chromatography ($SiO_2$, 2.5 cm×30.5 cm, 1:1 hexane-EtOAc) provided 25 (10.0 g, 12.8 g theoretical, 78%) as a white foam: $R_f$ 0.45 ($SiO_2$, 1:1 hexane-EtOAc): LRMS m/z 338 ($M^+$, $C_{20}H_{22}N_2O_3$, requires 338).

Example 13

Synthesis of Piperidine-3-R-carboxilic acid phenylamide

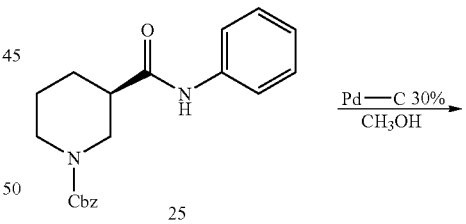

25

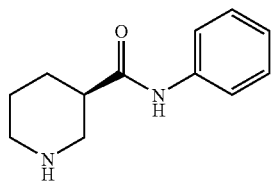

26

A solution of 25 (0.015 mol, 5.0 g) and Pd—C 30% (100 mg) in $CH_3OH$ at 25° C. was added to a Paar hydrogenator low pressure reaction vessel. The mixture was reacted at 55 psi with vigorous shaking until hydrogen uptake subsided (2 h). The catalyst was filtered through a pad of Celite. The filtrate was concentrated in vacuo which provided 26 (3.0 g,

Example 14

Synthesis of 1-[1-(4-Chloro-phenyl)-cyclobutanecarbonyl]-piperidine-3-R-carboxylic acid phenylamide

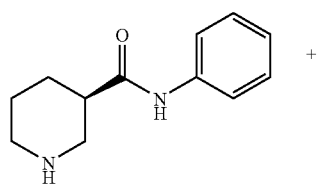

26

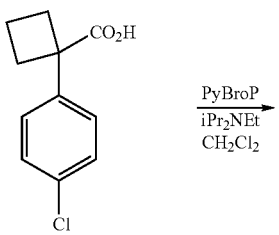

PyBroP
iPr₂NEt
CH₂Cl₂

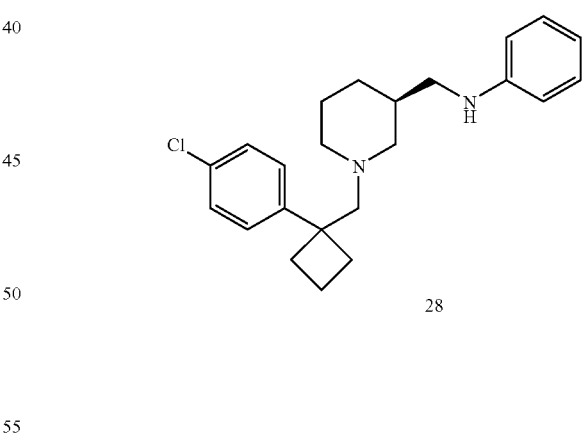

27

A solution of 26 (2.95 mmol, 603 mg), 1-(4-chlorophenyl)-1-cyclobutane carboxylic acid (1.5 equiv, 4.43 mmol, 932 mg) and iPr₂NEt (3.0 equiv, 8.85 mmol, 1.5 mL) in CH₂Cl₂ (10 mL) was treated with PyBroP (1.5 equiv, 4.43 mmol, 2.07 g) under Ar at 0° C. After warming to 25° C., and stirring for 12 h, the reaction mixture was quenched with 10% aqueous HCl and extracted with EtOAc (3×25 mL). The organic layer was then washed with NaHCO$_{3(sat)}$ and dried with NaCl$_{(sat)}$ and MgSO$_{4(s)}$. Chromatography (SiO₂, 2.5 cm×30.5 cm, 2:1 hexane-EtOAc) provided 27 (0.851 g, 1.17 g theoretical, 73%) as a white foam: R$_f$ 0.17 (SiO₂, 2:1 hexane-EtOAc); LRMS m/z 396 (M⁺, C₂₃H₂₅ClN₂O₂, requires 396).

Example 15

Synthesis of {1-[1-(4-Chloro-phenyl)-cyclobutylmethyl]-piperidin-3-R-ylmethyl}-phenyl-amine

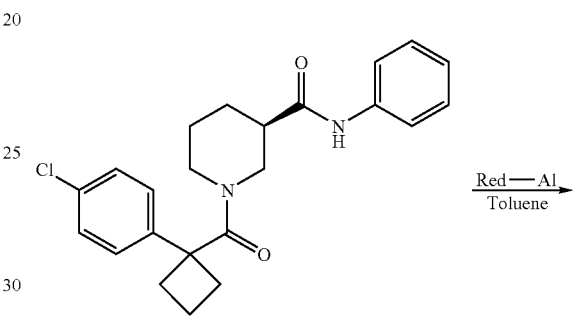

A solution of 27 (0.504 mmol, 200 mg) in toluene (2 mL) at 0° C. was treated with 3.0 M Red-Al (3.5 equiv, 1.76 mmol) under Ar. The reaction mixture stirred for 12 h, and returned to 25° C. The reaction mixture was then cooled to 0° C., quenched with 10% aqueous NaOH and extracted with EtOAc (3×25 mL). The organics were dried with NaCl$_{(sat)}$ and Na₂SO$_{4(s)}$. The reaction mixture was purified by chromatography (PTLC, SiO₂, 20 cm×20 cm, 1 mm, 2:1 hexane-EtOAc) which provided 28 (170 mg, 186 mg theoretical, 91%) as a colorless oil: R$_f$ 0.61 (SiO₂, 2:1 hexane-EtOAc); LRMS m/z 368 (M⁺, C₂₃H₂₉ClN₂, requires 368).

Example 16

Synthesis of 3-Phenoxymethyl-piperidine-1-carboxylic acid tert-butyl ester

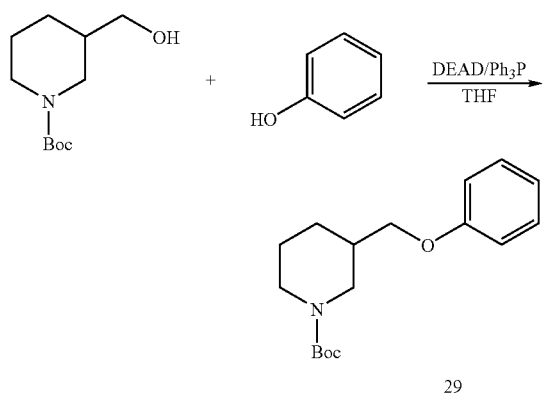

A solution of 3-hydroxymethyl-piperidine-1-carboxylic acid tert-butyl ester (4.64 mmol, 1.00 g), phenol (3.0 equiv, 13.92 mmol, 1.2 mL) and triphenylphosphine (3.0 equiv, 13.92 mmol, 3.65 g) in THF at 0° C. was treated with DEAD (3.0 equiv, 13.92 mol, 2.2 mL) under Ar. The reaction mixture was allowed to warm to 25° C., and stirred for 5 h. The reaction mixture was quenched with 10% NaOH (20 mL) and then extracted with EtOAc (2×25 mL). The combined organics were dried with $NaCl_{(sat)}$ and $Na_2SO_{4(s)}$. The solvents were removed in vacuo and chromatography ($SiO_2$, 2.5 cm×30.5 cm, 6:1 hexane-EtOAc) provided 29 (0.626 g, 1.35 g theoretical, 46%) as a white solid: $R_f$ 0.46 ($SiO_2$, 6:1 hexane-EtOAc); LRMS m/z 291 ($M^+$, $C_{17}H_{25}NO_3$, requires 291).

Example 17

Synthesis of 3-Phenoxymethyl-piperidine

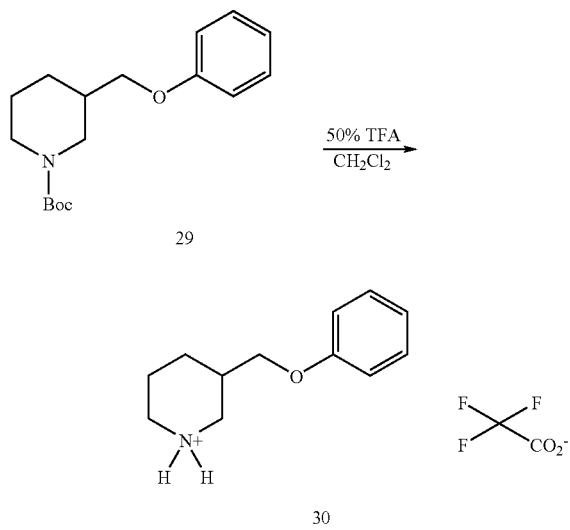

A solution of 29 (0.343 mmol, 100 mg) in $CH_2Cl_2$ (500 µL) at 0° C. was treated with TFA (500 µL). The reaction mixture was allowed to warm to 25° C., and stirred for 1 h. The solvent was removed under a stream of $N_2$ which provided 30 (105 mg, 105 mg theoretical, 99%) as a white solid: LRMS m/z 192 ($M^+$, $C_{12}H_{18}NO^+$, requires 192).

Example 18

Synthesis of 1-(4-Chloro-phenyl)-2-(3-phenoxymethyl-piperidin-1-yl)-ethanone

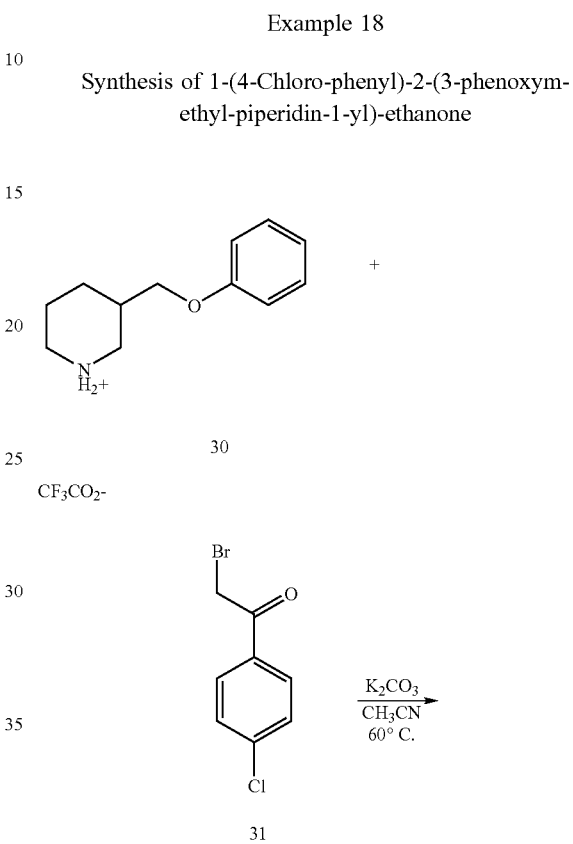

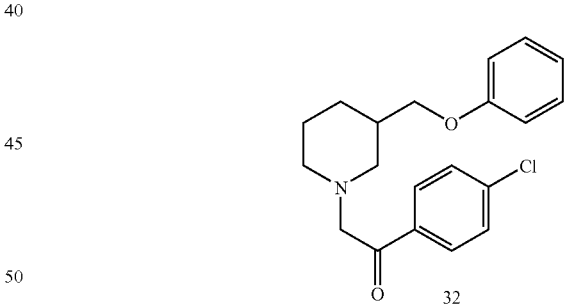

A solution of 3-phenoxymethyl-piperidine 30 (0.343 mmol, 105 mg), 2-bromo-4'-chloroacetophenone (31) (1.5 equiv, 0.515 mmol, 120 mg) and $K_2CO_3$ (3.0 equiv, 1.03 mmol, 142 mg) in $CH_3CN$ was heated to 60° C. and stirred for 12 h. The reaction mixture was quenched with $H_2O$ (10 mL), and then extracted with EtOAc (2×15 mL). The combined organics were dried with $NaCl_{(sat)}$ and $Na_2SO_{4(s)}$. The solvents were removed in vacuo and chromatography (PTLC, $SiO_2$, 20 cm×20 cm, 1 mm, 9:1 hexane-acetone) provided 32 (106 mg, 118 g theoretical, 46%) as a colorless oil: $R_f$ 0.52 ($SiO_2$, 9:1 hexane-acetone); LRMS m/z 344 ($M^+$, $C_{20}H_{22}ClNO_2$, requires 344).

Example 19

Synthesis of 1-(4-Chloro-phenyl)-2-(3-phenoxym-ethyl-piperidin-1-yl)-ethanol

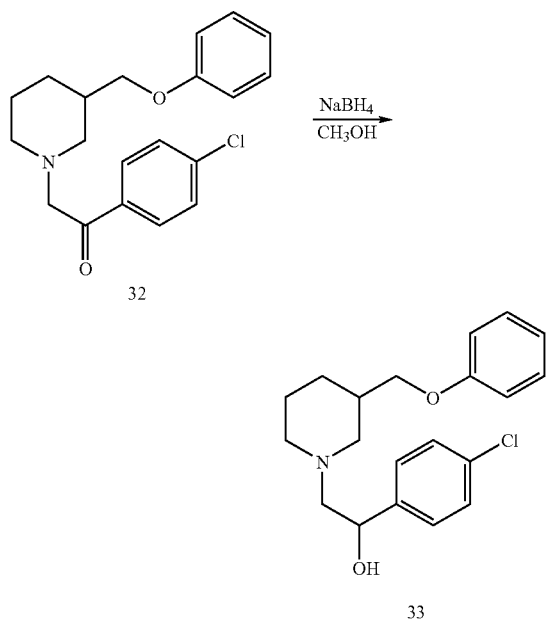

A solution of 32 (0.259 mmol, 89 mg) in CH₃OH was treated with NaBH₄ (3.0 equiv, 0.777 mmol, 30 mg) at 0° C. and stirred for 2 h. The reaction mixture was quenched with 10% HCl (5 mL) and then neutralized with NaHCO₃(sat) and extracted with EtOAc (2×10 mL). The combined organics were dried with NaCl$_{(sat)}$ and Na₂SO$_{4(s)}$. The solvents were removed in vacuo and chromatography (PTLC, SiO₂, 20 cm×20 cm, 1 mm, 9:1 EtOAc-CH₃OH) provided 33 (72 mg, 90 mg theoretical, 80%) as a colorless oil: R$_f$ 0.60 (SiO₂, 9:1 EtOAc-CH₃OH); LRMS m/z 346 (M⁺, C₂₀H₂₄ClNO₂, requires 346).

Example 20

Synthesis of 3-Phenoxymethyl-1-(1-phenyl-cyclobu-tylmethyl)-piperidine

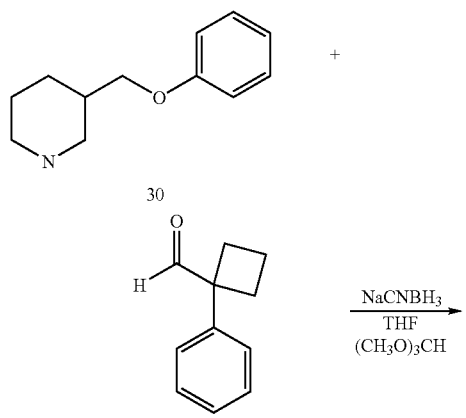

-continued

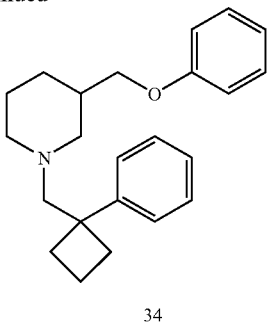

A solution of 30 (0.343 mmol, 105 mg) and 1-phenyl-cyclobutanecarbaldehyde (1.5 equiv, 0.515 mmol, 83 mg) in benzene were heated to reflux utilizing a Dean-Stark trap. The benzene was replaced three times. After the last reflux period, the solvents were removed in vacuo. The resulting oil was dissolved in THF (1 mL) and treated with NaCNBH₃ (3.0 equiv, 1.03 mmol, 65 mg) and trimethylorthoformate (1 mL) at 25° C. After stirring for 12 h, the reaction mixture was quenched with 10% HCl (5 mL) and then neutralized with NaHCO₃(sat) and extracted with EtOAc (2×10 mL). The combined organics were dried with NaCl$_{(sat)}$ and Na₂SO$_{4(s)}$. The solvents were removed in vacuo, and chromatography (PTLC, SiO₂, 20 cm×20 cm, 1 mm, 3:1 hexanes-EtOAc) provided 34 (68 mg, 115 mg theoretical, 59%) as a colorless oil: R$_f$ 0.54 (SiO₂, 3:1 hexanes-EtOAc); LRMS m/z 335 (M⁺, C₂₃H₂₉NO, requires 335).

Example 21

{1-[1-(4-Chloro-phenyl)-cyclobutylmethyl]-piperi-din-3-R-ylmethyl}-methyl-phenyl-amine

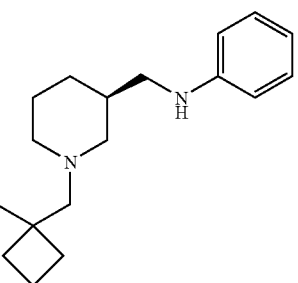

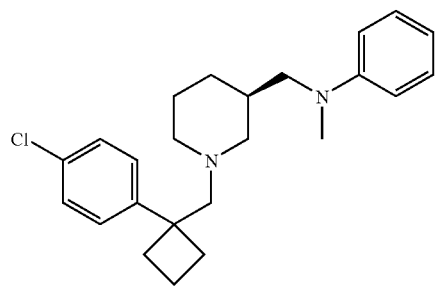

A solution of the 28 (0.228 mmol, 84 mg) in THF (1 mL) at −78° C. was treated with 1.6 M nBuLi (1.5 equiv, 0.342 mmol, 214 μL) under Ar. The reaction mixture was warmed to 0° C. for 30 min and then cooled again to −78° C. CH₃I (1.5 equiv, 0.342 mmol, 21 μL) was then added and the reaction mixture stirred at 0° C. for 5 min. The reaction was quenched with NaHCO₃(sat) and extracted with EtOAc. The combined organics were dried with NaCl(sat) and Na₂SO₄(s). The solvents were removed in vacuo and chromatography (PTLC, SiO₂, 20 cm×20 cm, 1 mm, 3:1 hexanes-EtOAc) provided 35 (87 mg, 87 mg theoretical, 99%) as a yellow oil: R$_f$ 0.38 (SiO₂, 3:1 hexanes-EtOAc); LRMS m/z 383 (M⁺, C₂₄H₃₁ClN₂, requires 383).

Example 22

Synthesis of 1-[1-(4-Chloro-phenyl)-cyclobutylmethyl]-3-[2-(4-trifluoromethyl-phenoxy)-ethyl]-piperidine

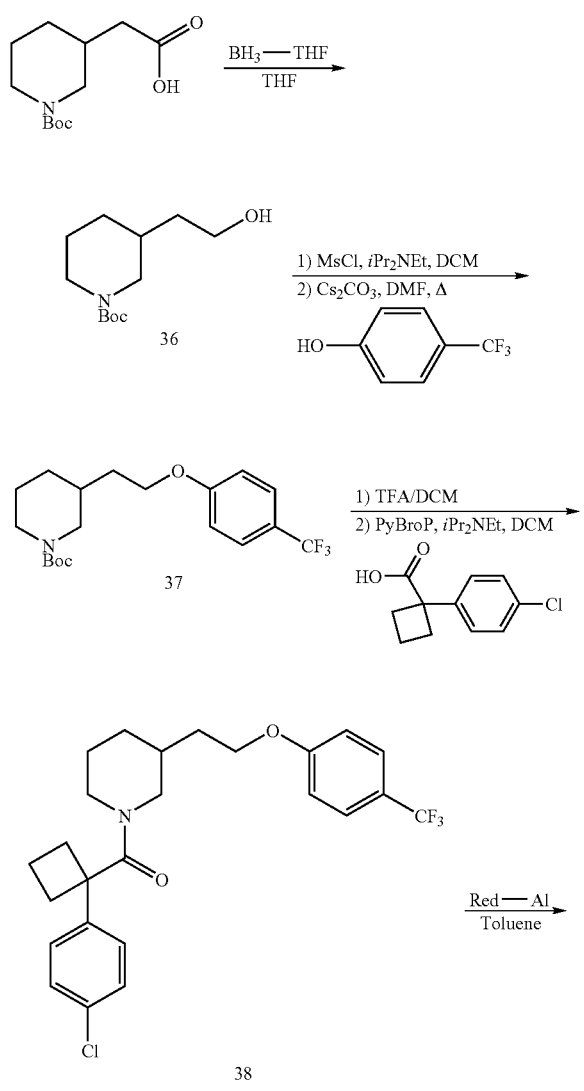

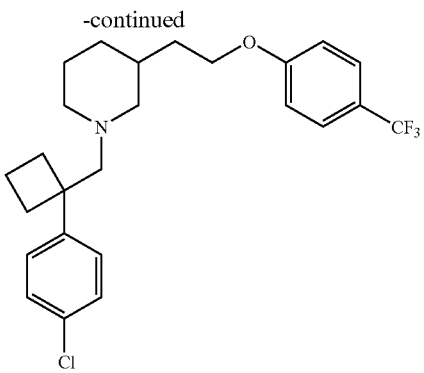

To a solution of N-Boc-3-piperidine acetic acid (500 mg, 2.1 mmol) in THF (10 mL) at room temperature was added BH₃-THF complex (5.1 mL of a 1.0 M solution, 5.1 mmol) dropwise. The reaction was allowed to stir at this temperature for two-and-a-half hours before quenching by the addition of 2 M HCl (approx. 10 mL). This mixture was allowed to stir for fifteen minutes before neutralizing by the addition of 2 M NaOH and extracting with ethyl acetate. The organic layer was dried (MgSO₄), filtered and concentrated in vacuo to provide the desired product 36 (488 mg, 100%) which required no further purification. LRMS calculated for C₁₂H₂₃NO₃ 229.17, found 229.71.

To a solution of primary alcohol 36 (300 mg, 1.3 mmol) in dichloromethane (6 mL) at room temperature was added iPr₂NEt (0.57 mL, 3.3 mmol) followed by MsCl (0.11 mL, 1.4 mmol). The reaction mixture was allowed to stir for one hour before concentrating and purifying the resulting residue by flash column chromatography using a gradient of 30 to 50% ethyl acetate/petroleum ether to provide the desired mesylate (not shown) (336 mg, 83%). LRMS calculated for C₁₃H₂₅NO₅S 307.15, found 307.34. To the mesylate (336 mg, 1.1 mmol) in DMF (5 mL) was added α,α,α-trifluoro-p-cresol (355 mg, 2.2 mmol) followed by Cs₂CO₃ (1.8 g, 5.5 mmol). The reaction mixture was heated to 75° C. for thirty minutes before cooling to room temperature, diluting with ethyl acetate and washing several times with brine. The organic layer was then dried (MgSO₄), filtered and concentrated in vacuo. The resulting residue was purified by flash column chromatography using a gradient of 6 to 10% acetone/hexane to provide 37 (342 mg, 84%). LRMS calculated for C₁₉H₂₆F₃NO₃ 373.19, found 373.96.

N-Boc-protected 37 (342 mg, 0.92 mmol) was then stirred in 40% TFA/DCM (5 mL) for one hour before concentrating in vacuo. The resulting residue was diluted with dichloromethane, washed with saturated aqueous sodium bicarbonate. The organic layer was then dried (MgSO₄), filtered and concentrated in vacuo. To the resulting free amine (not shown) in dichloromethane (5 mL) was then added 1-(4-chlorophenyl)-1-cyclobutane carboxylic acid (289 mg, 1.4 mmol) and iPr₂NEt (0.80 mL, 4.6 mmol) followed by PyBroP (641 mg, 1.4 mmol). The resulting solution was allowed to stir overnight at room temperature before quenching with 10% KOH and washing with ethyl acetate. The organic layer was then dried (MgSO$_4$), filtered, concentrated in vacuo and the resulting residue purified by flash column chromatography using a gradient of 20 to 30% ethyl acetate/hexane to provide amide 38 (238 mg, 56% for two steps). LRMS calculated for C$_{25}$H$_{27}$ClF$_3$NO$_2$ 465.17, found 466.18.

To amide 38 (100 mg, 0.22 mmol) in toluene (1 mL) was cautiously added Red-Al (0.23 mL, 0.75 mmol). The resulting solution was allowed to stir at room temperature for one hour before diluting with ethyl acetate and quenching with 10% aqueous KOH. The layers were separated and the aqueous layer further washed with ethyl acetate. The combined organic layers were then dried (MgSO$_4$), filtered, concentrated in vacuo and the resulting residue purified by flash column chromatography using 1% 2M NH$_3$ in EtOH/DCM to provide amine 39 (54 mg, 56%). LRMS calculated for C$_{25}$H$_{29}$ClF$_3$NO 451.19, found 451.48. $^1$H NMR (300 MHz, CDCl$_3$): δ 7.53 (d, J=8.5 Hz, 2H), 7.18 (d, J=8.4 Hz, 2H), 7.07 (d, J=8.3 Hz, 2H), 6.89 (d, J=8.54 Hz, 2H), 3.72–3.83 (m, 2H), 2.40–2.65 (m, 2H), 2.38 (m, 1H), 1.95–2.26 (m, 7H), 1.39–1.88 (m, 8H), 0.80–0.93 (m, 1H). $^{13}$C NMR (75 MHz, CDCl$_3$): δ 161.4, 148.5, 137.4, 130.8, 127.7, 127.6, 126.8, 122.8 (m), 114.4, 68.6, 66.0, 61.7, 56.4, 46.9, 33.2, 33.1, 31.6, 31.4, 30.5, 25.2, 15.9.

Example 23

Synthesis of 1-[2-(chloro-phenyl)-2-methyl-propyl]-3-(4-trifluoromethyl-phenoxymethyl)-piperidine

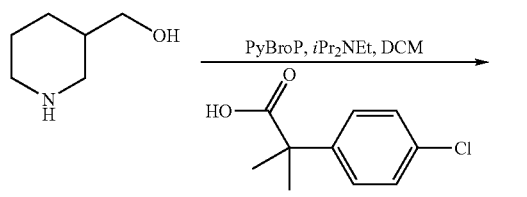

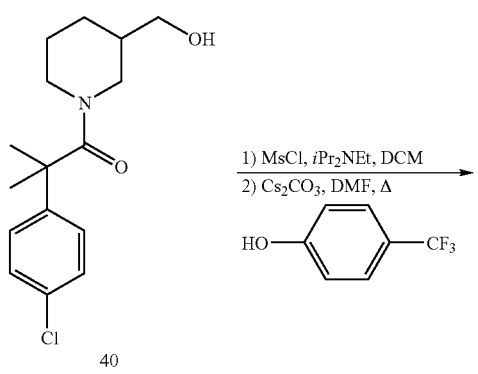

To 3-piperidine methanol (1.0 g, 8.7 mmol) in dichloromethane (40 mL) was added 2-(4-chlorophenyl)-2-methyl propionic acid (2.6 g, 13.0 mmol) and iPr$_2$NEt (4.5 mL, 26.0 mmol) followed by PyBroP (6.1 g, 13.0 mmol). The resulting solution was allowed to stir overnight at room temperature before diluting with ethyl acetate and quenching with 10% KOH. The layers were separated and the aqueous layer further washed with ethyl acetate. The combined organic layers were then dried (MgSO$_4$), filtered and concentrated in vacuo. The resulting residue was purified by flash column chromatography using a gradient of 40 to 50% ethyl acetate/petroleum ether to provide amide 40 (1.92 g, 75%). LRMS calculated for C$_{16}$H$_{22}$ClNO$_2$ 295.13, found 295.85.

To a solution of 40 (536 mg, 1.8 mmol) in dichloromethane (8 mL) at room temperature was added iPr$_2$NEt (0.79 mL, 4.5 mmol) followed by MsCl (0.15 mL, 2.0 mmol). The reaction mixture was allowed to stir for one hour before concentrating and purifying the resulting residue by flash column chromatography using a gradient of 30 to 50% ethyl acetate/petroleum ether to provide the desired mesylate (not shown) (569 mg, 84%). LRMS calculated for C$_{17}$H$_{24}$ClNO$_4$S 373.11, found 374.45. To the mesylate (569 mg, 1.5 mmol) in DMF (7 mL) was added α,α,α-trifluorop-creso (259 mg, 1.6 mmol) followed by Cs$_2$CO$_3$ (1.5 g, 4.6 mmol). The reaction mixture was heated to 75° C. for two hours before cooling to room temperature, diluting with ethyl acetate and washing several times with brine. The organic layer was then dried (MgSO$_4$), filtered and concentrated in vacuo. The resulting residue was purified by flash column chromatography using 30% ethyl acetate/hexane to provide ether 41 (477 mg, 71%). LRMS calculated for C$_{23}$H$_{25}$ClF$_3$NO$_2$ 439.15, found 440.27.

To 41 (100 mg, 0.23 mmol) in toluene (1 mL) was cautiously added Red-Al (0.24 mL, 0.80 mmol). The resulting solution was allowed to stir at room temperature for one hour before adding an additional portion of Red-Al (0.10 mL, 0.34 mmol) and stirring at room temperature overnight. The reaction was then diluted with ethyl acetate and quenched with 10% aqueous KOH. The layers were separated and the aqueous layer further washed with ethyl acetate. The combined organic layers were then dried (MgSO$_4$), filtered, concentrated in vacuo and the resulting residue purified by flash column chromatography using 0.5% 2M NH$_3$ in EtOH/DCM to provide amine 42 (52 mg, 54%). LRMS calculated for C$_{23}$H$_{27}$ClF$_3$NO 425.17, found 425.78. $^1$H NMR (300 MHz, CDCl$_3$): 7.57 (d, J=8.7 Hz, 2H), 7.35 (d, J=8.8 Hz, 2H), 7.27 (d, J=8.7 Hz, 2H), 6.93 (d, J=8.5 Hz, 2H), 3.72–3.84 (m, 2H), 2.53–2.55 (m, 1H), 2.41 (m, 3H), 2.13–2.21 (m, 1H), 2.01–2.03 (m, 2H), 1.48–1.71 (m, 3H), 1.32 (s, 6H), 1.06–1.19 (m, 1H).

Example 24

Synthesis of [3-(Benzo[1,3]dioxol-5-yloxymethyl)-piperidin-1-yl]-[1-(4-chloro-phenyl)-cyclobutyl]-methanone (44)

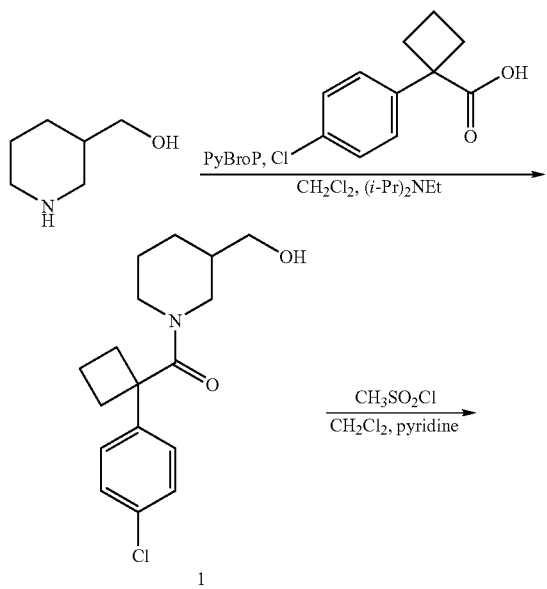

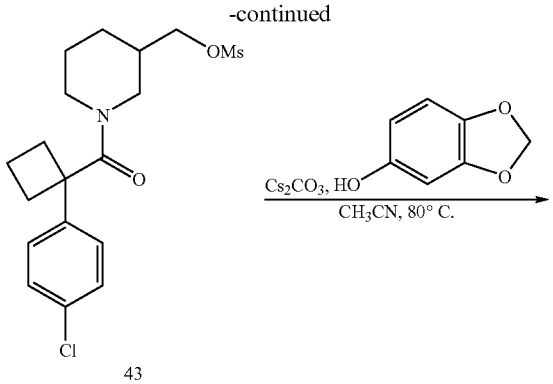

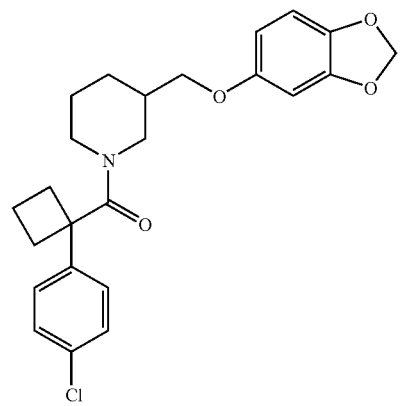

Methanesulonic acid 1-[1-(4-chloro-phenyl)-cyclobutanecarbonyl]-piperidin-3-ylmethyl ester (43).

To a solution of 3-piperidinemethanol (5.0 g, 43.4 mmol), 1-(4-chlorophenyl)-1-cyclobutanecarboxylic acid (9.14 g, 43.4 mmole), and diisopropylethylamine (11.22 g, 86.8 mmol) in dichloromethane (100 mL) at 0° C. was added PyBroP® (22.26 g, 47.8 mmol). The reaction was stirred at 0° C. for 1 h and then at room temperature for 4 h. The reaction mixture was washed successively with water, 1 N HCl, water, sat. sodium bicarbonate solution, and water (100 mL each). The organic layer was dried over anhydrous sodium sulfate, filtered and concentrated by rotary evaporation. The residue was purified by chromatography on silica gel, eluting with dichloromethane/methanol (96:4) to give 5.8 g of the amide 1 as a thick gum.

The amide 1 (5.0 g) was dissolved in dichloromethane (50 mL) and cooled to 0° C. To this solution was added pyridine (5.0 mL) followed by dropwise addition of methanesulfonyl chloride (2.05 g, 17.9 mmol). The reaction was stirred at for 1 h and then at room temperature overnight. The reaction mixture was washed successively with water, 1 N HCl, water, sat. sodium bicarbonate solution, and water (100 mL each). The reaction mixture was washed successively with water, sat. sodium bicarbonate solution, and water (100 mL each). The organic layer was dried over anhydrous sodium sulfate, filtered and concentrated by rotary evaporation. The residue was purified by chromatography on silica gel, eluting with hexane/ethyl acetate (2:1) to give 4.45 g of 43 as a tan gum. $C_{18}H_{24}ClNO_4S$, MS (m/z)=386 (MH+).

[3-(Benzo[1,3]dioxol-5-yloxymethyl)-piperidin-1-yl]-[1-(4-chloro-phenyl)-cyclobutyl]-methanone (44).

To a solution of 43 (1.0 g, 2.59 mmol) in acetonitrile (25 mL) was added sesamol (0.36 g, 2.59 mmol) and cesium carbonate (1.27 g, 3.89 mmol). The reaction was stirred and refluxed for 20 h. After cooling to room temperature, the reaction mixture was filtered and most of the solvent was removed by rotary evaporation. The residue was partitioned between dichloromethane and water, and the organic layer was washed with sat. sodium carbonate (2×50 mL) and water. The organic layer was dried over anhydrous sodium sulfate, filtered and concentrated by rotary evaporation. The residue was purified by chromatography on silica gel, eluting with dichloromethane/methanol (98:2) to give 0.68 g of the amide 44 as a crystalline solid. $C_{24}H_{26}ClNO_4$, MS (m/z)=428 (MH+).

Example 25

Synthesis of 1-Phenylcyclobutylcarboxaldehyde (47)

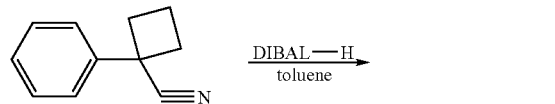

A solution of 3.018 g (19.2 mmol) of 1-phenylcyclobutanecarbonitrile in 60 mL of toluene was cooled to −70° C. and 38 mL of 1 M DIBAL-H in hexane was added dropwise in 30 min. The mixture was stirred at −70° C. for 30 min and at ambient temperature for 4 hours, whereupon 3 mL of ethyl formate was added and stirring was continued for 1 hour. The mixture was poured into saturated ammonium chloride solution (70 mL); after 30 min, 2M aqueous sulfuric acid (100 mL) was added and the product was isolated with ether (3×75 mL). The organic phase was dried over $MgSO_4$ and filtered. Evaporation to dryness furnished the crude product which was purified by column chromatography leading to 2.5 g aldehyde 47, 83% yield. $^1H$ NMR ($CDCl_3$) 1.92–2.13 (m, 2H), 2.40–2.51 (m, 2H), 2.74–2.83 (m, 2H), 7.18–7.22 (m, 2H), 7.28–7.34 (m, 1H), 7.39–7.45 (m, 2H), 9.58 (s, 1H). $^{13}C$ NMR ($CDCl_3$) 16.1, 28.6, 57.8, 126.7, 127.3, 129.1, 141.2, 199.7.

Example 26

Synthesis of 1-(4-Methoxyphenyl)cyclobutanecarbonitrile (48)

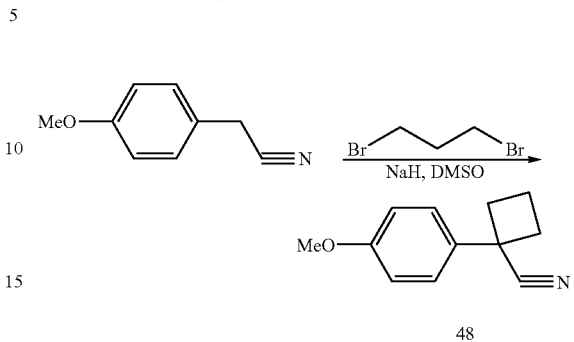

A solution of 3.27 g (22.2 mmol) of (4-methoxyphenyl)acetonitrile and 4.93 g (24.4 mmol) of 1,3-dibromopropane in 15 mL of ether was added dropwise into 1.17 g (48.8 mmol) of NaH in 60 mL of DMSO. The temperature was held between 25° and 35° by water bath cooling. The mixture was stirred at room temperature for 18 hours. The mixture was cooled in ice water and 3 mL of 2-propanol was added dropwise, followed by the addition of 50 mL of water. The mixture was extracted with hexane (3×100 mL), and the combined extracts were washed with water (3×75 mL), dried over anhydrous magnesium sulfate, filtered, and concentrated to yield 2.6 g (62%) product as colorless oil. $^1H$ NMR ($CDCl_3$) δ 2.01–2.14 (m, 1H), 2.35–2.50 (m, 1H), 2.55–2.66 (m, 2H), 2.77–2.87 (m, 2H), 3.83 (s, 3H), 6.94 (d, J=9.0 Hz, 2H), 7.36 (d, J=9.0 Hz, 2H). $^{13}C$ NMR ($CDCl_3$) δ 17.3, 35.1, 39.9, 55.6, 114.5, 124.9, 127.0, 132.1, 159.4.

Synthesis of 1-(4-Chlorophenyl)cyclobutanecarbonitrile (49)

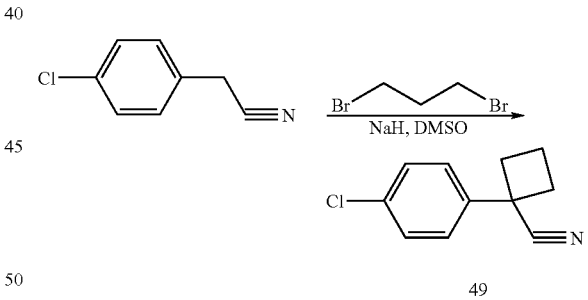

A solution of 3.37 g (22.2 mmol) of 4-Chlorobenzyl cyanide and 4.93 g (24.4 mmol) of 1,3-dibromopropane in 15 mL of ether was added dropwise into 1.17 g (48.8 mmol) of NaH in 60 mL of DMSO. The temperature was held between 25° and 35° by water bath cooling. The mixture was stirred at room temperature for 18 hours. The mixture was cooled in ice water and 3 mL of 2-propanol was added dropwise, followed by the addition of 50 mL of water. The mixture was extracted with hexane (3×100 mL), and the combined extracts were washed with water (3×75 mL), dried over anhydrous magnesium sulfate, filtered, and concentrated to yield 2.9 g (70%) product as colorless oil. $^1H$ NMR ($CDCl_3$) δ 2.04–2.15 (m, 1H), 2.39–2.52 (m, 1H), 2.55–2.65 (m, 2H), 2.79–2.88 (m, 2H), 7.38 (s, 4H). $^{13}C$ NMR ($CDCl_3$) 17.3, 34.9, 40.0, 124.2, 127.3, 129.4, 134.1, 138.6.

Synthesis of 1-(3-Chlorophenyl)cyclobutanecarbonitrile (50)

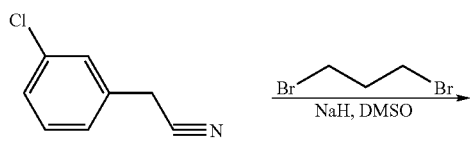

A solution of 3.37 g (22.2 mmol) of 3-Chlorobenzyl cyanide and 4.93 g (24.4 mmol) of 1,3-dibromopropane in 15 mL of ether was added dropwise into 1.17 g (48.8 mmol) of NaH in 60 mL of DMSO. The temperature was held between 25° and 35° by water bath cooling. The mixture was stirred at room temperature for 18 hours. The mixture was cooled in ice water and 3 mL of 2-propanol was added dropwise, followed by the addition of 50 mL of water. The mixture was extracted with hexane (3×100 mL), and the combined extracts were washed with water (3×75 mL), dried over anhydrous magnesium sulfate, filtered, and concentrated to yield 3.0 g (71%) product as colorless oil. $^1$H NMR (CDCl$_3$) δ 2.04–2.16 (m, 1H), 2.38–2.50 (m, 1H), 2.56–2.67 (m, 2H), 2.79–2.89 (m, 2H), 7.29–7.36 (m, 3H), 7.41–7.43 (m, 1H). $^{13}$C NMR (CDCl$_3$) 17.3, 34.8, 40.1, 124.2, 126.2, 128.4, 130.5, 135.2, 142.0.

Synthesis of 1-(4-Fluorophenyl)cyclobutanecarbonitrile (65)

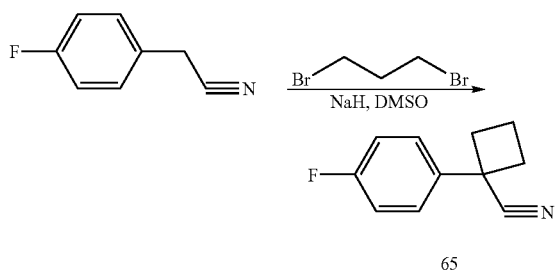

A solution of 3.00 g (22.2 mmol) of 4-fluorophenylacetonitrile and 4.93 g (24.4 mmol) of 1,3-dibromopropane in 15 mL of ether was added dropwise into 1.17 g (48.8 mmol) of NaH in 60 mL of DMSO. The temperature was held between 25° and 35° by water bath cooling. The mixture was stirred at room temperature for 18 hours. The mixture was cooled in ice water and 3 mL of 2-propanol was added dropwise, followed by the addition of 50 mL of water. The mixture was extracted with hexane (3×100 mL), and the combined extracts were washed with water (3×75 mL), dried over anhydrous magnesium sulfate, filtered, and concentrated to yield 2.35 g (61%) product as colorless oil. $^1$H NMR (CDCl$_3$) δ 2.03–2.16 (m, 1H), 2.38–2.53 (m, 1H), 2.58–2.67 (m, 2H), 2.80–2.90 (m, 2H), 7.11 (dd, J=9.0, 8.4 Hz, 2H), 7.41 (dd, J=9.1, 5.1 Hz, 2H). $^{13}$C NMR (CDCl$_3$) 17.3, 35.0, 39.9, 116.1 (d, J=21.5 Hz), 124.5, 127.7, 135.9, 162.5 (d, J=230 Hz).

Example 27

Synthesis of 1-[1-(4-Chloro-phenyl)-cyclobutylmethyl]-3-(4-trifluoromethyl-phenoxymethyl)-azepane

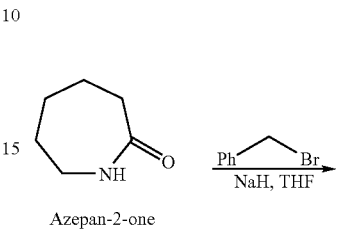

Azepan-2-one

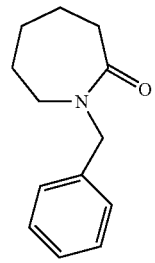

1-Benzyl-azepan-2-one

1-Benzyl-azepane-2-one

To a stirring 0° C. suspension of NaH (18.3 g, 763 mmol) in THF (195 mL) was added by addition funnel azepan-2-one (75.0 g, 667 mmol) in THF. An additional 2L of solvent was added as the reaction progressed in order to maintain agitation of the very viscous reaction suspension. Following addition, the reaction was allowed to warm to room temperature, and when the evolution of H$_2$ gas ceased after stirring overnight, benzyl bromide was added dropwise by addition funnel and the reaction was stirred overnight. The crude product was filtered through Celite and concentrated in vacuo. Recrystallization from hexanes and ethyl acetate provided pure 1-benzyl-azepan-2-one as a white fluffy solid. $^1$H NMR (CDCl$_3$, 300 MHz) 7.38–7.24 (5H, m), 4.61 (2H, s), 3.33–3.29 (2H, m), 2.65–2.61 (2H, m), 1.77–1.66 (4H, m), 1.56–1.46 (2H, m) ppm. $^{13}$C NMR (CDCl$_3$, 75 MHz) 176.13, 138.06, 128.67, 128.31, 127.43, 51.20, 49.04, 37.33, 30.12, 28.26, 23.58 ppm.

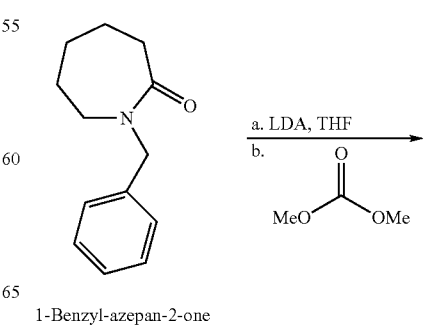

1-Benzyl-azepan-2-one

-continued

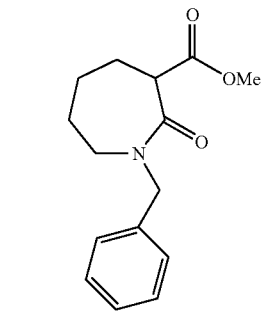

1-Benzyl-2-oxo-azepane-3-carboxylic acid
methyl ester

1-Benzyl-2-oxo-azepane-3-carboxylic methyl ester

LDA was prepared as follows: Diisopropyl amine (15.2 mL, 110 mmol) freshly distilled under N₂ and over CaH₂ was added to 110 mL of anhydrous THF in a dry flask, and the solution was cooled to 0° C. in an ice bath. nBuLi (73.3 mL, 111 mmol) was added dropwise, and the reaction was stirred at 0° C. for 1 hour. The freshly prepared LDA was added dropwise to a −70° C. solution of 1-benzyl-azepan-2-one (10.98 g, 544.0 mmol) dissolved in anhydrous Et₂O (70 mL). The reaction was stirred at −70° C. for 1 hour, then dimethyl carbonate (4.55 mL, 544 mmol) was added dropwise. The reaction was allowed to warm to room temperature overnight. The reaction was judged complete by HPLC, and was slowly poured into 5N HCl stirring in an ice bath. The organic layer was extracted. The aqueous layer was washed with CH₂Cl₂ two times, and the combined organics were dried with Na₂SO₄ and concentrated in vacuo. Crude material was purified on an automated flash column with 80:20 Hexanes:EtOAc to obtain 10.85 g, (77%) of 1-benzyl-2-oxo-azepane-3-carboxylic acid methyl ester as a pale yellow oil. ¹H NMR (CDCl₃, 300 MHz) 7.42–7.10 (5H, broad s), 4.61 (1H, d, J=14.7 Hz), 4.50 (1H, d, J=14.7 Hz), 3.74 (3H, s), 3.7–3.64 (1H, m), 3.40–3.13 (2H, m), 2.12–1.98 (1H, m), 1.92–1.73 (2H, m), 1.66–1.42 (2H, m), 1.32–1.16 (1H, m) ppm. ¹³C NMR (CDCl₃, 75 MHz) 171.94, 171.04, 137.28, 128.55, 128.24, 127.43, 52.15 (2), 51.27, 48.31, 27.87, 27.41, 25.91 ppm. LRMS: 261.73.

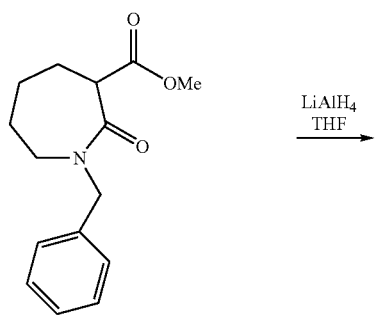

1-Benzyl-2-oxo-azepane-3-carboxylic acid
methyl ester

LiAlH₄
THF
→

-continued

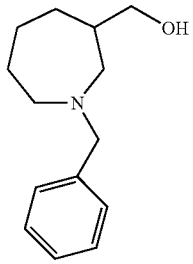

(1-Benzyl-azepane-3-yl)-methanol (1-Benzyl-azepan-3-yl)-methyl

1-Benzyl-2-oxo-azepan-2-carboxylic acid methyl ester (0.2154 g, 0.8243 mmol) dissolved in anhydrous THF (2.9 mL) was added to a stirring suspension of LiAlH₄ in THF (1.5 mL) over approx. 1.5 hours. The reaction was stirred overnight. The reaction was judged complete by TLC and was quenched by the sequential addition of H₂O (0.4 mL), then 2N NaOH (1.0 mL) and H₂O (0.4 mL). The reaction was stirred at room temperature for 30 minutes, then was filtered, dried with Na₂SO₄, and concentrated in vacuo. Crude material was purified by automated silica gel chromatography with 15:85:5 CH₂Cl₂:Hexanes:2N NH₃ in ethyl alcohol to obtain 0.1062 g (59%) of pure (1-benzyl-azepan-3-yl)-methanol. ¹H NMR (CDCl₃, 300 MHz) 7.40–7.23 (5H, m), 3.65 (2H, s), 3.54 (1H, dd, J=10.4, 3.5 Hz), 3.43 (1H, dd, J=10.4, 5.4 Hz), 2.82 (1H, J=13.3, 3.1 Hz), 2.77 (2H, m), 2.44 (1H, ddd, J=12.2, 8.6, 3.3 Hz), 1.90–1.45 (6H, m) ppm. ¹³C NMR (CDCl₃, 75 MHz) 139.14, 128.97, 128.14, 126.91, 67.20, 63.85, 58.49, 56.87, 39.59, 29.68, 29.43, 25.23 ppm. LRMS: 219.64.

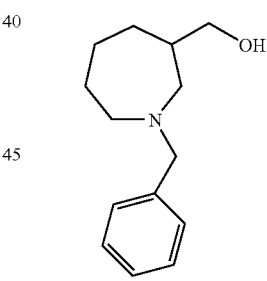

H₂, 10% Pd/C
MeOH
→

(1-Benzyl-azepan-3-yl)-methanol

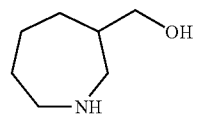

Azepan-3-yl-methanol

Azepan-3-yl-methanol (1-Benzyl-azepan-3-yl)-methanol (0.0922 g, 0.4192 mmol) dissolved in MeOH (1 mL) was added to a stirring suspension of 10% Pd/C (14.4 mg) in 5 mL MeOH. The reaction was purged with H₂, and the reaction was stirred at room temperature overnight. The reaction was judged complete by $^1$H-NMR analysis of an aliquot from the reaction. The reaction was filtered through a pad of Celite wet with MeOH and was rinsed with MeOH, and concentrated in vacuo to obtain pure azepan-3-yl-methanol in 60% yield (0.0323 g), which was used in the next step without further purification. $^1$H NMR (CDCl$_3$, 300 MHz, partial) 3.14–2.70 (4H, m), 1.92–1.73 (4H, m), 1.68–1.42 (3H, m) ppm. $^{13}$C NMR (CDCl$_3$, 75 MHz) 67.32, 52.01, 50.33, 41.31, 31.05, 29.76, 25.44 ppm.

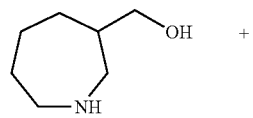

Azepan-3-yl-methanol

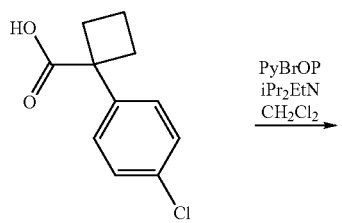

1-(4-Chloro-phenyl)-cyclobutanecarboxylic acid

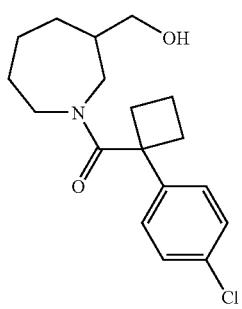

[1-(4-Chloro-phenyl)-cyclobutyl]-(3-hydroxymethyl-azepan-1-yl)-methanone

[1-(4-Chloro-phenyl)-cyclobutyl]-(3-hydroxynm-ethyl-azepan-1-yl)-methanone iPrEtN (1.78 mL, 10.2 mmol) and pyBrOP (2.39 g, 5.12 mmol) were added at room temperature to a stirring solution of azepan-3-yl-methanol (0.4392 g, 3.41 mmol) and 1-(4-Chlorophenyl)-cyclobutanecarboxylic acid (1.0778 g, 5.12 mmol) in CH$_2$Cl$_2$ under N$_2$. When the reaction was complete, the reaction was subjected to aqueous work-up. Silica gel purification (4:1 to 2:3 Hexanes:Ethyl acetate) provided the desired product in 95% yield (1.0395 g). LRMS: 321.91.

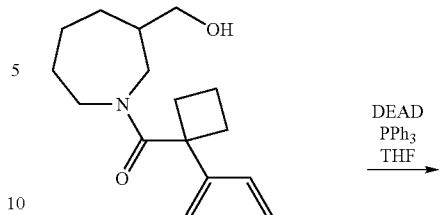

[1-(4-Chloro-phenyl)-cyclobutyl]-(3-hydroxymethyl-azepan-1-yl)-methanone

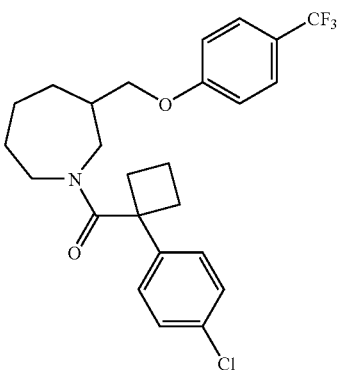

[1-(4-Chloro-phenyl)-cyclobutyl]-[3-(4-trifluoromethyl-phenoxymethyl)-azepan-1-yl]-methanone

[1-(4-Chloro-phenyl-cyclobutyl]-[3-(4-trifluorom-ethyl-phenoxymethyl-azepan-1-yl]-methanone To a room temperature solution of [1-(4-Chloro-phenyl)-cyclobutyl]-(3-hydroxymethyl-azepan-1-yl)-methanone (0.3307 g, 1.15 mmol) in tetrahydrofuran (5.75 mL, 0.2M) under N$_2$ was added triphenyl phosphine (0.9050 g, 3.45 mmol) and 4-trifluoromethylphenol (0.56 mL, 3.45 mmol). The solution was cooled to 0° C., then diethyl azodicarboxylate (0.54 mL, 3.1 mmol) was added dropwise over 10 minutes. When the reaction was complete by HPLC (2 hours), ethyl acetate and 10% aqueous NaOH was added. The organics were removed, dried with Na$_2$SO$_4$, concentrated, then taken up in Hexanes/ethyl acetate (70:30) and filtered to remove triphenyl phosphine oxide. The remaining yellow oil was purified by silica gel chromatography (3:1 to 2:3 Hexanes:ethyl acetate). The product was further purified by silica gel chromatography with 9:1 hexanes:ethyl acetate to obtain pure product in 26% yield (0.1301 g). Partial $^1$H NMR (CDCl$_3$, 300 MHz) 7.55 (2H, t, J=8.7 Hz), 7.36–7.26 (4H, m), 6.92 (2H, dd, J=34.9, 8.7 Hz), 4.00–3.85 (2H, m), ppm. Partial $^{13}$C NMR (CDCl$_3$, 75 MHz) 174.95, 161.66, 142.17, 132.35, 129.10, 126.95, 126.77, 114.61, 114.61, 71.50, 71.10 ppm. LRMS: 465.26.

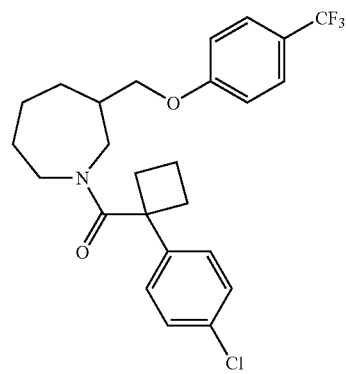

[1-(4-Chloro-phenyl)-
cyclobutyl]-[3-(4-trifluoromethyl-phenoxymethyl)-
azepan-1-yl]-methanone RedAl
toluene
→

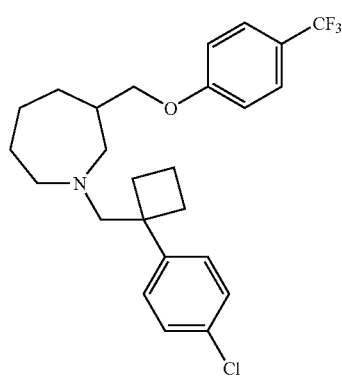

1-[1-(4-Chloro-phenyl)-
cyclobutylmethyl]-3-(4-trifluoromethyl-
phenoxymethyl)-azepane (168)

1-[1-(4-Chloro-phenyl-cyclobutylmethyl]-3-(4-trifluoromethyl-phenoxymethyl)-azepane (168)

To a stirring 0° C. solution of [1-(4-Chloro-phenyl)-cyclobutyl]-[3-(4-trifluoromethyl-phenoxymethyl)-azepan-1-yl]-methanone (0.13 g, 0.28 mmol) under $N_2$ in toluene (2.8 mL, 0.1M) was added sodium bis(2-methoxyethoxy)aluminum hydride (65+ weight % in toluene) (0.30 mL, 0.98 mmol) dropwise with stirring. When the reaction was complete by HPLC, the reaction was quenched with $H_2O$. 10% NaOH and ethyl acetate were added, and the organic was removed, dried with $Na_2SO_4$, and concentrated. The crude reaction mixture was purified by silica gel chromatography (90:8:2 Hexanes:methylene chloride:2N $NH_3$ in ethyl alcohol). A 40% yield (0.0504 g) of pure material was obtained as well as other impure fractions. $^1$H NMR (CDCl$_3$, 300 MHz) 7.54 (2H, d, J=8.9 Hz), 7.22 (2H, d, J=8.4 Hz), 7.09 (2H, d, J=8.3 Hz), 6.87 (2H, d, J=8.8 Hz), 3.62–3.45 (2H, m), 2.89 (1H, d, J=13.7 Hz), 2.80 (1H, d, J=13.7 Hz), 2.60 (1H, td, J=13.3, 3.7 Hz), 2.55–2.36 (3H, m), 2.30–2.10 (4H, m), 2.08–1.90 (2H, m), 1.90–1.25 (7H, m) ppm. $^{13}$C NMR (CDCl$_3$, 75 MHz) 161.75, 148.53, 130.96, 128.00, 127.91, 127.03, 126.98, 122.98, 114.61, 71.38, 70.53, 60.37, 58.87, 48.07, 39.52, 31.84, 31.64, 30.23, 29.50, 24.97, 16.24 ppm. LRMS: 451.53.

Example 28

Synthesis of {1-[1-(4-Chloro-phenyl)-cyclobutylmethyl]-azepan-3-yl}-methanol

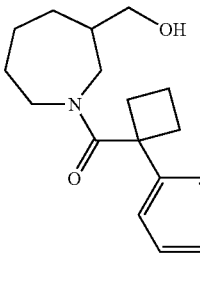

[1-(4-Chloro-phenyl)-
cyclobutyl]-(3-hydroxymethyl-
azepan-1-yl)-methanone

RedAl
Toluene
→

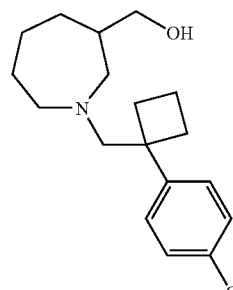

{1-[1-(4-Chloro-phenyl)-
cyclobutylmethyl]-azepan-3-yl}-
methanol
169

To a stirring 0° C. solution of [1-(4-Chloro-phenyl)-cyclobutyl]-(3-hydroxymethyl-azepan-1-yl)-methanone (0.075 g, 0.26 mmol) under $N_2$ in toluene (2.6 mL, 0.1M) was added sodium bis(2-methoxyethoxy)aluminum hydride (65+ weight % in toluene) (0.28 mL, 0.91 mmol) dropwise with stirring. When the reaction was complete by HPLC, the reaction was quenched with $H_2O$. 10% NaOH and ethyl acetate were added, and the organic was removed, dried with $Na_2SO_4$, and concentrated. The crude reaction mixture was purified by silica gel chromatography (90:8:2 Hexanes:methylene chloride:2N $NH_3$ in ethyl alcohol). A 39% yield (0.0290 g) of pure material was obtained as well as other impure fractions. $^1$H NMR (CDCl$_3$, 300 MHz) 7.28–7.25 (2H, m), 7.15–7.09 (2H, m), 3.44 (1H, dd, J=10.5, 4.5 Hz), 3.27 (1H, dd, J=10.3, 5.5 Hz), 2.89 (1H, d, J=13.9 Hz), 2.83 (1H, d, J=13.9 Hz), 2.72–2.60 (1H, m), 2.50–1.10 (16H, m) ppm. $^{13}$C NMR (CDCl$_3$, 75 MHz) 146.5, 131.22, 128.10, 127.93, 70.95, 67.49, 61.85, 59.10, 47.62, 40.59, 32.12, 31.90, 29.92, 25.41, 16.20 ppm. LRMS: 308.24.

Example 29

Synthesis of 3-(4-Methoxy-phenoxymethyl)-1-(1-phenyl-cyclobutylmethyl)piperidine

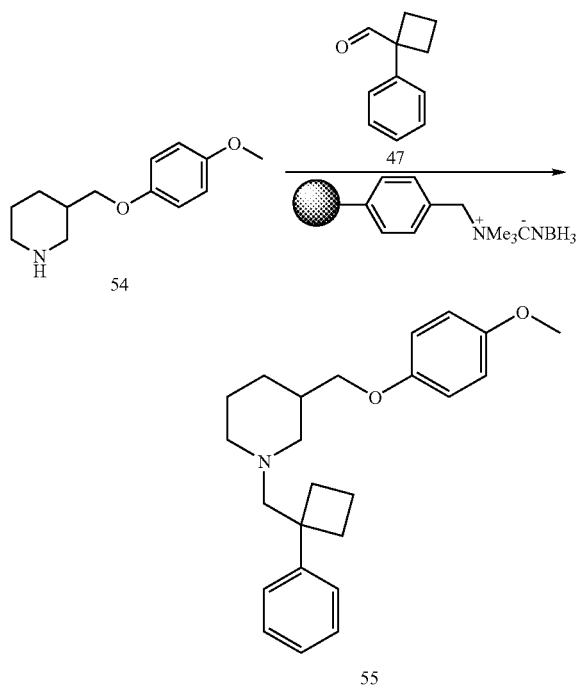

To a solution of 54 (TFA salt 35.7 mg 0.11 mmol) in trimethyl orthoformate (0.5 mL) was added 1-phenylcyclobutanecarboxaldehyde (18 mg, 011 mmol). After stirring at room temperature for one hour, 0.1 g of (polystyrylmethyl)trimethylammonium cyanoborohydride (2.85 mmol/g) was added, and the reaction mixture was agitated at room temperature for 18 hours. Another 18 mg of 1-phenylcyclobutanecarboxaldehyde was added into the reaction mixture. After shaking at room temperature for 18 hours, the reaction mixture was filtered and the resin was washed with MeOH (3×0.5 mL). After conditioning a SPE column (SCX cation exchange, 0.5 g of sorbent, 2.0 mequiv/g) with MeOH (5 mL), the reaction contents were loaded onto the column. The column was washed with MeOH (2×5 mL), and eluted with 4 mL of 2 M ammonia in MeOH. The effluent was collected into a receiving tube, concentrated and dried in vacuo to afford 25 mg of 55, 65% yield, LRMS m/z 366.

Example 30

In Vivo Evaluation of 4

Compound 4 was administered i.v. to a group of 3 ICR derived male or female mice (~22 gms) and observed for the presence of acute toxic symptoms (mortality, convulsions, tremors, muscle relaxation, sedation, etc.) and autonomic effects (diarrhea, salvation, lacrimation, vasodilation, piloerection, etc) during first 5 min (i.v). The number of animal deaths was observed at the subsequent 3, 24, 48, 72 hours after compound treatment.

Compound 4 was administered at doses of 5, 10, 20, and 30 mk/kg. No obvious change was observed in autonomic signs of behavior for all four doses. After monitoring daily for 3 days, no mortality was observed.

Example 31

Antagonism of Dopamine Receptors or Transporters & Functional Activity

The ability of compounds of the invention to displace norephinephrine ligands in vitro was determined by the methods of Galli et al. (J. Exp. Biol. 198:2197, 1995) using desipramine ($IC_{50}$=920 nM) as a reference compound. The displacement of dopamine, and serotonin ligands in vitro was determined by the methods of Gu et al. (J. Biol. Chem. 269;7124, 1994) using GBR-12909 ($IC_{50}$(DA uptake)=490 nM, $IC_{50}$ (5-HT uptake)=110 nM) as a reference compound. Functional activity of the compounds was determined in vitro in cellular assays using recombinant human cell lines. Measurements of functional activity for serotonin uptake inhibition was determined in human HEK-293 cell lines according to the procedures of Gu H. et al. (J. Biol. Chem. 269: 27124, 1994) using fluoxetine ($EC_{50}$=57 nM) as the reference compound. Determination of functional activity for norephinephrine uptake inhibition was accomplished using a MDCK cell lines according to the methods of Galli A. et al. (J. Exp. Biol. 198:2197, 1995) with desipramine ($EC_{50}$=7 nM) as a reference compound. For determination of dopamine functional activity, a hDAT cell line was used as described by Giros B. et al. (Mol. Pharmacol. 42:383, 1992) with nomifensine ($EC_{50}$=11 nM) as the reference compound.

| Compound | Uptake Profile ($IC_{50}$, nM) | | | Functional Assays (antagonism, $EC_{50}$, nM) | | |
|---|---|---|---|---|---|---|
| | NE Uptake | DA Uptake | 5-HT Uptake | NE Uptake | DA Uptake | 5-HT Uptake |
| 35 | >1,000 | >1,000 | >1,000 | NA | NA | NA |
| 28 | <1,000 | <1,000 | <1,000 | <1,000 | <100 | <1,000 |
| 20 | <1,000 | <1,000 | <1,000 | NA | NA | NA |
| 21 | <100 | <100 | <1,000 | NA | NA | NA |
| 7 | >1,000 | <100 | >1,000 | NA | <100 | NA |
| 15 | >1,000 | >1,000 | >1,000 | NA | NA | NA |
| 16 | >1,000 | >1,000 | >1,000 | NA | NA | NA |
| 11 | >1,000 | <1,000 | >1,000 | NA | NA | NA |
| 1 | >1,000 | >1,000 | >1,000 | NA | NA | NA |
| 2 | >1,000 | <1,000 | >1,000 | NA | <100 | NA |
| 4 | >1,000 | <1,000 | >1,000 | NA | <1,000 | NA |
| 5 | NA | <1,000 | NA | NA | NA | NA |
| 33 | <1,000 | <100 | <1,000 | NA | NA | NA |
| 34 | <1,000 | <1,000 | <1,000 | NA | NA | NA |
| 6 | NA | <1,000 | NA | NA | NA | NA |
| 32 | <1,000 | >1,000 | >1,000 | NA | NA | NA |
| 23 | <1,000 | <100 | >1,000 | NA | NA | NA |
| 24 | <10 | <10 | <1,000 | NA | NA | NA |
| 39 | <100 | <10 | >1,000 | NA | NA | NA |
| 55 | >1,000 | <1,000 | >1,000 | NA | NA | NA |
| 72 | NA | <1,000 | NA | NA | NA | NA |
| 76 | <1,000 | <1,000 | >1,000 | NA | NA | NA |
| 89 | <1,000 | <1000 | >1,000 | NA | NA | NA |
| 42 | <1,000 | <100 | >1,000 | NA | NA | NA |
| 80 | >1,000 | >1,000 | >1,000 | NA | NA | NA |
| 81 | >1,000 | >1,000 | >1,000 | NA | NA | NA |
| 82 | <1,000 | <100 | <1,000 | NA | NA | NA |
| 8 | >1,000 | >1,000 | NA | NA | NA | NA |
| 78 | <1,000 | <1,000 | >1,000 | NA | NA | NA |
| 79 | <1,000 | <1,000 | <100 | NA | NA | NA |
| 83 | <1,000 | <100 | <1,000 | <1,000 | <10 | <100 |
| 86 | <1,000 | <100 | <1,000 | <1,000 | <10 | <1,000 |
| 93 | >1,000 | >1,000 | <1,000 | NA | NA | NA |
| 95 | >1,000 | <1,000 | <1,000 | NA | NA | NA |

| Compound | NE Uptake | DA Uptake | 5-HT Uptake | NE Uptake | DA Uptake | 5-HT Uptake |
|---|---|---|---|---|---|---|
| | Uptake Profile (IC$_{50}$, nM) | | | Functional Assays (antagonism, EC$_{50}$, nM) | | |
| 99 | <1,000 | <100 | <1,000 | <1,000 | <10 | >1,000 |
| 102 | >1,000 | <100 | >1,000 | <10 | <10 | >1,000 |
| 105 | <100 | <10 | <1,000 | NA | NA | NA |
| 107 | <1,000 | <1,000 | >1,000 | NA | NA | NA |
| 110 | <1,000 | <100 | <1,000 | <1,000 | <10 | >1,000 |
| 113 | <1,000 | <100 | <1,000 | <1,000 | <10 | >1,000 |
| 114 | <1,000 | <100 | >1,000 | <1,000 | <10 | >1,000 |
| 115 | <1,000 | <100 | >1,000 | <1,000 | <10 | >1,000 |
| 118 | <1,000 | <10 | >1,000 | <100 | <10 | >1,000 |
| 119 | <100 | <10 | >1,000 | <100 | <10 | >1,000 |
| 122 | >1,000 | <1,000 | >1,000 | NA | NA | NA |
| 128 | <1,000 | <100 | <1,000 | <1,000 | <10 | <1,000 |
| 123 | <1,000 | <10 | <1,000 | <1,000 | <10 | <1,000 |
| 129 | <100 | <10 | >1,000 | <100 | <10 | <100 |
| 130 | <1,000 | <100 | <1,000 | <100 | <10 | >1,000 |
| 82 | <1,000 | <100 | <1,000 | <1,000 | <100 | NA |
| 131 | <1,000 | <100 | <1,000 | NA | NA | NA |
| 132 | <100 | <10 | <1,000 | NA | NA | NA |
| 133 | <1,000 | <1,000 | >1,000 | NA | NA | NA |
| 125 | <100 | <10 | <1,000 | <1,000 | <10 | <1,000 |
| 124 | <100 | <10 | <1,000 | <1,000 | <10 | <1,000 |
| 127 | <100 | <10 | >1,000 | <1,000 | <10 | >1,000 |
| 126 | <100 | <10 | <1,000 | <1,000 | <10 | <1,000 |
| 136 | <1,000 | <1,000 | <100 | NA | NA | NA |
| 140 | <100 | <100 | <100 | NA | NA | NA |
| 141 | <1,000 | <1,000 | <1,000 | NA | NA | NA |
| 142 | <1,000 | <1,000 | <100 | NA | NA | NA |
| 143 | <100 | <100 | <10 | NA | NA | NA |
| 144 | <100 | <10 | <10 | NA | NA | NA |
| 145 | <1,000 | <1,000 | <1,000 | NA | NA | NA |
| 147 | <100 | <1,000 | >1,000 | NA | NA | NA |
| 150 | >1,000 | >1,000 | >1,000 | NA | NA | NA |
| 151 | <1,000 | <1,000 | <1,000 | NA | NA | NA |
| 152 | <1,000 | <1,000 | <100 | NA | NA | NA |
| 153 | <100 | <100 | <10 | NA | NA | NA |
| 154 | <100 | <10 | <10 | NA | NA | NA |
| 155 | >1,000 | <100 | >1,000 | NA | NA | NA |
| 158 | >1,000 | <1,000 | >1,000 | NA | NA | NA |
| 159 | <1,000 | <100 | <1,000 | NA | NA | NA |
| 163 | >1,000 | <10 | <1,000 | NA | NA | NA |
| 162 | >1,000 | <100 | <1,000 | NA | NA | NA |
| 160 | >1,000 | <100 | <1,000 | NA | NA | NA |
| 161 | <1,000 | <10 | <1,000 | NA | NA | NA |
| 164 | <1,000 | <10 | <100 | NA | NA | NA |
| 165 | <100 | <10 | <100 | NA | NA | NA |
| 166 | <100 | <10 | >1,000 | NA | NA | NA |
| 167 | >1,000 | >1,000 | >1,000 | NA | NA | NA |
| 170 | <1,000 | <10 | <1,000 | NA | NA | NA |
| 171 | <1,000 | <10 | <1,000 | NA | NA | NA |
| 168 | <1,000 | <100 | >1,000 | NA | NA | NA |
| 169 | >1,000 | <1,000 | >1,000 | NA | NA | NA |
| 173 | >1,000 | <1,000 | <100 | NA | NA | NA |
| 175 | >1,000 | <1,000 | <1,000 | NA | NA | NA |
| 174 | <1,000 | <100 | <100 | NA | NA | NA |
| 189 | >1,000 | >1,000 | >1,000 | NA | NA | NA |
| 180 | <1,000 | <1,000 | <1,000 | NA | NA | NA |
| 181 | <1,000 | >1,000 | <100 | NA | NA | NA |
| 183 | <1,000 | <1,000 | <1,000 | NA | NA | NA |
| 182 | >1,000 | <100 | <1,000 | NA | NA | NA |
| 186 | <1,000 | <1,000 | <1,000 | NA | NA | NA |
| 185 | >1,000 | <1,000 | >1,000 | NA | NA | NA |
| 184 | <1,000 | <1,000 | <1,000 | NA | NA | NA |
| 191 | >1,000 | >1,000 | >1,000 | NA | NA | NA |
| 233 | <100 | <10 | <10 | <10 | <10 | <10 |
| 192 | <1,000 | <10 | <1,000 | NA | NA | NA |
| 193 | <10 | <10 | <10 | NA | NA | NA |
| 194 | <100 | <10 | <10 | NA | NA | NA |
| 195 | <1,000 | <100 | <1,000 | NA | NA | NA |
| 196 | <1,000 | <100 | <10 | NA | NA | NA |
| 197 | <1,000 | <1,000 | <10 | NA | NA | NA |
| 201 | <1,000 | <10 | <1,000 | NA | NA | NA |
| 206 | <1,000 | <100 | <1,000 | NA | NA | NA |
| 210 | <100 | <10 | <1,000 | NA | NA | NA |
| 212 | <1,000 | <100 | <1,000 | NA | NA | NA |
| 213 | <1,000 | <1,000 | <100 | NA | NA | NA |
| 218 | >1,000 | <10 | <1,000 | NA | NA | NA |
| 220 | <1,000 | <1,000 | <100 | NA | NA | NA |
| 222 | >1,000 | >1,000 | <1,000 | NA | NA | NA |
| 227 | >1,000 | <1,000 | <1,000 | NA | NA | NA |
| 224 | >1,000 | >1,000 | >1,000 | >1,000 | >1,000 | <1,000 |
| 228 | >1,000 | >1,000 | >1,000 | NA | NA | NA |
| 230 | >1,000 | <100 | >1,000 | NA | NA | NA |
| 176 | >1,000 | <1,000 | <1,000 | NA | NA | NA |
| 178 | <1,000 | <1,000 | <1,000 | NA | NA | NA |
| 179 | <1,000 | >1,000 | <1,000 | NA | NA | NA |
| 177 | >1,000 | >1,000 | <1,000 | NA | NA | NA |
| 225 | >1,000 | <10 | <1,000 | >1,000 | >1,000 | >1,000 |
| 232 | <1,000 | <1,000 | <1,000 | NA | NA | NA |

Example 32

Synthesis of (R)-3-Methanesulfonyloxymethyl-piperidine-1-carboxylic acid tert-butyl ester To a stirred solution of N-BOC-3-piperidinemethanol (0.50 g, 0.002 mmole) in DCM (10 mL) was added dropwise pyridine (2.42 mL, 0.03 mmole) followed by the addition of methanesulfonyl chloride (0.774 mL, 0.01 mmole). The reaction mixture continued stirring at RT overnight. The reaction mixture was quenched with water. The aqueous layer was extracted with EtOAc (3×5 mL). Combined organic layers were dried over Na$_2$SO$_4$ and concentrated to yield a crude oil, 68, which was used in the next step without further purification. LRMS: 193 (M+-BOC group).

Example 33

Synthesis of (R)-3-Phenoxymethyl-piperidine-1-carboxylic acid tert-butyl ester

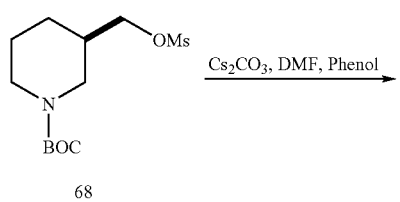

68

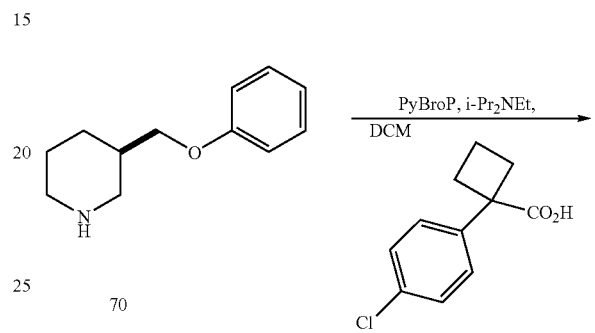

A solution of 68 (0.7 g, 2.4 mmole), $Cs_2CO_3$ (3.91 g, 12 mmole), and phenol (0.452 g, 4.8 mmole) in DMF (10 mL) was heated to 75° C. After 2 h the reaction mixture was cooled down to RT and quenched with water. The aqueous layer was extracted with EtOAc (3×20 mL). Combined organic layers were dried over $Na_2SO_4$ and concentrated to yield a crude oil. Chromatography with basic alumina (95:5 hexane:$Et_2O$) afforded 69 (196.6 mg) as an oil. $^1H$ (300 MHz, $CDCl_3$) δ 7.33–7.27 (2H. m), 6.99–6.90 (3H, m), 3.86–3.80 (2H, m), 2.98–2.77 (4H, m), 2.0–1.20 (5H, M), 1.50 (s, 9H).

Example 34

Synthesis of (R)-3-Phenoxymethyl-piperidine

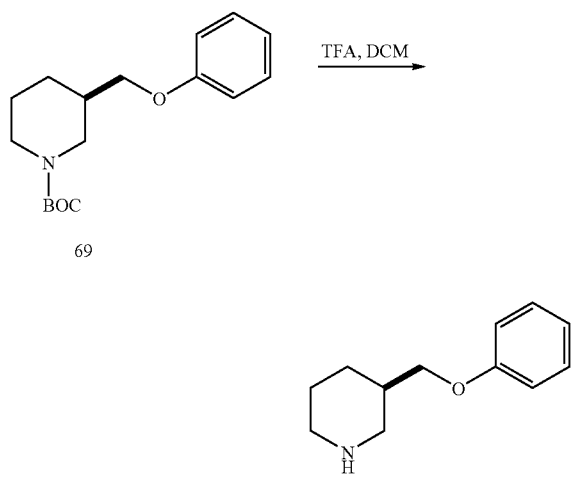

Compound 69 (98.3 mg) was dissolved in DCM (2 mL) and cooled to 0° C. in an ice bath. TFA (0.8 mL) was added dropwise to the stirred cooled reaction mixture. After completion of addition the reaction continued stirring at RT. Reaction progress was monitored by TLC and upon reaction completion reaction mixture was concentrated to yield the TFA salt of 70 (98.3 mg). LRMS: M+ 192.

Example 35

Synthesis of (R)-[1-(4-Chloro-phenyl)-cyclobutyl]-(3-phenoxymethyl-piperidin-1-yl)-methadone

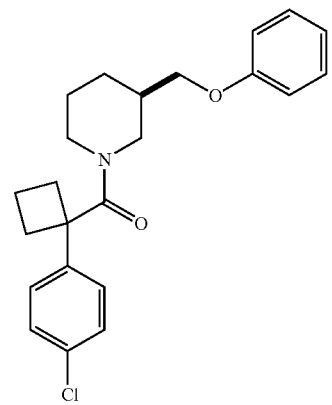

A solution of 70 (98.3 mg, 0.336 mmole), 1-(4-chlorophenyl)-cyclobutanecarboxylic acid (106.3 mg, 0.505 mmole), diisopropylethyl amine (0.234 mL, 1.34 mmole) in DCM (2 mL) was stirred at RT. PyBroP (235.4 mg, 0.505 mmole) was added and the reaction mixture continued stirring at RT. After 6 h the reaction mixture was quenched with 10% KOH. Aqueous layer was extracted with EtOAc (3×2 mL). Combined organic layers were dried over $Na_2SO_4$ and concentrated to yield a crude oil. Silica gel chromatography (4:1 hexane:EtOAc-1:4 hexane:EtOAc) afforded 71 (64.6 mg) as an oil. LRMS: M+384. $^1H$ (300 MHz, $CDCl_3$) δ 7.39–7.29 (4H, m), 6.97 (2H, m), 6.90 (2H, m), 6.82 (1H, m), 4.58 (2H, d, J=12.5 Hz), 3.81–3.24 (4H, m), 2.97–1.161 (11H, m).

Example 36

Synthesis of (R)-[1-(4-Chloro-phenyl)-cyclobutyl]-3-phenoxymethyl-piperidine

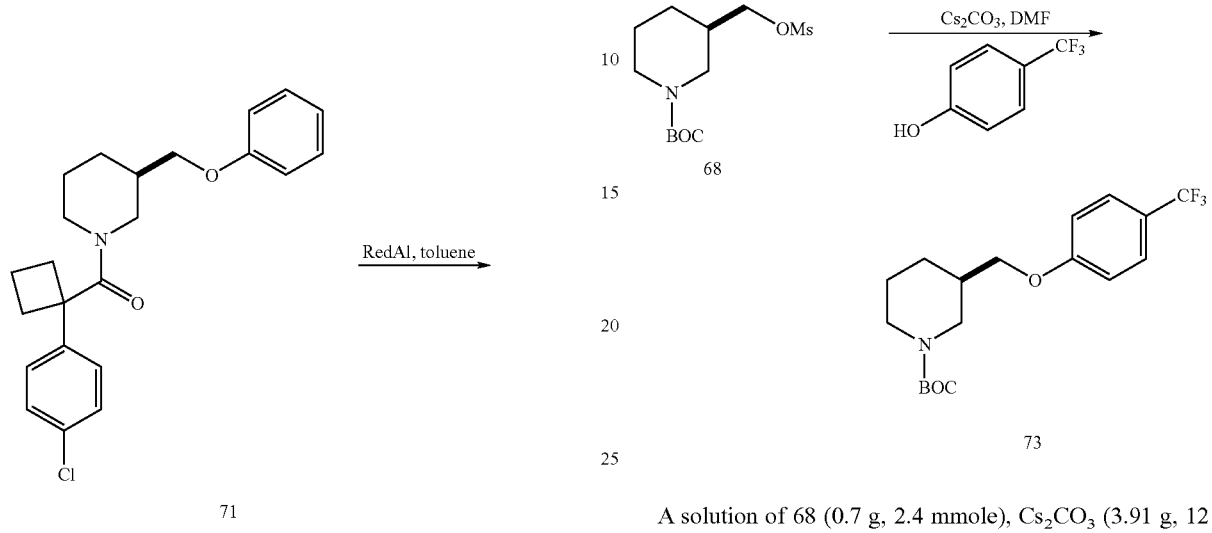

A solution of 71 (62.8 mg, 0.16 mmole) in toluene (3 mL) was cooled to 0° C. in an ice bath. RedAl (155.7 mg, 0.57 mmole) was added to the cooled reaction mixture. After completion of addition the reaction mixture continued stirring at RT. After 2 h the reaction mixture was quenched with water. The aqueous layer was extracted with EtOAc (3×2 mL). Combined organic layers were dried over $Na_2SO_4$ and concentrated to yield a crude oil. Silica gel chromatography (9:1 hexane:$Et_2O$) afforded 72 (52 mg) as an oil. LRMS: M+371.

Example 37

Synthesis of (R)-3-(4-Trifluoromethyl)-phenoxymethyl-piperidine-1-carboxylic acid tert-butyl ester

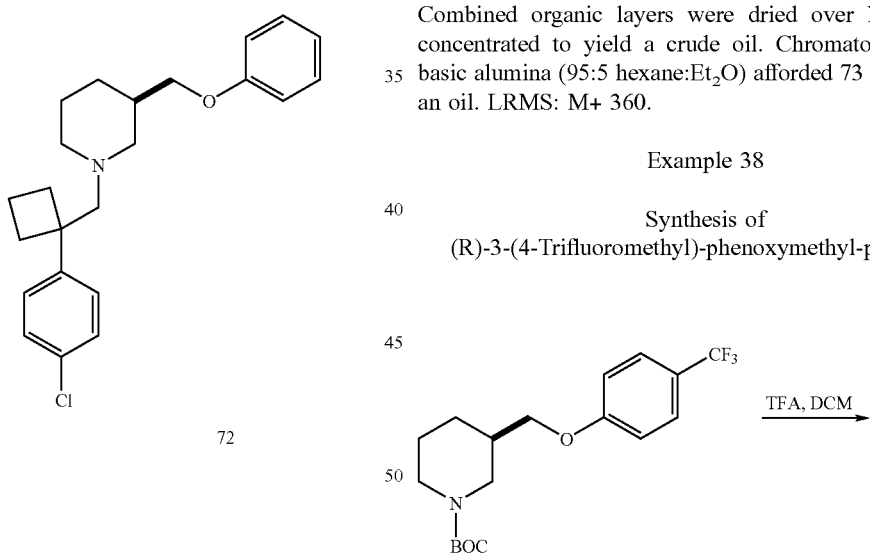

A solution of 68 (0.7 g, 2.4 mmole), $Cs_2CO_3$ (3.91 g, 12 mmole), and 4-trifluoromethyl phenol (0.389 g, 2.4 mmole) in DMF (10 mL) was heated to 75° C. After 4 h the reaction mixture was cooled down to RT and quenched with water. The aqueous layer was extracted with EtOAc (3×20 mL). Combined organic layers were dried over $Na_2SO_4$ and concentrated to yield a crude oil. Chromatography with basic alumina (95:5 hexane:$Et_2O$) afforded 73 (70.3 mg) as an oil. LRMS: M+ 360.

Example 38

Synthesis of (R)-3-(4-Trifluoromethyl)-phenoxymethyl-piperidine

Compound 73 (66.9 mg) was dissolved in DCM (2 mL) and cooled to 0° C. in an ice bath. TFA (0.8 mL) was added dropwise to the stirred cooled reaction mixture. After completion of addition the reaction continued stirring at RT. Reaction progress was monitored by TLC and upon reaction completion reaction mixture was concentrated to yield the TFA salt of 74 (98.3 mg). LRMS: M+260.

Example 39

Synthesis of (R)-[1-(4-Chloro-phenyl)-cyclobutyl]-(3-(4-fluoromethyl)-phenoxymethyl-piperidin-1-yl)-methadone Example 40

Synthesis of (R)-[1-(4-Chloro-phenyl)-cyclobutyl]-3-(4-trifluoromethyl)-phenoxymethyl-piperidine

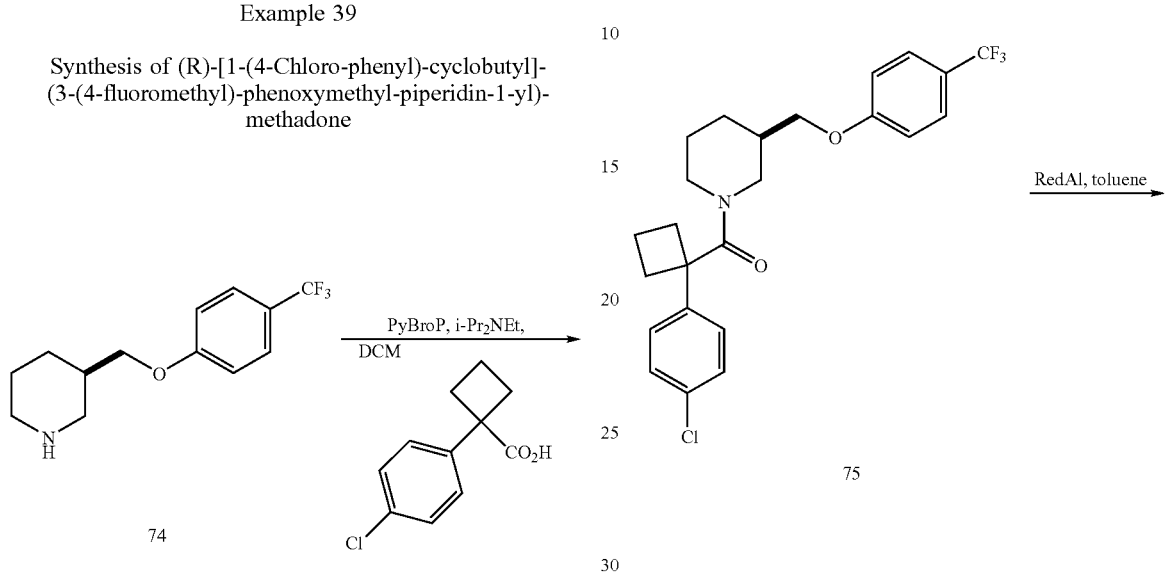

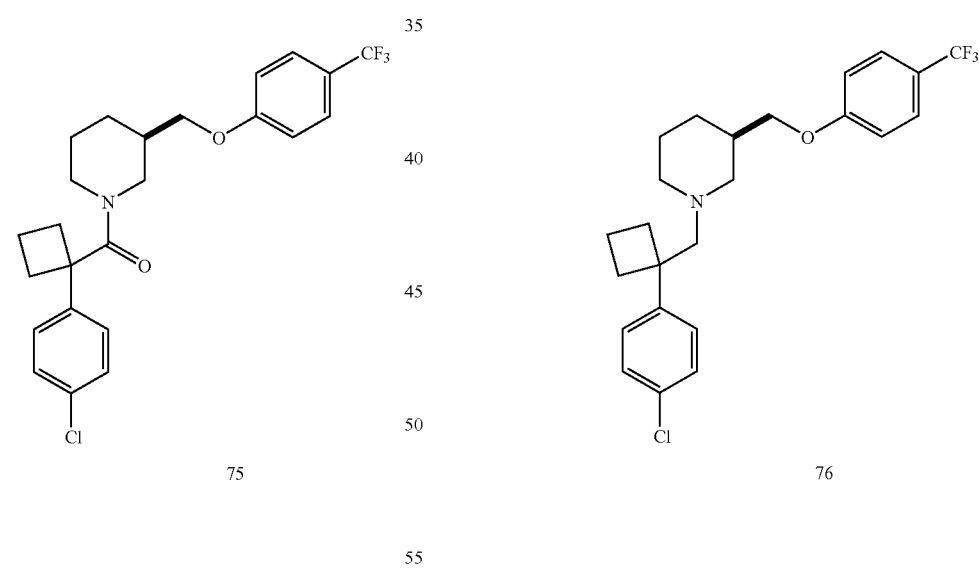

A solution of 74 (98.3 mg, 0.362 mmole), 1-(4-chlorophenyl)-cyclobutanecarboxylic acid (114.3 mg, 0.543 mmole), diisopropylethyl amine (0.252 mL, 1.45 mmole) in DCM (2 mL) was stirred at RT. PyBroP (253.1 mg, 0.543 mmole) was added and the reaction mixture continued stirring at RT. After 12 h the reaction mixture was quenched with 10% KOH. Aqueous layer was extracted with EtOAc (3×2 mL). Combined organic layers were dried over Na$_2$SO$_4$ and concentrated to yield a crude oil. Silica gel chromatography (100% hexane-100% EtOAc) afforded 75 (20 mg) as an oil. LRMS: M+ 452.

A solution of 75 (450 mg, 0.996 mmole) in toluene (15 mL) was cooled to 0° C. in an ice bath. RedAl (950.6 mg, 3.48 mmole) was added to the cooled reaction mixture. After completion of addition the reaction mixture continued stirring at RT. After 2 h the reaction mixture was quenched with water. The aqueous layer was extracted with EtOAc (3×20 mL). Combined organic layers were dried over Na$_2$SO$_4$ and concentrated to yield a crude oil. Silica gel chromatography (85:15 hexane:EtOAc) afforded 76 (134 mg) as an oil. LRMS: M+437.

Example 41

Synthesis of [1-(4-Chloro-phenyl)-cyclobutyl]-[3(4-trifluoromethyl-phenylsulfanylmethyl)-piperidin-1-yl]-methanone

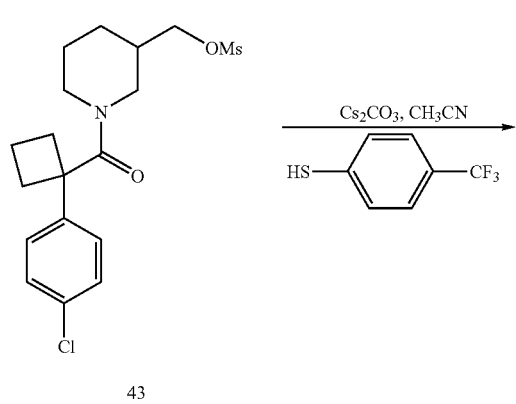

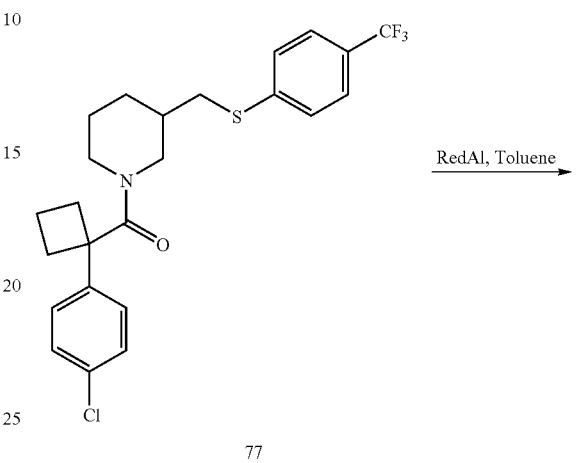

A solution of 43 (1.4 g, 3.6 mmole), Cs$_2$CO$_3$ (5.86 g, 18 mmole), and 4-trifluoromethylthiol phenol (0.646 g, 3.6 mmole) in CH$_3$CN (50 mL) was heated to 75° C. After 4 h the reaction mixture was cooled down to RT and quenched with water. The aqueous layer was extracted with EtOAc (3×30 mL). Combined organic layers were dried over Na$_2$SO$_4$ and concentrated to yield a crude oil. Chromatography using silica gel (4:1 hexane:EtOAc) afforded 77 (196.6 mg) as an oil. LRMS: M+467.

Example 42

Synthesis of [1-(4-Chloro-phenyl)-cyclobutyl]-[3(4-trifluoromethyl-phenylsulfanylmethyl)-piperidine

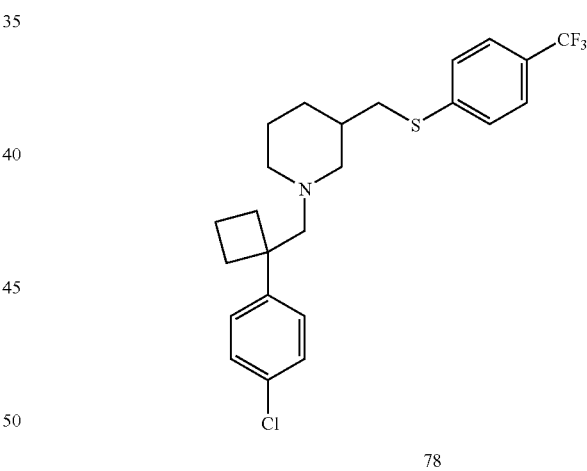

A solution of 77 (500 mg, 1.07 mmole) in toluene (13 mL) was cooled to 0° C. in an ice bath. RedAl (750 mg, 3.74 mmole) was added to the cooled reaction mixture. After completion of addition the reaction mixture continued stirring at RT. After 1.5 h the reaction mixture was quenched with water. The aqueous layer was extracted with EtOAc (20 mL, 3×). Combined organic layers were dried over Na$_2$SO$_4$ and concentrated to yield a crude oil. Silica gel chromatography (90:10 hexane:EtOAc) afforded 78 (180 mg) as an oil. LRMS: M+452.

Example 43

Synthesis of 2-(4-Chloro-phenyl)-1-(3-phenoxymethyl-piperidin-1-yl)-propan-2-ol

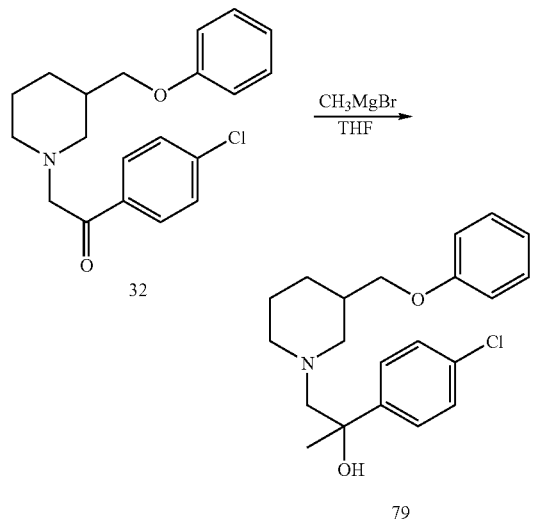

A solution of 32 (0.343 mmol, 118 mg) in THF (1 mL) was treated with CH$_3$MgBr (3.0 M in ether) (3.0 equiv, 1.03 mmol, 343 µL) at 0° C. and stirred for 12 h. The reaction mixture was quenched with 10% HCl (5 mL) and then neutralized with NaHCO$_3$(sat) and extracted with EtOAc (2×10 mL). The combined organics were dried with NaCl$_{(sat)}$ and Na$_2$SO$_{4(s)}$. The solvents were removed in vacuo and chromatography (PTLC, SiO$_2$, 20 cm×20 cm, 1 mm, 3:1 Hexane-EtOAc) provided 79 (29 mg, 123 mg theoretical, 24%) as a colorless oil: R$_f$ 0.44 (SiO$_2$, 3:1 Hexane-EtOAc); LRMS m/z 361 (M$^+$+1, C$_{21}$H$_{26}$ClNO$_2$, requires 361).

Example 44

Synthesis of {1-[2-(4-Chloro-phenyl)-2-methyl-propyl]-piperidin-3-yl]}-methanol

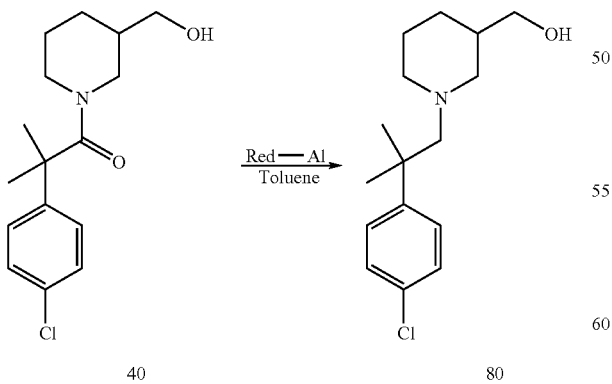

To amide 40 (100 mg, 0.34 mmol) in toluene (1 mL) was cautiously added Red-Al (0.36 mL, 1.2 mmol). The resulting solution was allowed to stir at room temperature overnight. The reaction was then diluted with ethyl acetate and quenched with 10% aqueous KOH. The layers were separated and the aqueous layer further washed with ethyl acetate. The combined organic layers were then dried (MgSO$_4$), filtered, concentrated in vacuo and the resulting residue purified by flash column chromatography using 4% 2M NH$_3$ in EtOH/DCM to provide the desired amine 80 (44 mg, 46%). LRMS calculated for C$_{16}$H$_{24}$ClNO 281.15, found (M+) 282.82. $^1$H NMR (300 MHz, CDCl$_3$): 7.34 (d, J=8.7 Hz, 2H), 7.28 (d, J=8.7 Hz, 2H), 3.47–3.61 (m, 2H), 2.47–2.52 (m, 1H), 2.42 (s, 2H), 2.12–2.29 (m, 4H), 1.38–1.70 (m, 4H), 1.33 (s, 3H), 1.32 (s, 3H), 1.15–1.22 (m, 1H). $^{13}$C NMR (75 MHz, CDCl$_3$): 147.0, 131.4, 127.8, 127.6, 71.3, 67.1, 59.8, 56.6, 39.1, 37.5, 27.0, 26.9, 26.6, 24.5.

Example 45

Synthesis of Methanesulfonic acid 1-[1-(4-chlorophenyl)-cyclobutanecarbonyl]-piperidin-3-ylmethyl ester

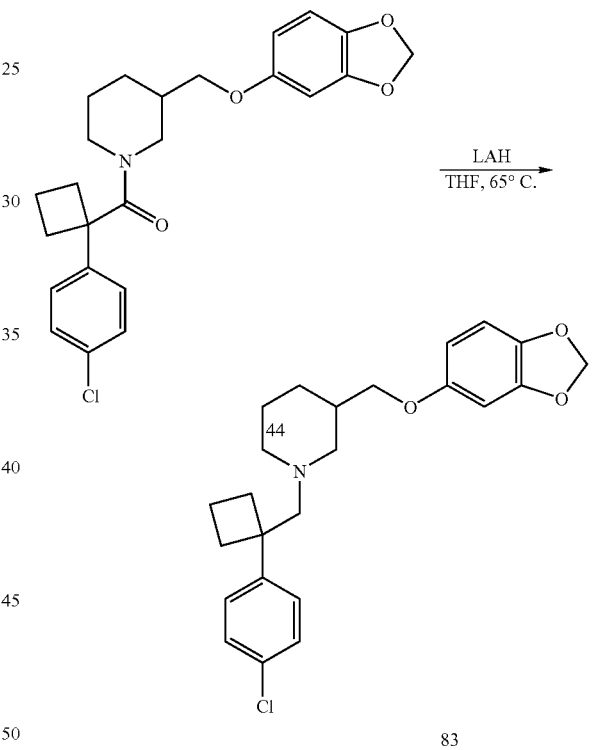

To a suspension of lithium aluminum hydride (0.089 g, 2.34 mmol) in anhydrous tetrahydrofuran (25 mL) at 0° C. was added 44 (0.50 g, 1.17 mmol). The reaction mixture was then stirred and refluxed for 6 h. The mixture was cooled to 0° C., and the reaction was quenched with slow addition of water. The resulting salts were removed by vacuum filtration through Celite, and the filtrate was partitioned between water and diethyl ether (50 mL each). The aqueous layer was extracted well with diethyl ether (4×50 mL), and the combined organic portions were dried over anhydrous magnesium sulfate, filtered and concentrated by rotary evaporation. The organic residue was purified by flash chromatographey on silica gel, eluting with dichloromethane/2.0 M ammonia in ethyl alcohol (96:4) to give 83 (0.15 g, 31%) as a pale yellow gum; C$_{24}$H$_{28}$ClNO$_3$, LRMS (m/z)=414 (MH+).

Example 46

Synthesis of [1-(4-Chlorophenyl)-cyclobutyl]-[3-(4-fluorophenoxymethyl)-piperidin-1-yl]-methanone (84)

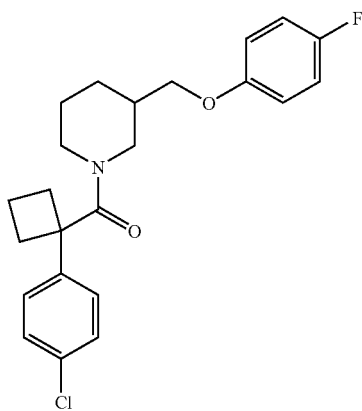

Compound 84 was synthesized from 4-fluorophenol (0.29 g, 2.60 mmol), cesium carbonate (1.27 g, 3.89 mmol) and compound 43 (1.0 g, 2.60 mmol), using the method described for the synthesis of compound 44 to give 0.60 g of the desired product 84. $C_{23}H_{25}ClFNO_2$, LRMS (m/z) =402 (MH+).

Example 47

Synthesis of [1-(4-Chloro-phenyl)-cyclobutyl]-[3-(pyridin-3-yloxymethyl)-piperidin-1-yl]-methanone (85)

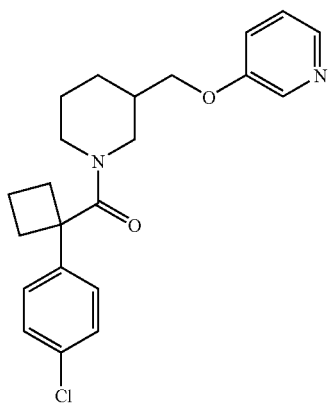

Compound 85 was synthesized from 3-hydroxypyridine (0.25 g, 2.60 mmol), cesium carbonate (1.27 g, 3.89 mmol) and compound 43 (1.0 g, 2.60 mmol), using the method described for the synthesis of compound 44 to give 0.52 g of the desired product 85. $C_{22}H_{25}ClN_2O_2$, LRMS (m/z)=385 (MH+).

Example 48

Synthesis of 1-[1-(4-Chloro-phenyl)-cyclobutylmethyl]-3-(4-fluoro-phenoxymethyl)-piperidine (86)

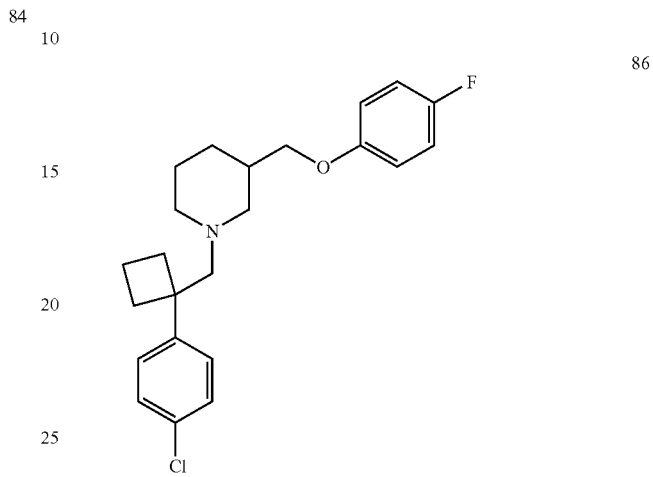

Compound 86 was synthesized from compound 84 (0.50 g, 1.25 mmol) and lithium aluminum hydride (0.10 g), using the method described for the synthesis of compound 83 to give 0.24 g of the desired product 86. $C_{23}H_{27}ClFNO$, LRMS (m/z)=388 (MH+).

Example 49

Synthesis of 3-{1-[1-(4-Chloro-phenyl)-cyclobutylmethyl]-piperidin-3-ylmethoxy}-pyridine (87)

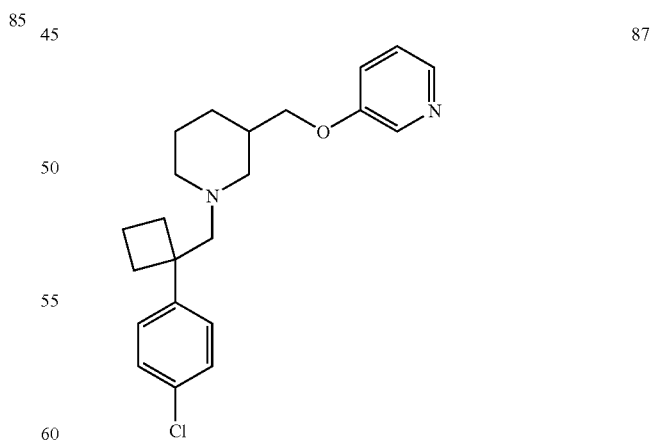

Compound 87 was synthesized from compound 85 (0.50 g, 1.25 mmol) and lithium aluminum hydride (0.10 g), using the method described for the synthesis of compound 83 to give 0.19 g of the desired product 87. $C_{22}H_{27}ClN_2O$, LRMS (m/z)=371 (MH+).

Example 50

Synthesis of 1-[1-(4-Chlorophenyl)cyclobutylmethyl]piperidin-3-ol (89)

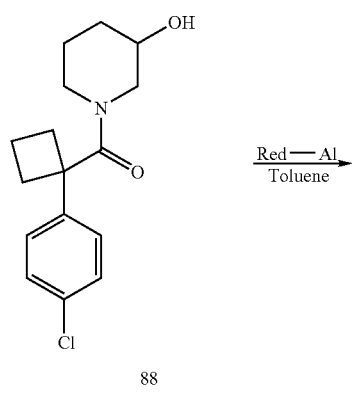

88

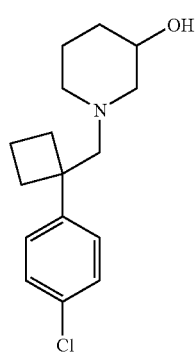

89

The synthesis of amide 88 from commercially-available 3-hydroxypiperidine hydrochloride and 1-(4-chloro-phenyl)-cyclobutanecarboxylic acid is described in Example 72.

To amide 88 (100 mg, 0.34 mmol) in toluene (1 mL) was cautiously added Red-Al (0.36 mL, 1.2 mmol). The resulting solution was allowed to stir at room temperature for one and one half hours before diluting with ethyl acetate and quenching with 10% aqueous KOH. The layers were separated and the aqueous layer further washed with ethyl acetate. The combined organic layers were then dried (MgSO$_4$), filtered and concentrated in vacuo. The resulting residue was purified by flash column chromatography using 4% 2M NH$_3$ in EtOH/DCM to provide the desired amine 89 (51 mg, 54%). LRMS calculated for C$_{16}$H$_{22}$ClNO 279.14, found (M+) 280.87. $^1$H NMR (300 MHz, CDCl$_3$): 7.28 (d, J=8.3 Hz, 2H), 7.11 (d, J=8.3 Hz, 2H), 3.67–3.69 (m, 1H), 2.73 (m, 1H), 2.66 (s, 2H), 2.14–2.44 (m, 7H), 1.97–2.11 (m, 2H), 1.79–1.90 (m, 1H), 1.24–1.66 (m, 4H). $^{13}$C NMR (75 MHz, CDCl$_3$): 147.6, 131.1, 127.9, 127.4, 68.2, 66.0, 62.2, 55.3, 46.9, 31.8, 31.7, 30.8, 21.2, 16.0.

Example 51

Synthesis of 3-[1-(4-Chloro-phenyl)-cyclobutanecarbonyl]-cyclohexanecarbaldehyde

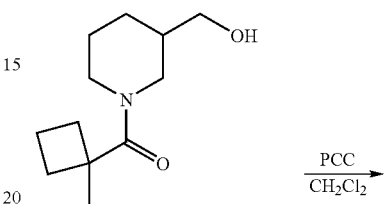

1

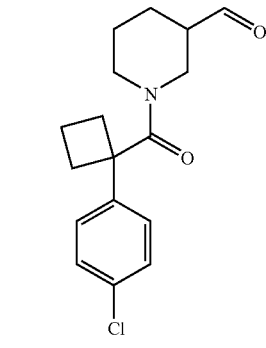

90

To a stirred solution of pyridinium chlorochromate (210 mg, 0.98 mmole) in anhydrous dichloromethane (5 mL) was added alcohol 1 (200 mg, 0.65 mmole) dissolved in anhydrous dichloromethane (5 mL). After completion of addition the reaction mixture continued stirring at RT for 5 h. The reaction mixture was then filtered though a presaturated silica gel plug (1:1 hexane:EtOAc) to obtain the aldehyde 90 as a clear oil (100 mg, 50%).

Example 52

Synthesis of 3-[1-(4-Chloro-phenyl)-cyclobutyl]-{3-{2-(4-trifluoromethyl-phenyl)-vinyl]-cyclohexyl}-methanone

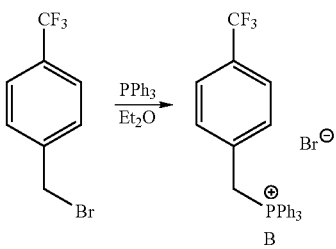

B

Example 53

Synthesis of (1-phenyl-cyclobutyl]-{3-{2-(4-trifluoromethyl-phenyl)-ethyl]-cyclohexyl}-methanone

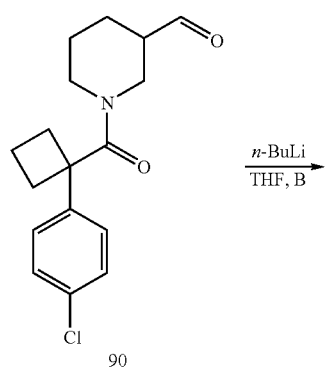

90

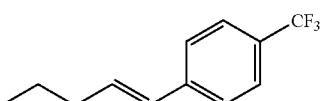

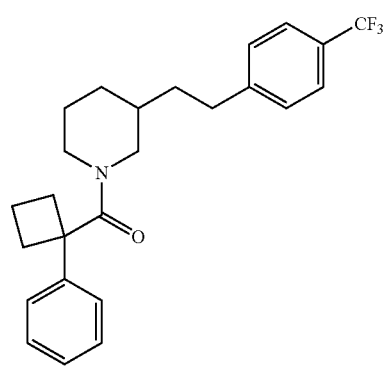

91

92

To a stirring solution of triphenylphosphine (2.2 g, 8.4 mmole) in anydrous diethylether (8 mL) was added 4-trifluoromethyl-benzyl bromide (2 g, 8.4 mmole) dissolved in anydrous diethylether (7 mL). The reaction mixture continued stirring at RT for 72 h. The phosphine salt, B, was collected via filtration of the reaction mixture. The salt, white solid, was dried under vacuum (2.52 g).

A solution of B (2.5 mmol, 754 mg) in THF (10 mL) was treated with nBuLi (1.6M in hexanes, 3.7 mmole, 2.3 mL) at −78° C. The solution was warmed to 0° C. for 30 min and then cooled again to −78° C. A solution of 90 (3.7 mmol, 1.85 g) in THF (10 mL) was added to the above reaction mixture at −78° C. The reaction was stirred for 2 h. The reaction mixture was quenched with water and then extracted with EtOAc (3×20 mL). The combined organics were dried over $Na_2SO_{4(s)}$. The solvents were removed in vacuo and the crude material was purified using silica gel chromatography (100% hexanes-85:15 hexanes:EtOAc) to provide 91 (176 mg, 17%) as an oil. LRMS: M+ 415.

A solution of 91 (592 mmol, 190 mg) in $CH_3OH$ (5 mL) was treated with 10% Pd—C (60 mg) and $H_2$ (Parr Hydrogenator, 65 psi). The reaction was shaken for 4 h. The reaction mixture was filtered, and the solvents were removed in vacuo to provide 92 (180 mg). $^1H$ (300 MHz, $CDCl_3$) δ 7.55 (2H, t, J=9 Hz), 7.38–7.29 (m, 3H), 7.24 (2H, d, J=7.3 Hz), 7.14 (2H, d, J=9 Hz), 4.64 (2H, m), 4.42 (2H, m), 3.80–0.78 (m, 15H).

Example 54

Synthesis of 1-(1-phenyl-cyclobutylmethyl)-3-[2-(4-trifluoromethyl-phenyl)-ethyl]-piperidine

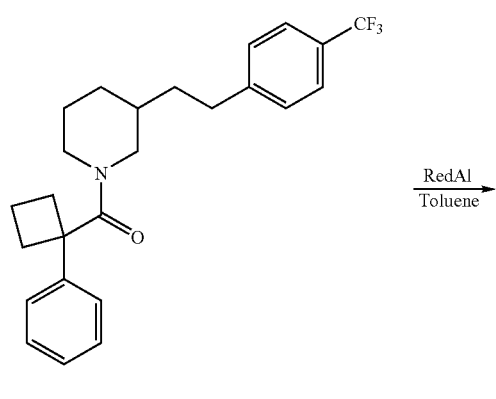

Example 55

Synthesis of 1-(4-Chloro-phenyl)-cyclobutyl]-[3-(4-trifluoromethyl-phenoxymethyl)-piperidin-1-yl]-methanone

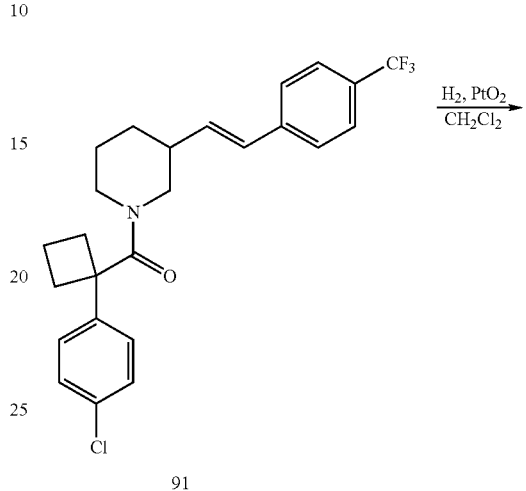

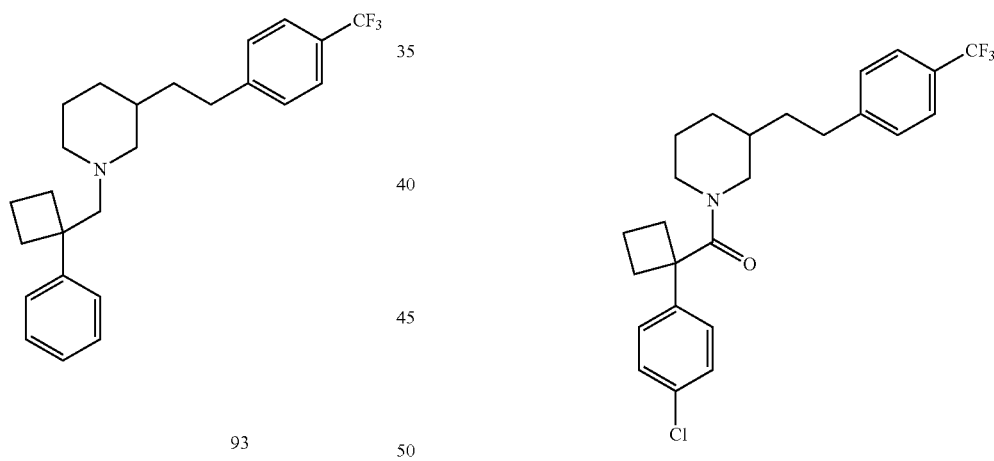

A solution of amide 92 (180 mg, 0.50 mmole) in anhydrous toluene (5 mL) was cooled to 0° C. RedAl (356 mg, 1.76 mmole) was added to the cooled stirring reaction mixture. After completion of addition, the reaction continued stirring at RT. After 2 h, the reaction mixture was diluted with EtOAc and quenched with water. The aqueous layer was extracted with EtOAc (3×10 mL). The combined organic layers were dried over $Na_2SO_4$ and concentrated to yield an oil. The crude material was purified using silica gel chromatography (100% hexane-80:20 Hexanes:EtOAc) to yield 93. LRMS: M+ 402.

The olefin 91 (100 mg, 0.28 mmole) was dissolved in anhydrous dichloromethane (3 mL) and placed in a two-neck flask. To this solution platinum oxide (16 mg, 0.07 mmole) was added. The system was alternately evacuated and filled with nitrogen, then hydrogen from a balloon. The reaction mixture was stirred vigorously under hydrogen for 4 h. The crude solution was filtered and concentrated to yield 94 as a milky white oil (97 mg, 77%). $^1$H (300 MHz, $CDCl_3$) δ 7.55 (2H, d, J=8.3 Hz), 7.34–7.31 (m, 4H), 7.17 (2H, d, J=7.6 Hz), 4.62 (2H, m), 4.41 (2H, m), 3.00–0.85 (m, 15H).

Example 56

Synthesis of 1-[1-(4-Chloro-phenyl)-cyclobutylmethyl]-3-[2-(4-trifluoromethyl-phenyl)-ethyl]-piperidine

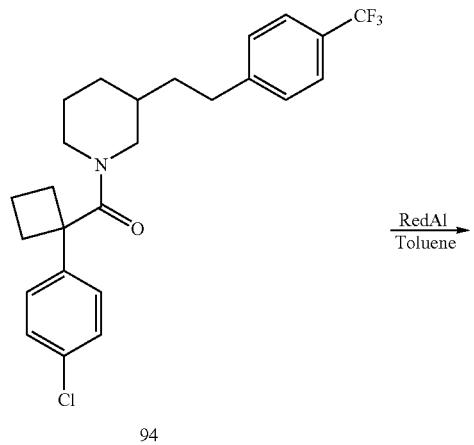

94

95

A solution of amide 94 (97 mg, 0.27 mmole) in anhydrous toluene (2 mL) was cooled to 0° C. RedAl (192 mg, 0.94 mmole) was added to the cooled stirring reaction mixture. After completion of addition, the reaction continued stirring at RT. After 2 h, the reaction mixture was diluted with EtOAc (4 mL) and quenched with water. The aqueous layer was extracted with EtOAc (3×5 mL). The combined organic layers were dried over Na$_2$SO$_4$ and concentrated to yield an oil. The crude material was purified using silica gel chromatography (100% hexane-80:20:0.2% hexanes:EtOAc:2M NH$_3$ in EtOH) to yield 95. LRMS: M+435.

Example 57

Synthesis of 3-(1-hydroxy-ethyl)-piperidine-1-carboxylic Acid 2,2-dimethyl-propyl ester

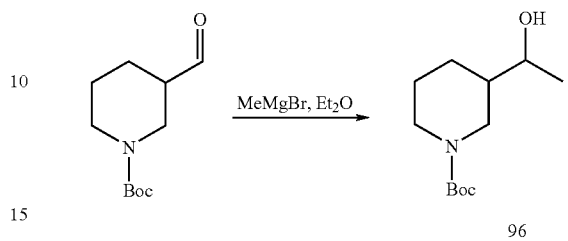

96

To a cooled solution of N-BOC-piperidine-3-carboxaldehyde dissolved in diethyl ether (50 mL) was added the methyl grignard reagant (10.55 mL, 10.5 mmol, 1 M in diethyl ether). After completion of addition the reaction mixture continued stirring at 0° C. for 15 min. and was then warmed to RT. After 15 min. of stirring at RT the reaction mixture was quenched with water. The aqueous layer was extracted with EtOAc (3×100 mL). The combined organic layer was then dried over Na$_2$SO$_4$, filtered and concentrated in vacuo. The resulting residue was purified by silica gel chromatography using a gradient (100% hexanes-1:1 hexanes:EtOAc) to obtain the desired alcohol 96. $^1$H NMR (300 MHz, CDCl$_3$): δ 3.94 (m, 1H), 3.65 (t, 1H, J=6.1 Hz), 2.73 (m, 2H), 2.65 (m, 2H), 1.94 (m, 2H), 1.70 (m, 2H), 1.50 (s, 9H), 1.29 (m, 3H).

Example 58

Synthesis of [1-(4-chlorophenyl)-cyclobutyl]-[3-(1-hydroxy-ethyl)-piperidin-1-yl]-methanone

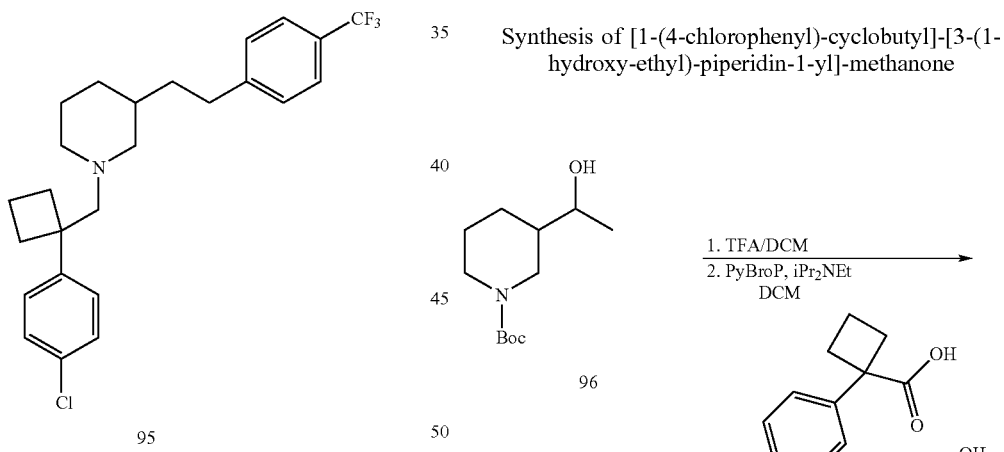

96

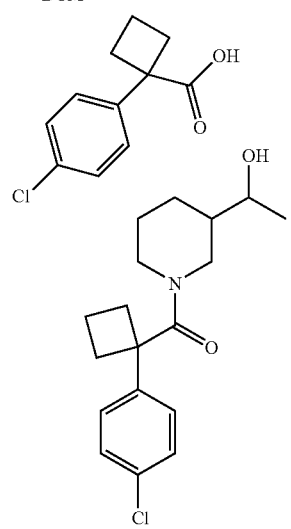

97

To a cooled solution of the protected amine 96 (750 mg, 3.3 mmol) dissolved in DCM (4 mL) was added concentrated TFA (4 mL) dropwise. After completion of addition the reaction continued stirring at 0° C. After 1.5 h the reaction mixture was concentrated in vacuo to yield the TFA salt as a brown oil.

This salt was dissolved in DCM (16.5 mL) and solid 1-(4-chloro-phenyl)-cyclobutane carboxylic acid (1.43 g, 4.95 mmole) followed by di-isopropyl ethyl amine (2.3 mL 13.2 mmol) were added. After completion of addition solid PyBroP (2.29 g, 4.95 mmole) was added to the stirring reaction mixture. The reaction mixture continued stirring at RT for 10 h and was quenched with water and 10% KOH. The aqueous layer was extracted with EtOAc (3×20 mL). Combined organic layers were dried over $Na_2SO_4$ and concentrated to yield an oil. This crude material was purified using silica gel chromatography (1:1 hexane:EtOAc) to yield 97 as an oil. LRMS: M+ 321.

Example 59

Synthesis of 1-[1-(4-chloro-phenyl)-cyclobutyl]-{3-[1-(4-trifluoromethyl-phenoxy)-ethyl]-piperidin-1-yl}-methanone

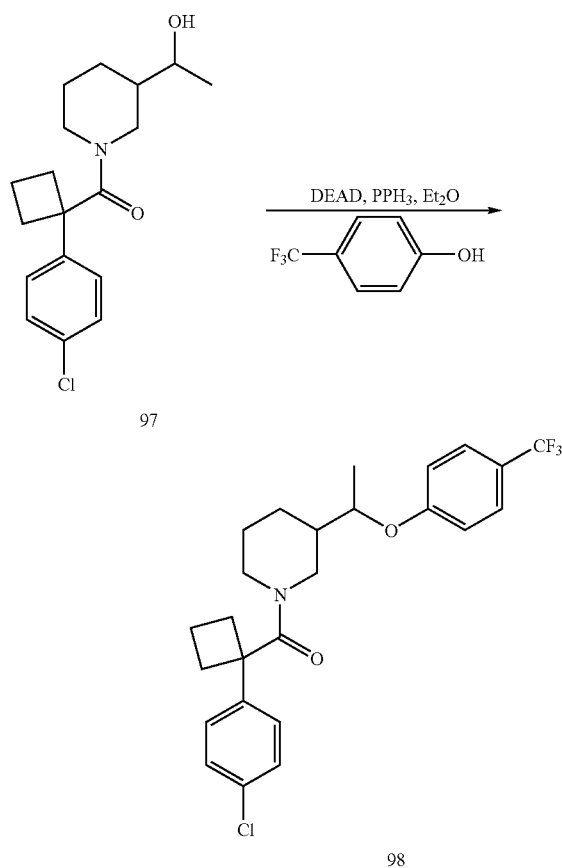

A solution of 97 (300 mg, 0.932 mmoles), triphenylphosphine (370 mg, 1.40 mmole), and phenol (300 mg, 1.86 mmoles) dissolved in anhydrous ether (2.5 mL) was cooled in a brine bath to −5° C. DEAD (240 mg, 1.40 mmoles) dissolved in ether (2.5 mL) was added to the cooled stirring reaction mixture. After completion of addition the reaction mixture continued stirring at −5° C. After 4 h the reaction mixture was concentrated and crude material was dissolved in a hexane/ethyl acetate mixture (70% hexanes:30% ethyl acetate, 30 mL). Phosphine by-products precipitated and were filtered off. Filtrate was concentrated to yield an oil. This oil was purified using silica gel chromatography (3:2 hexanes:EtOAc-100% EtOAc) to yield 98. LRMS: M+ 367.

Example 60

Synthesis of 1-[1-(4-chloro-phenyl)-cyclobutylmethyl]-3-[1-(4-trifluoromethyl-phenoxy)-ethyl]-piperidine

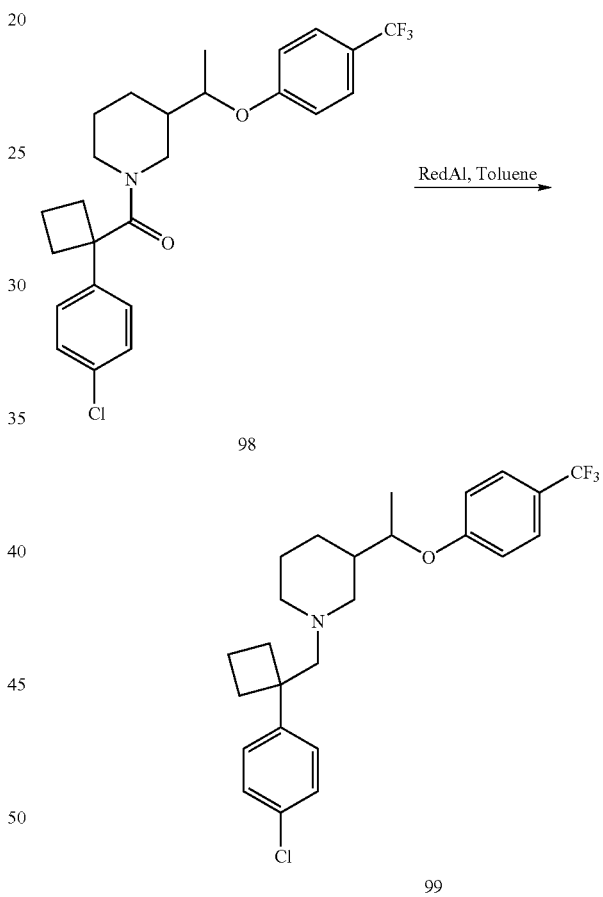

A solution of 98 (215 mg, 0.461 mmoles) dissolved in anhydrous toluene (2.3 mL) was cooled to 0° C. RedAl (326 mg, 1.62 mmoles) was added dropwise to the cooled stirring reaction mixture. After completion of addition the reaction continued stirring at RT. After 1.5 h water was added to the reaction mixture. The aqueous layer was extracted with EtOAc 3× (5 mL). Combined organic layers were dried over $Na_2SO_4$ and concentrated to yield an oil. The crude material was purified using silica gel chromatography (1:1 Hexanes: EtOAc) to yield 99. $^1$H NMR (300 MHz, CDCl$_3$): δ 7.54 (dd, 2H, J=8.7 Hz), 7.27 (d, 2H, J=6.2 Hz), 7.10 (m, 2H), 6.86 (d, 2H, J=8.5 Hz), 4.10 (m, 1H), 2.69–1.08 (m, 20H).

Example 61

Synthesis of 2-benzyl aminoethanol

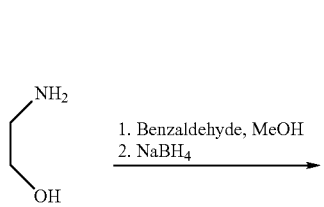

To a stirring solution of benzaldehyde (41.60 g, 393 mmole) dissolved in anhydrous MeOH (350 mL) was added 2-amino ethanol (20 g, 327 mmole) dropwise. After completion of addition the reaction mixture was heated to 75° C. After 0.5 h the reaction mixture was cooled to RT and placed in an ice bath. Solid NaBH$_4$ (18.58 g, 491 mmole) was added over 20 min. After completion of addition the reaction mixture continued stirring at RT. After 10 h the reaction mixture was concentrated and the white crude material was taken up in DCM (300 mL). The organic layer was extracted with water (1×200 mL). The aqueous layer was acidified with 10% HCl and then extracted with DCM (3×200 mL). Combined organic layers were dried over Na$_2$SO$_4$ and concentrated to yield 2-benzyl aminoethanol (55.21 g, 0.363 moles, 92%). LRMS: M+ 152.

Example 62

Synthesis of 4-benzyl-2-chloromethyl-morpholine

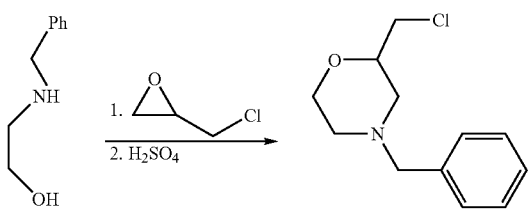

A solution of 2-benzyl aminoethanol (7.0 g, 46.3 mmoles) and epichlorohydrin (42.8 g, 463 mmoles) was heated to 40° C. After 2.5 h the reaction was cooled to RT and the excess epichlorohydrin was evaporated in vacuo. Sulfuric acid (14 mL) was added slowly to the crude mixture. After completion of addition the reaction flask was placed in a preheated oil bath (150° C.). The reaction mixture was heated for 30 minutes, cooled to RT, and quenched with ice. The aqueous layer was basified with 10% KOH and extracted with EtOAc 3× (300 mL). Combined organic layers were dried over Na$_2$SO$_4$ and concentrated to yield a crude oil. This oil was purified using silica gel chromatography (90:8:2 hexanes: DCM:2M NH$_3$ in EtOH) to obtain the morpholine (3.41 g, 15.16 mmole, 33%). $^{13}$C NMR (100 MHz, CDCl$_3$) δ 137.7, 129.4, 128.6, 127.6, 75.4, 67.1, 63.4, 56.1, 53.0, 45.2. LRMS: 225.

Example 63

Synthesis of 2 chloromethyl-morpholine

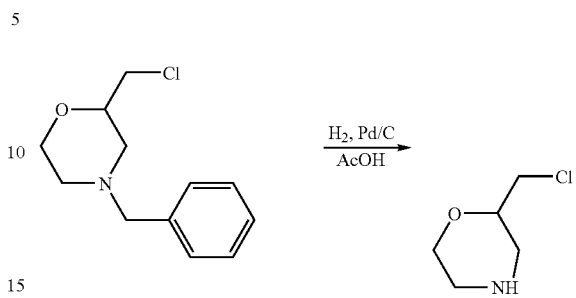

4-Benzyl-2-chloromethyl-morpholine (316 mg, 1.40 mmole) dissolved in acetic acid (3.16 mL) was hydrogenated in the presence of palladium on charcoal (10%, 94.8 mg) under pressure (50 psi) at RT. After 5 h the reaction catalyst was removed by filtration and the filtrate was concentrated to yield 2-chloromethyl-morpholine as an oil. $^{13}$C NMR (100 MHz, CDCl$_3$) δ 74.6, 66.5, 47.0, 44.7, 44.1. LRMS: M+ 136.

Example 64

Synthesis of (2-chloromethyl-morpholin-4-yl)-[1-(4-chloro-phenyl)-cyclobutyl]-methanone

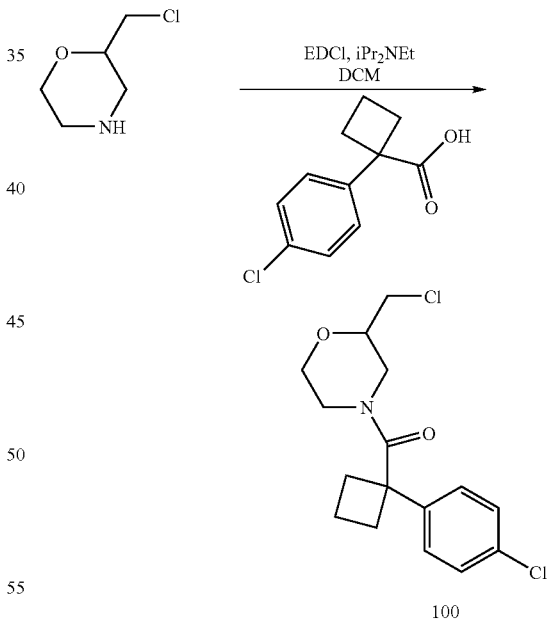

To a solution of 2-chloromethyl-morpholine (163 mg, 1.2 mmole) and EDCI (280 mg, 1.8 mmole) dissolved in DCM (5 mL) was added solid 1-(4-chloro-phenyl)-cyclobutane carboxylic acid (304 mg, 1.44 mmole) followed by di-isopropyl ethyl amine (310 mg, 2.4 mmol). The reaction mixture continued stirring at RT for 10 h and was quenched with water. The aqueous layer was extracted with EtOAc (3×10 mL). Combined organic layers were dried over Na$_2$SO$_4$ and concentrated to yield an oil. This crude material was purified using silica gel chromatography (1:1 hexane: EtOAc) to yield 100 (100 mg, 12.7%). LRMS: M+ 328.

Example 65

Synthesis of [1-(4-chloro-phenyl)-cyclobutyl]-[2-(4-trifluoromethyl-phenoxymethyl)-morpholin-4-yl] methanone

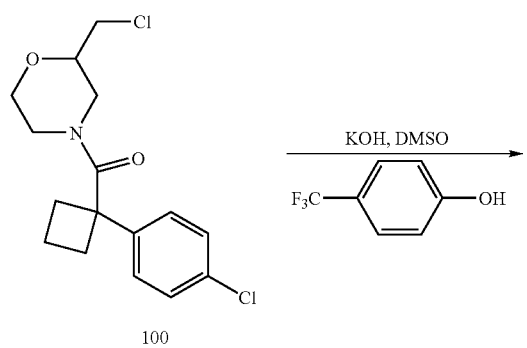

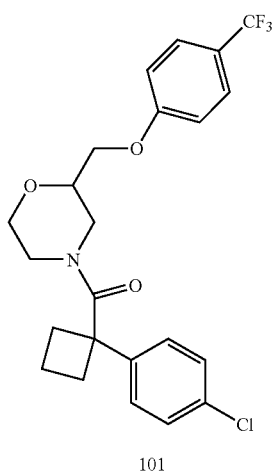

To a solution of KOH (34 mg, 0.61 mmoles) dissolved in DMSO (1.5 mL) was added the phenol (49 mg, 0.30 mmoles) followed by the halide 100 (100 mg, 0.30 mmoles). After completion of addition the reaction mixture was heated to 55° C. After 12 h the reaction mixture was cooled to RT and quenched with water. The aqueous layer was extracted with EtOAc 3× (2 mL) and combined organic layers were dried over Na₂SO₄ and concentrated to yield a crude oil. The crude material was purified using silica gel chromatography (1:1 hexane:EtOAc) to yield 101 (16 mg, 0.035 mmole, 12.3%). LRMS: M+ 353.

Example 66

Synthesis of [1-(4-chloro-phenyl)-cyclobutyl]-[2-(4-trifluoromethyl-phenoxymethyl)-morpholin-4-yl] methanone

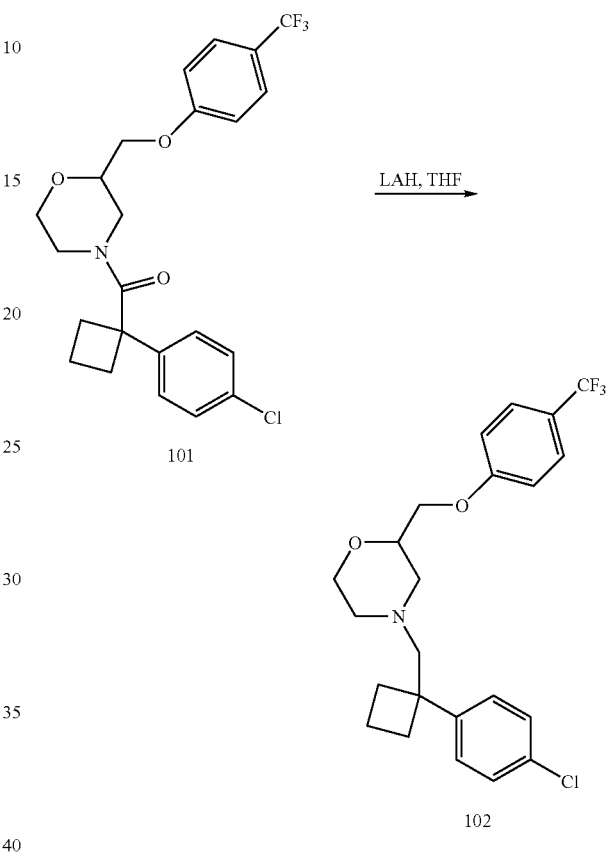

To a cooled solution of LAH (0.053 mL, 0.053 mmol, 1 M solution in THF) in anhydrous THF was added 101 (16 g, 0.035 mmole) dissolved in anhydrous THF (0.175 mL). After completion of addition the reaction continued stirring at RT. After 4 h the reaction mixture was quenched with 5% HCl (aq.). The aqueous layer was extracted with EtOAc (3×2 mL) and combined organic layers were dried over Na₂SO₄ and then concentrated to yield an oil. The crude material was purified using a silica gel prep plate (90:10 Hexanes:EtOAc) to yield 102. LRMS: M+ 440.

Example 67

Synthesis of azetidine-3-carboxylic acid ethyl ester hydrochloride

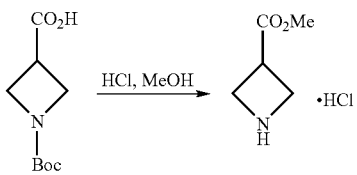

Hydrogen chloride gas was gently bubbled into a solution of azetidine-3-carboxylic acid (1 g, 9.85 mmole) in methanol (20 mL). After 3 min. the HCl gas source was removed from the solution and the reaction flask was capped. The reaction mixture continued stirring at RT. After 2 days the reaction mixture was concentrated in vacuo to yield the HCl salt as a yellow oil (762 mg, 4.60 mmole, 47%). $^{13}$C NMR (100 MHz, CDCl$_3$) δ 171.1, 53.2, 48.2, 34.7.

Example 68

Synthesis of 1-[1-(4-chloro-phenyl)-cyclobutanecarbonyl]-azetidine-3-carboxylic acid methyl ester

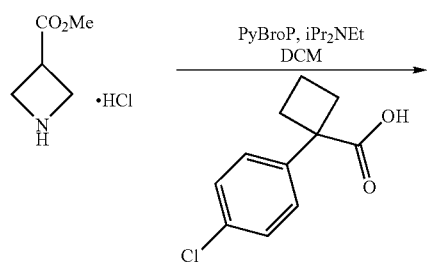

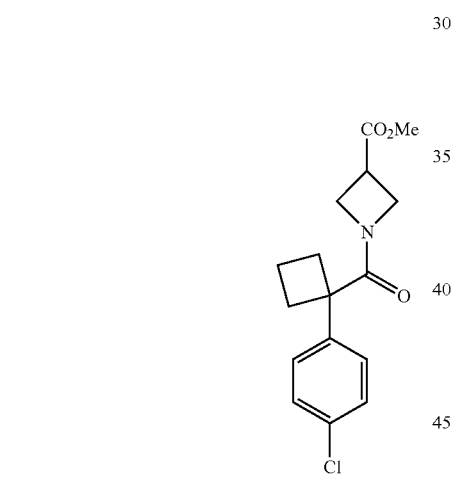

To a stirred solution of azetidine-3-carboxylic acid methyl ester hydrochloride (762 mg, 4.60 mmoles) and 1-(4-chlorophenyl)-cyclobutane carboxylic acid (2.09 g, 9.90 mmoles) in anhydrous DCM (20 mL) was added di-isopropyl ethyl amine (4.6 mL, 26.4 mmoles) dropwise. After completion of addition solid PyBroP (4.63 g, 9.94 mmoles) was added to the stirring reaction mixture. The reaction mixture continued stirring at RT for 10 h and was quenched with water. The aqueous layer was extracted with EtOAc (3×20 mL). Combined organic layers were dried over Na$_2$SO$_4$ and concentrated to yield an oil. This crude material was purified using silica gel chromatography (9:1 hexanes:EtOAc-1:1 hexane:EtOAc) to yield the desired amide (1.0 g, 65%). $^1$H NMR (300 MHz, CDCl$_3$): δ 7.38–7.29 (m, 4H), 4.16 (m, 2H), 3.88 (m, 1H), 3.72 (s, 3H), 3.31–1.63 (m, 8H). LRMS: M+309.

Example 69

Synthesis of {1-[1-(4-chloro-phenyl)-cyclobutylmethyl]-azetidin-3-yl}-methanol

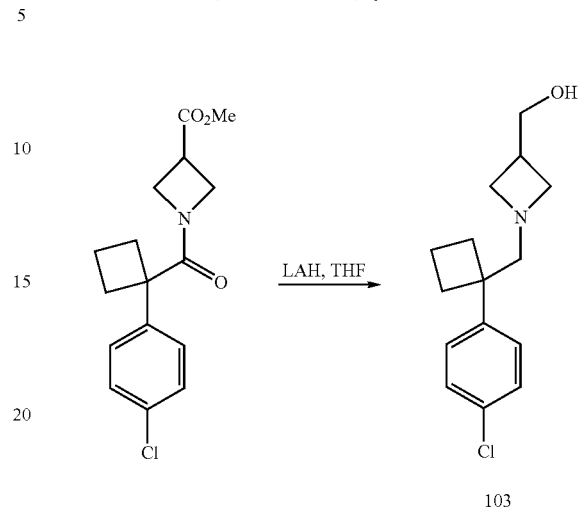

To a cooled (0° C.) solution of LAH (9.8 mL, 9.8 mmol, 1 M solution in THF) in anhydrous THF was added the ester (1 g, 3.0 mmole) dissolved in anhydrous THF (20 mL). After completion of addition the reaction continued stirring at RT. After 3 h the reaction mixture was quenched with 10% HCl (aq.). The aqueous layer was extracted with EtOAc (3×200 mL) and combined organic layers were dried over Na$_2$SO$_4$ and then concentrated to yield 103 as an oil. LRMS: M+ 265.

Example 70

Synthesis of Methanesulfonic acid 1-[1-(4-chlorophenyl)-cyclobutylmethyl]-azetidin-3-ylmethyl ester

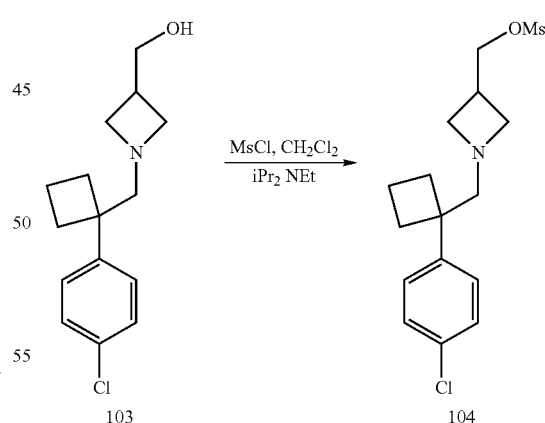

To a solution of primary alcohol 103 (1.8 g, 6.77 mmol) in DCM (30 mL) at room temperature was added iPr$_2$NEt (3 mL, 16.93 mmol) followed by MsCl (0.6 mL, 7.44 mmol). The reaction mixture was allowed to stir for one hour before purifying the crude mixture using a presaturated silica gel plug (4:1 hexanes:EtOAc) to provide the desired mesylate 104, which was used in the next reaction without further purification. LRMS: M+ 344.

Example 71

Synthesis of Methanesulfonic acid 1-[1-(4-chlorophen 1)-cyclobutylmethyl]-3-(4-trifluoromethyl-phenoxymethyl)-azetidine

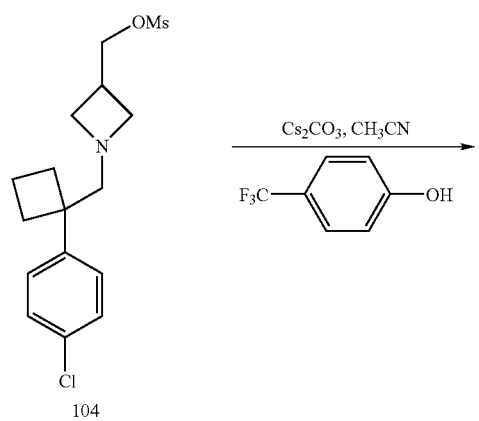

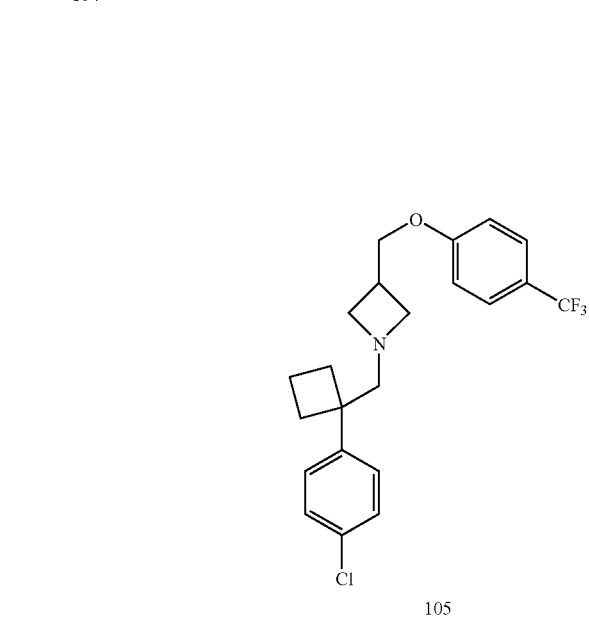

To the mesylate 104 (2.3 g, 6.70 mmol) in anhydrous acetonitrile (33 mL) was added α,α,α-trifluoro-p-cresol (1.1 g, 6.70 mmol) followed by $Cs_2CO_3$ (10.90 g, 33.44 mmol). The reaction mixture was heated to 75° C. and the reaction progress was monitored by HPLC. Upon completion the reaction mixture was quenched with water and the aqueous layer was extracted with EtOAc (3×20 mL). The combined organic layer was then dried over $Na_2SO_4$, filtered and concentrated in vacuo. The resulting residue was purified by silica gel chromatography using a gradient (30% hexanes: 70% EtOAc) to obtain the desired ether 105. LRMS: M+410.

Example 72

Synthesis of 1-[1-(4-Chloro-phenyl)-cyclobutylmethyl]-3-(4-trifluoromethyl-benzyloxy)-piperidine

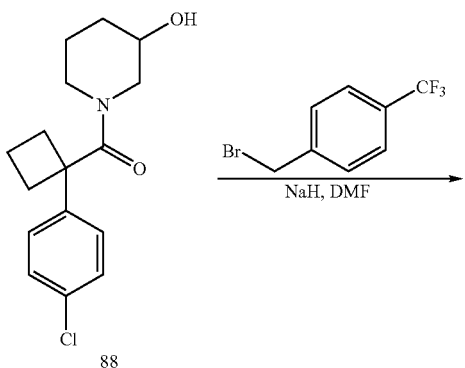

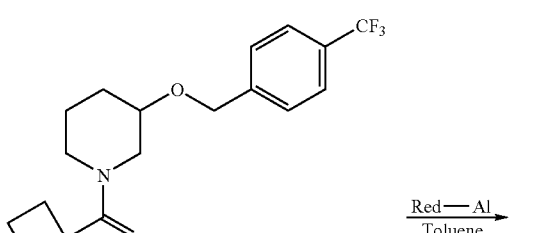

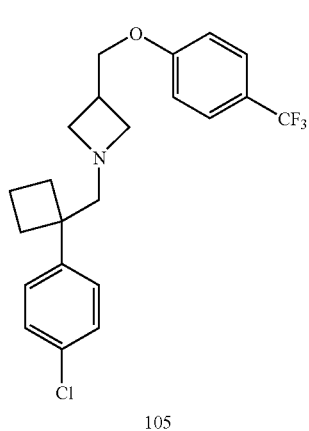

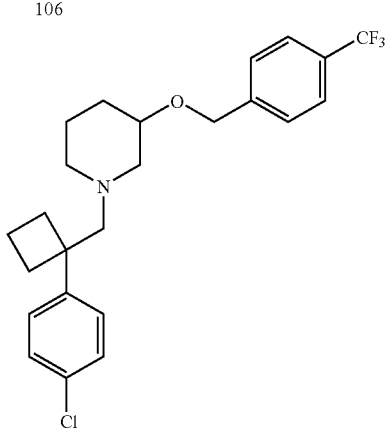

Amide 88 was prepared from commercially-available 3-hydroxypiperidine hydrochloride and 1-(4-chloro-phenyl)-cyclobutane carboxylic acid, using the procedure outlined for the synthesis of 1 in Example 1: 3-hydroxypiperidine hydrochloride (1.0 g, 7.29 mmol), 1-(4-chlorophenyl)-1-cyclobutane carboxylic acid (2.29 g, 10.9 mmol), PyBroP (5.08 g, 10.9 mmol), $iPr_2NEt$ (6.33 mL, 36.3 mmol), DCM (40 mL). Purification by flash column chromatography using 40% ethyl acetate/petroleum ether provided the desired amide 88 (1.74 g, 82%). $^{13}$C NMR (75 MHz, CDCl$_3$): δ (major rotamer only) 174.4, 141.9, 132.1, 128.9, 126.4, 65.8, 51.9, 49.3, 45.5, 32.6, 31.9, 22.0, 15.2.

To amide 88 (200 mg, 0.68 mmol) in DMF (3 mL) was cautiously added sodium hydride (82 mg, 2.0 mmol). The resulting mixture was allowed to stir at room temperature for 45 minutes before adding 4-(trifluoromethyl)benzoyl bromide (179 mg, 0.75 mmol). The reaction was allowed to continue stirring at room temperature overnight before diluting with ethyl acetate and quenching with a saturated aqueous sodium chloride solution. The layers were separated and the aqueous layer further washed with ethyl acetate. The combined organic layers were then dried (MgSO$_4$), filtered, concentrated in vacuo and the resulting residue purified by flash column chromatography using 30% ethyl acetate/hexane to provide the desired ether 106 (192 mg, 62%).

Amide 106 was reduced as per the procedure for the reduction of 88, see Example 50: 106 (91 mg, 0.202 mmol), Red-Al (0.212 mL, 0.706 mmol), toluene (1 mL). Purification by flash column chromatography using 1% 2M NH$_3$ in EtOH/DCM provided the desired amine 107. LRMS calculated for C$_{24}$H$_{27}$ClF$_3$NO 437.17, found 437.71. $^1$H NMR (300 MHz, CDCl$_3$): δ 7.58 (d, J=8.0 Hz, 2H), 7.36 (d, J=7.9 Hz, 2H), 7.22 (d, J=8.3 Hz, 2H), 7.06 (d, J=7.9 Hz, 2H), 4.36 (s, 2H), 3.2 (m, 1H), 2.66–2.71 (m, 1H), 2.50–2.55 (m, 1H), 2.35–2.37 (m, 2H), 1.97–2.26 (m, 6H), 1.77–1.94 (m, 3H), 1.53–1.58 (m, 1H), 1.29–1.44 (m, 1H), 1.04–1.18 (m, 1H).

Example 73

Synthesis of (R)-3-(Benzo[1,3]dioxol-5-yloxymethyl)-1-[1-(4-chloro-phenyl)-cyclobutylmethyl]-piperidine

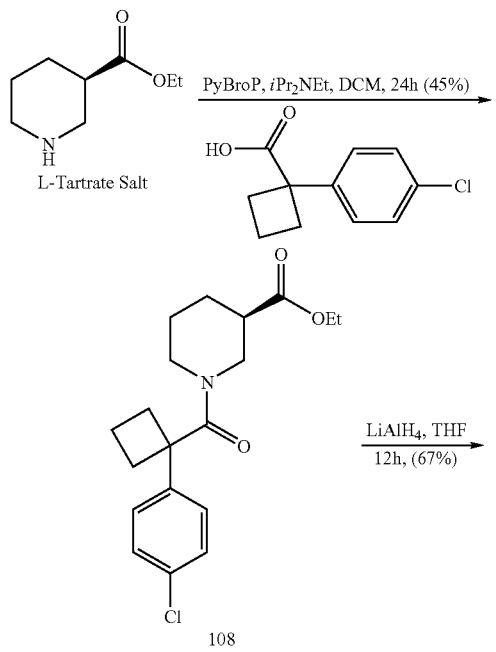

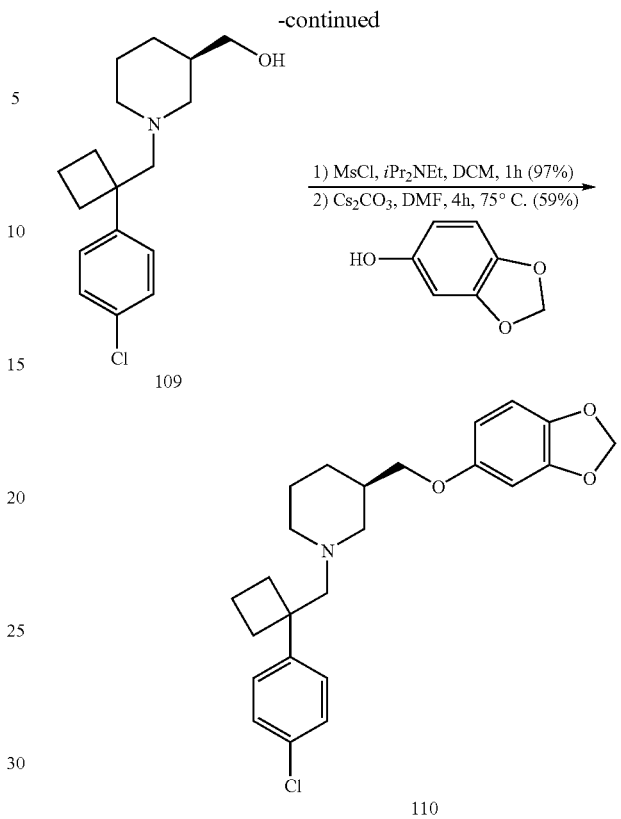

Amide 108 was prepared from commercially-available (R)-ethyl nipecotate L-tartrate and 1-(4-chlorophenyl)-1-cyclobutane carboxylic acid, using the procedure outlined for the synthesis of 1 in Example 1: (R)-ethyl nipecotate L-tartrate (10.0 g, 32.6 mmol), 1-(4-chlorophenyl)-1-cyclobutane carboxylic acid (10.3 g, 48.9 mmol), PyBroP (22.8 g, 48.9 mmol), iPr$_2$NEt (28.0 mL, 163 mmol), DCM (170 mL). Purification by flash column chromatography using 35% ethyl acetate/hexane provided the desired amide 108 (5.1 g, 45%).

To a flask containing LiAlH$_4$ (1.66 g, 43.8 mmol), charged with Argon at 0° C. was added tetrahydrofuran (50 mL). After the addition was complete, the suspension was allowed to warm to room temperature for five minutes before recooling to 0° C. Next, a solution of amide 108 (5.1 g, 14.6 mmol) in tetrahydrofuran (25 mL) was added over five minutes. After continuing at this temperature for fifteen minutes, the reaction was allowed to warm to room temperature and stir overnight before recooling to 0° C. and cautiously quenching by the addition of 1N H$_2$SO$_4$. The aqueous layer was then basified by the addition of saturated aqueous NaHCO$_3$. The resulting mixture was filtered through a pad of celite, washing with ethyl acetate. The layers were separated and the aqueous layer further washed with ethyl acetate. The combined organic layers were dried (MgSO$_4$), filtered, concentrated in vacuo and the resulting residue purified by flash column chromatography using a gradient of 2 to 4% 2M NH$_3$ in EtOH/DCM to provide the desired 109 (2.87 g, 67%). $^1$H NMR (300 MHz, CDCl$_3$): δ 7.26–7.29 (m, 2H), 7.12–7.16 (m, 2H), 3.58–3.64 (m, 1H), 3.47–3.53 (m, 1H), 3.00 (m, 1H), 2.64 (s, 2H), 2.43–2.48 (m, 1H), 2.15–2.32 (m, 7H), 1.99–2.09 (m, 1H), 1.79–1.92 (m, 1H), 1.36–1.69 (m, 4H), 1.16–1.29 (m, 1H). $^{13}$C NMR (75

MHz, CDCl$_3$): δ 147.9, 131.0, 127.9, 127.4, 69.1, 67.6, 59.7, 56.2, 46.7, 37.0, 31.8, 31.5, 27.2, 24.3, 15.9.

Alcohol 109 could be converted to the desired 110 using the procedure outlined for the conversion of 36 to 37 in Example 22 with the substitution of sesamol for α,α,α-trifluoro-p-cresol. Mesylate formation: 109 (2.82 g, 9.61 mmol), iPr$_2$NEt (4.18 mL, 24.0 mmol), MsCl (0.818 mL, 10.6 mmol), DCM (44 mL). After purification by flash column chromatography using 2% 2M NH$_3$ in EtOH/DCM the desired mesylate was provided (3.46 g, 97%). Mesylate displacement: mesylate (3.46 g, 9.31 mmol), Cs$_2$CO$_3$ (7.59 g, 23.4 mmol), sesamol (1.29 g, 9.31 mmol), DMF (50 mL). Purification by flash column chromatography using 1% 2M NH$_3$ in EtOH/DCM followed by a second column using a gradient of 10 to 20% ethyl acetate/hexane provided the desired 110. LRMS calculated for C$_{24}$H$_{28}$ClNO$_3$ 413.18, found (M+) 414.27. $^1$H NMR (300 MHz, CDCl$_3$): δ 7.21 (d, J=8.5 Hz, 2H), 7.07 (d, J=8.4 Hz, 2H), 6.69 (d, J=8.4 Hz, 1H), 6.43 (d, J=2.4 Hz, 1H), 6.23 (dd, J=2.4, 8.4 Hz, 1H), 5.89 (s, 2H), 3.53–3.65 (m, 2H), 2.44–2.57 (m, 3H), 2.16–2.31 (m, 5H), 1.79–2.08 (m, 5H), 1.56–1.62 (m, 1H), 1.42–1.48 (m, 2H), 0.95–1.09 (m, 1H). $^{13}$C NMR (75 MHz, CDCl$_3$): δ 154.6, 148.3, 148.1, 141.3, 130.7, 127.7, 127.5, 107.8, 105.4, 101.0, 97.9, 71.4, 68.7, 58.9, 56.3, 47.0, 36.1, 31.6, 26.7, 24.6, 16.0. ee determination: 96.4%

The HCl salt of 110 could be prepared by dissolving the basic amine in acetonitrile and adding an excess of 2M HCl. The acetonitrile could then be removed in vacuo and the sample frozen and liophilized to provide the desired salt as a white solid. LRMS calculated for C$_{24}$H$_{28}$ClNO$_3$ (free base) 413.18, found 413.88. $^1$H NMR (300 MHz, CDCl$_3$): δ 7.31–7.39 (m, 4H), 6.63 (d, J=8.4 Hz, 1H), 6.31 (d, J=2.0 Hz, 1H), 6.11–6.15 (m, 1H), 5.86 (s, 2H), 3.66 (dd, J=3.8, 9.5 Hz, 1H), 3.48–3.54 (m, 3H), 3.08–3.22 (m, 2H), 2.76–2.91 (m, 1H), 2.20–2.64 (m, 7H), 2.05–2.15 (m, 1H), 1.84–1.94 (m, 1H), 1.63–1.75 (m, 2H), 1.15–1.28 (m, 1H). $^{13}$C NMR (75 MHz, CDCl$_3$): δ 153.7, 148.2, 144.1, 141.9, 132.8, 129.2, 127.8, 107.8, 105.3, 101.1, 97.9, 70.1, 68.0, 57.4, 54.9, 44.2, 33.3, 32.8, 24.6, 21.8, 15.8. [α]=–6.1 (c=0.74, MeOH).

Example 74

Synthesis of (S)-3-(Benzo[1,3]dioxol-5-yloxymethyl)-1-[1-(4-chloro-phenyl)-cyclobutylmethyl]-piperidine

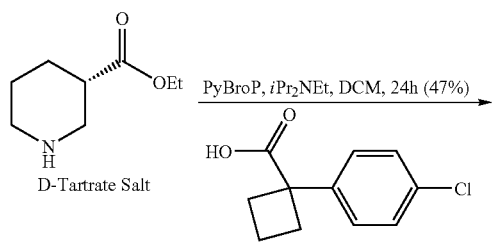

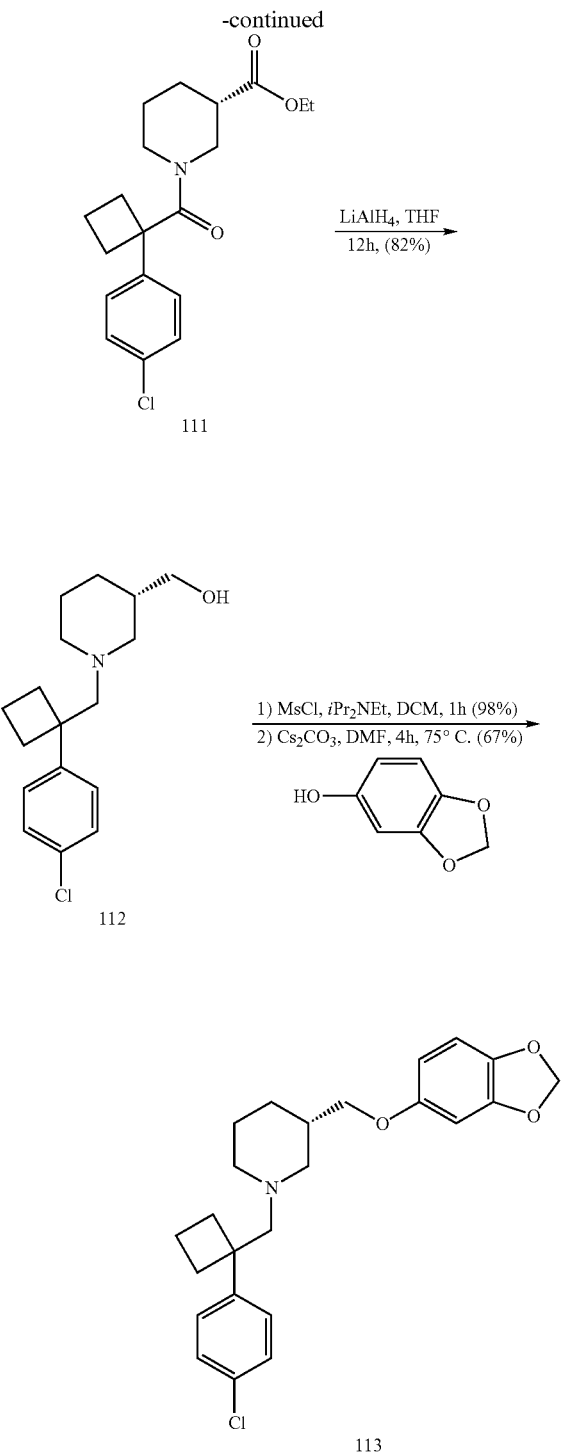

113 was prepared from ethyl (S)-nipecotate D-tartrate and 1-(4-chloro-phenyl)-cyclobutanecarboxylic acid, using the procedure outlined in Example 73 for the synthesis of 110.

Preparation of 111: (S)-ethyl nipecotate L-tartrate (10.3 g, 33.6 mmol), 1-(4-chlorophenyl)-1-cyclobutane carboxylic acid (10.6 g, 50.4 mmol), PyBroP (23.5 g, 50.4 mmol), iPr$_2$NEt (29.3 mL, 168 mmol), DCM (170 mL). Purification by flash column chromatography using 35% ethyl acetate/hexane provided the desired amide 111 (5.5 g, 47%).

Preparation of 112: 111 (5.50 g, 15.8 mmol), LiAlH₄ (1.79 g, 47.3 mmol), THF (75 mL). Purification by flash column chromatography using a gradient of 2 to 4% 2M NH₃ in EtOH/DCM provided the desired 112 (3.79 g, 82%).

Preparation of 113. Mesylate formation: amino alcohol (3.79 g, 12.9 mmol), iPr₂NEt (5.63 mL, 32.3 mmol), MsCl (1.10 mL, 14.2 mmol), DCM (60 mL). After purification by flash column chromatography using 2% 2M NH₃ in EtOH/DCM the desired mesylate was provided (4.73 g, 98%). Mesylate displacement: mesylate (4.73 g, 12.7 mmol), Cs₂CO₃ (10.3 g, 31.8 mmol), sesamol (1.76 g, 12.7 mmol), DMF (65 mL). Purification by flash column chromatography using a gradient of 5 to 10% ethyl acetate/hexane followed by a second column using 1% 2M NH₃ in EtOH/DCM provided the desired 113 (3.52 g, 67%). LRMS calculated for $C_{24}H_{28}ClNO_3$ 413.18, found 413.73. $^1$H NMR (300 MHz, CDCl₃): δ 7.20 (d, J=8.6 Hz, 2H), 7.07 (d, J=8.3 Hz, 2H), 6.69 (d, J=8.5 Hz, 1H), 6.43 (d, J=2.4 Hz, 1H), 6.23 (dd, J=2.4, 8.4 Hz, 1H), 5.89 (s, 2H), 3.54–3.65 (m, 2H), 2.34–2.57 (m, 3H), 2.16–2.31 (m, 5H), 1.74–2.08 (m, 5H), 1.56–1.62 (m, 1H), 1.35–1.51 (m, 2H), 0.97–1.09 (m, 1H). $^{13}$C NMR (75 MHz, CDCl₃): δ 154.6, 148.3, 148.1, 141.3, 130.7, 127.7, 127.5, 107.8, 105.4, 101.0, 97.9, 71.5, 68.7, 58.9, 56.3, 47.0, 36.1, 31.6, 26.7, 24.6, 16.0. ee determination: 98.7%

The HCl salt of 113 could be prepared by dissolving the basic amine in acetonitrile and adding an excess of 2 M HCl. The acetonitrile could then be removed in vacuo and the sample frozen and lyopholized to provide the desired salt as a white solid. LRMS calculated for $C_{24}H_{28}ClNO_3$ (free base) 413.18, found 413.44. $^1$H NMR (300 MHz, CDCl₃): δ 7.32–7.37 (m, 4H), 6.62 (d, J=8.4 Hz, 1H), 6.31 (d, J=2.4 Hz, 1H), 6.11–6.15 (m, 1H), 5.86 (s, 2H), 3.64–3.69 (m, 1H), 3.49–3.54 (m, 3H), 3.10–3.23 (m, 2H), 2.81 (m, 1H), 2.26–2.61 (m, 7H), 2.03–2.14 (m, 1H), 1.83–1.93 (m, 1H), 1.63–1.74 (m, 2H), 1.14–1.27 (m, 1H). $^{13}$C NMR (75 MHz, CDCl₃): δ. 153.7, 148.2, 144.0, 141.9, 132.8, 129.2, 127.8, 107.8, 105.3, 101.1, 97.9, 70.1, 68.0, 57.4, 54.9, 44.2, 33.4, 32.8, 24.6, 21.8, 15.8. [α]=+5.4 (c=0.78, MeOH).

Example 75

Synthesis of (R)-1-[1-(4-chloro-phenyl)-cyclobutylmethyl]-3-(4-trifluoromethyl-phenoxymethyl)-piperidine

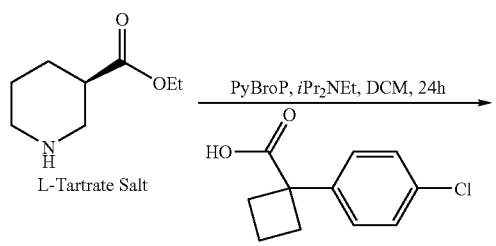

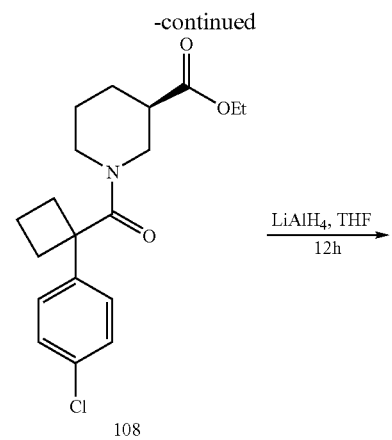

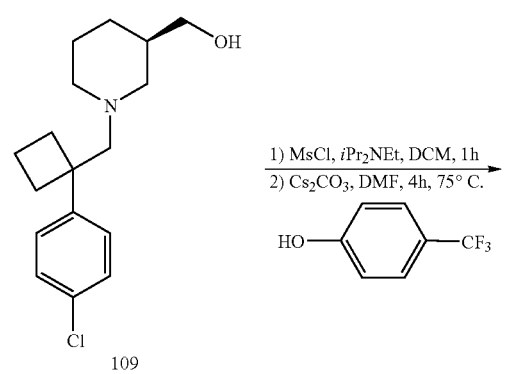

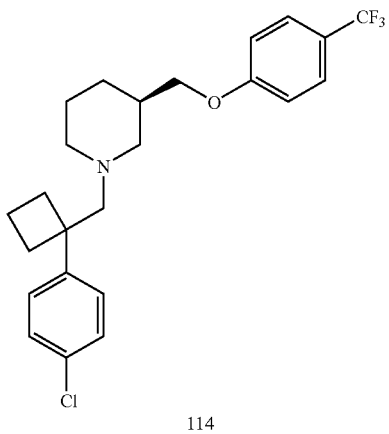

Amide 108 was prepared from commercially-available (R)-ethyl nipecotate L-tartrate and 1-(4-chlorophenyl)-1-cyclobutane carboxylic acid, using the procedure outlined for the synthesis of 1 in Example 1: (R)-ethyl nipecotate L-tartrate (17.0 g, 55 mmol), 1-(4-chlorophenyl)-1-cyclobutan carboxylic acid (17.43 g, 83 mmol), PyBroP (38.51 g, 83 mmol), iPr₂NEt (68 mL), DCM (240 mL). Purification by flash column chromatography using 10% ethyl acetate/hexane provided the desired amide 108 (9.56 g, 44%).

To a flask containing LiAlH₄ (2.75 g, 72.0 mmol), charged with Argon at 0° C. was added tetrahydrofuran (50 mL). After the addition was complete, the suspension was cooled to 0° C. Next, a solution of amide 108 (9.56 g, 24 mmol) in tetrahydrofuran (50 mL) was added dropwise. After completion of addition, the reaction was allowed to warm to room temperature and stir overnight before quenching by the addition of EtOAc and water. The aqueous layer was extracted with EtOAc (3×300 mL). The combined organic layers were dried (MgSO₄), filtered, concentrated in vacuo and the resulting residue purified by flash column chromatography using a gradient of 0 to 4% 2M NH₃ in EtOH/DCM to provide the desired 109 (5.36 g, 76%). ¹H NMR (300 MHz, CDCl₃): δ 7.26–7.29 (m, 2H), 7.12–7.16 (m, 2H), 3.58–3.64 (m, 1H), 3.47–3.53 (m, 1H), 3.00 (m, 1H), 2.64 (s, 2H), 2.43–2.48 (m, 1H), 2.15–2.32 (m, 7H), 1.99–2.09 (m, 1H), 1.79–1.92 (m, 1H), 1.36–1.69 (m, 4H), 1.16–1.29 (m, 1H). ¹³C NMR (75 MHz, CDCl₃): δ 147.9, 131.0, 127.9, 127.4, 69.1, 67.6, 59.7, 56.2, 46.7, 37.0, 31.8, 31.5, 27.2, 24.3, 15.9.

Alcohol 109 could be converted to the desired 114 using the procedure outlined for the conversion of 36 to 37 in Example 22. Mesylate formation: 109 (7.25 g, 25 mmol), iPr₂NEt (10.90 mL, 63.0 mmol), MsCl (2.11 mL, 27 mmol), DCM (100 mL). After purification by flash column chromatography using a gradient of 0 to 4% 2M NH₃ in EtOH/DCM the desired mesylate was provided (8.42 g, 90%). Mesylate displacement: mesylate (8.42 g, 22.60 mmol), Cs₂CO₃ (18.40 g, 56.5 mmol), phenol (4.03 g, 24.9 mmol), DMF (100 mL). Purification by silica gel column chromatography using a gradient of 0 to 5% ethyl acetate/hexane provided the desired 114. The enantiomeric excess could be determined via a chiral AD column (100% MeOH) and was found to be 98%. LRMS: M+438. ¹H NMR (300 MHz, CDCl₃): δ 7.56 (2H, d, J=8.6 Hz), 7.23 (2H, d, J=8.5 Hz), 7.10 (2H, d, J=7.7 Hz), 6.91 (2H, d, J=9.0 Hz), 4.74 (2H, m), 2.68–1.49 (17H, m).

Example 76

Synthesis of (S)-1-[1-(4-chloro-phenyl)-cyclobutyl-methyl]-3-(4-trifluoromethyl-phenoxymethyl)-piperidine

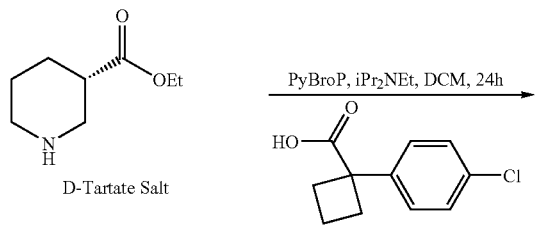

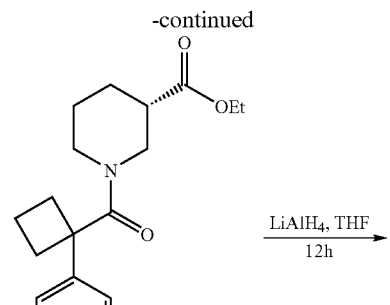

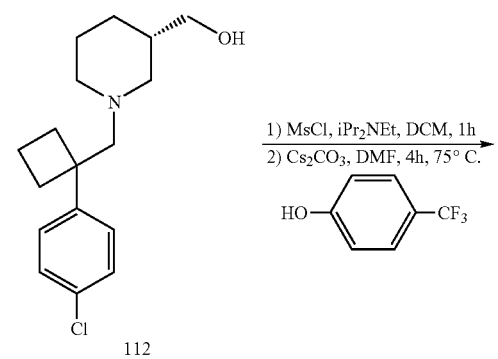

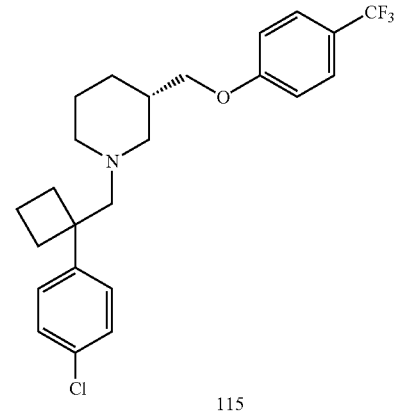

115 was prepared from ethyl (S)-nipecotate D-tartrate and 1-(4-chloro-phenyl)-cyclobutanecarboxylic acid, using the procedure outlined in Example 75 for the synthesis of 114.

Preparation of 111: (S)-ethyl nipecotate L-tartrate (11.96 g, 38.8 mmol), 1-(4-chlorophenyl)-1-cyclobutane carboxylic acid (12.23 g, 58 mmol), PyBroP (27.16 g, 58.0 mmol), iPr₂NEt (34 mL, 194 mmol), DCM (170 mL). Purification by flash column chromatography using 35% ethyl acetate/hexane provided the desired amide 111 (7.73 g, 56%).

Preparation of 112: 111 (7.73 g, 22 mmol), LiAlH₄ (2.51 g, 66 mmol), THF (75 mL). Purification by flash column chromatography using a gradient of 1 to 4% 2M NH₃ in EtOH/DCM provided the desired 112 (4.78 g, 74%).

Preparation of 115. Mesylate formation: amino alcohol (4.78 g, 16 mmol), iPr$_2$NEt (7.10 mL, 40 mmol), MsCl (1.40 mL, 18 mmol), DCM (66 mL). After purification by flash column chromatography using a gradient of 1–4% 2M NH$_3$ in EtOH/DCM the desired mesylate was provided (4.74 g, 80%). Mesylate displacement: mesylate (4.74 g, 13.0 mmol), Cs$_2$CO$_3$ (10.6 g, 33 mmol), phenol (2.27 g, 14 mmol), DMF (60 mL). The compound was purified using silica gel chromatography using a gradient of 0 to 5% ethyl acetate/hexane provided the desired 115. The enantiomeric excess could be determined via a chiral AD column (100% MeOH) and was found to be 94%. LRMS: M+438. $^1$H NMR (300 MHz, CDCl$_3$): δ 7.56 (2H, d, J=8.6 Hz), 7.23 (2H, d, J=8.5 Hz), 7.10 (2H, d, J=7.7 Hz), 6.91 (2H, d, J=9.0 Hz), 4.74 (2H, m), 2.68–1.49 (17H, m). $^{13}$C (partial, 100 MHz, CDCl$_3$): δ 161.2, 144.4, 128.0, 127.8, 17.1, 114.6, 70.9, 69.0, 58.6, 36.2, 32.0, 31.8, 26.9, 24.9, 16.3.

Example 77

Synthesis of 118 and 119

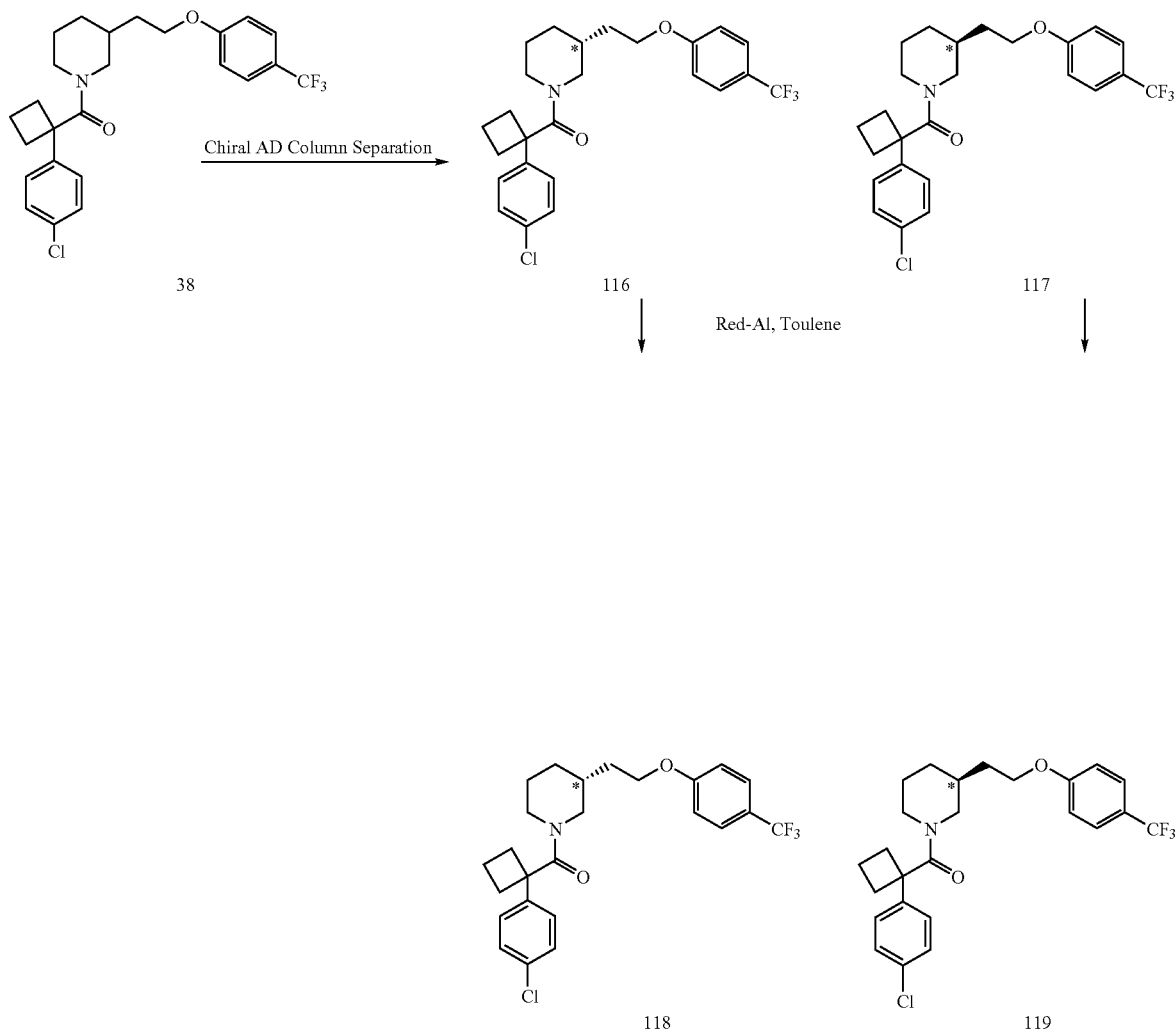

*denotes stereochemistry randomly assigned.

The two enantiomers of amide 38 were separated on a 2 cm AD chiral column using 85% hexane (with 0.2% diethylamine)/15% isopropyl alcohol with a flow rate of 6 mL/min. 116 retention time approx. 31 minutes. LRMS calculated for $C_{25}H_{27}ClF_3NO_2$ 465.17, found 465.55. 117 retention time approx. 41 minutes. LRMS calculated for $C_{25}H_{27}ClF_3NO_2$ 465.17, found 465.68.

116 was reduced as per the procedure outlined for the reduction of amide 38 to amine 39 in Example 22: 116 (39 mg, 0.0839 mmol), Red-Al (0.088 mL, 0.294 mmol), toluene (0.5 mL). Purification by flash column chromatography using 1% 2M $NH_3$ in EtOH/DCM provided 118 (18 mg, 47%). LRMS calculated for $C_{25}H_{29}ClF_3NO$ 451.19, found 451.28.

117 was reduced as per the procedure outlined for the reduction of amide 38 to amine 39 in Example 22: 117 (38 mg, 0.0817 mmol), Red-Al (0.086 mL, 0.286 mmol), toluene (0.5 mL). Purification by flash column chromatography using 1% 2M $NH_3$ in EtOH/DCM provided 119 (15 mg, 41%). LRMS calculated for $C_{25}H_{29}ClF_3NO$ 451.19, found 451.85.

Example 78

Synthesis of (R)-1-[2-(4-Chloro-phenyl)-2-methyl-propyl]-3-(4-trifluoromethyl-phenoxymethyl)-piperidine)

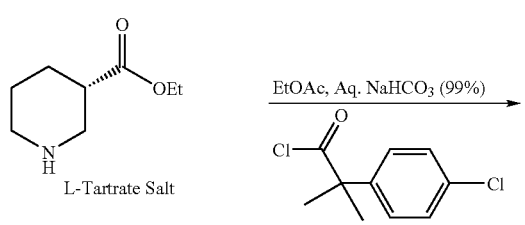

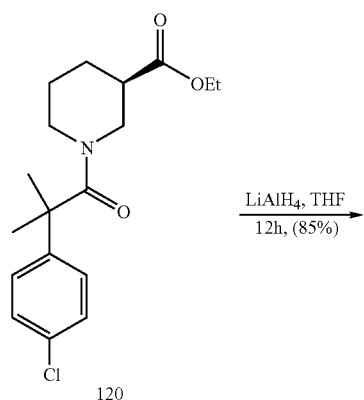

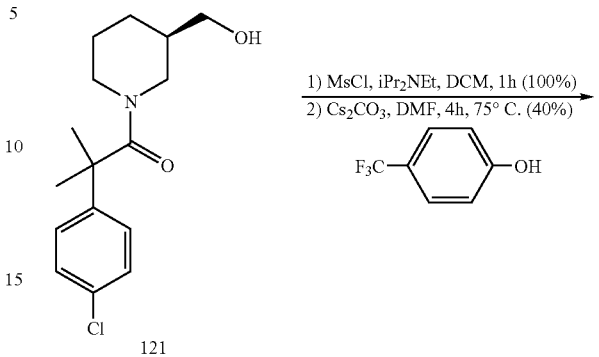

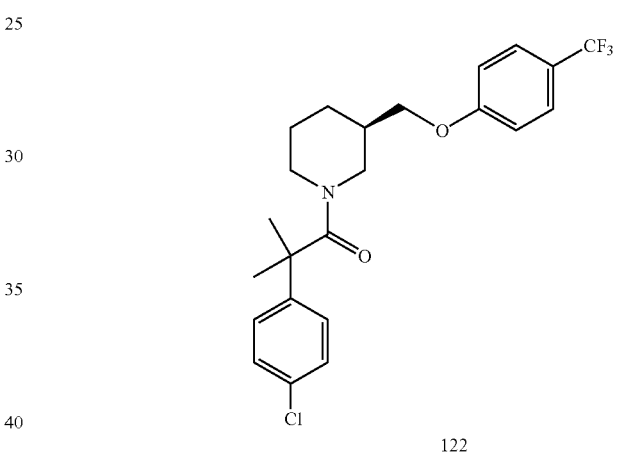

2-(4-chlorophenyl)-2-methyl propionyl chloride was prepared as follows: To a flask containing 2-(4-chlorophenyl)-2-methyl propionic acid (15.0 g, 75.6 mmol) was added thionyl chloride (approx. 6 mL). Dichloromethane (20 mL) was then added before adding an additional portion of thionyl chloride (approx. 12 mL). The reaction was allowed to heat to 40° C. for two hours before cooling to room temperature and concentrating in vacuo (azeotroping with tetrahydrofuran). The resulting acid chloride was used in the following acylation step without further purification or characterization.

To a solution of (R)-ethyl nipecotate L-tartrate (5.8 g, 18.9 mmol) in saturated aqueous $NaHCO_3$ (50 mL) was added a solution of 2-(4-chlorophenyl)-2-methyl propionyl chloride (assume 100% yield from above preparation, 75.6 mmol) in ethyl acetate (50 mL). The reaction was allowed to stir at room temperature for two hours before further diluting with ethyl acetate and saturated aqueous $NaHCO_3$. The layers were separated and the aqueous layer further washed with ethyl acetate. The combined organic extracts were dried ($MgSO_4$), filtered, concentrated in vacuo and the resulting residue purified by flash column chromatography using a gradient of 20 to 35% ethyl acetatehexane to provide the desired amide 120 (6.3 g, 99%).

The reduction of 120 to 121 could be accomplished as per the procedure for the reduction of 108 to 109 outlined in Example 75 above: 120 (6.30 g, 18.7 mmol), LiAlH$_4$ (2.13 g, 56.1 mmol), THF (85 mL). Purification by flash column chromatography using a gradient of 2 to 4% 2M NH$_3$ in EtOH/DCM provided the desired amide 121 (1.74 g, 82%). LRMS calculated for C$_{16}$H$_{24}$ClNO 281.15, found 281.96. $^1$H NMR (300 MHz, CDCl$_3$): δ 7.32 (m, 4H), 3.49–3.64 (m, 2H), 2.74 (m, 1H), 2.48–2.53 (m, 1H), 2.43 (s, 2H), 2.14–2.31 (m, 3H), 1.65–1.73 (m, 2H), 1.53–1.64 (m, 1H), 1.41–1.50 (m, 1H), 1.35 (s, 3H), 1.34 (s, 3H), 1.21 (m, 1H). $^{13}$C NMR (75 MHz, CDCl$_3$): δ 147.0, 131.0, 127.8, 127.6, 71.3, 67.3, 59.8, 56.6, 39.1, 37.5, 27.0, 26.8, 26.6, 24.6.

Alcohol 121 could be converted to the desired 122 using the procedure outlined for the conversion of 36 to 37 in Example 22. Mesylate formation: 121 (4.48 g, 15.9 mmol), iPr$_2$NEt (6.94 mL, 39.8 mmol), MsCl (1.36 mL, 17.5 mmol), DCM (71 mL). After purification by flash column chromatography using 2% 2M NH$_3$ in EtOH/DCM the desired mesylate was provided (5.71 g, 100%). Mesylate displacement: mesylate (5.71 g, 15.9 mmol), Cs$_2$CO$_3$ (12.9 g, 39.6 mmol), α,α,α-trifluoro-p-cresol (2.57 g, 15.9 mmol), DMF (81 mL). Purification by flash column chromatography using a gradient of 0.5 to 1% 2M NH$_3$ in EtOH/DCM provided the desired 122 (2.67 g, 40%). LRMS calculated for C$_{23}$H$_{27}$ClF$_3$NO 425.17, found (M+) 426.26. $^1$H NMR (300 MHz, CDCl$_3$): δ 7.56 (d, J=8.7 Hz, 2H), 7.35 (d, J=8.7 Hz, 2H), 7.26 (d, J=8.7 Hz, 2H), 6.92 (d, J=8.7 Hz, 2H), 3.71–3.83 (m, 2H), 2.50–2.55 (m, 1H), 2.35–2.45 (m, 3H), 2.13–2.20 (m, 1H), 2.00–2.02 (m, 2H), 1.45–1.70 (m, 3H), 1.31 (s, 6H), 1.05–1.15 (m, 1H). $^{13}$C NMR (75 MHz, CDCl$_3$): δ 161.5, 147.3, 131.2, 127.7, 126.8, 126.7, 126.3, 122.5 (m), 114.3, 71.0, 70.6, 59.0, 56.6, 39.3, 36.1, 26.6, 26.5, 24.7.

Example 79

Synthesis of [2-{3-[1-(4-Chloro-phenyl)-cyclobutyl-methyl]-cyclohexyl}-2-(4-trifluoromethyl-phenoxy)-ethyl]-piperdine

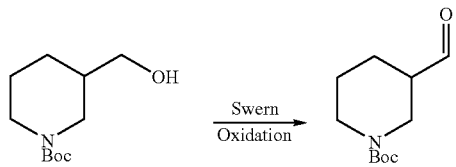

Oxalyl chloride (18.5 mL) in 250 mL of CH$_2$Cl$_2$ was cooled down to −78° C., and DMSO (22.7 mL) was added slowly. The reaction mixture was stirred for 10 minutes. The primary alcohol (30.0 g) in 300 mL of CH$_2$Cl$_2$ was added dropwise to the cooled stirring reaction mixture. After completion of addition the reaction mixture was stirred for an additional 15 minutes. At last, triethylamine (66.0 mL) was added slowly. The reaction mixture was warmed to r.t. and stirred for 2 hours. The reaction mixture was washed with 500 mL of brine, 1.0 M NaHSO$_4$ (2×100 mL), dried over anhydrous Na$_2$SO$_4$, and filtered. After removal of the solvent, the aldehyde was purified by a flash column chromatography (silica gel, Hexane/EtOAc, 8:2, yield, 95%).

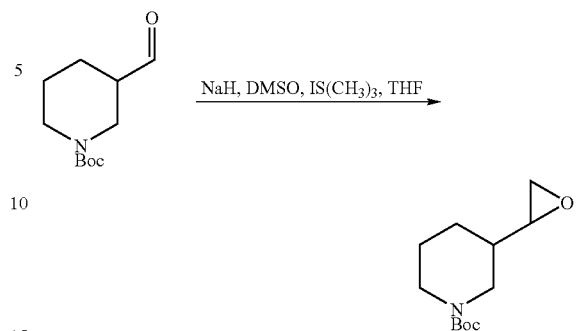

Sodium hydride (4.12 g, 60% in mineral oil) in 100 mL of DMSO was heated at 55° C. for 90 minutes and then cooled down to 0° C. A solution of trimethylsulfonium iodide (21.62 g) in 100 mL of THF was added dropwise and the resulting mixture was stirred for additional 15 minutes. The aldehyde (10.0 g) in 100 mL of DMSO was then added. The reaction mixture was stirred first at 0° C. for 15 minutes then at r.t. for 90 minutes. The mixture was quenched with 50 mL of water and extracted with hexane (3×100 mL). The combined organic layer was washed with brine, dried over anhydrous Na$_2$SO$_4$, filtered, and concentrated. The epoxide was used in the next step without purification (yield: 94%).

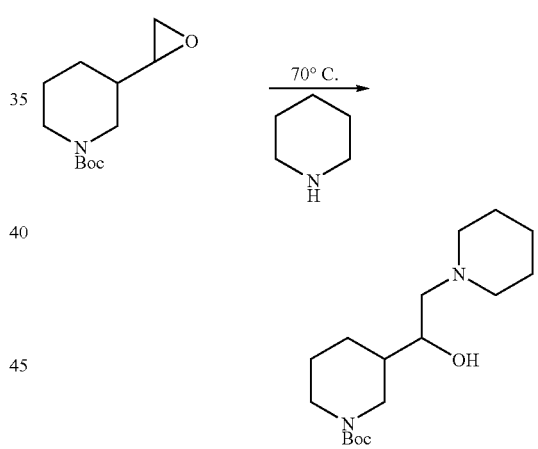

The epoxide (1.0 g) was dissolved in 50 mL of piperidine in a sealed tube. The reaction mixture was heated at 70° C. overnight. Removal of excess piperidine gave the secondary alcohol (1.37 g). LRMS 312. The crude product was taken to the next step without further purification.

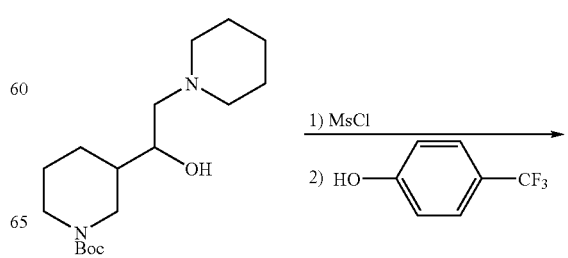

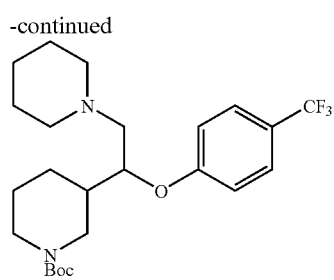

To the secondary alcohol (1.37 g) in 10 mL of CH$_2$Cl$_2$ was added 1.86 mL of N,N-Diisopropylethylamine (2 eq.). The mixture was cooled down to 0° C., then methanesulfonyl chloride (0.619 mL, 1.5 eq.) was added. The reaction mixture was stirred at r.t. for 2 hours and the solvent was removed. The crude residual was dissolved in 20 mL of CH$_3$CN and 3.66 g of potassuim carbonate (5 eq.) and 1.72 g of α,α,α,trifluoro-p-cresol (2 eq.) were added. The mixture was heated at 60° C. overnight. The reaction mixture was quenched with 10% NaOH (5 mL) and extracted with EtOAc (3×10 mL). The combined organic layer was washed with brine and dried over Na$_2$SO$_4$. After filtration and removal of the solvent, the flash column chromatography (silica gel, Hexane/EtOAc, 4:1) gave the phenyl ether as a colorless oil (400 mg, LRMS 456,).

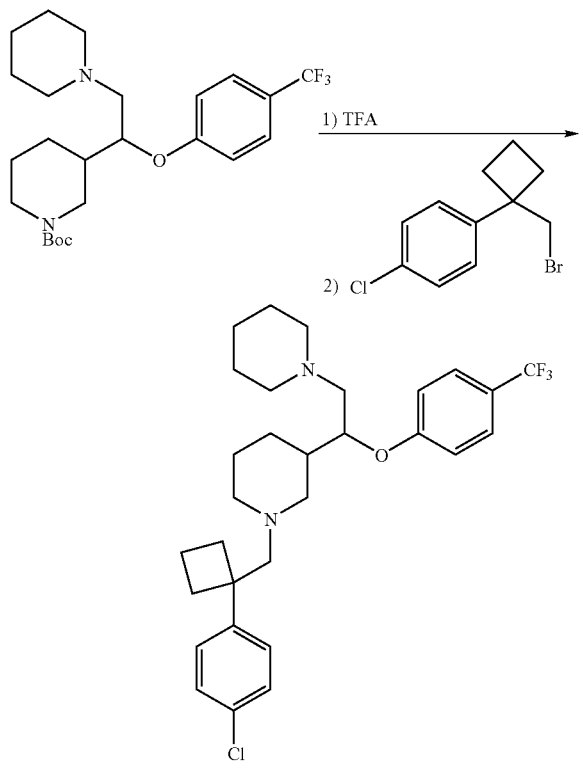

172

To the phenyl ether (400 mg) in 1 mL of CH$_2$CL$_2$, 1.5 mL of Trifluoroacetic acid was added at 0° C. The mixture was stirred at r.t. for 1 hour. The solvent was removed. 5 mL of 10% NaOH was added and aqueous solution was extracted with EtOAc (3×10 mL). The organic layer was washed with brine and dried over Na$_2$SO$_4$. After removal of the solvent, the residual was used in the next step. The crude product obtained from previous step (313 mg), potassium carbonate (608 mg, 5 eq.) and 1-(1-Bromomethyl-cyclobutyl)-4-chloro-benzene (685 mg, 3 eq.), were dissolved in 2.0 mL of CH$_3$CN. The reaction mixture was stirred at 70° C. overnight. The reaction mixture was quenched with 10% NaOH (5 mL) and extracted with EtOAc (3×10 mL). The combined organic layer was washed with brine and dried over Na$_2$SO$_4$. After filtration and removal of the solvent, the preparative TLC (silica gel, hexane/EtOAc 7:3) gave 1-[2-{3-1-[(4-Chloro-phenyl)-cyclobutylmethyl]-cyclohexyl}-2-4-trifluoromethyl-phenoxy)-ethyl]-piperidine as a colorless oil (LRMS 535).

Example 80

Synthesis of (S)-piperidine-1,3-dicarboxylic acid 1 Benzyl Ester 3-ethyl ester

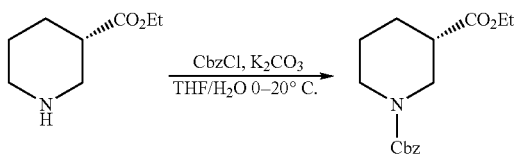

A 250 mL round-bottom flask was charged with K$_2$CO$_3$ (13.5 g, 97.6 mmol), piperidine (10 g, 32.5 mmol), and a 1:1 mixture of THF/H$_2$O (100 mL). A 50 mL addition funnel was placed on the flask and charged with CbzCl (6.67 g, 39.0 mmol). The flask was cooled to 0° C. and then CbzCl was added dropwise over 5 minutes. The reaction mixture was warmed to 20° C. and stirred for 12 h. The reaction mixture was extracted with EtOAc (250 mL) and the organic layer was washed with saturated NaCl (250 mL), dried (MgSO$_4$), filtered and concentrated in vacuo. The crude material (9.5 g, 100% yield) was carried on without further purification.

Example 81

Synthesis of S-3-Methanesulfonyloxymethyl-piperidine-1-carboxylic acid benzyl ester

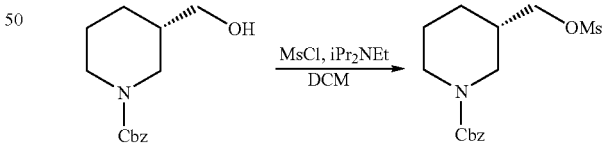

A 250 mL round-bottom flask was charged with alcohol (4.17 g, 16.7 mmol), DCM (100 mL) and diisopropylethylamine (7.3 mL, 42 mmol). The flask was cooled to 0° C. and methanesulfonyl chloride (1.55 mL, 20 mmol) was added dropwise. The reaction was warmed to 20° C. and stirred for 12 h. The reaction mixture was diluted with DCM (150 mL). The organic layer was washed with 5% HCl (250 mL), saturated NaCl (250 mL), dried (MgSO$_4$), filtered and concentrated in vacuo. The crude material was purified by flash chromatography (silica gel, hexanes/EtOAc 2:1) to give pure product (5.46 g, 100% yield).

Example 82

Synthesis of S-3-(4-Trifluoromethyl-phenoxymethyl)-piperidine-1-carboxylic acid benzyl ester

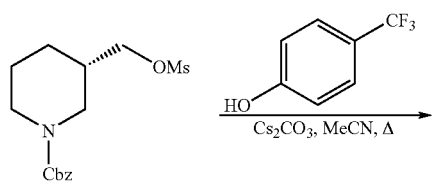

A 250 mL round-bottom flask was charged with mesylate (4.17 g, 12.7 mmol), α,α,α-trifluoromethyl-p-cresol (2.27 g, 14.0 mmol), MeCN (100 mL) and Cs₂CO₃ (10.4 g, 31.8 mmol). The reaction mixture was heated to reflux for 12 h. The reaction mixture was cooled and diluted with EtOAc (250 mL). The organic layer was washed with H₂O (250 mL), saturated NaCl (250 mL), dried (Na₂SO₄), filtered and concentrated in vacuo. The crude material was purified by flash chromatography (silica gel, hexanes/EtOAc 3:1) to give pure product (3.97 g, 79% yield).

Example 83

Synthesis of S-3-(4-Trifluoromethyl-phenoxymethyl)-piperidine

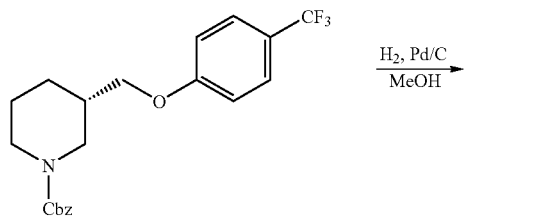

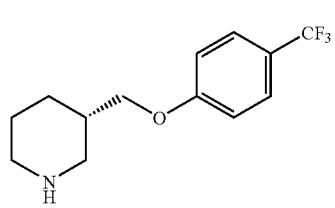

A 100 mL round-bottom flask was charged with Cbz-protected amine (4.0 g, 10 mmol) and methanol (20 mL). The flask was blanketed under argon and 10% w/w palladium on carbon (1.08 g, 1 mmol) was added. The flask was placed under hydrogen gas (1 atmosphere) and stirred for 3 h. The reaction mixture was filtered through celite and concentrated in vacuo to give crude product (2.91 g, 79% yield) that was used without purification.

Example 84

Synthesis of S-1-[1-(4-Chloro-phenyl)-cyclobutyl]-2-[3-(4-trifluoromethyl-phenoxymethyl)-piperidin-1-yl]-ethanone

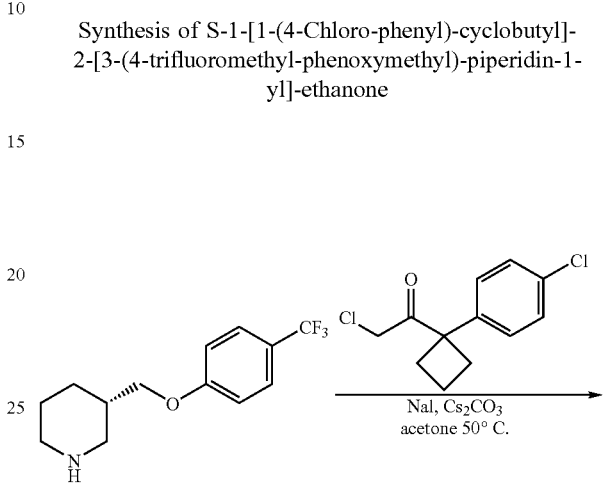

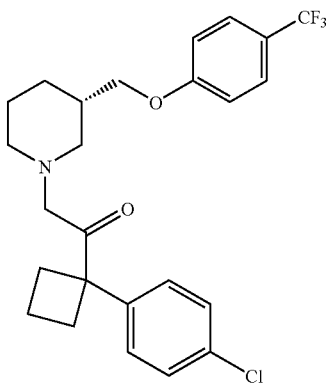

123

A 50 mL pear-bottom flask was charged with α-chloroketone (700 mg, 2.9 mmol), acetone (10 mL) and sodium iodide (432 mg, 2.9 mmol). The reaction mixture was heated to reflux for 10 minutes and then a solution of amine (622 mg, 2.4 mmol) in acetone (15 mL) was added followed by Cs₂CO₃ (1.6 g, 4.8 mmol). The reaction mixture was heated to reflux for 6 h and then diluted with EtOAc (50 mL). The organic layer was washed with saturated NaCl (50 mL), dried (Na₂SO₄), filtered and concentrated in vacuo. The crude material was purified by flash chromatography (silica gel, hexanes/EtOAc 85:15 w/5% 2.0 M NH₃ in EtOH) to give 123 (622 mg, 56% yield).

Example 85

Synthesis of 1R-1-[1-(4-Chloro-phenyl)-cyclobutyl]-2-[(3S)-3-(4-trifluoromethyl-phenoxymethyl)-piperidin-1-yl]-ethanol and 1S-1-[1-(4-Chloro-phenyl)-cyclobutyl]-2-[(3S)-3-(4-trifluoromethyl-phenoxymethyl)-piperidin-1-yl]-ethanol

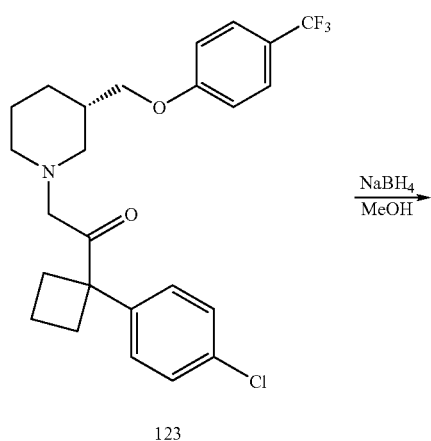

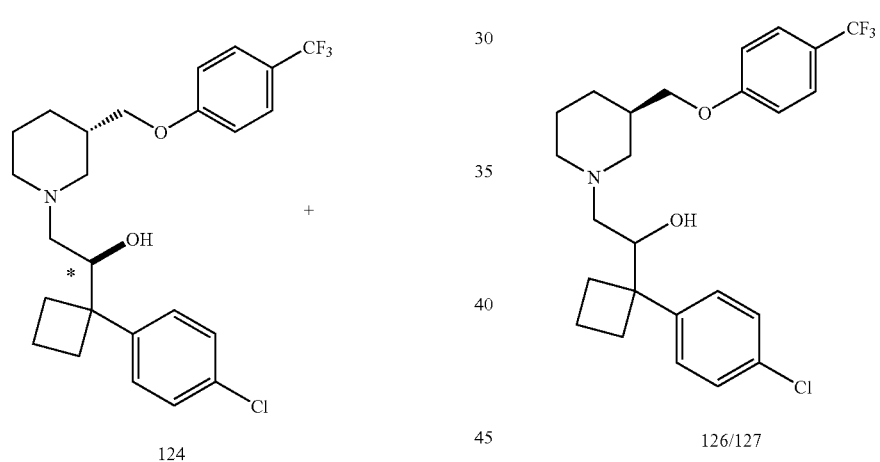

*denotes stereochemistry randomly assigned

A 100 mL round-bottom flask was charged with 123 (622 mg, 1.33 mmol), methanol (10 mL) and sodium borohydride (56 mg, 1.47 mmol). The reaction mixture was stirred for 2 h and then quenched with $H_2O$ (10 mL) and extracted with EtOAc (50 mL). The organic layer was washed with 5% HCl (50 mL), saturated NaCl (50 mL), dried ($Na_2SO_4$), filtered and concentrated in vacuo. The curde material was purified by flash chromatography (hexanes/EtOAc 1:1 w/5% 2.0 M $NH_3$ in EtOH) to give the alcohol as a ~1:1 mixture of diastereomers (534 mg). The diastereomers were separated by first recrystalization from hot methanol to give 124 (140 mg) followed by preparatory HPLC (chiral AD column, hexanes/ethanol/diethylamine 95:5:0.1) to give additional 124 (70 mg, RT=33 min) and 125 (212 mg, RT=39 min).

Example 86

Synthesis of 1R-1-[1-(4-Chloro-phenyl)-cyclobutyl]-2-[(3R)-3-(4-trifluoromethyl-phenoxymethyl)-piperidin-1-yl]-ethanol and 1S-1-[1-(4-Chloro-phenyl)-cyclobutyl]-2-[(3R)-3-(4-trifluoromethyl-phenoxymethyl-piperidin-1-yl]-ethanol Synthesis of S-1-[1-(4-Chloro-phenyl)-cyclobutyl]-2-[3-(4-trifluoromethyl-phenoxymethyl)-piperidin-1-yl]-ethanone

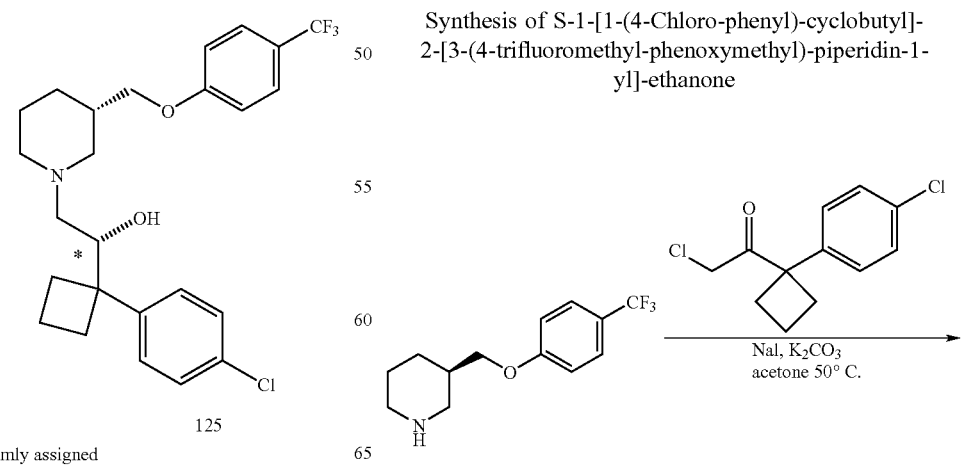

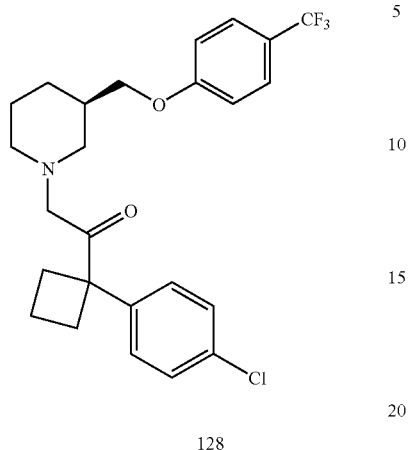

128

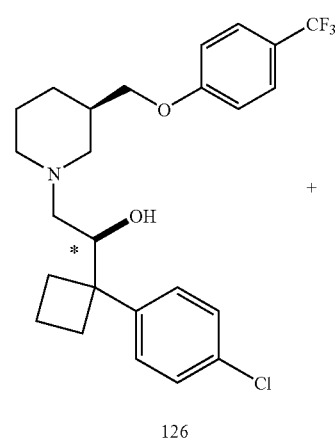

126

A solution of amine 74 (7.6 g) and potassium carbonate (8.40 g) in acetone (50 mL) was stirred at RT for 30 min. The α-chloroketone (5 g) dissolved in acetone (50 mL) was stirred at RT in a separate reaction vessel. After 5 min. of stirring, the α-chloroketone solution was added to the reaction mixture containing the amine and potassium carbonate. After completion of addition the reaction mixture was heated to 50 C. After 18 h the reaction mixture was poured into water (400 mL) and the aqueous layer was extracted with EtOAc. Combined organics were dried ($Na_2SO_4$), filtered and concentrated in vacuo. The crude material was purified by flash chromatography (silica gel, hexanes/EtOAc 80:16 w/4% 2.0 M $NH_3$ in EtOH) to give 128 (8 g).

Synthesis of 1R-1-[1-(4-Chloro-phenyl)-cyclobutyl]-2-[(3R)-3-(4-trifluoromethyl-phenoxymethyl)-piperidin-1-yl]-ethanol and 1S-1-[1-(4-Chloro-phenyl)-cyclobutyl]-2-[(3R)-3-(4-trifluoromethyl-phenoxymethyl)-piperidin-1-yl]-ethanol

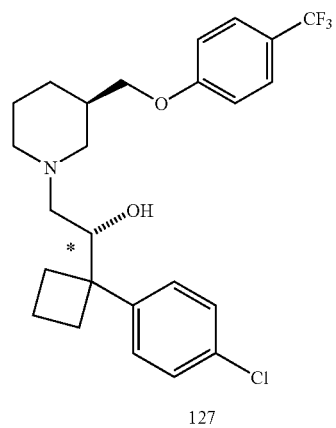

127

*denotes stereochemistry randomly assigned

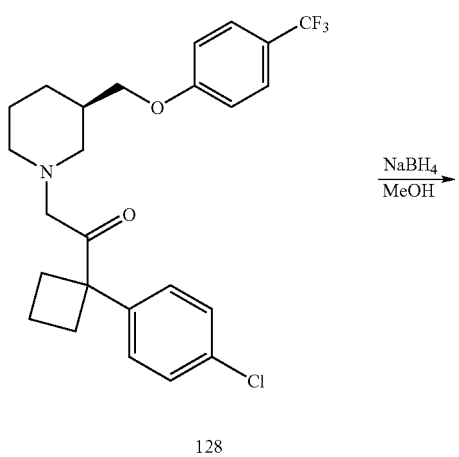

128

A 100 mL round-bottom flask was charged with 128 (4.65 g, 9.98 mmol), methanol (69 mL) and sodium borohydride (566 mg, 14.98 mmol). Progress of the reaction was monitored by TLC. Upon completion, the reaction mixture was concentrated to yield a yellow residue. This residue was taken up in EtOAc and then diluted with water. The aqueous layer was extracted with EtOAc (3×50 mL). The combined organic layers were dried ($Na_2SO_4$), filtered and concentrated in vacuo. The crude material was purified by flash chromatography (80:16:4 hexane:EtOAc:2.0 M $NH_3$ in EtOH) to give the alcohol as a ~1:1 mixture of diastereomers (2.5 g). The diastereomers were separated by first recrystalization from methanol to give isomer 126 followed by preparatory HPLC (chiral AD collumn, hexanes/ethanol/diethylamine 95:5:0.1) to give additional pure isomer 126 (RT=28 min) and pure isomer 127 (RT=45 min).

Example 87

Synthesis of S-1-[1-(4-Chloro-phenyl)-cyclobutan-ecarbonyl]-piperidine-3-carboxylic acid ethyl ester

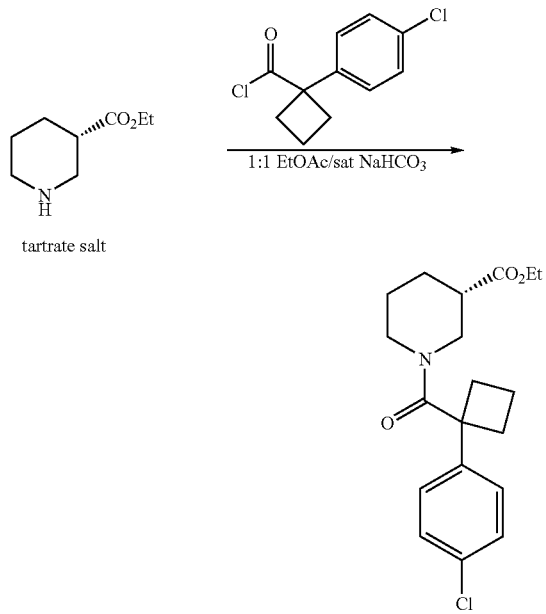

The acid chloride was prepared from the corresponding acid (8.5 g, 40/7 mmol) by treatment with oxalyl chloride (35.5 mL, 407 mmol) and DMF (1 drop) in a 50 mL round-bottom flask at 20° C. for 3 h. The acid chloride was concentrated in vacuo and used immediately. A 250 mL round-bottom flask was charged with amine tartrate (2.5 g, 8.16 mmol), EtOAc (50 mL) and saturated NaHCO$_3$ (50 mL). Acid chloride (40.7 mmol) was added while stirring vigorously. The reaction was stirred for 1 h and then the organic layer was separated, dried (Na$_2$SO$_4$), filtered and concentrated in vacuo. The crude material was purified by flash chromatography (silica gel, hexanes/EtOAc 3:1) to give pure product (2.35 g, 82% yield).

Example 88

Synthesis of S-{1-[1-(4-Chloro-phenyl)-cyclobutyl-methyl]-piperidin-3-yl}-methanol

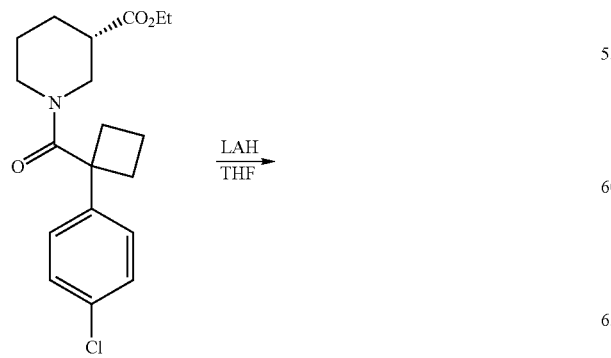

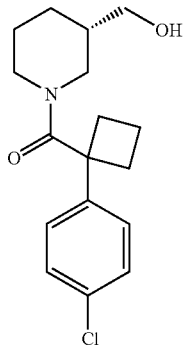

A 100 mL round-bottom flask was charged with ester (2.35 g, 6.7 mmol) and THF (30 mL). The reaction flask was cooled to 0° C. and a 1.0 M solution of LAH in THF (20.2 mL, 20.2 mmol) was added dropwise. The reaction mixture was allowed to warm to 20° C. and stirred for 12 h. The reaction mixture was quenched slowly with 10% HCl (1 mL). The pH was adjusted to 8 with 10% NaOH and extracted with EtOAc (2×50 mL). The organic layer was washed with saturated NaCl (50 mL), dried (Na$_2$SO$_4$), filtered and concentrated in vacuo. The crude material was purified by flash chromatography (silica gel, DCM w/5% 2.0 M NH$_3$ in EtOH) to give pure product (1.9 g, 88% yield).

Example 89

Synthesis of S-1-[1-(4-Chloro-phenyl)-cyclobutylm-ethyl]-3-(4-trifluoromethyl-benzyloxymethyl)-piperidine

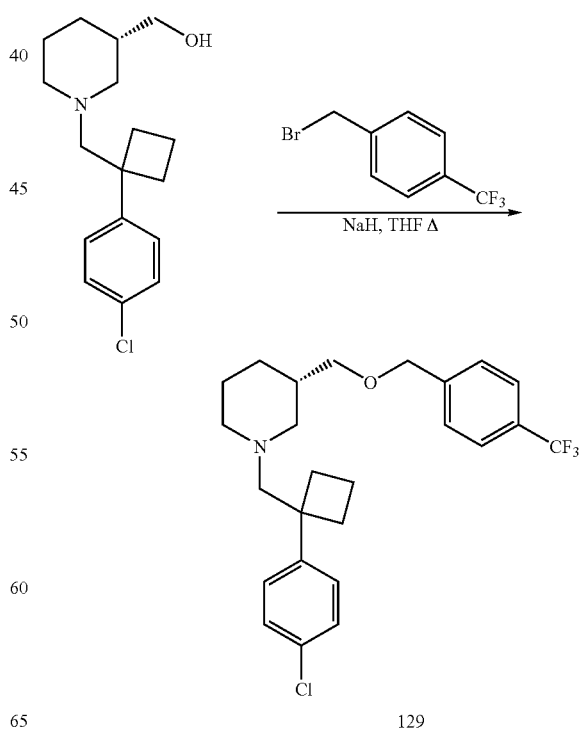

A 100 mL round-bottom flask was charged with NaH (237 mg, 7.76 mmol) and THF (25 mL). The reaction flask was cooled to 0° C. and alcohol was added (1.9 g, 6.5 mmol). The reaction mixture was stirred for 15 minutes and then benzylbromide (1.86 g, 7.76 mmol) was added. The reaction was heated to 60° C. and stirred for 12 h. The reaction mixture was cooled to 20° C., quenched with water (25 mL) and extracted with EtOAc (50 mL). The organic layer was washed with saturated NaCl (50 mL), dried (Na$_2$SO$_4$), filtered and concentrated in vacuo. The crude material was purified by flash chromatography (silica gel, hexanes/EtOAc 3:1) to give 129 (2.3 g, 78% yield). $^1$H-NMR (CDCl$_3$) (300 MHz) δ 7.65 (d, 2H), 7.42 (d, 2H), 7.24 (d, 2H), 7.15 (d, 2H), 5.51 (s, 2H), 3.24 (m, 2H), 2.63 (s, 2H), 2.50 (d, 1H), 2.40–2.18 (m, 5H), 2.07 (m, 2H), 1.96 (m, 3H), 1.58 (m, 1H), 1.43 (m, 2H), 0.98 (m, 1H). $^{13}$C-NMR (CDCl$_3$) (300 MHz) δ 148.7, 143.2, 131.0, 127.9, 127.8, 127.6, 125.6, 125.5, 74.1, 72.3, 69.0, 59.6, 56.5, 47.4, 36.9, 31.8, 27.3, 25.1, 16.3. MS (APCI) m/z 451.8 [MH]$^+$.

Example 90

Synthesis of R-1-[1-(4-Chloro-phenyl)-cyclobutylmethyl]-3-(4-trifluoromethyl-benzyloxymethyl)-piperidine

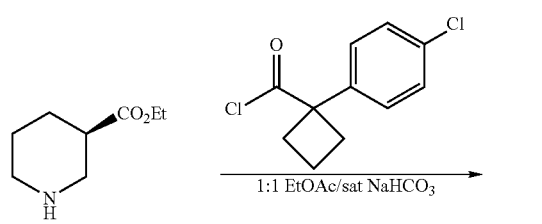

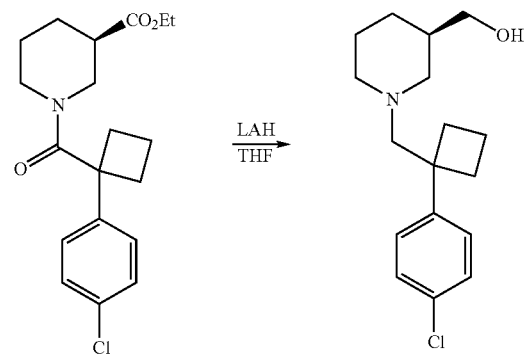

R-1-[1-(4-Chloro-phenyl)-cyclobutanecarbonyl]-piperidine-3-carboxylic acid ethyl ester A 250 mL round-bottom flask was charged with amine tartrate (3.44 g, 11.2 mmol), EtOAc (50 mL) and saturated NaHCO$_3$ (50 mL). Acid chloride (56.0 mmol) was added while stirring vigorously. The reaction was stirred for 1 h and then the organic layer was separated, dried (Na$_2$SO$_4$), filtered and concentrated in vacuo. The crude material was purified by flash chromatography (silica gel, hexanes/EtOAc 3:1) to give pure product (3.8 g, 97% yield)

R-{1-[1-(4-Chloro-phenyl)-cyclobutylmethyl]-piperidin-3-yl}-methanol

A 100 mL round-bottom flask was charged with ester (3.80 g, 10.9 mmol) and THF (25 mL). The reaction flask was cooled to 0° C. and a 1.0 M solution of LAH in THF (32.6 mL, 32.6 mmol) was added dropwise. The reaction mixture was allowed to warm to 20° C. and stirred for 12 h. The reaction mixture was quenched slowly with 10% HCl (1 mL). The pH was adjusted to 8 with 10% NaOH and extracted with EtOAc (2×50 mL). The organic layer was washed with saturated NaCl (50 mL), dried (Na$_2$SO$_4$), filtered and concentrated in vacuo. The crude material was purified by flash chromatography (silica gel, DCM w/5% 2.0 M NH$_3$ in EtOH) to give pure product (2.8 g, 88% yield).

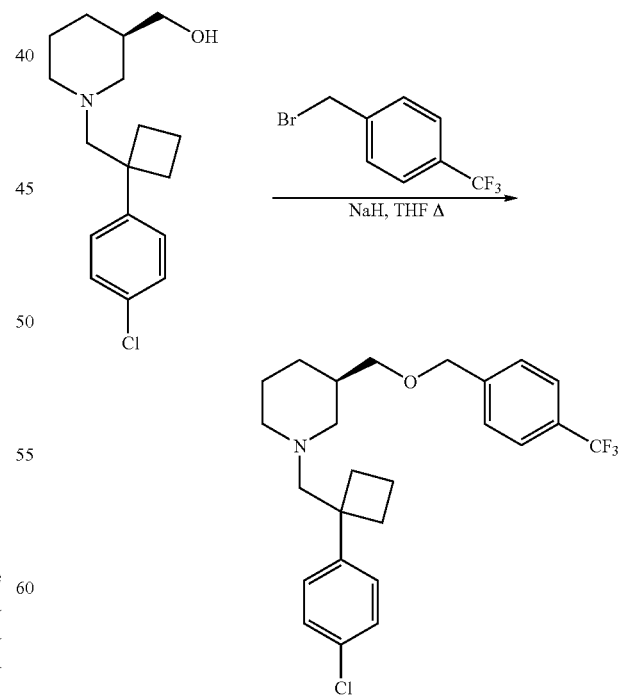

130

R-1-[1-(4-Chloro-phenyl)-cyclobutylmethyl]-3-(4-trifluoromethyl-benzyloxymethyl)-piperidine A 100 mL round-bottom flask was charged with NaH (348 mg, 11.4 mmol) and THF (35 mL). The reaction flask was cooled to 0° C. and alcohol (2.8 g, 9.5 mmol) was added. The reaction mixture was stirred for 15 minutes and then benzylbromide (2.73 g, 11.4 mmol) was added. The reaction was heated to 60° C. and stirred for 12 h. The reaction mixture was cooled to 20° C., quenched with water (25 mL) and extracted with EtOAc (50 mL). The organic layer was washed with saturated NaCl (50 mL), dried (Na$_2$SO$_4$), filtered and concentrated in vacuo. The crude material was purified by flash chromatography (silica gel, hexanes/EtOAc 3:1) to give 130 (3.1 g, 73% yield). $^1$H-NMR (CDCl$_3$) (300 MHz) δ 7.65 (d, 2H), 7.42 (d, 2H), 7.24 (d, 2H), 7.15 (d, 2H), 5.51 (s, 2H), 3.24 (m, 2H), 2.63 (s, 2H), 2.50 (d, 1H), 2.40–2.18 (m, 5H), 2.07 (m, 2H), 1.96 (m, 3H), 1.58 (m, 1H), 1.43 (m, 2H), 0.98 (m, 1H). $^{13}$C-NMR (CDCl$_3$) (300 MHz) δ 148.7, 143.2, 131.0, 127.9, 127.8, 127.6, 125.6, 125.5, 74.1, 72.3, 69.0, 59.6, 56.5, 47.4, 36.9, 31.8, 27.3, 25.1, 16.3. MS (APCI) m/z 451.8 [MH]$^+$.

Example 91

Synthesis of cis-1-[1-(4-Chloro-phenyl)-cyclobutyl-methyl]-3-(4-trifluoromethyl-phenoxymethyl)-piperidin-2-yl]-methanol, as a racemate and as single enantiomers (absolute stereochemistry randomly assigned to all single enantiomers)

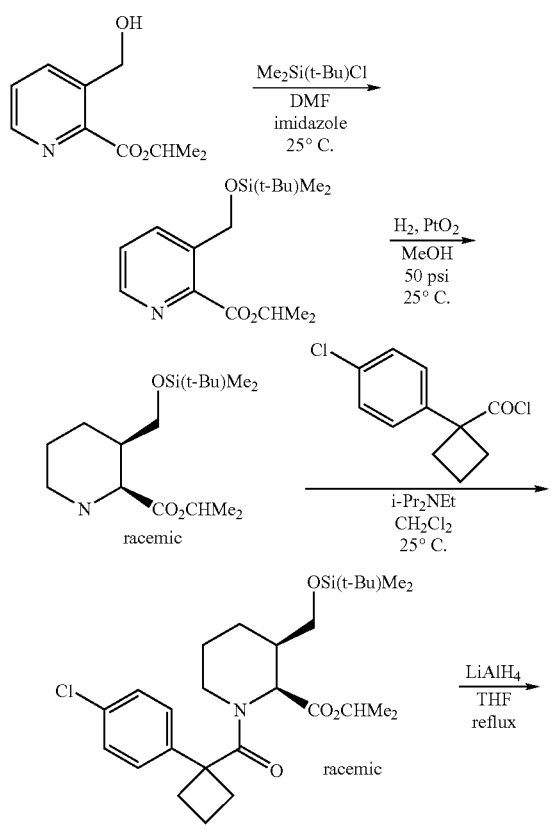

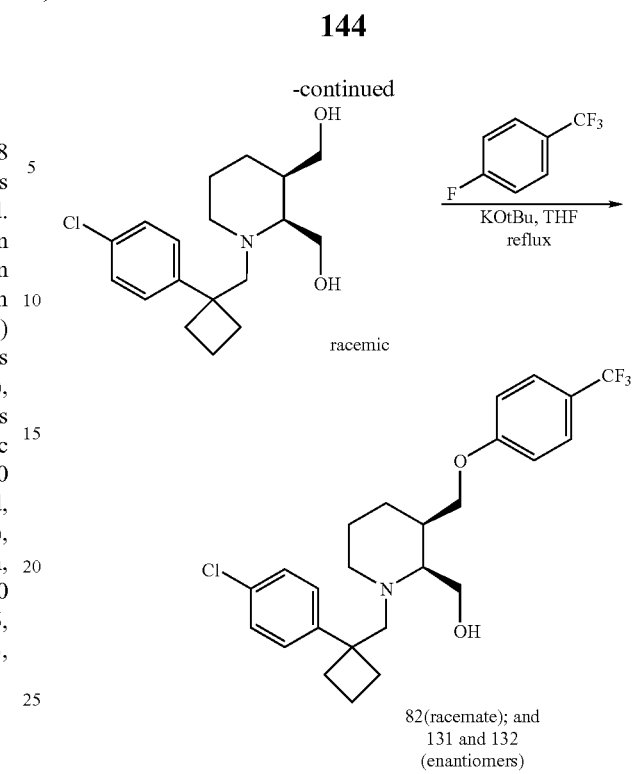

82(racemate); and
131 and 132
(enantiomers)

3-Hydroxymethyl-pyridine-2-carboxylic acid isopropyl ester (1.0 g, 5.1 mmol, prepared as in Ornstein, et al., *J. Med. Chem.* 1989, 32, 827) was converted to its t-butyldimethyl-silyl ether under standard conditions (5.6 mmol Me$_2$Si(t-Bu)Cl, 11.2 mmol imidazole, 25 mL DMF, room temperature, overnight). Dilution with 50 mL of water, addition of 100 mL ether, and extractive workup gave, after concentration of the organic layers in vacuo and chromatography on silica gel, the desired compound, 3-(tert-Butyl-dimethyl-silanyloxymethyl)-pyridine-2-carboxylic acid isopropyl ester (1.15 g, 73%). MS 310 (M+1); $^1$H NMR (300 MHz, CDCl$_3$): δ 8.59 (br. d, J=4.6 Hz, 1H), 8.17 (br.d, J=8.0 Hz, 1H), 7.41 (dd, J=8.0, 4.6 Hz, 1H), 5.22 (m, 1H), 5.02 (s, 2H), 1.39 (d, J=6.4 Hz, 6H), 0.91 (s, 9H), 0.03 (s, 6H).

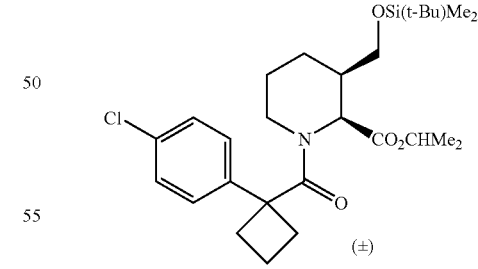

3-(tert-Butyl-dimethyl-silanyloxymethyl)-pyridine-2-carboxylic acid isopropyl ester (800 mg, 2.6 mmol) was dissolved in 6 mL of methanol in a pressure hydrogenation vessel to which 100 Mg of PtO$_2$ was added (Rh on alumina may also be used). The vessel was shaken under 50 psi of hydrogen for 5 hrs. The suspension was filtered through Celite and the solution was concentrated in vacuo to provide the desired compound, cis-3-(tert-butyl-dimethyl-silanyloxymethyl)-piperidine-2-carboxylic acid isopropyl ester. MS 316 (M+1). Without further purification the product was acylated under standard conditions with 1-(4-chloro-phenyl)-cyclobutanecarbonyl chloride (itself prepared from the carboxylic acid using excess thionyl chloride at reflux for 1 hr. followed by concentration in vacuo). Water/ether extractive workup gave, after concentration of the organic layers in vacuo and chromatography on silica gel, the desired compound, cis-3-(tert-Butyl-dimethyl-silanyloxymethyl)-1-[1-(4-chloro-phenyl)-cyclobutanecarbonyl]-piperidine-2-carboxylic acid isopropyl ester (720 mg, 55% for two steps) MS 508 (M+1). The cis stereochemistry was assigned based upon a $^1$H NMR coupling constant of 4 Hz for the proton at C-2 of the piperidine ring.

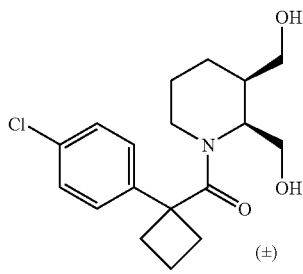

Cis-3-(tert-Butyl-dimethyl-silanyloxymethyl)-1-[1-(4-chloro-phenyl)-cyclobutanecarbonyl]-piperidine-2-carboxylic acid isopropyl ester (460 mg, 0.9 mmol) was dissolved in 10 mL of THF. Lithium aluminum hydride (171 mg, 4.5 mmol) was added slowly and the suspension was brought to reflux for 1 hr. The suspension was cooled to 0° C. and cold 0.5 M NaOH (0.75 mL) was added dropwise. The slurry was vigorously stirred at room temperature for 30 minutes, filtered through Celite, and the solution was concentrated in vacuo to provide, after chromatography on silica gel, the desilylated and reduced compound, cis-{1-[1-(4-Chloro-phenyl)-cyclobutylmethyl]-3-hydroxymethyl-piperidin-2-yl}-methanol (176 mg, 60%) MS 324 (M+1).

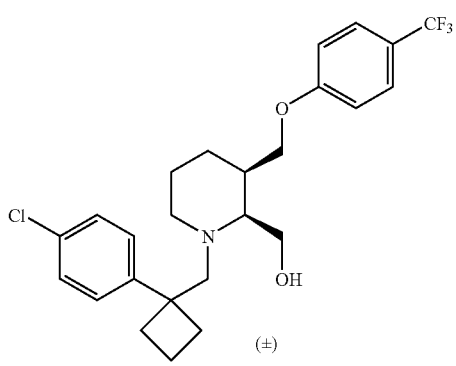

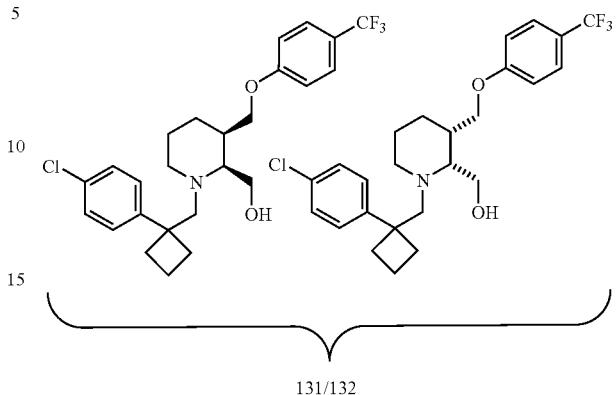

131/132

Cis-{1-[1-(4-Chloro-phenyl)-cyclobutylmethyl]-3-hydroxymethyl-piperidin-2-yl}-methanol (95 mg, 0.29 mmol) was dissolved in 5 mL of THF. KOtBu (0.58 mmol, 66 mg) and 1-fluoro-4-trifluoromethyl-benzene (0.29 mmol, 48 mg) was added and the solution was brought to reflux for 4 hours. Water/ether extractive workup gave, after concentration of the organic layers in vacuo and chromatography on silica gel, the desired mono-arylated compound, cis-[1-[1-(4-chloro-phenyl)-cyclobutylmethyl]-3-(4-trifluoromethyl-phenoxymethyl)-piperidin-2-yl]-methanol (82) (39 mg, 28%). The enantiomeric mixture of compounds was separated by preparative HPLC using a Chiralpak OD™ column from Chiral Technologies, Inc., eluting with an 85:15 mixture of hexane and isopropyl alcohol containing ca. 0.2% diethylamine. The products (131 and 132) were isolated and converted individually into their HCl salts by exposure to a solution of HCl in ether. Data for HCl salt form: MS 468 (M+1). $^1$H NMR (300 MHz, CDCl$_3$): δ 9.23 (br. s, 1 H, NH of protonated tertiary amine), 7.56 (d, J=7.4 Hz, 2H), 7.39–7.49 (m, 4 H), 6.85 (d, J=7.4 Hz, 2H), 3.6–3.95 (br. m, 7H), 1.45–3.25 (br. overlapping multiplets, total 14 H). $^{13}$C NMR (CDCl$_3$, 75 MHz): δ 160.4, 143.0, 133.5, 129.7, 128.2, 127.3 (CF3), 124.2, 114.8, 114.6, 68.3, 65.0, 63.4, 56.0, 50.6, 45.1, 33.9, 32.9, 30.9, 21.5, 19.1, 16.1.

To confirm the identity of the final products as the enantiomers of cis-[1-[1-(4-chloro-phenyl)-cyclobutylmethyl]-3-(4-trifluoromethyl-phenoxymethyl)-piperidin-2-yl]-methanol rather than the regioisomers [1-[1-(4-chloro-phenyl)-cyclobutylmethyl]-2-(4-trifluoromethyl-phenoxymethyl)-piperidin-3-yl]-methanol, the Scheme 1 synthesis was modified as shown in Scheme 2. Experimental procedures employed are standard and generally follow procedures outlined for Scheme 1 with the exception that the hydroxyl "protecting group" strategies are altered in a straightforward fashion. This modified route uses an ethoxyethyl group rather than a tert-butyl-dimethyl-silanyl group for blocking the hydroxyl function of the starting material 3-hydroxymethyl-pyridine-2-carboxylic acid isopropyl ester. The ethoxyethyl group, unlike the tert-butyl-dimethyl-silanyl group, is stable to the lithium aluminum hydride reduction. By employing a triisopropyl-silanyl group for the functionalization of the hydroxymethyl group at the 2 position of the piperidine system, the alcohol functions remain differentially blocked. Thus it was unambiguously determined that the aryl ether present in the final product is off the 3 position rather than the two position of the piperidine ring system. This modified synthesis of cis-1-[1-(4-Chloro-phenyl)-cyclobutylmethyl]-3-(4-trifluoromethyl-phenoxymethyl)-piperidin-2-yl]-methanol (82 as the racemate, 131 and 132 as single enantiomers) is shown in Scheme 2.

Scheme 2

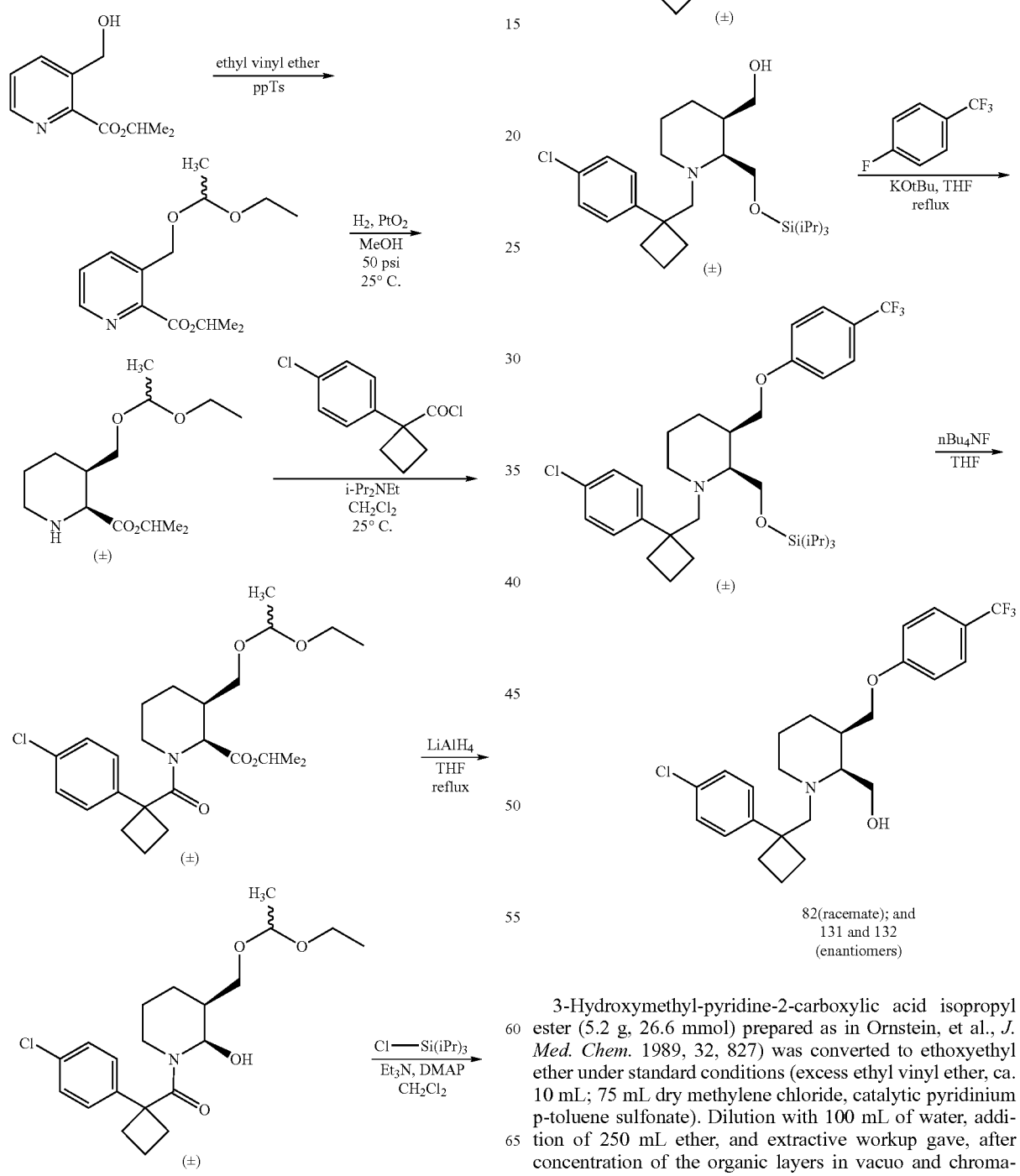

82(racemate); and
131 and 132
(enantiomers)

3-Hydroxymethyl-pyridine-2-carboxylic acid isopropyl ester (5.2 g, 26.6 mmol) prepared as in Ornstein, et al., *J. Med. Chem.* 1989, 32, 827) was converted to ethoxyethyl ether under standard conditions (excess ethyl vinyl ether, ca. 10 mL; 75 mL dry methylene chloride, catalytic pyridinium p-toluene sulfonate). Dilution with 100 mL of water, addition of 250 mL ether, and extractive workup gave, after concentration of the organic layers in vacuo and chromatography on silica gel, the desired compound 3-(1-Ethoxyethoxymethyl)-pyridine-2-carboxylic acid isopropyl ester, 6.13 g (86%). Data: MS 268 (M+1); $^1$H NMR (300 MHz, CDCl$_3$): δ 8.63 (br. d, J=4.6 Hz, 1H), 8.09 (br. d, J=7.9 Hz, 1H), 7.43 (dd, J=7.9, 4.6 Hz), 5.17 (m, 1H), 5.02 and 4.94(AB d, J=14.9 Hz, 2 H), 4.81 (q, J=7.0 Hz, 1H), 3.50–3.75 (m, 2H), 1.40–1.45 (overlapping doublets, 9H), 1.21 (t, J=7.0 Hz, 3H); $^{13}$C NMR (CDCl$_3$, 75 MHz): δ 165.7, 147.9, 146.3, 136.8, 136.1, 126.0, 100.1, 69.6, 63.7, 61.4, 21.9, 20.1, 15.4.

Hydrogenation of compound 3-(1-ethoxy-ethoxymethyl)-pyridine-2-carboxylic acid isopropyl ester, following the method used for the corresponding silyl ether as in scheme 1, gave the desired product 3-(1-ethoxy-ethoxymethyl)-piperidine-2-carboxylic acid isopropyl ester. The starting pyridine compound (5.1 g, 19.1 mmol) was dissolved in 60 mL of methanol in a pressure hydrogenation vessel to which 2 g of PtO$_2$ was added. The vessel was shaken under 60 psi of hydrogen for 5 days. The suspension was filtered through Celite and the solution was concentrated in vacuo to provide the desired compound, 3-(1-ethoxy-ethoxymethyl)-piperidine-2-carboxylic acid isopropyl ester (5.1 g, ca. 100%). Data: MS 274 (M+1); $^1$H NMR (300 MHz, CDCl$_3$): δ 5.50 (br. s, 1H, NH), 5.07 (m, 1H, CH of ester), 4.60–4.64 (overlapping q's, J=7.0 Hz, 1 H), 3.41–3.73 (m, 5H), 3.10 (m, 1H), 2.69 (m, 1H), 2.30 (m, 1H), 1.80–1.95 (m, 2H), 1.41–1.63 (m, 3H), 1.19–1.30 (m, 12 H); $^{13}$C NMR (CDCl$_3$, 75 MHz): δ 172.4, 172.3, 100.0, 99.9, 68.1, 68.0, 64.4, 63.7, 61.1, 61.0, 60.4, 46.0, 45.9, 36.81, 36.76, 26.3, 26.1, 22.14, 22.07, 22.0, 21.9, 19.92, 19.85, 15.45, 15.39.

Acylation and LAH reduction, were accomplished following the same procedures used in the scheme 1 route, affording the desired products in 88% (15 mmol scale of the amine) and 73% yields (13.5 mmol scale of the amide), respectively. Mass spectral data for these intermediates are as follows: 1-[1-(4-chloro-phenyl)-cyclobutanecarbonyl]-3-(1-ethoxy-ethoxymethyl)-piperidine-2-carboxylic acid isopropyl ester MS 466 (M+1), [1-[1-(4-Chloro-phenyl)-cyclobutylmethyl]-3-(1-ethoxy-ethoxymethyl)-piperidin-2-yl]-methanol MS 396 (M+1). Protection of the alcohol function as the triisopropylsilyl ester followed the procedure for the t-butyldimethylsilyl ester protection in scheme 1 (92 yield, 12.2 mmol scale of the alcohol, 1-[1-(4-chloro-phenyl)-cyclobutylmethyl]-3-(1-ethoxy-ethoxymethyl)-2-triisopropylsilanyloxymethyl-piperidine MS 552 (M+1). Hydrolysis of the ethoxyethyl function (11.1 mmol starting ether, 50 mL MeOH, 5 mL TFA, 30 min, concentrated in vacuo) gave the free alcohol Chloro-phenyl)-cyclobutylmethyl]-2-triisopropylsilanyloxymethyl-piperidin-3-yl}-methanol in 88% yield after chromatographic purification on silica gel. Data: MS 480 (M+1). This alcohol (960 mg, 2.0 mmol) was dissolved in 15 mL of THF. KOtBu (4.1 mmol) and 1-Fluoro-4-trifluoromethyl-benzene (5.1 mmol) was added and the solution was brought to reflux for 4 hours. Water/ether extractive workup gave, after concentration of the organic layers in vacuo and chromatography on silica gel, the desired arylated compound 1-[1-(4-chloro-phenyl)-cyclobutylmethyl]-3-(4-trifluoromethyl-phenoxymethyl)-2-triisopropylsilanyloxymethyl-piperidine (968 mg, 78%); Data: MS 624 (M+1). Finally, this compound (746 mg, 1.19 mmol) was dissolved in 5 mL of tetrahydrofuran and 1.5 mL of a 1M solution of tetrabutylammonium fluoride in THF was added dropwise via syringe. The solution was stirred overnight at ambient temperature. Water/ether extractive workup gave, after concentration of the organic layers in vacuo and chromatography on silica gel, the desired compound 82. The final products obtained via the route in Scheme 2 (131 and 132, obtained after HPLC purification as described above, 82 as the racemate) were identical in all respects to products obtained via the route in Scheme 1.

Example 92

Synthesis of (R)-1-[1-(4-Chloro-phenyl)-cyclobutanecarbonyl]-piperidine-3-carboxylic acid ethyl ester

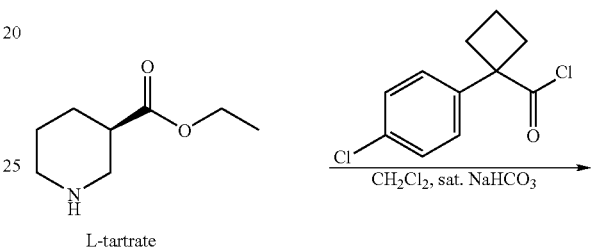

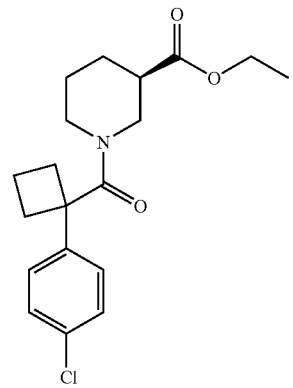

Ethyl (R)-nipecotate L-tartrate (15.0 g, 48.8 mmol) was added to a stirred mixture of dichloromethane and saturated sodium bicarbonate solution (100 mL each) at 0° C. After 10 min 1-(4-chloro-phenyl)-cyclobutanecarbonyl chloride (11.13 g, 48.8 mmol) was slowly added at 0° C. The reaction was then allowed to stir for 2 h at room temperature. The organic layer was separated and the aqueous layer was washed once with dichloromethane (100 mL). The organic material was combined and washed once with water (100 mL), dried over anhydrous sodium sulfate, filtered and concentrated by rotary evaporation. The residue was purified by chromatography on silica gel, eluting with hexane/ethyl acetate (2:1) to give 9.2 g of the amidester as a thick clear gum; $C_{19}H_{24}ClNO_3$, LRMS (m/z)=350 (MH+).

Example 93

Synthesis of (R)-[1-(4-Chloro-phenyl)-cyclobutyl]-(3-hydroxymethyl-piperidin-1-yl)-methanone

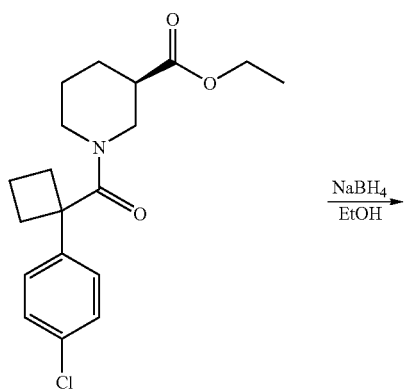

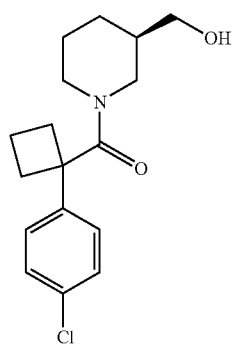

To a solution of the amidester (6.0 g, 17.2 mmol) in absolute ethanol (100 mL) at 0° C. was slowly added sodium borohydride (0.65 g, 17.2 mmol). The reaction was then allowed to warm to room temperature and stirred overnight. The reaction was quenched by slow addition of water, and then most of the ethanol was removed by rotary evaporation. The residue was partitioned between dichloromethane and water (100 mL each), and the aqueous layer was extracted once with dichloromethane (100 mL). The organic material was combined and dried over anhydrous sodium sulfate, filtered and concentrated by rotary evaporation. The residue was purified by chromatography on silica gel, eluting with dichloromethane/methanol (98:2) to give 4.9 g of the alcohol as a thick clear gum; $C_{17}H_{22}ClNO_2$, LRMS (m/z)=308 (MH+).

Example 94

Synthesis of Methanesulfonic acid (R)-1-[1-(4-chloro-phenyl)-cyclobutanecarbonyl]-piperidin-3-ylmethyl ester

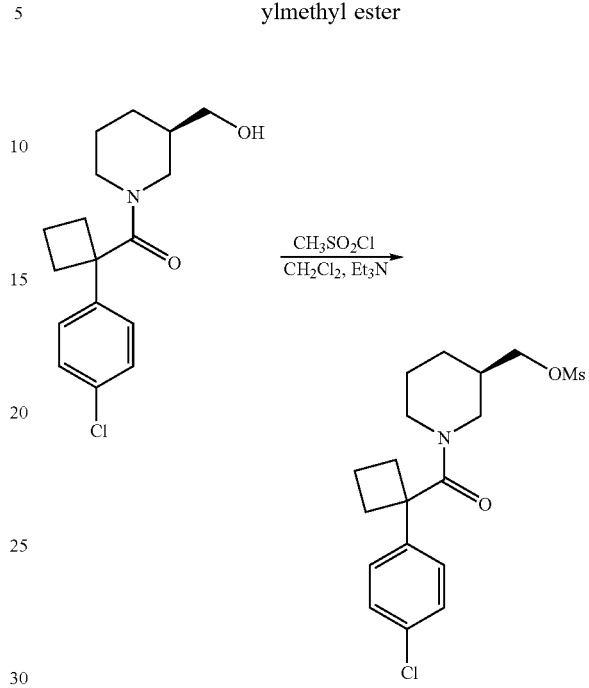

The alcohol derivative (4.5 g, 14.7 mmol)) was dissolved in dichloromethane (100 mL) and cooled to 0° C. To this solution was added triethylamine (5.0 mL) followed by dropwise addition of methanesulfonyl chloride (1.68 g, 14.7 mmol) at 0° C. The reaction was stirred at 0° C. for 1 h and then at room temperature for 4 h. The reaction mixture was washed successively with water, 1 N HCl, water, sat. sodium bicarbonate solution, and water (100 mL each). The organic layer was dried over anhydrous sodium sulfate, filtered and concentrated by rotary evaporation. The residue gave 5.0 g of the mesylate as a thick yellow gum which was used in the following step without further purification; $C_{18}H_{24}ClNO_4S$, LRMS (m/z)=386 (MH+).

Example 95

Synthesis of (R)-[1-(4-Chloro-phenyl)-cyclobutyl]-[3-(4-fluoro-phenoxymethyl)-piperidin-1-yl]-methanone

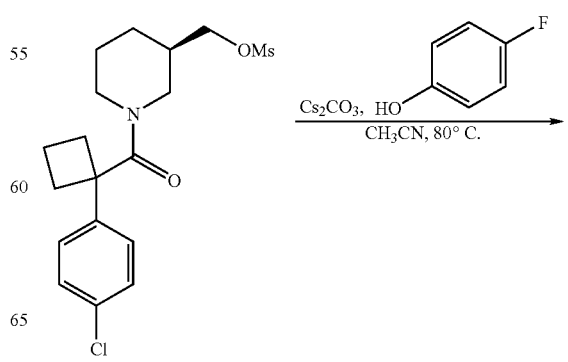

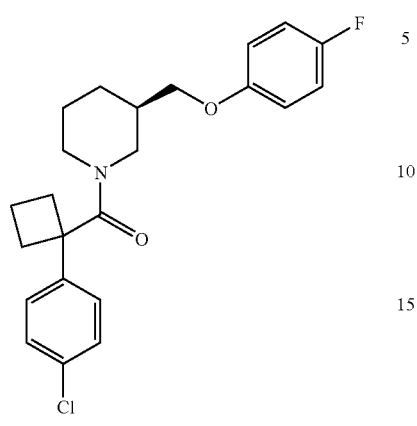

To a solution of the mesylate (4.0 g, 10.4 mmol) in acetonitrile (100 mL) was added 4-fluorophenol (1.17 g, 10.4 mmol) and cesium carbonate (3.40 g, 10.4 mmol). The reaction was stirred and refluxed for 20 h. After cooling to room temperature, the reaction mixture was filtered and most of the solvent was removed by rotary evaporation. The residue was partitioned between dichloromethane and water, and the organic layer was washed with sat. sodium carbonate (2×50 mL) and water. The organic layer was dried over anhydrous sodium sulfate, filtered and concentrated by rotary evaporation. The residue was purified by chromatography on silica gel, eluting with dichloromethane/methanol (98:2) to give 3.2 g of the amide as a white solid; $C_{23}H_{25}ClFNO_2$, LRMS (m/z)=402 (MH+).

Example 96

Synthesis of (R)-1-[1-(4-Chloro-phenyl)-cyclobutyl-methyl]-3-(4-fluoro-phenoxymethyl)-piperidine

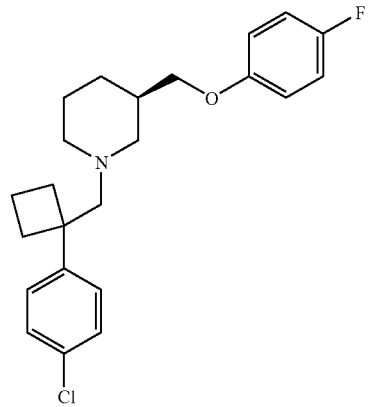

133

To a suspension of lithium aluminum hydride (0.19 g, 5.0 mmol) in anhydrous tetrahydrofuran (50 mL) at 0° C. was added the amide (2.0 g, 4.99 mmol). The reaction mixture was then stirred at 0° C. for 4 h. The reaction mixture was then quenched at 0° C. with slow addition of water and 1 N NaOH. The residue was extracted well with ethyl acetate (4×100 mL), and the combined organic portions were dried over anhydrous magnesium sulfate, filtered and concentrated by rotary evaporation. The organic residue was purified by flash chromatographey on silica gel, eluting with dichloromethane/2.0 M ammonia in ethyl alcohol (98:2) to give 1.35 g of 133 as a pale yellow oil; $C_{23}H_{27}ClFNO$, LRMS (m/z)=388 (MH+). Enantiomeric excess was determined via Chiral HPLC using a Chiralpak®AD Column (Chiral Technologies, Inc.; 10 μm, 4.6 mm I.D.×250 mm) eluting with methanol/water/diethylamine (95:5:0.1) with a flow rate of 1.0 ml/min. and was found to be >98% (retention time of 133: 9.51 min.).

Example 97

Synthesis of (R)-[1-(4-Chloro-phenyl)-cyclobutyl]-[3-(4-fluoro-phenoxymethyl)-piperidin-1-yl]-methanone, and (S)-[1-(4-Chloro-phenyl)-cyclobutyl]-[3-(4-fluoro-phenoxymethyl)-piperidin-1-yl]-methanone

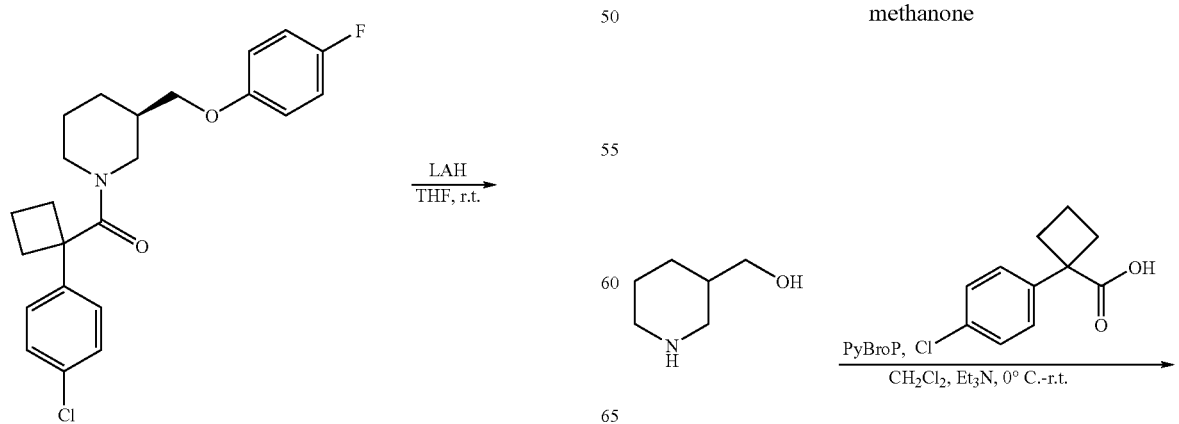

-continued

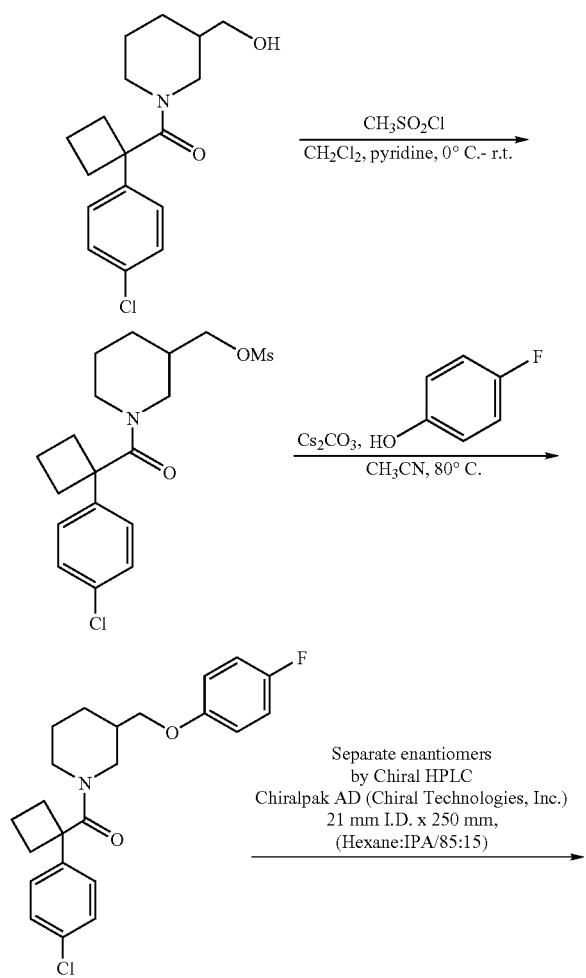

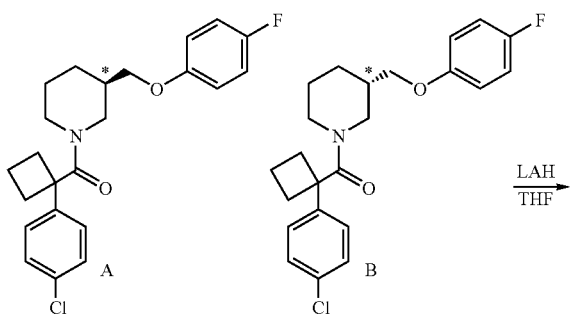

* denotes stereochemistry randomly assigned.

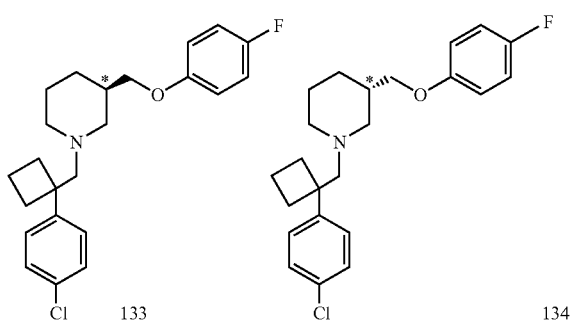

Methanesulfonic acid 1-[1-(4-chloro-phenyl)-cyclobutanecarbonyl]-piperidin-3-ylmethyl ester To a solution of 3-piperidinemethanol (5.0 g, 43.4 mmol), 1-(4-chlorophenyl)-1-cyclobutanecarboxylic acid (9.14 g, 43.4 mmol), and diisopropylethylamine (11.22 g, 86.8 mmol) in dichloromethane (100 mL) at 0° C. was added PyBroP® (22.26 g, 47.8 mmol). The reaction was stirred at 0° C. for 1 h and then at room temperature for 4 h. The reaction mixture was washed successively with water, 1 N HCl, water, sat. sodium bicarbonate solution, and water (100 mL each). The organic layer was dried over anhydrous sodium sulfate, filtered and concentrated by rotary evaporation. The residue was purified by chromatography on silica gel, eluting with dichloromethane/methanol (96:4) to give 5.8 g of the hydroxyl amide as a thick gum.

The hydroxyl amide (5.0 g) was dissolved in dichloromethane (50 mL) and cooled to 0° C. To this solution was added pyridine (5.0 mL) followed by dropwise addition of methanesulfonyl chloride (2.05 g, 17.9 mmol). The reaction was stirred at for 1 h and then at room temperature overnight. The reaction mixture was washed successively with water, 1 N HCl, water, sat. sodium bicarbonate solution, and water (100 mL each). The reaction mixture was washed successively with water, sat. sodium bicarbonate solution, and water (100 mL each). The organic layer was dried over anhydrous sodium sulfate, filtered and concentrated by rotary evaporation. The residue was purified by chromatography on silica gel, eluting with hexane/ethyl acetate (2:1) to give 4.45 g of the mesylate amide as a tan gum; $C_{18}H_{24}ClNO_4S$, LRMS (m/z)=386 (MH+).

[1-(4-Chloro-phenyl)-cyclobutyl]-[3-(4-fluoro-phenoxymethyl)-piperidin-1-yl]-methanone To a solution of mesylate amide (1.0 g, 2.60 mmol) in acetonitrile (25 mL) was added 4-fluorophenol (0.29 g, 2.60 mmol) and cesium carbonate (1.27 g, 3.90 mmol). The reaction was stirred and refluxed for 20 h. After cooling to room temperature, the reaction mixture was filtered and most of the solvent was removed by rotary evaporation. The residue was partitioned between dichloromethane and water, and the organic layer was washed with sat. sodium carbonate (2×50 mL) and water. The organic layer was dried over anhydrous sodium sulfate, filtered and concentrated by rotary evaporation. The residue was purified by chromatography on silica gel, eluting with dichloromethane/methanol (98:2) to give the ether amide (0.54 g, 52%) as a crystalline solid; $C_{23}H_{25}ClFNO_2$, LRMS (m/z)=402 (MH+).

(R)-[1-(4-Chloro-phenyl)-cyclobutyl]-[3-(4-fluoro-phenoxymethyl)-piperidin-1-yl]-methanone, and (S)-[1-(4-Chloro-phenyl)-cyclobutyl]-[3-(4-fluoro-phenoxymethyl)-piperidin-1-yl]-methanone Ether amide was separated via Chiral HPLC using a Chiralpak®AD Column (Chiral Technologies, Inc.; 21 mm I.D.×250 mm) eluting with hexane/2-propanol (85:15) to give enantiomers A and B.

Compounds 133 and 134 were separated via Chiral HPLC using a Chiralpak®AD Column (Chiral Technologies, Inc.; 10 μm, 4.6 mm I.D.×250 mm) eluting with methanol/water/diethylamine (95:5:0.1) with a flow rate of 1.0 ml/min. Retention time of 133: 9.51 min. Retention time of 134: 10.8 min.

Example 98

Synthesis of Polymer Supported Methanesulfonic Acid Piperidin-3-ylmethyl Ester

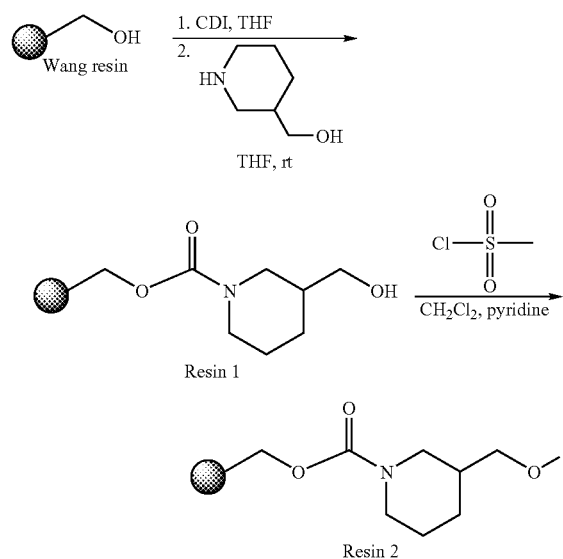

To the Wang resin (12 g, 1.1 mmol/g) in a 250 mL peptide synthesis vessel was added 120 mL of 0.4 N CDI in anhydrous THF, and shaken at room temperature for 17 hours. The resin was thoroughly washed with $CH_2Cl_2$ (3×100 mL) and THF (3×100 mL) to remove the excess CDI and then treated with 120 mL of 0.4 N 3-piperidinemethanol in THF at room temperature for 17 hours. The resulting resin 1 was washed with DMF (3×100 mL), MeOH (4×100 mL), and $CH_2Cl_2$ (4×100 mL) and dried in vacuo. To the alcohol resin 1 was added methanesulfonyl chloride (5.11 ml, 66 mmol) in 100 mL $CH_2Cl_2$ followed by 20 mL of pyridine, and the resulting slurry was shaken at room temperature for 17 hours. The resulting mesylate resin 2 was washed with DMF (3×100 mL), MeOH (4×100 mL), and $CH_2Cl_2$ (4×100 mL) and dried in vacuo.

Synthesis of 3-(4-Methoxy-phenoxymethyl)piperidine (1)

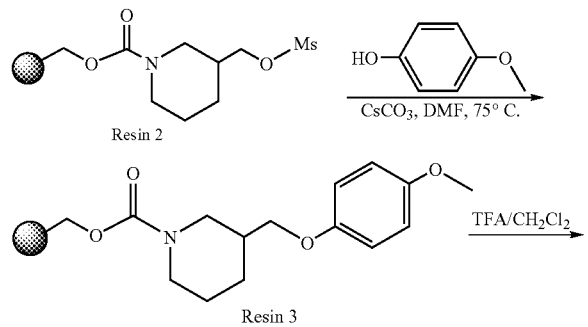

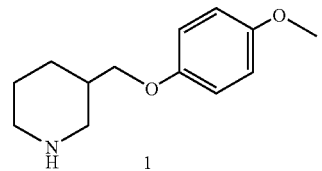

To mesylate resin 2 (1.0 g, 1.1 mmol) was added cesium carbonate (1.79 g, 5.5 mmol) followed by 4-methoxyphenol (0.682 g, 5.5 mmol) in 10 mL of DMF, and the mixture was shaken at 75° C. for 24 hours. The resulting resin 3 was extensively washed with DMF (3×10 mL), water (3×10 mL), MeOH (4×10 mL), and $CH_2Cl_2$ (4×10 mL). The resin was dried in vacuo and treated with a solution of 50% TFA in $CH_2Cl_2$ at room temperature for 30 min to release polymer-bound 3-(4-Methoxy-phenoxymethyl)piperidine. Removal of the volatiles under a stream of nitrogen followed by drying in vacou afforded 1 as a TFA salt, LRMS m/z 222. Piperidine derivatives 2, 3, 4, 5, 6, 7, 8, 9, 10, 11, and 12 were prepared using the same general procedure.

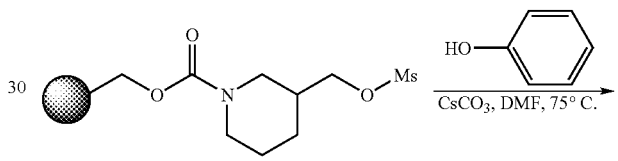

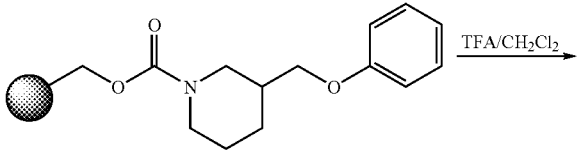

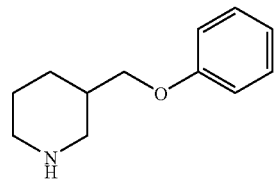

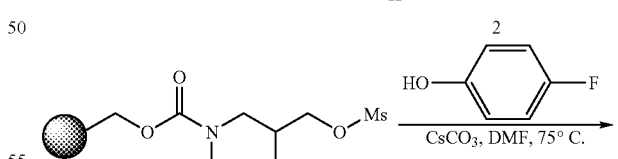

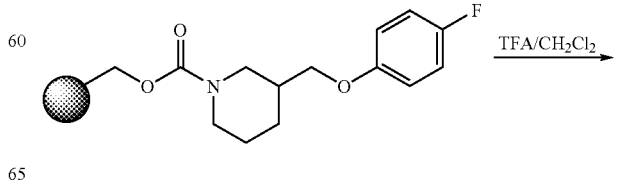

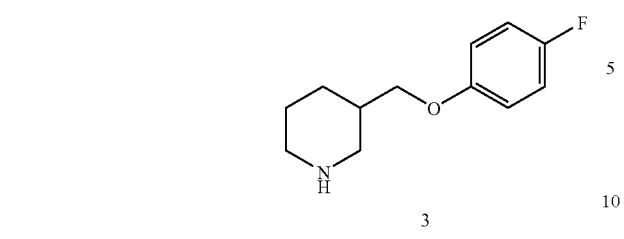
3
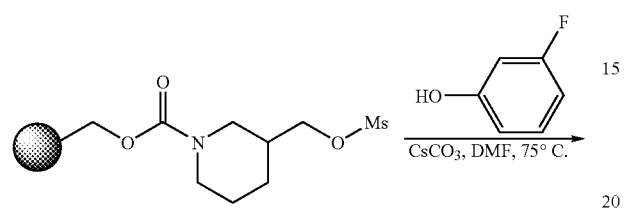
Resin 2
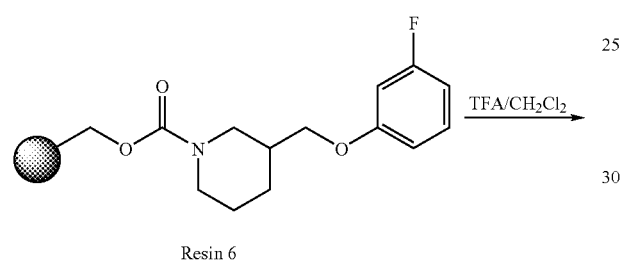
Resin 6
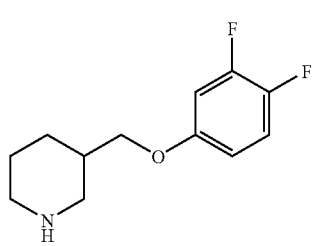
5
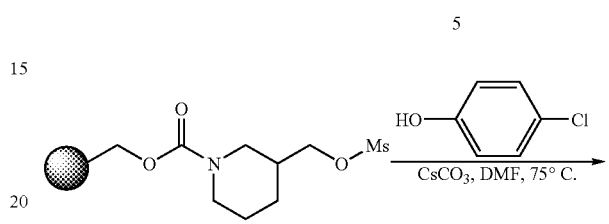
Resin 2
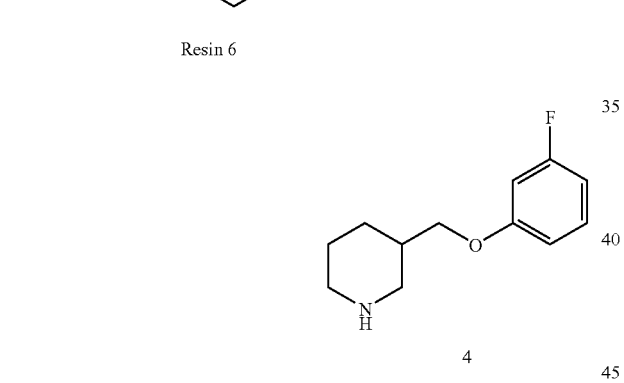
4
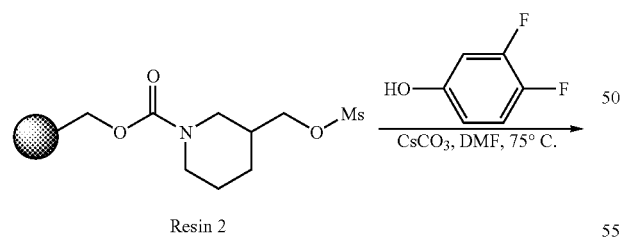
Resin 2
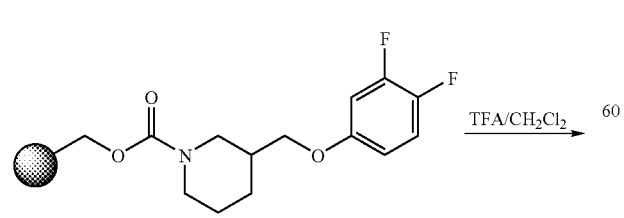
Resin 7
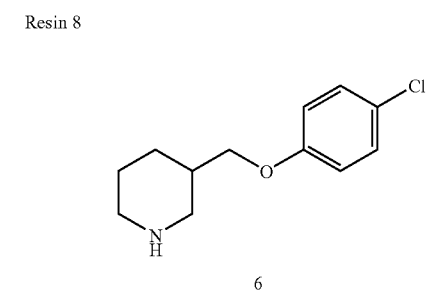
6
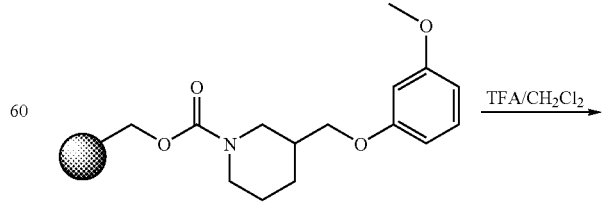
Resin 9

-continued
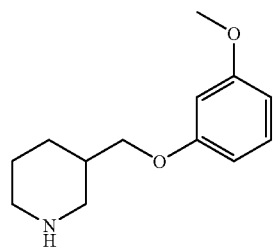
7
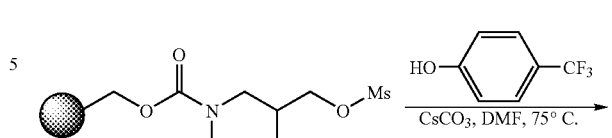
Resin 2
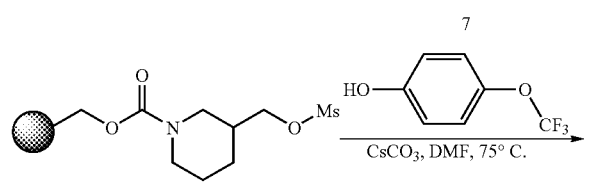
Resin 10
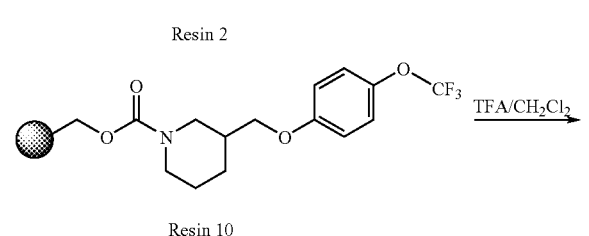
8
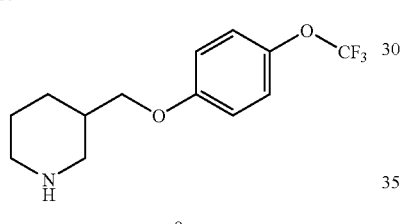
Resin 2
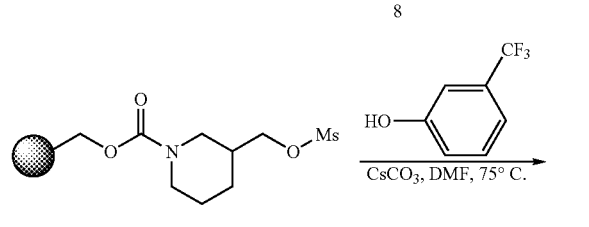
Resin 11
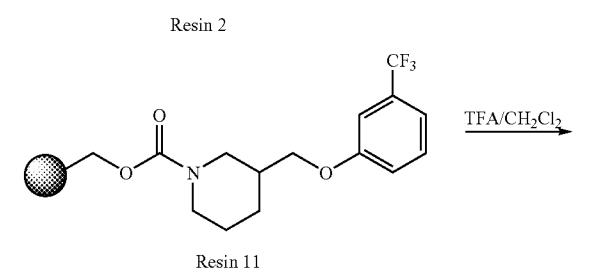
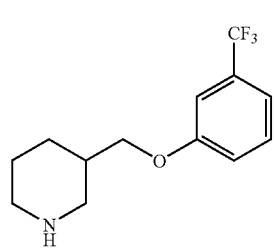
9
-continued
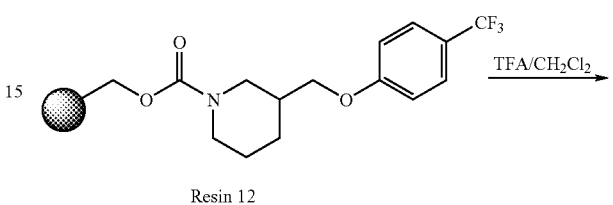
Resin 2
Resin 12
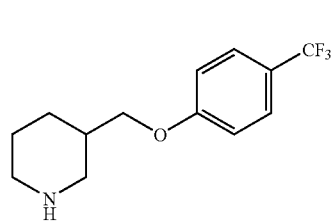
10
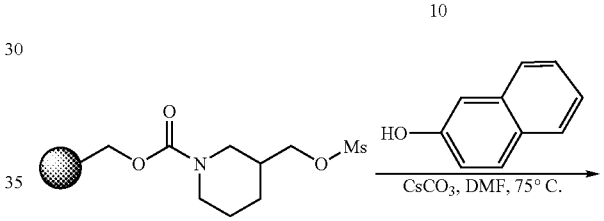
Resin 2
Resin 13
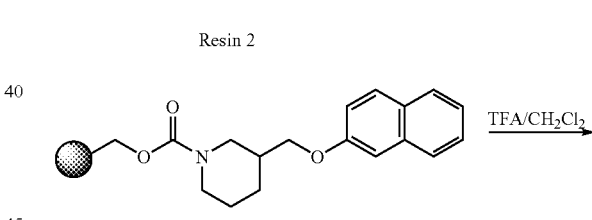
11
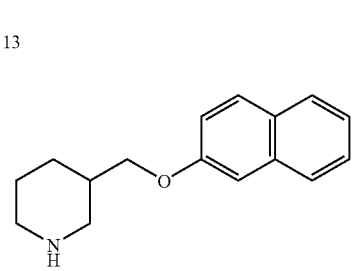
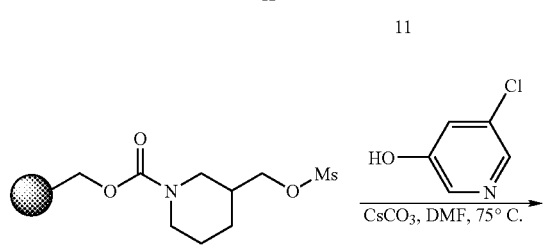
Resin 2

Synthesis of Combinatorial Library of Compounds of the Present Invention

Twelve piperidines (1 to 12) were dissolved in TMOF (4 mL), and respectively dispensed into 96-well reaction block from column 1 to column 12 at 0.5 ml/well (Scheme 1). Eight aldehydes (A to H) in TMOF were respectively dispensed into eight rows, from row A to row H at 0.33 ml/well (containing 0.11 mmol aldehyde). The mixtures were shaken at rt for one hour, then (polystyrylmethyl) trimethylammonium cyanoborohydride (4.25 mmol/g) was dispensed into 96 wells at 0.1 g/well. The mixtures were shaken at rt for 24 hours. Eight aldehydes were dispensed again into the reaction block, and the shaking continued for another 24 hours. The reaction mixtures were filtered and the resins were washed with MeOH (3×0.5 ml/well). After conditioning SPE columns (SCX cation exchange, 0.5 g of sorbent, 2.0 mequiv/g) with 5 mL of MeOH, the reaction contents were loaded onto the column. The column was washed with 2×5 mL of MeOH, and eluted with 4 mL of 2.0 M ammonia in MeOH. The effluents were collected into receiving tubes, concentrated and dried in vacou to afford 96 final compounds, which were submitted to HPLC and mass spectra analyses.

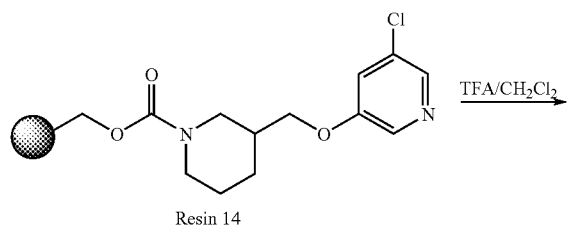

Resin 14

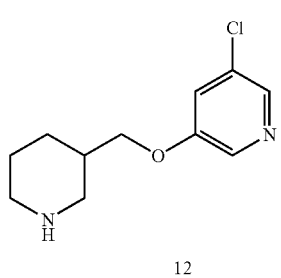

12

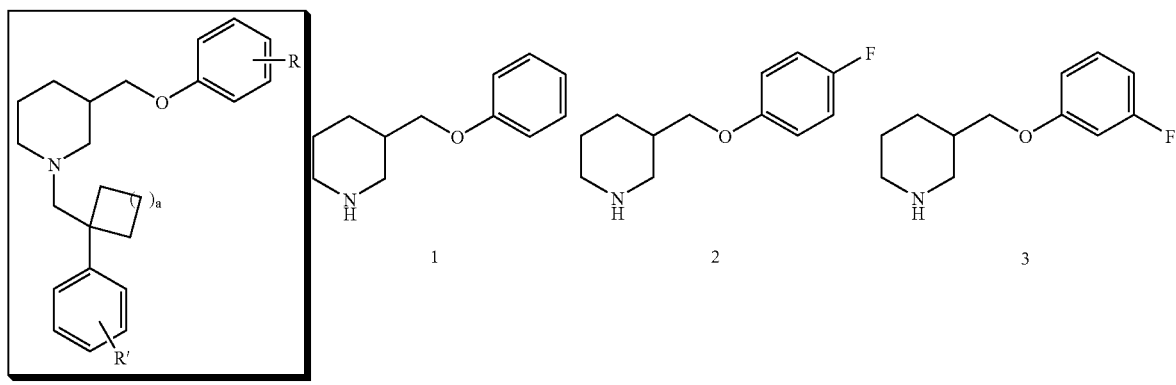

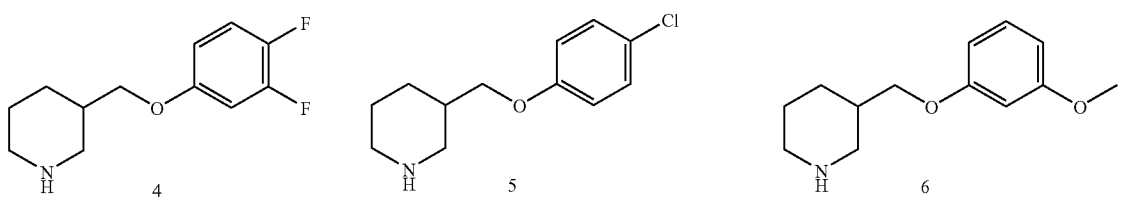

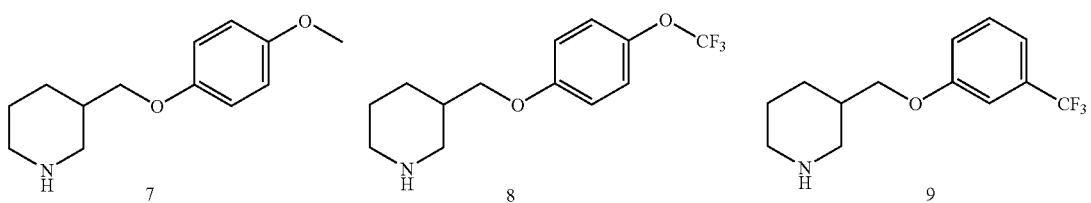

-continued

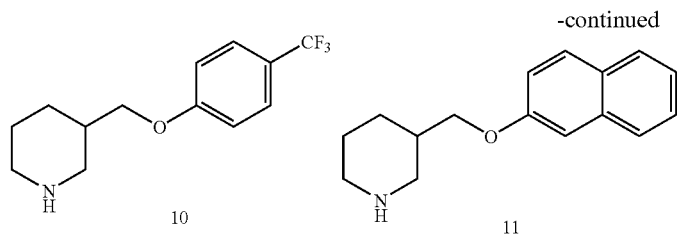

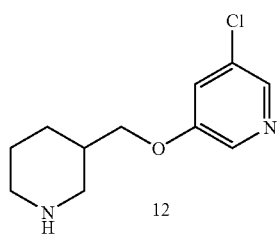

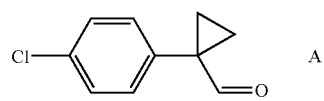

A

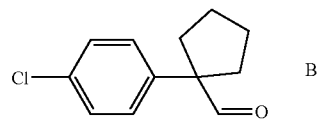

B

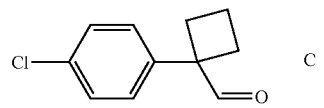

C

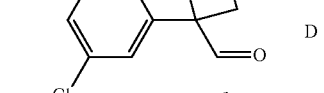

D

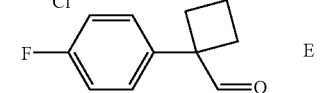

E

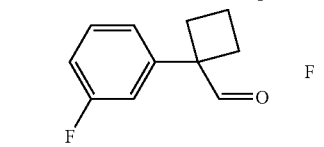

F

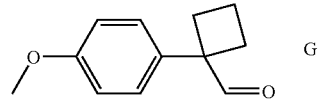

G

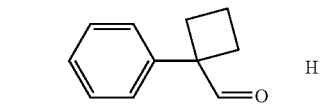

H

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   |   |   |   |   |   |   |   |   |    |    |    |
| C |   |   |   |   |   |   |   |   |   |    |    |    |
| D |   |   |   |   |   |   |   |   |   |    |    |    |
| E |   |   |   |   |   |   |   |   |   |    |    |    |
| F |   |   |   |   |   |   |   |   |   |    |    |    |
| G |   |   |   |   |   |   |   |   |   |    |    |    |
| H |   |   |   |   |   |   |   |   |   |    |    |    |

Example 99

The compounds prepared in the combinatorial library in Example 98 were screened for their ability to inhibit the uptake of human monoamines. The ability of test compounds in this library to displace norephinephrine ligands in vitro was determined by the methods of Galli et al (*J. Exp. Biol.* 198:2197, 1995) using desipramine ($IC_{50}$=920 nM) as a reference compound. The displacement of dopamine, and serotonin ligands in vitro was determined by the methods of Gu et al (J. Biol. Chem. 269;7124, 1994) using GBR-12909 ($IC_{50}$(DA uptake)=490 nM, $IC_{50}$ (5-HT uptake)=110 nM) as a reference compound. The test compounds were tested at 1 µM (n=1) for dopamine (DA) uptake, norephinephrine (NE) uptake, and serotonin (5-HT) uptake. The table is a representation of their % inhibition at that test concentration.

| Well # | Uptake Profile (% Inhibition @ 1 μM) | | |
|---|---|---|---|
| | DA uptake | NE uptake | 5-HT uptake |
| A1 | 90 | 87 | 49 |
| A2 | 91 | 61 | 56 |
| A3 | 86 | 78 | 59 |
| A4 | 91 | 67 | 42 |
| A5 | 96 | 64 | 73 |
| A6 | 90 | 94 | 44 |
| A7 | 92 | 70 | 60 |
| A8 | 90 | 60 | 32 |
| A9 | 93 | 89 | 48 |
| A10 | 93 | 71 | 56 |
| A11 | 74 | 81 | 53 |
| A12 | 84 | 51 | 31 |
| B1 | 88 | 88 | 48 |
| B2 | 93 | 68 | 60 |
| B3 | 85 | 85 | 52 |
| B4 | 89 | 73 | 64 |
| B5 | 97 | 68 | 77 |
| B6 | 88 | 73 | 59 |
| B7 | 94 | 60 | 59 |
| B8 | 92 | 69 | 60 |
| B9 | 74 | 71 | 60 |
| B10 | 92 | 69 | 78 |
| B11 | 78 | 68 | 75 |
| B12 | 76 | 60 | 62 |
| C1 | 79 | 71 | 42 |
| C2 | 90 | 52 | 54 |
| C3 | 90 | 72 | 58 |
| C4 | 85 | 61 | 57 |
| C5 | 97 | 67 | 77 |
| C6 | 86 | 64 | 55 |
| C7 | 91 | 66 | 53 |
| C8 | 87 | 55 | 57 |
| C9 | 91 | 75 | 59 |
| C10 | 95 | 74 | 86 |
| C11 | 61 | 57 | 78 |
| C12 | 78 | 66 | 68 |
| D1 | 67 | 54 | 30 |
| D2 | 78 | 57 | 55 |
| D3 | 71 | 76 | 51 |
| D4 | 86 | 61 | 46 |
| D5 | 87 | 57 | 73 |
| D6 | 70 | 65 | 29 |
| D7 | 83 | 61 | 54 |
| D8 | 83 | 58 | 68 |
| D9 | 76 | 69 | 59 |
| D10 | 81 | 61 | 92 |
| D11 | 52 | 54 | 39 |
| D12 | 68 | 52 | 76 |
| E1 | 75 | 67 | 55 |
| E2 | 86 | 47 | 63 |
| E3 | 83 | 70 | 65 |
| E4 | 86 | 55 | 67 |
| E5 | 97 | 65 | 75 |
| E6 | 81 | 77 | 67 |
| E7 | 86 | 72 | 56 |
| E8 | 92 | 53 | 73 |
| E9 | 85 | 57 | 71 |
| E10 | 92 | 54 | 73 |
| E11 | 63 | 64 | 60 |
| E12 | 80 | 50 | 83 |
| F1 | 76 | 70 | 64 |
| F2 | 77 | 56 | 51 |
| F3 | 80 | 84 | 64 |
| F4 | 87 | 66 | 59 |
| F5 | 90 | 65 | 67 |
| F6 | 77 | 68 | 70 |
| F7 | 74 | 60 | 70 |
| F8 | 87 | 60 | 82 |
| F9 | 85 | 65 | 56 |
| F10 | 84 | 46 | 52 |
| F11 | 89 | 56 | 57 |
| F12 | 77 | 49 | 75 |
| G1 | 88 | 82 | 78 |
| G2 | 97 | 64 | 51 |
| G3 | 90 | 77 | 75 |
| G4 | 99 | 74 | 78 |
| G5 | 93 | 62 | 62 |
| G6 | 91 | 85 | 74 |
| G7 | 94 | 68 | 70 |
| G8 | 99 | 87 | 74 |
| G9 | 96 | 91 | 73 |
| G10 | 95 | 85 | 65 |
| G11 | 89 | 79 | 81 |
| G12 | 89 | 64 | 73 |
| H1 | 65 | 65 | 39 |
| H2 | 86 | 59 | 61 |
| H3 | 77 | 77 | 54 |
| H4 | 89 | 70 | 64 |
| H5 | 87 | 69 | 80 |
| H6 | 81 | 72 | 53 |
| H7 | 82 | 44 | 52 |
| H8 | 86 | 55 | 67 |
| H9 | 87 | 65 | 56 |
| H10 | 89 | 56 | 74 |
| H11 | 85 | 60 | 47 |
| H12 | 72 | 43 | 45 |

Example 100

Synthesis of 1-(4-Chloro-phenyl)-2-[3-(4-trifluoromethyl-phenoxymethyl)-piperidin-1-yl]-ethanone

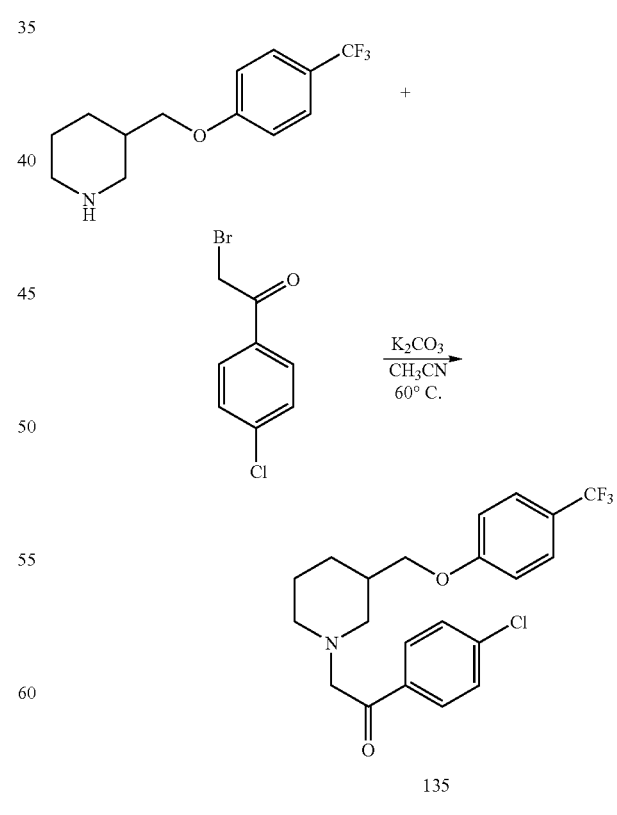

135

A solution of 3-(4-trifluoromethyl-phenoxymethyl)-piperidine (0.189 mmol, 49 mg), 2-bromo-4'-chloroacetophenone (1.5 equiv, 0.284 mmol, 66 mg) and $K_2CO_3$ (2.0 equiv, 0.378 mmol, 52 mg) in $CH_3CN$ (1 mL) was heated to 60° C. and stirred for 12 h. The reaction mixture was quenched with $H_2O$ (10 mL) and then extracted with EtOAc (2×15 mL). The combined organics were dried with $NaCl_{(sat)}$ and $Na_2SO_{4(s)}$. The solvents were removed in vacuo and chromatography (PTLC, $SiO_2$, 20 cm×20 cm, 1 mm, 5:1 hexane-EtOAc) provided 135 (37 mg, 78 mg theoretical, 47%) as a colorless oil: $R_f$ 0.38 ($SiO_2$, 5:1 hexane-EtOAc); LRMS m/z 412 ($M^++1$, $C_{20}H_{21}ClF_3NO_2$, requires 412).

Example 101

Synthesis of 1-(4-Chloro-phenyl)-2-[3-(4-trifluoromethyl-phenoxymethyl)-piperidin-1-yl]-ethanol

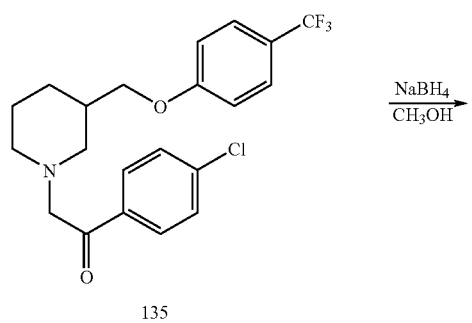

A solution of 135 (0.0898 mmol, 37 mg) in $CH_3OH$ (400 µL) was treated with $NABH_4$ (3.0 equiv, 0.269 mmol, 10 mg) at 0° C. The reaction mixture was allowed to warm to rt and stirred for 12 h. The reaction mixture was quenched with pH 7 phosphate buffer (5 mL) and extracted with EtOAc (2×10 mL). The combined organics were dried with $NaCl_{(sat)}$ and $Na_2SO_{4(s)}$. The solvents were removed in vacuo and chromatography (PTLC, $SiO_2$, 20 cm×20 cm, 1 mm, 6:1 Hexane-EtOAc) provided 136 (23 mg, 37 mg theoretical, 62%) as a colorless oil: $R_f$ 0.32 ($SiO_2$, 6:1 Hexane-EtOAc); LRMS m/z 414 ($M^++1$, $C_{21}H_{23}ClF_3NO_2$, requires 414).

Example 102

Synthesis of 3-Styryl-piperidine-1-carboxylic acid benzyl ester

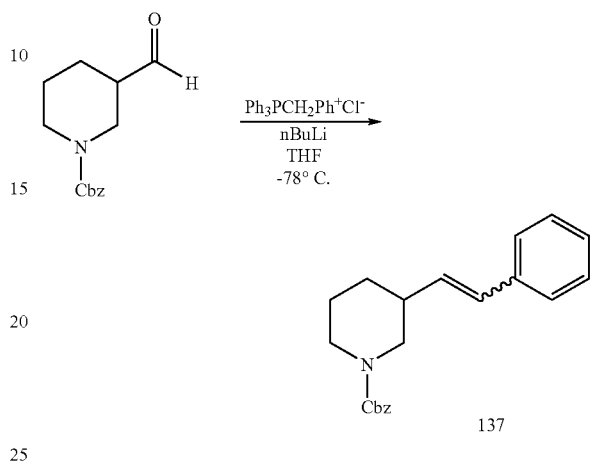

A solution of $Ph_3PCH_2Ph^+Cl^-$ (1.5 equiv, 1.82 mmol, 708 mg) in THF (4 mL) was treated with nBuLi (1.5 equiv, 1.6M, 1.82 mmol, 1.14 mL) at −78° C. The solution was warmed to 0° C. for 30 min and then cooled again to −78° C. A solution of CBZ-piperdine-3-carbaldehyde (1.21 mmol, 300 mg) in THF (2 mL) was added to the above reaction mixture at −78° C. The reaction stirred for 12 h. The reaction mixture was quenched with 10% HCl (10 mL) and then extracted with EtOAc (2×25 mL). The combined organics were dried with $NaCl_{(sat)}$ and $Na_2SO_{4(s)}$. The solvents were removed in vacuo and chromatography (Isco Combi-Flash, 110 g cartridge, 9:1 Hexane-EtOAc) provided 137 (328 mg, 388 mg theoretical, 85%) as a colorless oil: $R_f$ 0.41 ($SiO_2$, 6:1 hexane-EtOAc); LRMS m/z 322 ($M^++1$, $C_{21}H_{23}NO_2$, requires 322).

Example 103

Synthesis of 3-Phenethyl-piperidine

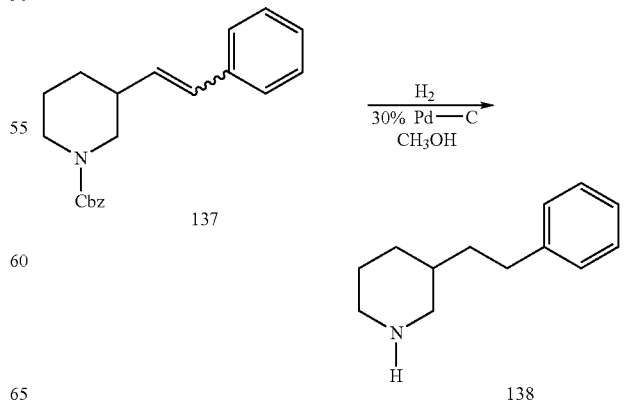

A solution of 137 (0.815 mmol, 262 mg) in CH₃OH (10 mL) was treated with 30% Pd—C (50 mg) and H₂ (Parr Hydrogenator, 65 psi). The reaction was shaken for 4 h. The reaction mixture was filtered through celite, and the solvents were removed in vacuo to provide 138 (154 mg, 154 mg theoretical, quantitative) as a colorless oil: LRMS m/z 190 (M$^+$+1, $C_{13}H_{19}N$, requires 190).

Example 104

Synthesis of 1-(4-Chloro-phenyl)-2-(3-phenethyl-piperidin-1-yl)-ethanone

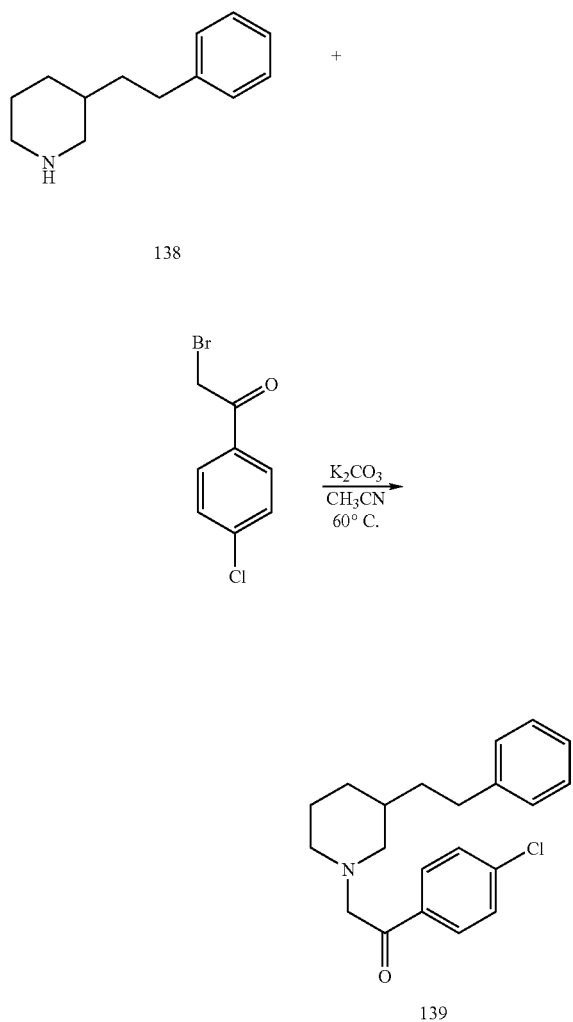

A solution of 138 (0.481 mmol, 91 mg), 2-bromo-4'-chloroacetophenone (1.5 equiv, 0.722 mmol, 169 mg) and K₂CO₃ (2.0 equiv, 0.962 mmol, 133 mg) in CH₃CN (1 mL) was heated to 60° C. and stirred for 12 h. The reaction mixture was quenched with H₂O (10 mL) and then extracted with EtOAc (2×25 mL). The combined organics were dried with NaCl$_{(sat)}$ and Na₂SO₄$_{(s)}$. The solvents were removed in vacuo and chromatography (PTLC, SiO₂, 20 cm×20 cm, 1 mm, 5:1 hexane-EtOAc) provided 139 (139 mg, 164 mg theoretical, 85%) as a colorless oil: R$_f$ 0.37 (SiO₂, 5:1 hexane-EtOAc); LRMS m/z 342 (M$^+$+1, $C_{21}H_{24}ClNO$, requires 342).

Example 105

Synthesis of 1-(4-Chloro-phenyl)-2-(3-phenethyl-piperidin-1-yl)-ethanol

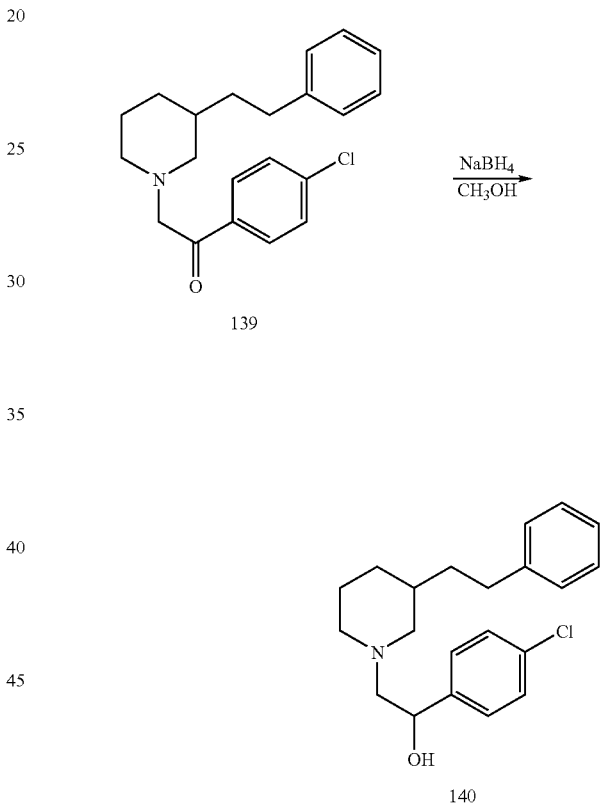

A solution of 139 (0.407 mmol, 139 mg) in CH₃OH (1 mL) was treated with NaBH₄ (3.0 equiv, 1.22 mmol, 46 mg) at 0° C. The reaction mixture was allowed to warm to rt and stirred for 12 h. The reaction mixture was quenched with pH 7 phosphate buffer (5 mL) and extracted with EtOAc (2×10 mL). The combined organics were dried with NaCl$_{(sat)}$ and Na₂SO₄$_{(s)}$. The solvents were removed in vacuo and chromatography (PTLC, SiO₂, 20 cm×20 cm, 1 mm, 3:1 Hexane-EtOAc) provided 140 (74 mg, 140 mg theoretical, 53%) as a colorless oil: R$_f$ 0.36 (SiO₂, 3:1 Hexane-EtOAc); LRMS m/z 344 (M$^+$+1, $C_{21}H_{26}ClNO$, requires 344).

Example 106

Separation of 140 into its Four Constituent Diastereomers, 141, 142, 143 and 144

141
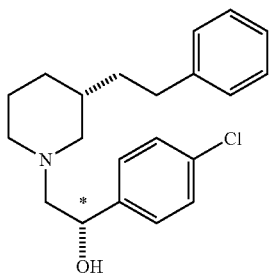

142
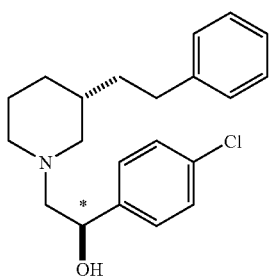

143
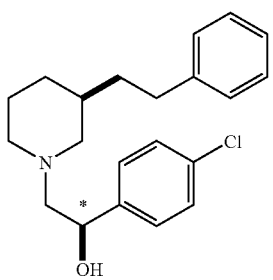

144
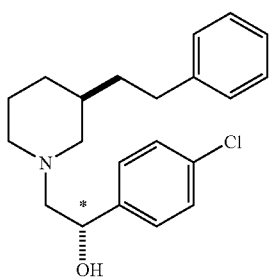

*denotes stereochemistry randomly assigned 140 was dissolved in 90:10 hexane (0.2% DEA) and isopropanol at a concentration of 90 mg/mL. The compounds were separated on a Chiralpak AD column using the same solvent system as above providing the following retention times: 141 (20.5 min), 142 (24.1 min), 143 (29.4 min) and 144 (60.1 min). Syntheses starting with chiral R and S Ethyl nipecotate tartrates confirmed the stereochemistry at the 3-position of the piperidine ring. The resulting diastereomers were separated utilizing the same conditions.

Example 107

Synthesis of (S)-3-Styryl-piperidine-1-carboxylic acid benzyl ester

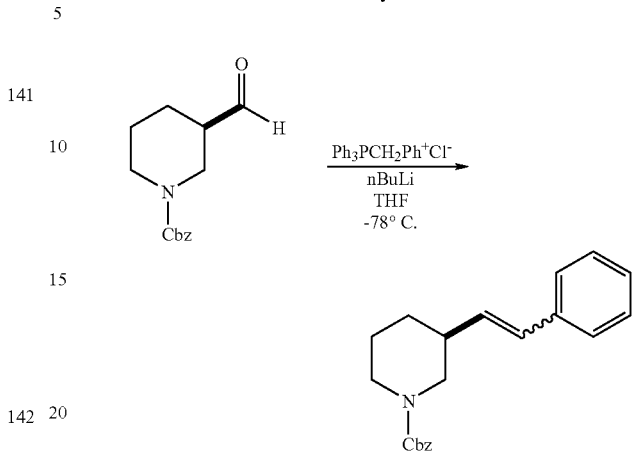

A solution of $Ph_3PCH_2Ph^+Cl^-$ (1.5 equiv, 5.12 mmol, 1.99 g) in THF (10 mL) was treated with nBuLi (1.5 equiv, 1.6M, 3.25 mmol, 2.04 mL) at −78° C. The solution was warmed to 0° C. for 30 min and then cooled again to −78° C. A solution of CBZ-piperdine-3-carboxaldehyde (3.41 mmol, 844 mg) in THF (5 mL) was added to the above reaction mixture at −78° C. The reaction stirred for 12 h. The reaction mixture was quenched with 10% HCl (20 mL) and then extracted with EtOAc (2×50 mL). The combined organics were dried with $NaCl_{(sat)}$ and $Na_2SO_{4(s)}$. The solvents were removed in vacuo and chromatography (Isco Combi-Flash, 35 g cartridge, 9:1 Hexane-EtOAc) provided the olefin (647 mg, 1.10 mg theoretical, 59%) as a colorless oil: $R_f$ 0.41 ($SiO_2$, 6:1 hexane-EtOAc); LRMS m/z 322 (M$^+$+1, $C_{21}H_{23}NO_2$, requires 322).

Example 108

Synthesis of (R)-3-Phenethyl-piperidine

A solution of the olefin (0.0638 mol, 20.51 g) in $CH_3OH$ (120 mL) was treated 30% Pd—C (200 mg) and $H_2$ (Parr Hydrogenator, 65 psi). The reaction was shaken for 4 h. The reaction mixture was filtered through celite, and the solvents were removed in vacuo to provide 3-phenethyl-piperidine (12.08 g, 12.08 g theoretical, quantitative) as a colorless oil: LRMS m/z 190 (M$^+$+1, $C_{13}H_{19}N$, requires 190).

Example 109

Synthesis of (R)-1-(4-Chloro-phenyl)-2-(3-phenethyl-piperidin-1-yl)-ethanone

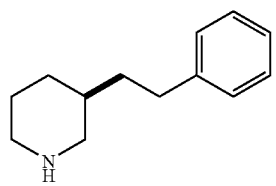

+

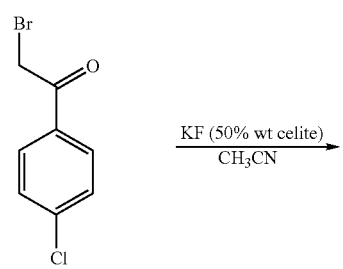

KF (50% wt celite)
———————→
CH₃CN

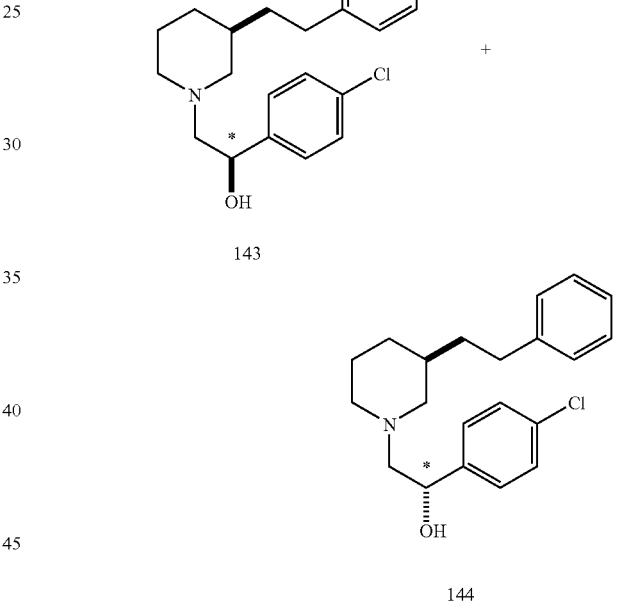

A solution of 3-phenethyl piperidine (0.0158 mol, 3.00 g), 2-bromo-4'-chloroacetophenone (1.0 equiv, 0.0158 mmol, 3.69 g) and KF (50% wt on celite) (8.0 equiv, 0.127 mol, 14.73 g) in CH₃CN (50 mL) was stirred at rt for 12 h. The reaction mixture was then filtered, and the solvents were removed in vacuo. Chromatography (Isco Combi-Flash, 35 g cartridge, 7:1 Hexane-EtOAc) provided 145 (2.88 g, 5.40 g theoretical, 53%) as a colorless oil: $R_f$ 0.37 (SiO₂, 5:1 hexane-EtOAc); LRMS m/z 342 (M⁺+1, C₂₁H₂₄ClNO, requires 342).

Example 110

Synthesis of 1-(4-Chloro-phenyl)-2-(3-phenethyl-piperidin-1-yl)-ethanol

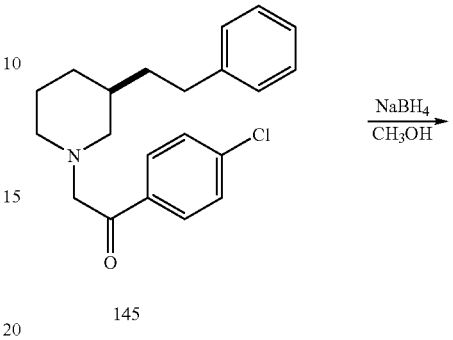

* denotes stereochemistry randomly assigned

A solution of 145 (8.16 mmol, 2.79 g) in CH₃OH (40 mL) was treated with NaBH₄ (2.0 equiv, 16.32 mmol, 617 mg) at 0° C. The reaction mixture was allowed to warm to rt and stirred for 12 h. The reaction mixture was quenched with pH 7 phosphate buffer (100 mL) and extracted with EtOAc (2×100 mL). The combined organics were dried with NaCl$_{(sat)}$ and Na₂SO₄$_{(s)}$. The solvents were removed in vacuo and chromatography (Isco Combi-Flash, 110 g cartridge, CH₂Cl₂ with 2% CH₃OH) provided 143 and 144 as a mixture of diastereomers (1.91 g, 2.81 g theoretical, 68%) as a colorless oil: $R_f$ 0.36 (SiO₂, 3:1 Hexane-EtOAc); LRMS m/z 344 (M⁺+1, C₂₁H₂₆ClNO, requires 344). 143 and 144 were separated on a Chiralpak AD column using 85:15 hexane (0.2% DEA) and isopropanol as the eluent. The retention times are as follow: 143 (30.35 min) and 144 (65.32 min).

Example 111

Synthesis of (S)-3-Styryl-piperidine-1-carboxylic acid benzyl ester

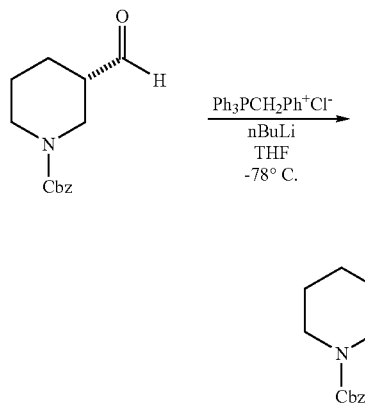

A solution of $Ph_3PCH_2Ph^+Cl^-$ (3.0 equiv, 28.05 mmol, 10.90 g) in THF (20 mL) was treated with nBuLi (3.0 equiv, 2.5M, 28.05 mol, 11.2 mL) at −78° C. The solution was warmed to 0° C. for 30 min and then cooled again to −78° C. A solution of S-piperdine carboxaldehyde (9.35 mmol, 2.31 g) in THF (20 mL) was added to the above reaction mixture at −78° C. The reaction stirred for 12 h. The reaction mixture was quenched with 10% HCl (10 mL) and then extracted with EtOAc (2×25 mL). The combined organics were dried with $NaCl_{(sat)}$ and $Na_2SO_{4(s)}$. The solvents were removed in vacuo and chromatography (Isco Combi-Flash, 110 g cartridge, 9:1 Hexane-EtOAc) provided the olefin (1.36 g, 3.01 g theoretical, 45%) as a colorless oil: $R_f$ 0.41 ($SiO_2$, 6:1 hexane-EtOAc); LRMS m/z 322 ($M^+$+1, $C_{21}H_{23}NO_2$, requires 322).

Example 112

Synthesis of (S)-3-Phenethyl-piperidine

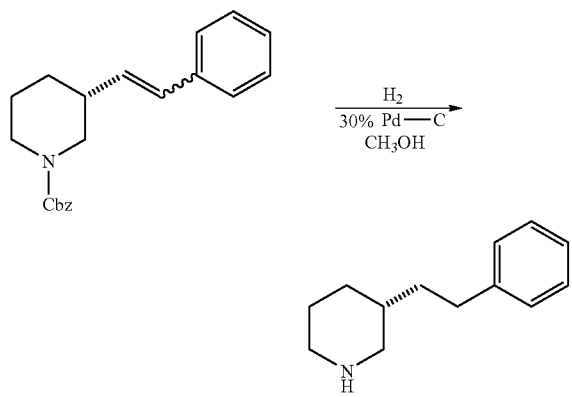

A solution of the olefin (4.23 mmol, 1.36 mg) in $CH_3OH$ (10 mL) was treated 30% Pd—C (50 mg) and $H_2$ (Parr Hydrogenator, 65 psi). The reaction was shaken for 4 h. The reaction mixture was filtered through celite, and the solvents were removed in vacuo to provide 3-phenethyl-piperidine (801 mg, 801 mg theoretical, quantitative) as a colorless oil: LRMS m/z 190 ($M^+$+1, $Cl_{13}H_{19}N$, requires 190).

Example 113

Synthesis of (S)-1-(4-Chloro-phenyl)-2-(3-phenethyl-piperidin-1-yl)-ethanone

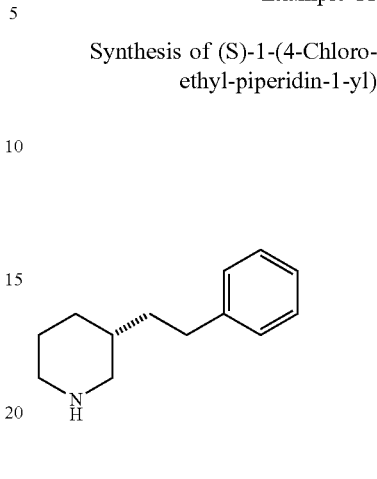

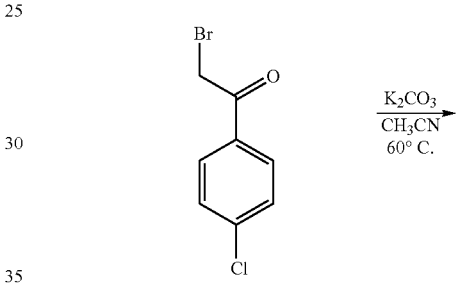

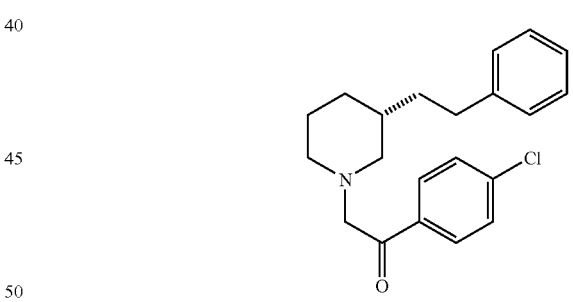

A solution of (S)-3-phenethyl-piperidine (4.23 mmol, 801 mg), 2-bromo-4'-chloroacetophenone (1.5 equiv, 6.35 mmol, 1.48 g) and $K_2CO_3$ (2.0 equiv, 8.46 mmol, 1.17 g) in $CH_3CN$ (10 mL) was heated to 60° C. and stirred for 12 h. The reaction mixture was quenched with $H_2O$ (25 mL) and then extracted with EtOAc (2×50 mL). The combined organics were dried with $NaCl_{(sat)}$ and $Na_2SO_{4(s)}$. The solvents were removed in vacuo and chromatography (Isco Combi-Flash, 110 g cartridge, 9:1 Hexane-EtOAc) provided the desired product (0.556 mg, 1.45 mg theoretical, 38%) as a colorless oil: $R_f$ 0.37 ($SiO_2$, 5:1 hexane-EtOAc); LRMS m/z 342 ($M^+$+1, $C_{21}H_{24}ClNO$, requires 342).

Example 114

Synthesis of 1-(4-Chloro-phenyl)-2-(3-phenethyl-piperidin-1-yl)-ethanol

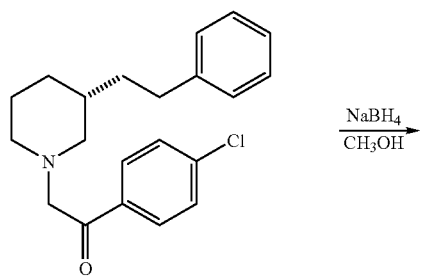

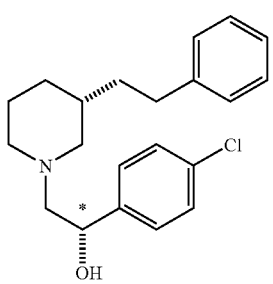

141

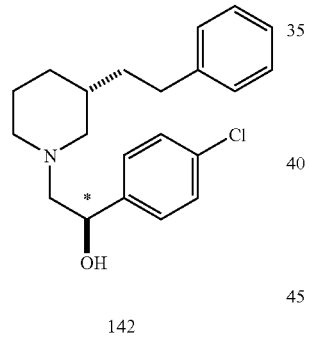

142

* denotes stereochemistry randomly assigned

A solution of the ketone (1.63 mmol, 556 mg) in CH$_3$OH (5 mL) was treated with NaBH$_4$ (3.0 equiv, 4.89 mmol, 185 mg) at 0° C. The reaction mixture was allowed to warm to rt and stirred for 12 h. The reaction mixture was quenched with pH 7 phosphate buffer (20 mL) and extracted with EtOAc (2×30 mL). The combined organics were dried with NaCl$_{(sat)}$ and Na$_2$SO$_{4(s)}$. The solvents were removed in vacuo and chromatography (Isco Combi-Flash, 35 g cartridge, 1:1 Hexane-EtOAc) provided 141 and 142 as a mixture of diastereomers (366 mg, 561 mg theoretical, 65%) as a colorless oil: R$_f$ 0.36 (SiO$_2$, 3:1 Hexane-EtOAc); LRMS m/z 344 (M$^+$+1, C$_{21}$H$_{26}$ClNO, requires 344). 141 and 142 were separated on a Chiralpak AD column using 85:15 hexane (0.2% DEA) and isopropanol as the eluent. The retention times are as follow: 141 (20.19 min) and 142 (23.22 min).

Example 115

Synthesis of [1-(4-Chloro-phenyl)-cyclobutyl]-(3-phenethyl-piperidin-1-yl)-methanone

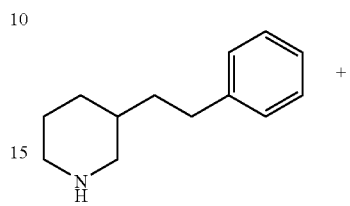

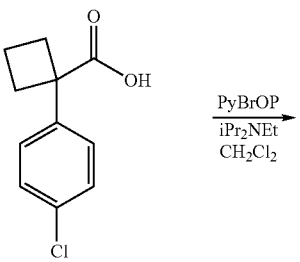

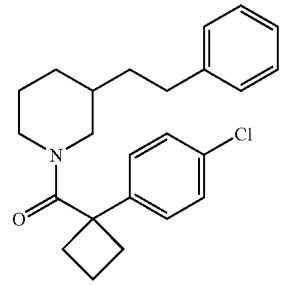

146

A solution of 3-phenethyl piperdine (0.449 mmol, 85 mg) and 1-(4-chloro-phenyl)-cyclobutanecarboxylic acid (1.5 equiv, 0.674 mmol, 142 mg) in CH$_2$Cl$_2$ (1 mL) was treated with PyBrOP (1.5 equiv, 0.674 mmol, 314 mg) and iPr$_2$Net (3.0 equiv, 1.35 mmol, 235 μL) at 0° C. The reaction mixture stirred for 12 h while warming to rt. The reaction mixture was quenched with 10% HCl (10 mL) and then extracted with EtOAc (2×15 mL). The combined organics were washed with NaHCO$_3$(sat) and dried with NaCl$_{(sat)}$ and Na$_2$SO$_{4(s)}$. The solvents were removed in vacuo and chromatography (PTLC, SiO$_2$, 20 cm×20 cm, 1 mm, 6:1 hexane-EtOAc) provided 146 (114 mg, 171 mg theoretical, 67%) as a colorless oil: R$_f$ 0.36 (SiO$_2$, 6:1 hexane-EtOAc); LRMS m/z 382 (M$^+$+1, C$_{24}$H$_{28}$ClNO, requires 382).

Example 116

Synthesis of 1-[1-(4-Chloro-phenyl)-cyclobutylmethyl]-3-phenethyl-piperidine

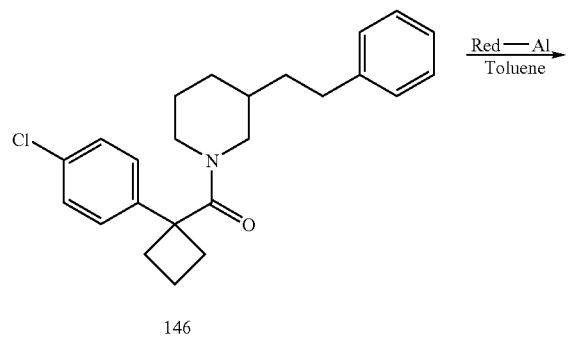

A solution of 146 (0.262 mmol, 100 mg) in toluene (1 mL) at 0° C. was treated with 3.0 M Red-Al (65% wt in toluene) (3.0 equiv, 0.815 mmol) under Ar. The reaction mixture stirred for 12 h and returned to 25° C. The reaction mixture was then cooled to 0° C., quenched with 10% aqueous NaOH and extracted with 3×EtOAc (25 mL). The organics were dried with NaCl$_{(sat)}$ and Na$_2$SO$_{4(s)}$. The reaction mixture was purified by chromatography (PTLC, SiO$_2$, 20 cm×20 cm, 1 mm, 6:1 hexane-acetone) which provided 147 (80 mg, 96 mg theoretical, 83%) as a colorless oil: R$_f$ 0.48 (SiO$_2$, 6:1 hexane-acetone); LRMS m/z 369 (M$^+$+1, C$_{24}$H$_{30}$ClN, requires 369).

Example 117

Synthesis of 3-[2-(4-Trifluoromethyl-phenyl)-vinyl]-piperidine-1-carboxylic acid benzyl ester

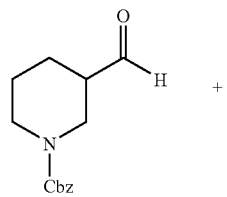

+

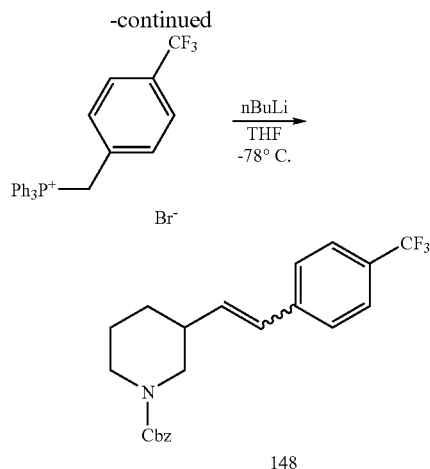

A solution of the wittig salt (1.5 equiv, 12.03 mmol, 6.03 g) in THF (40 mL) was treated with nBuLi (1.5 equiv, 2.5M, 12.03 mmol, 4.8 mL) at −78° C. The solution was warmed to 0° C. for 30 min and then cooled again to −78° C. A solution of piperidine-3-carbaldehyde (8.02 mmol, 1.98 g) in THF (10 mL) was added to the above reaction mixture at −78° C. The reaction stirred for 12 h. The reaction mixture was quenched with 10% HCl (20 mL) and then extracted with EtOAc (2×50 mL). The combined organics were dried with NaCl$_{(sat)}$ and Na$_2$SO$_{4(s)}$. The solvents were removed in vacuo and chromatography (Isco Combi-Flash, 110 g cartridge, 9:1 Hexane-EtOAc) provided 148 (2.08 g, 3.21 g theoretical, 67%) as a colorless oil: R$_f$ 0.44 (SiO$_2$, 6:1 hexane-EtOAc); LRMS m/z 390 (M$^+$+1, C$_{22}$H$_{22}$F$_3$NO$_2$, requires 390).

Example 118

Synthesis of 3-[2-(4-Trifluoromethyl-phenyl)-ethyl]-piperidine

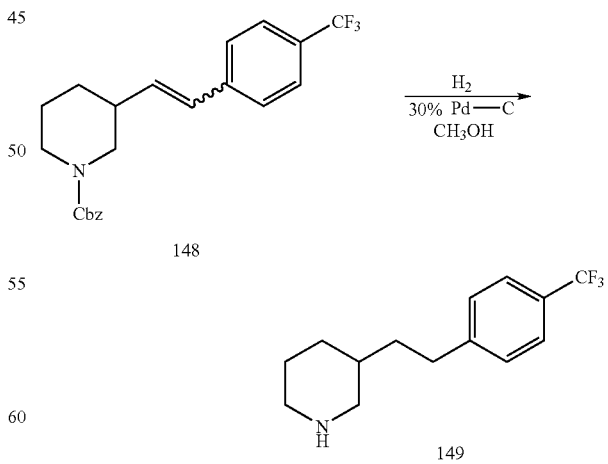

A solution of 148 (5.34 mmol, 2.08 g) in CH$_3$OH (30 mL) was treated with 30% Pd—C (500 mg) and H$_2$ (Parr Hydrogenator, 65 psi). The reaction was shaken for 4 h. The reaction mixture was filtered through celite, and the solvents were removed in vacuo to provide 149 (2.08 g, 2.08 g theoretical, quantitative) as a colorless oil: LRMS m/z 258 (M⁺+1, $C_{14}H_{18}F_3N$, requires 258).

Example 119

Synthesis of 1-(4-Chloro-phenyl)-2-{3-[2-(4-trifluoromethyl-phenyl)-ethyl]-piperidin-1-yl}-ethanone

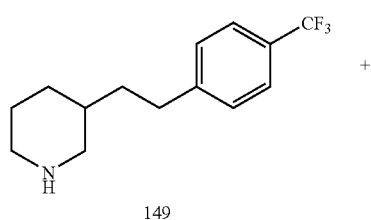

149

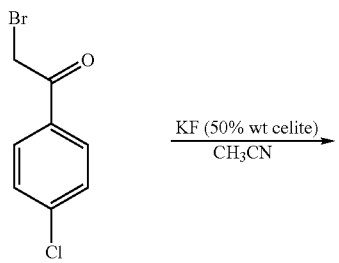

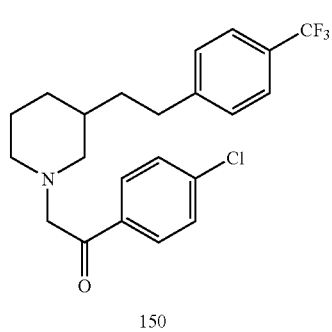

150

A solution of 149 (0.777 mmol, 200 mg), 2-bromo-4'-chloroacetophenone (1.0 equiv, 0.777 mmol, 182 mg) and KF (50% wt on celite) (7.0 equiv, 5.44 mol, 632 mg) in $CH_3CN$ (5 mL) was stirred for 12 h. The reaction mixture was filtered, and the solvents were removed in vacuo. Chromatography (Isco Combi-Flash, 35 g cartridge, 2:1 Hexane-EtOAc) provided 150 (178 mg, 318 mg theoretical, 56%) as a colorless oil: $R_f$ 0.24 (SiO₂, 2:1 hexane-EtOAc); LRMS m/z 410 (M⁺+1, $C_{22}H_{23}ClF_3NO$, requires 410).

Example 120

Synthesis of 1-(4-Chloro-phenyl)-2-{3-[2-(4-trifluoromethyl-phenyl)-ethyl]-piperidin-1-yl}-ethanol

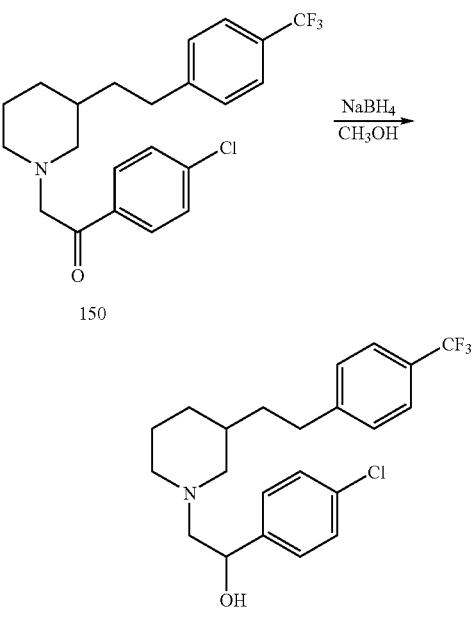

151/152/153/154

A solution of 150 (0.398 mmol, 163 mg) in $CH_3OH$ (2 mL) was treated with $NaBH_4$ (1.5 equiv, 0.597 mmol, 23 mg) at 0° C. The reaction mixture was allowed to warm to rt and stirred for 12 h. The reaction mixture was quenched with pH 7 phosphate buffer (5 mL) and extracted with EtOAc (2×10 mL). The combined organics were dried with $NaCl_{(sat)}$ and $Na_2SO_{4(s)}$. The solvents were removed in vacuo and chromatography (Isco Combi-Flash, 35 g cartridge, 1:1 Hexane-EtOAc) provided 151, 152, 153, and 154 as a mixture of diastereomers (124 mg, 164 mg theoretical, 76%) as a colorless oil: $R_f$ 0.38 (SiO₂, 2:1 Hexane-EtOAc); LRMS m/z 412 (M⁺+1, $C_{22}H_{25}ClF_3NO$, requires 412).

Example 121

Separation of 151, 152, 153, and 154

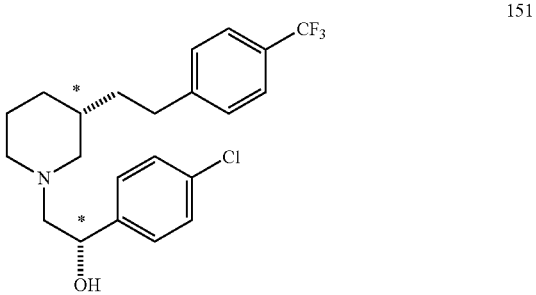

151

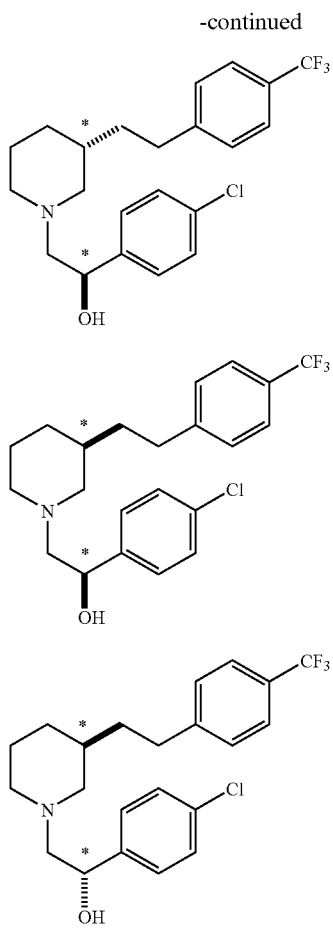

*denotes stereochemistry randomly assigned

The four diastereomers were dissolved in 90:10 hexane (0.2% DEA) and isopropanol at a concentration of 100 mg/mL. The compounds were separated on a Chiralpak AD column using 85:15 hexane (0.2% DEA) and isopropanol providing the following retention times: 151 (23.75 min), 152 (23.75 min), 153 (29.27 min) and 154 (45.1 min). Since 151 and 152 eluted as one peak, the compounds were separated using a Chiralpak AD column using 90:10 methanol, acetonitrile (0.1% DEA) providing the following retention times 151 (9.26 min), and 152 (10.68 min).

Example 122

Synthesis of 1-[1-(4-Chloro-phenyl)-cyclobutyl]-2-{3-[2-(4-trifluoromethyl-phenyl)-ethyl]-piperidin-1-yl}-ethanone

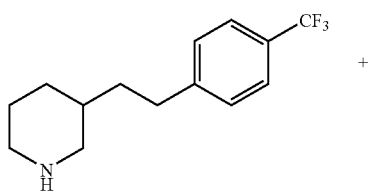

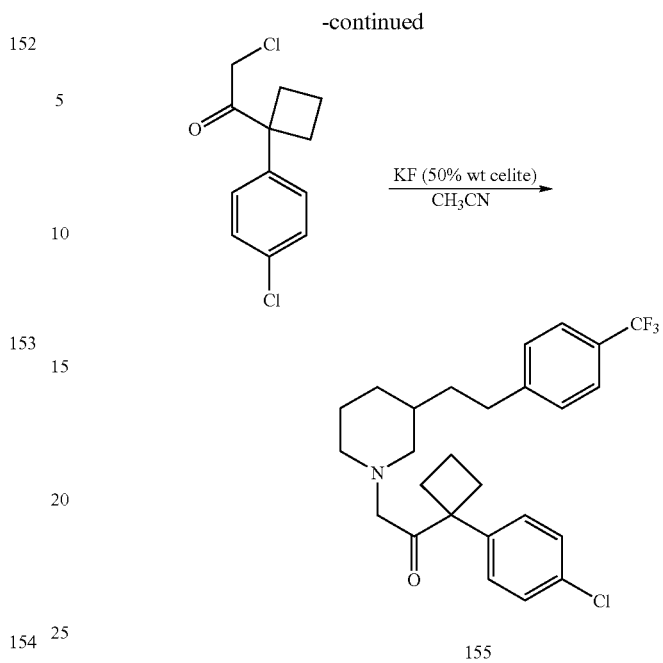

A solution of 149 (0.411 mmol, 106 mg), 2-chloro-1-[1-(4-chloro-phenyl)-cyclobutyl]-ethanone (1.0 equiv, 0.411 mmol, 100 mg) and KF (50% wt on Celite) (7.0 equiv, 2.88 mol, 335 mg) in $CH_3CN$ (3 mL) was stirred for 12 h. The reaction mixture was filtered, and the solvents were removed in vacuo. Chromatography (Isco Combi-Flash, 10 g cartridge, 2:1 Hexane-EtOAc) provided 155 (136 mg, 168 mg theoretical, 81%) as a colorless oil: $R_f$ 0.38 ($SiO_2$, 2:1 hexane-EtOAc); LRMS m/z 465 ($M^+$+1, $C_{26}H_{29}ClF_3NO$, requires 465).

Example 123

Spontaneous Locomotor Activity in Rats

Animals

Male Sprague-Dawley rats, (Iffa Crédo, Saint-Germain/L'Arbresle, France), weighing 200–250 g at the beginning of the study, were used.

During acclimatization period, rats were housed, 2 or 3 per cage, in Makrolon type III cages, in the animal room (temperature: 20±2° C., humidity: minimum 45%, air changes: >12 per hour, light/dark cycle of 12 h/12 h [on at 7:00 A.M.]). Animals were allowed a minimum of 5 days period before experiment for acclimatization.

Rats received food (TrouwNutrition, Vigny, France) and water (tap water in water bottle) ad libitum. Rats were placed on a sawdust bedding in their cages (Goldchips, Trouw Nutrition, Vigny, France). On the day before experiments, food was withdrawn to have animals fasted overnight.

Preparation of the Test Substance(s) Suspension and of the Reference Compound

On the day of experiment, test item(s) were solubilized in 5% dextrose (w/v)/polyethylene glycol (PEG) 400 (4:1 v/v).

Administrations

All test compounds were administered at 20 mg/kg as a single i.p. dose.

187

Locomotor Activity Measurements

Twenty, 60 and 120 minutes after administration, rats were placed in a plastic box 30×30 cm in a room with low light intensity (maximum 50 lux). Locomotor activity was determined during 20 min periods using a video image analyzer (Videotrack, View Point, France). Number of occurences, distance and duration of fast and slow movements, number of occurences and duration of periods of inactivity and number of rears were measured.

Results

Rats treated with compounds 114, 115, 113, and 110 exhibit a significant increase in locomotor activity compared to control animals at 60 minutes after i.p. administration at a dose of 20 mg/kg.

Example 124

Acute Toxicity Assessments

An in vivo evaluation was carried out to determine the maximum tolerated dose of numerous test compounds in two animal species (mouse and rat). The compounds were administered i.v. and the animals were then observed for 72 h. Compounds 114, 115, 113, 110, 124, 125, 129, and 130 were solubilized in 5% dextrose (w/v)/polyethylene glycol 400 (4:1 v/v). Compounds 126, 127, 131, and 132 were solubilized in 10% hydroxypropyl-β-cyclodextrin (w/v).

Compounds 114, 115, 113, 110, 125, 127, 131, 130, and 132 administered at 30 mg/kg i.v. were well tolerated by the animals and did not cause any mortality after 72 h in mice and rats. Compound 129 administered i.v. was well tolerated by mice and rats after 72 h at 20 mg/kg and 30 mg/kg respectively. Compounds 124 and 126 administered at 10 mg/kg i.v. were well tolerated by the animals and did not cause any mortality after 72 h in mice and rats.

Compounds 143 and 144 administered at 5 mg/kg i.v. were tolerated by the animals and did not cause any mortality after 72 h in mice and rats.

Example 125

Synthesis of 1-[1-(4-Chloro-phenyl)-cyclobutylmethyl]-3-94-trifluoromethyl-phenoxy)-piperidine

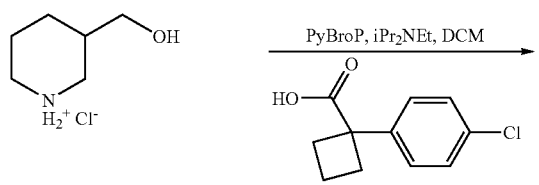

188

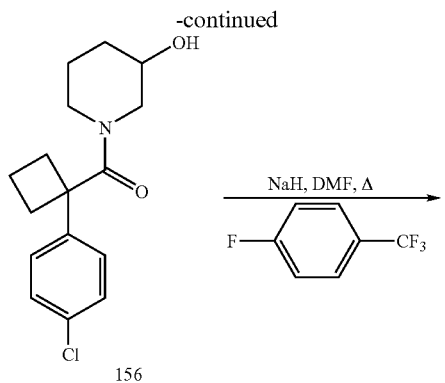

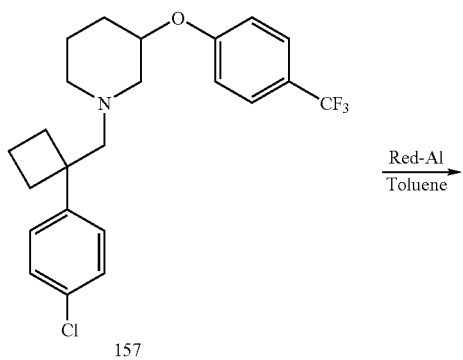

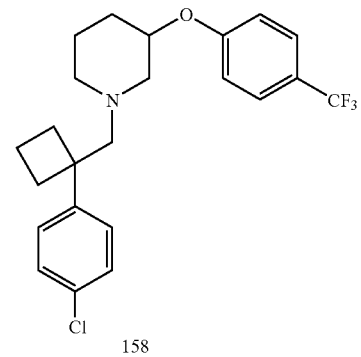

To 3-hydroxypiperidine hydrochloride (1.0 g, 7.3 mmol) in DCM (40 mL) was added 1-(4-chlorophenyl)-1-cyclobutane carboxylic acid (2.3 g, 10.9 mmol) and iPr$_2$NEt (6.3 mL, 36.3 mmol) followed by PyBroP (5.1 g, 10.9 mmol). The resulting solution was allowed to stir overnight at room temperature before diluting with ethyl acetate and quenching with 10% KOH. The layers were separated and the aqueous layer further washed with ethyl acetate. The combined organic layers were then dried (MgSO$_4$), filtered and concentrated in vacuo. The resulting residue was purified by flash column chromatography using 40% ethyl acetate/ petroleum ether to provide the desired amide 156 (1.74 g, 82%).

To a solution of 156 (500 mg, 1.7 mmol) in DMF (10 mL) at room temperature was added NaH (205 mg, 60% wt., 5.1 mmol) and the suspension allowed to heat to 70° C. After stirring at this temperature for 40 minutes, 4-fluorobenzenetrifluoride was added and the reaction allowed to continue at this temperature for two and one half hours before adding an additional portion of 4-fluorobenzenetrifluoride (0.10 mL) and stirring for an additional hour. The reaction mixture was then diluted with ethyl acetate and quenched by the addition of brine. The organic layer was separated and the aqueous layer further washed with ethyl acetate. The combined organic extracts were then dried (MgSO$_4$), filtered and concentrated in vacuo. The resulting residue was purified by flash column chromatography using 20% ethyl acetate/petroleum ether to provide the desired ether 157 (246 mg, 33%). LRMS calculated for $C_{23}H_{23}ClF_3NO_2$ 437.14, found (M+) 438.60.

To amide 157 (100 mg, 0.23 mmol) in toluene (1 mL) was cautiously added Red-Al (0.24 mL, 0.80 mmol). The resulting solution was allowed to stir at room temperature for one hour before adding an additional portion of Red-Al (0.10 mL, 0.34 mmol) and stirring at room temperature overnight. The reaction was then diluted with ethyl acetate and quenched with 10% aqueous KOH. The layers were separated and the aqueous layer further washed with ethyl acetate. The combined organic layers were then dried (MgSO$_4$), filtered and concentrated in vacuo. The resulting residue was purified by flash column chromatography using 1% 2M NH$_3$ in EtOH/DCM to provide the desired amine 158 (69 mg, 71%). LRMS calculated for $C_{23}H_{25}ClF_3NO$ 423.16, found (M+) 424.31. $^1$H NMR (300 MHz, CDCl$_3$): 7.50 (d, J=8.9 Hz, 2H), 7.24 (d, J=8.4 Hz, 2H), 7.08 (d, J=8.3 Hz, 2H), 6.71 (d, J=8.5 Hz, 2H), 4.06–4.16 (m, 1H), 2.71–2.76 (m, 1H), 2.53–2.58 (m, 2H), 2.42–2.46 (m, 1H), 1.92–2.25 (m, 8H), 1.75–1.88 (m, 1H), 1.60–1.68 (m, 1H), 1.41–1.56 (m, 1H), 1.25–1.38 (m, 1H). $^{13}$C NMR (75 MHz, CDCl$_3$): 160.0, 148.2, 130.9, 127.8, 127.6, 126.9, 122.6 (m), 119.1, 115.2, 73.1, 67.8, 59.2, 55.6, 47.0, 31.6, 31.2, 29.8, 23.7, 15.9.

Example 126

Synthesis of 1-[4-(4-Chloro-phenyl)-tetrahydropyran-4-ylmethyl]-3-(4-trifluoromethyl-phenoxymethyl)piperidine

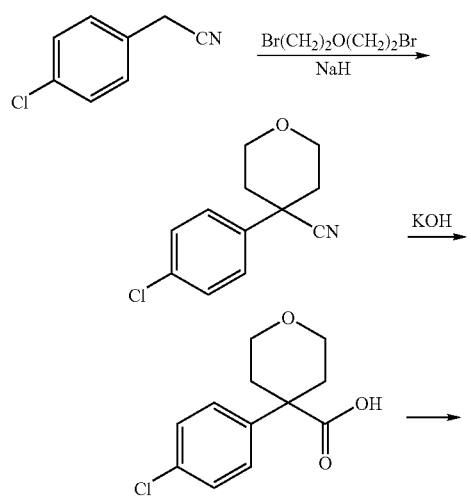

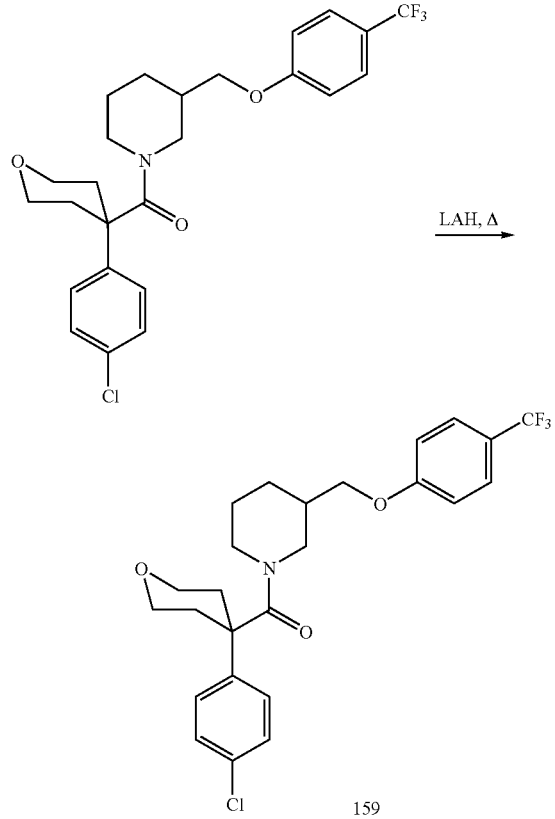

Into a round-bottom flask under argon fitted with an addition funnel and thermometer was added anhydrous dimethylsulfoxide (60 mL) and sodium hydride (1.17 g, 48.8 mmol, 95%). Then a solution of (4-chlorophenyl)acetonitrile (3.37 g, 22.2 mmol) and 2-bromoethyl ether (90%, 3.41 mL, 24.4 mmol) in diethyl ether (15 mL) was added slowly, while maintaining the reaction temperature at 20–30° C. The reaction mixture was maintained at room temperature for overnight. The reaction mixture was carefully quenched with water (50 mL) and then extracted with hexane (3×100 mL). The organic extracts were combined, washed with water (3×75 mL), brine (50 mL), dried over anhydrous magnesium sulfate, filtered, and concentrated to give a pale yellow oil. The oil was purified by column chromatography on silica gel using hexane/ethyl acetate (80:20) to give 4.7 g of 4-(4-chlorophenyl)tetrahydropyran-4-carbonitrile, as a colorless oil. $^1$H NMR (CDCl$_3$, 300 MHz): δ 2.00–2.15 (m, 4H); 3.89 (dt, 2H, J$_1$=12.6 Hz, J$_2$=3 Hz); 4.05–4.11 (m, 2H); 7.37–7.45 (m, 4H); $^{13}$C NMR (CDCl$_3$, 300 MHz): δ 36.66 (2C), 41.51, 64.98 (2C), 121.40, 127.03, 129.37, 134.31, 138.46.

Into a round-bottom flask was added 4-(4-chlorophenyl)tetrahydropyran-4-carbonitrile (0.442 g, 2 mmol), bis-(hydroxyethyl)ether (6 mL), and potassium hydroxide (0.337 g, 5.96 mmol). The reaction mixture was heated at 215° C. for 3 h. The reaction mixture was allowed to cool to room temperature, carefully quenched with water (20 mL) and then washed with diethyl ether (2×20 mL). The aqueous layer was made acidic with the addition of concentrated HCl. The aqueous layer was extracted with diethyl ether (2×20 mL). These extracts were combined, washed with brine (15 mL), dried over anhydrous sodium sulfate, filtered, and concentrated to give 0.32 g of 4-(4-chlorophenyl)tetrahydropyran-4-carboxylic acid, as a tan solid. $^1$H NMR (d$_4$-methanol, 300 MHz): δ 1.86–1.96 (m, 2H); 2.45–2.51 (m, 2H); 3.56–3.65 (m, 2H); 3.86–3.93 (m, 2H); 7.33–7.44 (m, 4H); $^{13}$C NMR (d$_4$-methanol, 300 MHz): δ 35.62 (2C), 66.76 (2C), 128.79, 129.77, 134.22, 143.34, 177.29.

Into a round-bottom flask was added 3-(4-trifluoromethylphenoxymethyl)piperidine (29.8 mg, 0.115 mmol), dichloromethane (0.5 mL), 4-(4-chlorophenyl)tetrahydropyran-4-carboxylic acid (30.4 mg, 0.127 mmol), diisopropylethylamine (0.0442 mL, 0.254 mmol), and bromotris(dimethylamino)phosphonium hexafluorophosphate (0.049 g, 0.127 mmol). The reaction mixture was stirred at room temperature overnight. The reaction mixture was diluted with 5% aqueous hydrochloric acid (10 mL) and then extracted with ethyl acetate (2×20 mL). The extracts were combined, washed with brine (7 mL), dried over anhydrous sodium sulfate, filtered, and concentrated to give a colorless oil. The oil was purified by column chromatography on silica gel using hexane/ethyl acetate (2:1) to give 30.8 mg of the amide, as a colorless oil.

Into a round-bottom flask was added the amide (30.8 mg, 0.064 mmol), tetrahydrofuran (2 mL), lithium aluminum hydride (0.160 mL of a 1M THF solution, 0.160 mmol). The reaction mixture was heated at reflux for 1 h and then allowed to cool to room temperature. The reaction mixture was carefully quenched with 2.5% aqueous sodium potassium tartrate (10 mL) and then extracted with ethyl acetate (2×10 mL). The extracts were combined, washed with brine (5 mL), dried over anhydrous sodium sulfate, filtered, and concentrated to give a colorless oil. The oil was purified by column chromatography on silica gel using hexane/ethyl acetate/2N ammonia in ethanol (85:14:1) to give 17.8 mg of 159, as a colorless oil. $^1$H NMR (CDCl$_3$, 300 MHz): δ 1.02–1.10 (m, 1H); 1.39–1.66 (m, 3H); 1.82–1.94 (m, 4H); 2.04–2.12 (m, 3H); 2.25–2.41 (m, 4H); 3.47–3.53 (m, 2H); 3.68–3.77 (m, 4H); 6.89 (d, 2H, J=8.4 Hz); 7.23–7.31 (m, 4H); 7.54 (d, 2H, J=8.4 Hz); $^{13}$C NMR (CDCl$_3$, 300 MHz): δ 25.09, 26.74, 34.10, 36.45, 41.34, 56.87, 59.41, 64.41, 70.27, 70.85, 114.56, 122.63, 122.90, 127.03, 128.43, 128.93, 131.83, 143.53, 161.67.

Example 127

Synthesis of (R) and (S) 2-bromo-1-[1-(4-chlorophenyl)-cyclobutyl]-ethanol

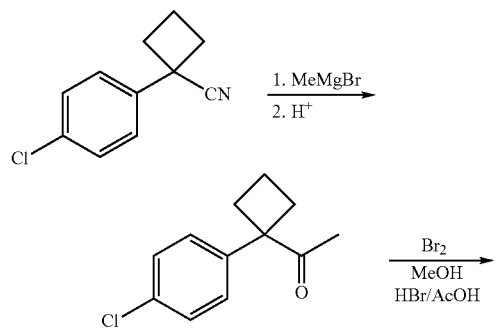

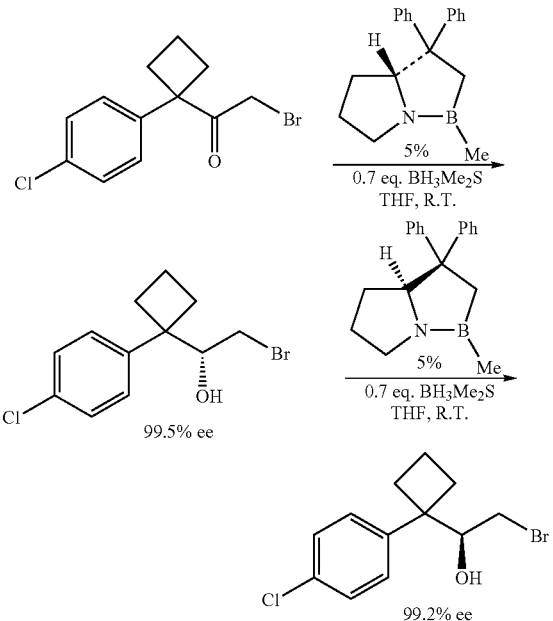

The methyl ketone was prepared from the corresponding nitrile as follows. To a solution of the carbonitrile (40 g) in 100 mL toluene solution was added 200 mL MeMgBr ether solution (3.0 M, 3 eq.). The reaction mixture was heated to boiling under nitrogen with a 95° C. oil bath to distill away the ether solvent and subsequently kept under that temperature overnight. The reaction mixture was cooled to room temperature and then poured into a second flask containing 500 mL water. It was acidified by the addition of 5 M hydrochloric acid (500 mL) and the mixture was brought to reflux for 2 h. The product was extracted into ether (3×200 mL) and the organic layers were combined and dried with Na$_2$SO$_4$. The solvent was then evaporated to supply pure methyl ketone (40 g, 92%). $^1$H NMR (CDCl$_3$, 300 MHz): δ (ppm) 7.36 (d, 2H), 7.19 (d, 2H), 2.72–2.81 (m, 2 H), 2.35–2.45 (m, 2H), 1.95 (s, 3H), 1.86–1.94 (m, 2H); $^{13}$C NMR (CDCl$_3$, 300 MHz): δ (ppm) 208.3, 141.9, 132.9, 129.1, 127.9, 59.0, 30.7, 24.6, 16.1.

The bromo ketone was prepared as follows. A mixture of methyl ketone (21.2 g, 0.102 mol) and methanol (80 mL) was cooled to 5° C. and acetic acid containing 30% HBr (0.8 mL) was added. Bromine (5 mL, 0.097 mol) was then added dropwise to this solution over a 20 min period while the temperature was maintained at 5° C. The reaction was kept at that temperature overnight. The reaction mixture was then poured into 250 mL water and the product was extracted into ether (3×250 mL). The organic layers were combined and dried with Na$_2$SO$_4$. The solvent was evaporated to supply pure bromo ketone (28 g, 96%), $^1$H NMR (CDCl$_3$, 300 MHz): δ (ppm) 7.40 (d, 2H), 7.22 (d, 2H), 3.90 (s, 2H), 2.51–2.90 (m, 2 H), 2.04–2.45 (m, 2H), 1.95–2.04 (m, 2H); $^{13}$C NMR (CDCl$_3$, 300 MHz): δ (ppm) 201.2, 140.6, 133.6, 129.4, 128.5, 57.8, 31.7, 31.4, 16.3.

Into a 500 mL three-necked flask, equipped with a magnetic stir bar, a nitrogen inlet, was charged with 150 mL anhydrous THF, (R)-2-methyl-CBS-oxazaborolidine (1.0 M in toluene, 4.35 mL, 4.35 mmol) and borane-methyl sulfide (2.0 M in THF, 2.2 mL, 4.4 mmol). The reaction flask was cooled to 0° C. A solution of the bromo ketone (25 g, 87 mmol) in anhydrous THF (50 mL) and more borane-methyl sulfide (2.0 M in THF, 28.2 mL, 56.4 mmol) were added simultaneously over a period of 2 h while the reaction was maintained at 0° C. Following the addition, the reaction was warmed up to room temperature and stirred for 10 h. The reaction was cooled to 0° C. again and MeOH (25 mL) was carefully added (gas evolution!). The reaction mixture concentrated in vacuo (Me$_2$S was trapped and oxidized with household bleach) and the residue dissolved in toluene (250 mL). The solution was washed with H$_2$SO$_4$ (0.2 M, 3×100 mL) and water (3×100 mL), dried (Na$_2$SO$_4$) and concentrated. The product was purified by column chromatography on silica gel using hexane/ethyl acetate (95:5) to give the (R)-bromo alcohol (23.1 g, 92%) as colorless oil, $[\alpha]^{25}_D$=−7.98 (c=1.19, CHCl$_3$), 99.5% ee; $^1$H NMR (CDCl$_3$, 300 MHz): δ (ppm) 7.32 (d, 2H), 7.14 (d, 2H), 4.09–4.13 (dd, 1H), 3.43–3.47 (dd, 1 H), 2.86–2.93 (t, 1H), 2.59–2.65 (m, 1H), 2.28–2.44 (m, 3H), 2.01–2.10 (m, 1H), 1.90–1.92 (m, 1H); $^{13}$C NMR (CDCl$_3$, 300 MHz): δ (ppm) 143.5, 132.4, 128.8, 128.4, 50.1, 37.4, 31.2, 30.6, 16.2.

Into a 500 mL three-necked flask, equipped with a magnetic stir bar, a nitrogen inlet, was charged with 150 ml anhydrous THF, (s)-2-methyl-CBS-oxazaborolidine (1.0 M in toluene, 4.35 mL, 4.35 mmol) and borane-methyl sulfide (2.0 M in THF, 2.2 mL, 4.4 mmol). The reaction flask was cooled to 0° C. A solution of the bromo ketone (25 g, 87 mmol) in anhydrous THF (50 mL) and more borane-methyl sulfide (2.0 M in THF, 28.2 mL, 56.4 mmol) were added simultaneously over a period of 2 h while the reaction was maintained at 0° C. Following the addition, the reaction was warmed up to room temperature and stirred for 10 h. The reaction was cooled to 0° C. again and MeOH (25 mL) was carefully added (gas evolution!). The reaction mixture concentrated in vacuo (Me$_2$S was trapped and oxidized with household bleach) and the residue dissolved in toluene (250 mL). The solution was washed H$_2$SO$_4$ (0.2 M, 3×100 mL) and water (3×100 mL), dried (Na$_2$SO$_4$) and concentrated. The product was purified by column chromatography on silica gel using hexane/ethyl acetate (95:5) to give the (S)-bromo alcohol (24.8 g, 99%) as colorless oil, $[\alpha]^{25}_D$=+8.24 (c=0.85, CHCl$_3$), 99.2% ee; $^1$H NMR (CDCl$_3$, 300 MHz): δ (ppm) 7.32 (d, 2H), 7.14 (d, 2H), 4.09–4.13 (dd, 1H), 3.43–3.47 (dd, 1 H), 2.86–2.93 (t, 1H), 2.59–2.65 (m, 1H), 2.28–2.44 (m, 3H), 2.01–2.10 (m, 1H), 1.90–1.92 (m, 1H); $^{13}$C NMR (CDCl$_3$, 300 MHz): δ (ppm) 143.5, 132.4, 128.8, 128.4, 50.0, 37.4, 31.2, 30.6, 16.1.

Example 128

Synthesis of 2R-2-[1-(4-Chloro-phenyl)-cyclobutyl]-oxirane

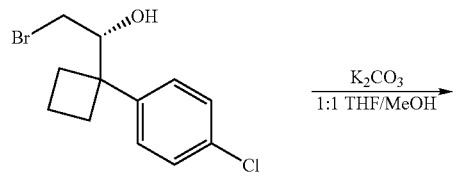

-continued

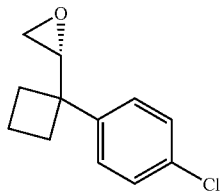

A 500 mL round bottom flask was charged with 2R-bromo-1-[1-(4-chloro-phenyl)-cyclobutyl]-ethanol (4.86 g; 16.8 mmol), THF (100 mL), MeOH (100 mL) and potassium carbonate (4.63 g; 33.6 mmol). The reaction mixture was stirred at 20° C. for 3 hours and then diluted with hexanes, filtered and concentrated in vacuo. The crude material was purified by flash chromatography (hexanes/EtOAc 97:3) to give pure product (3.0 g; 86% yield).

The enantiomeric epoxide (2S-2-[1-(4-Chloro-phenyl)-cyclobutyl]-oxirane) was also prepared according to the procedure described above, using 2S-bromo-1-[1-(4-chloro-phenyl)-cyclobutyl]-ethanol (5.0 g, 17.3 mmol), THF (100 mL), MeOH (100 mL), and potassium carbonate (4.77 g, 34.5 mmol). The crude material was purified by flash chromatography (hexanes/EtOAc 97:3) to give pure product (2.85 g; 79% yield).

Example 129

Synthesis of 1R-1-[1-(4-Chloro-phenyl)-cyclobutyl]-2-[(3S)-3-(4-trifluoromethyl-phenoxymethyl)-piperidin-1-yl]-ethanol

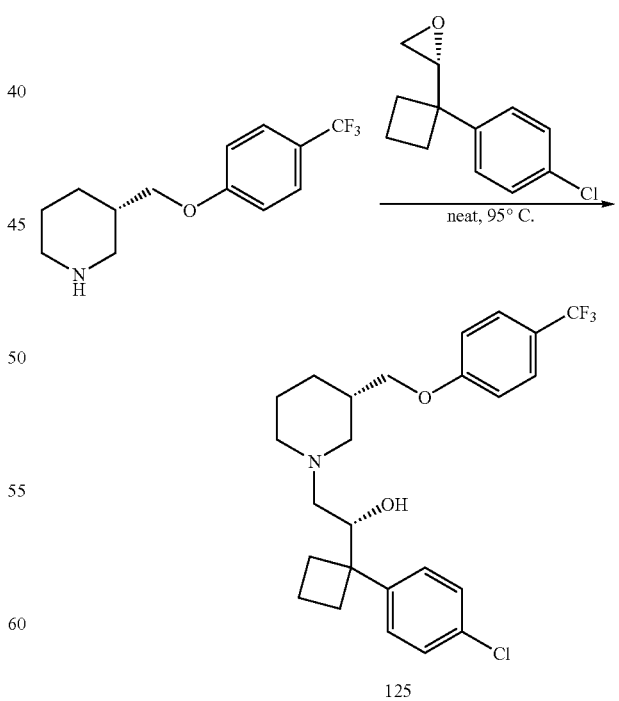

A 25 mL RB flask was charged with amine (3.79 g; 14.6 mmol) and 2R-2-[1-(4-Chloro-phenyl)-cyclobutyl]-oxirane (3.05 g; 14.6 mmol) and heated to 95° C. with stirring for 12

Example 130

Synthesis of 1R-1-[1-(4-Chloro-phenyl)-cyclobutyl]-2-[(3R)-3-(4-trifluoromethyl-phenoxymethyl)-piperidin-1-yl]-ethanol

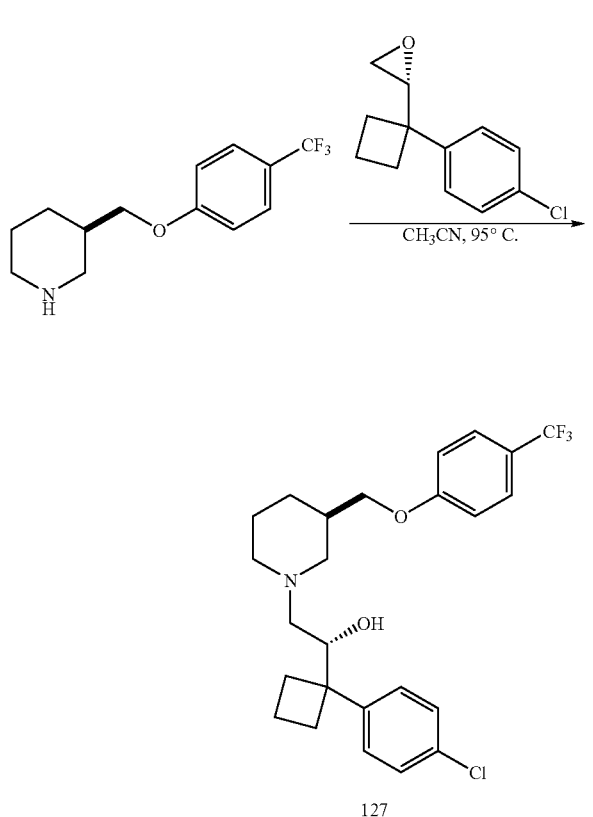

127

A 25 mL RB flask was charged with amine (1.0 g; 3.86 mmol) and 2R-2-[1-(4-chloro-phenyl)-cyclobutyl]-oxirane (0.8 g; 3.86 mmol), CH$_3$CN (4 mL) and heated to 95° C. with stirring for 5 hours. The reaction mixture was cooled to 20° C. and concentrated in vacuo. The crude material was purified via crystallization from hot methanol to yield pure product (998 mg, 56%). The diastereomeric purity was determined to be 100% de based on chiral HPLC analysis. $^1$H (300 MHz, CDCl$_3$) δ 7.55 (d, 2H, J=9 Hz), 7.30 (d, 2H, J=6.5 Hz), 7.13 (d, 2H, J=9 Hz), 6.94 (d, 2H, 9 Hz), 3.94–3.76 (m, 4H), 2.95–1.55 (m, 16H); $^{13}$C (100 MHz, CDCl$_3$) δ 161.7, 145.2, 131.7, 128.9, 128.1, 127.1, 114.6, 71.3, 71.1, 59.7, 59.0, 53.0, 48.9, 36.8, 31.0, 29.3, 27.3, 25.0, 16.3; IR (NaCl, cm$^-$): 3423, 2942, 1617, 1521, 1334, 1260, 1108, 1068, 836; MH$^+$ (468).

Example 131

Synthesis of 1S-1-[1-(4-Chloro-phenyl-cyclobutyl]-2-[(3S)-3-(4-trifluoromethyl-phenoxymethyl)-piperidin-1-yl]-ethanol

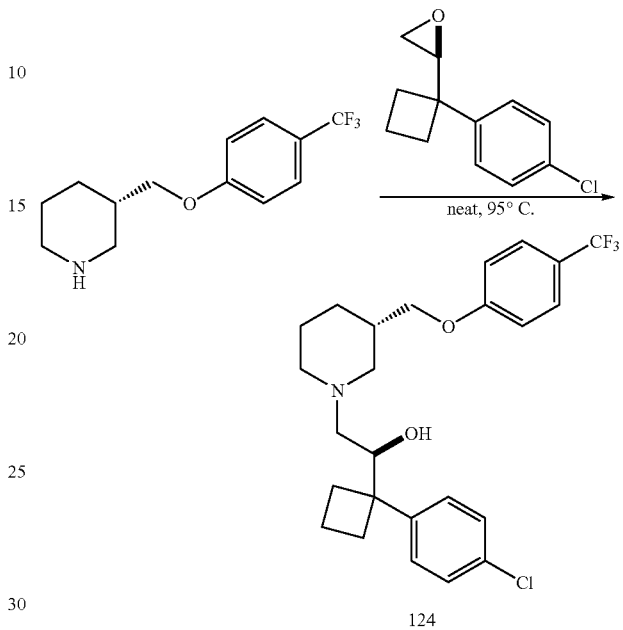

124

A 25 mL RB flask was charged with amine (239 mg; 0.92 mmol) and 2S-2-[1-(4-chloro-phenyl)-cyclobutyl]-oxirane (192 mg; 0.92 mmol), CH$_3$CN, and heated to 95° C. with stirring for 3 hours. The reaction mixture was cooled to 20° C. and concentrated. The crude material was purified by flash chromatography (hexanes/EtOAc 1:1 w/5% 2.0 M NH$_3$ in EtOH) to give pure material (324 g; 74% yield, 5de: 99.6%). $^1$H (300 MHz, CDCl$_3$) δ 7.55 (d, 2H, J=9 Hz), 7.30 (d, 2H, J=6.5 Hz), 7.13 (d, 2H, J=9 Hz), 6.94 (d, 2H, 9 Hz), 3.94–3.76 (m, 4H), 2.95–1.55 (m, 16H); $^{13}$C (100 MHz, CDCl$_3$) δ 161.7, 145.2, 131.7, 128.9, 128.1, 127.1, 114.6, 71.3, 71.1, 59.7, 59.0, 53.0, 48.9, 36.8, 31.0, 29.3, 27.3, 25.0, 16.3; IR (NaCl, cm$^{-1}$): 3423, 2942, 1617, 1521, 1334, 1260, 1108, 1068, 836; MH$^+$ (468).

Example 132

Synthesis of 1S-1-[1-(4-Chloro-phenyl)-cyclobutyl]-2-[(3R)-3-(4-trifluoromethyl-phenoxymethyl)-piperidin-1-yl]-ethanol

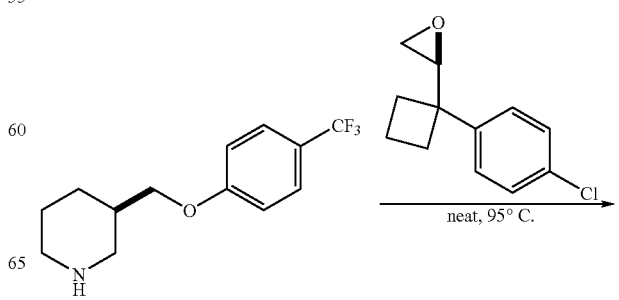

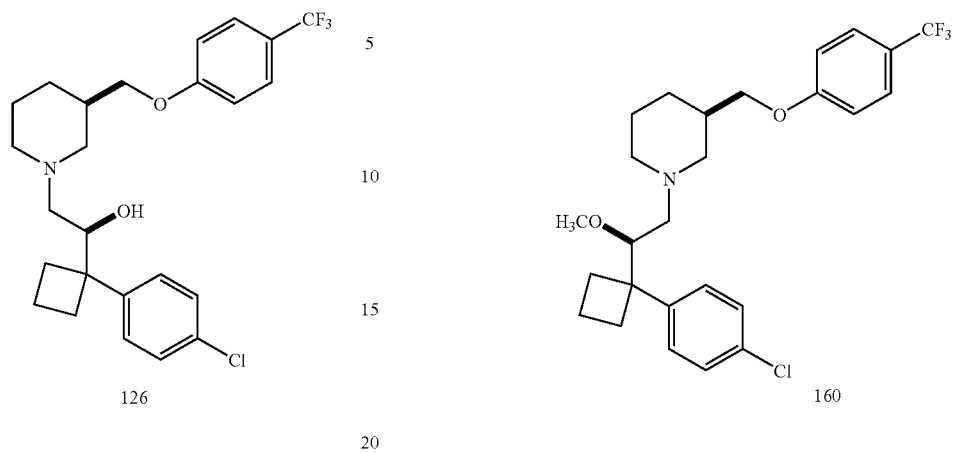

126

A 25 mL RB flask was charged with amine (1.5 g; 5.79 mmol) and 2S-2-[1-(4-chloro-phenyl)-cyclobutyl]-oxirane (1.2 g; 5.79 mmol) and heated to 95° C. with stirring for 5 hours. The reaction mixture was cooled to 20° C. and the crude material was purified by flash chromatography (hexanes/EtOAc 1:1 w/5% 2.0 M NH₃ in EtOH) to give pure material (2.31 g; 85% yield). The diastereomeric purity was determined to be 99.42% de based on chiral HPLC analysis. $^1$H (300 MHz, CDCl₃) δ 7.58 (m, 2H), 7.31 (m, 2H), 7.17 (m, 2H), 6.98 (m, 2H), 3.94–3.82 (m, 3H), 3.11 (m, 2H), 2.60–1.63 (m, 15H); $^{13}$C (100 MHz, CDCl₃) δ 161.7, 145.2, 131.8, 128.9, 28.1, 127.1, 114.6, 71.2, 59.6, 56.0, 49.0, 36.6, 31.0, 29.1, 27.4, 25.3, 16.3; IR (NaCl, cm$^{-1}$): 3428, 2932, 1623, 1320, 1259, 1155, 1105, 1061, 836; MH$^+$ (467).

Example 133

Synthesis of 1R-1-{2-[1-(4-Chloro-phenyl)-cyclobutyl]-2-methoxy-ethyl}-(3R)-3-(4-trifluoromethyl-phenoxymethyl)-piperidine

160

The alcohol (107.6 mg, 0.230 mmol) was dissolved in THF (2.5 mL). Methyl iodide (0.072 mL, 1.15 mmol) and potassium tert-butoxide (39 mg, 0.345 mmol) were added. The reaction continued stirring at RT and was monitored by HPLC. After completion the reaction mixture was diluted with water and the aqueous layer was extracted with EtOAc (3×, 20 mL). Combined organic layers were dried over Na₂SO₄ and concentrated. The crude material was purified using silica gel chromatography (80:16:4 hexanes; EtOAc: 2M ammonia in EtOH) to yield pure product. MH$^+$=481.

Example 134

Synthesis of 1S-1-{2-[1-(4-Chloro-phenyl)-cyclobutyl]-2-methoxy-ethyl}-(3R)-3-(4-trifluoromethyl-phenoxymethyl)-piperidine

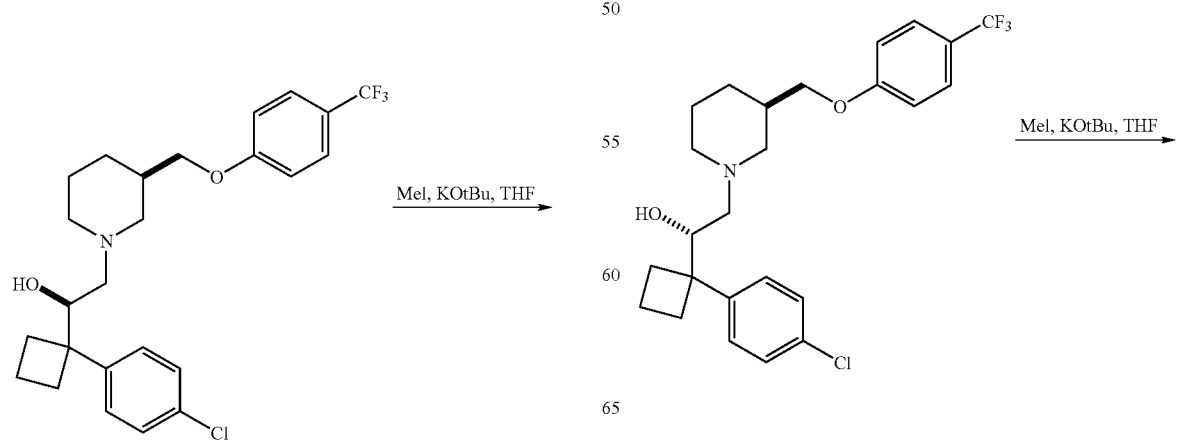

-continued

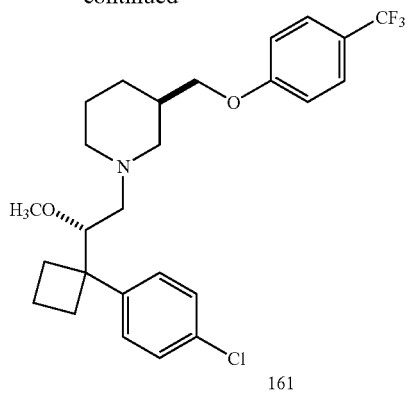

161

1S-1-{2-[1-(4-Chloro-phenyl)-cyclobutyl]-2-methoxy-ethyl}-(3R)-3-(4-trifluoromethyl-phenoxymethyl)-piperidine was prepared according to the procedure in Example 133: alcohol (100 mg, 0.21 mmol), potassium tert-butoxide (36 mg, 0.32 mmol), MeI (151.6 mg, 1.07 mmol), THF (2.2 mL). The crude material was purified using silica gel chromatography (80:16:4 hexanes:EtOAc:2M ammonia in EtOH) to yield pure product. MH$^+$=481.

Example 135

Synthesis of 1R-1-{2-[1-(4-Chloro-phenyl)-cyclobutyl]-2-methoxy-ethyl}-(3S)-3-(4-trifluoromethyl-phenoxymethyl)-piperidine

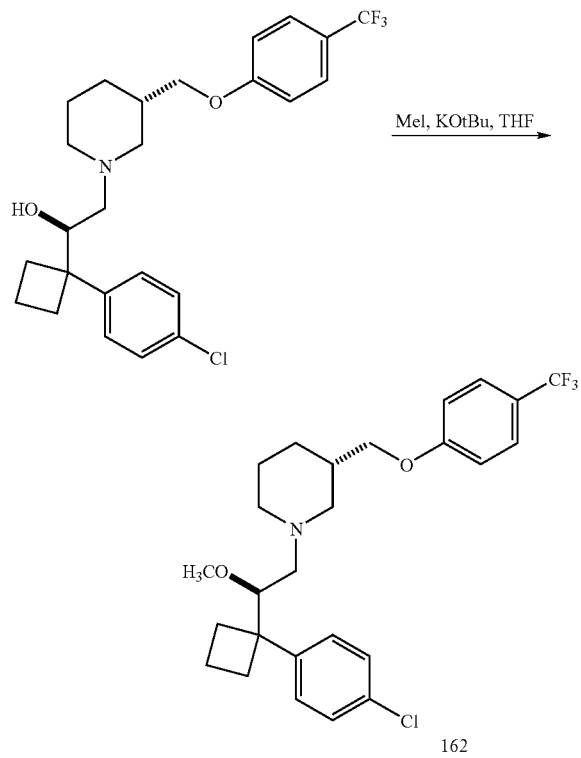

162

1R-1-{2-[1-(4-Chloro-phenyl)-cyclobutyl]-2-methoxy-ethyl}-(3S)-3-(4-trifluoromethyl-phenoxymethyl)-piperidine was prepared according to the procedure in Example 133: alcohol (289 mg, 0.62 mmol), potassium tert-butoxide (104 mg, 0.93 mmol), MeI (430 mg, 3.0 mmol), THF (5 mL). The crude material was purified using silica gel chromatography (1:1 hexanes:EtOAc in 2M ammonia in EtOH) to yield pure product (256 mg, 86%).

Example 136

Synthesis of 1S-1-{2-[1-(4-Chloro-phenyl)-cyclobutyl]-2-methoxy-ethyl}-(3S)-3-(4-trifluoromethyl-phenoxymethyl)-piperidine

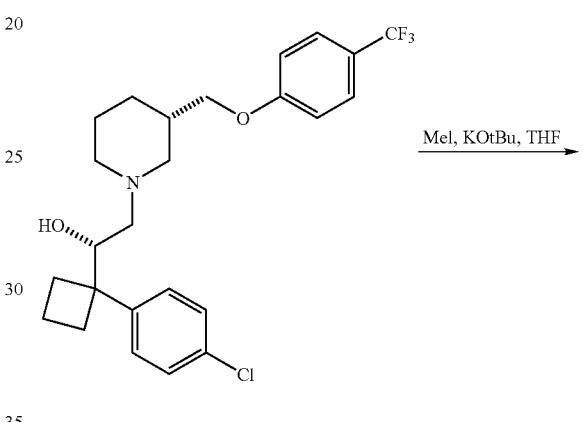

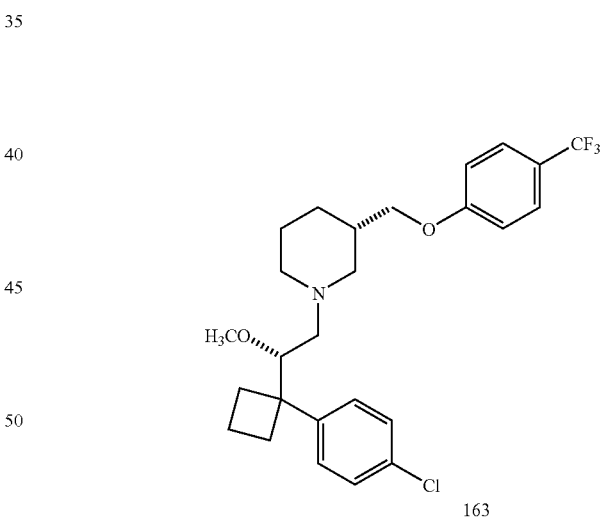

163

1S-1-{2-[1-(4-Chloro-phenyl)-cyclobutyl]-2-methoxy-ethyl}-(3S)-3-(4-trifluoromethyl-phenoxymethyl)-piperidine was prepared according to the procedure in Example 133: alcohol (200 mg, 0.43 mmol), potassium tert-butoxide (78 mg, 0.64 mmol), MeI (303 mg, 2.1 mmol), THF (5 mL). The crude material was purified using silica gel chromatography (1:1 hexanes:EtOAc in 2M ammonia in EtOH) to yield pure product (196 mg, 95%).

Example 137

Synthesis of [1-(4-Chloro-phenyl)-cyclobutylmethyl]-3-(4-trifluoromethyl-phenoxymethyl)-piperidin-3-ol (167)

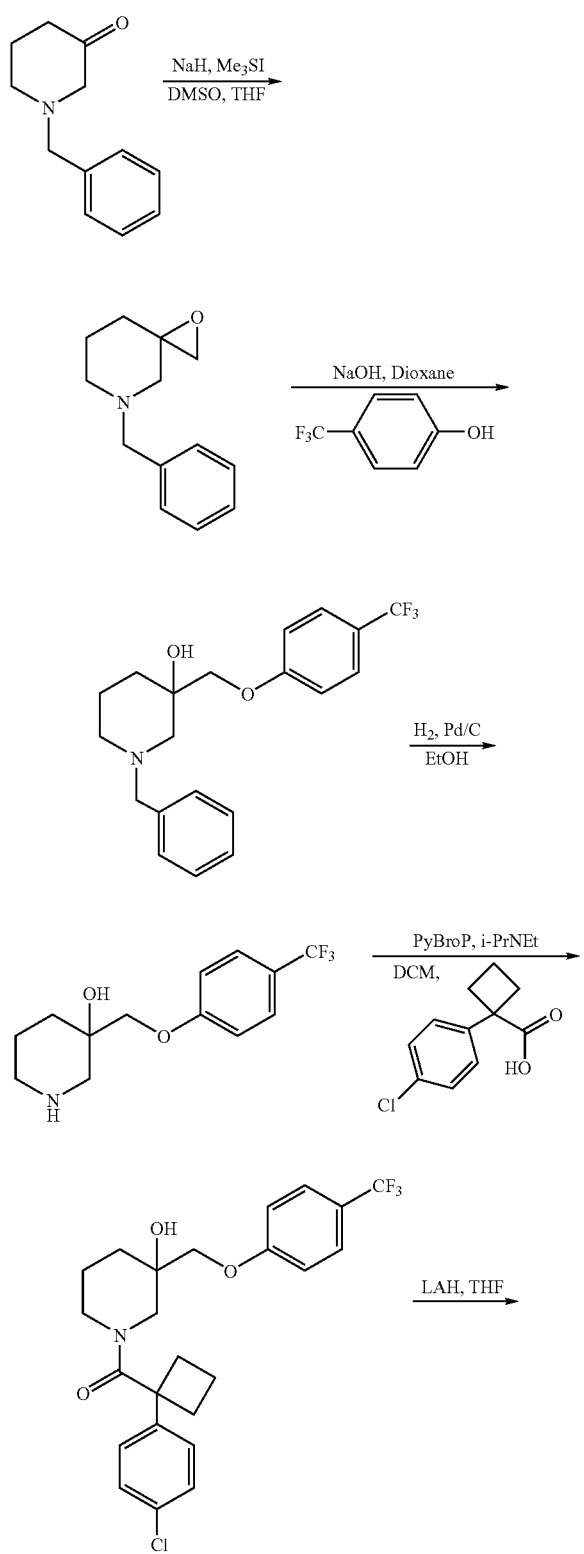

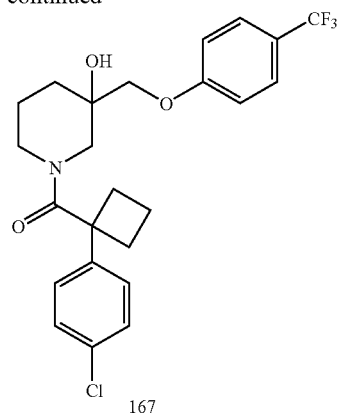

167

5-Benzyl-1-oxa-5-aza-spiro[2.5]octane

Sodium hydride (583 mg, 14.6 mmol) in DMSO (6 mL) was heated to 55° C. for 1 h. The reaction mixture is cooled to 0° C. and Me$_3$SI (3 g, 14.62 mmol) dissolved in THF (9.8 mL) was added dropwise. 1-Benzyl-piperidine-3-one (1.5 g, 6.64 mmol) dissolved in DMSO (10 mL) was added 15 minutes later. After completion of addition the reaction proceded at RT. After 30 min. the reaction was quenched with water. The aqueous layer was extracted with hexanes. Combined organic layers were dried over Na$_2$SO$_4$ and concentrated. The crude material was purified using silica gel chromatography (9:1 DCM:hexanes in 2 M ammonia in EtOH) to yield 5-benzyl-1-oxa-5-aza-spiro[2.5]octane (960 mg, 71%). MH$^+$ (204).

1-Benzyl-3-(4-trifluoromethyl-phenoxymethyl)-piperidin-3-ol 5-benzyl-1-oxa-5-aza-spiro[2.5]octane (960 mg, 4.74 mmol) dissolved in dioxane (3 mL) was added dropwise to a hot (105 C) stirring solution of NaOH (189 mg, 4.74 mmole), p-trifluoro-cresol (2.30 g, 14.2 mmol), and dioxane (3 mL). After completion of addition the reaction mixture was stirred at 110 C for 6 h and at RT for 12 h. The reaction mixture was diluted with 10% NaOH and extracted with diethyl ether. Combined organic layers were concentrated to yield a brown oil. The crude material was purified using silica gel chromatography (4:1 hexane:EtOAc in 2M ammonia in EtOH) to yield 1-benzyl-3-(4-trifluoromethyl-phenoxymethyl)-piperidin-3-ol (100 mg, 6%). MH$^+$ (365).

3-(4-Trifluoromethyl-phenoxymethyl)-piperidin-3-ol

The amine (100 mg 0.274 mmol) was dissolved in EtOH (3 mL). 10% Pd/C catalyst (37 mg) was added to the solution. The reaction mixture was stirred under H$_2$ atmosphere at 50 psi for 5 h. The catalyst was removed via filtration and the filtrate was concentrated to afford the desired compound as a yellow oil (75 mg, 100%).

[1-(4-Chloro-phenyl)-cyclobutyl]-[3-hydroxy-3-(4-trifluoromethyl-phenoxymethyl)-piperidin-1-yl]-methanone Into a round-bottom flask was added 3-(4-trifluoromethyl-phenoxymethyl)-piperidin-3-ol (100 mg, 0.36 mmol), dichloromethane (5 mL), diisopropylethylamine (0.190 mL, 1.08 mmol), 1-(4-chloro-phenyl)-cyclobutanecarboxylic acid (113.4 mg, 0.54 mmole), and PyBroP (0.252 g, 0.54 mmol). The reaction mixture was stirred at room temperature overnight. The reaction mixture was diluted with water and then extracted with ethyl acetate (3×10 mL). The extracts were combined, dried over anhydrous sodium sulfate, filtered, and concentrated to give a yellow oil. The oil was purified by column chromatography on silica gel using hexane/ethyl acetate (4:1) to give [1-(4-Chloro-phenyl)-cyclobutyl]-[3-hydroxy-3-(4-trifluoromethyl-phenoxymethyl)-piperidin-1-yl]-methanone (18.7 mg, 11%). MH+ (468).

[1-(4-Chloro-phenyl)-cyclobutylmethyl]-3-(4-trifluoromethyl-phenoxymethyl)-piperidin-3-ol The amide (18.7 mg, 0.40 mmol) was dissolved in THF (1 mL) and cooled in an ice bath. LAH (1M in THF, 0.048 mL, 0.048 mmol) was added to the cooled stirring reaction mixture. After completion of addition the reaction stirred at RT. After 12 h the reaction mixture was quenched with water. The aqueous layer was extracted with EtOAc (3×5 mL). The combined organic layers were dried over $Na_2SO_4$ and concentrated. The crude material was purified using silica gel prep plate (4:1 hexane EtOAc in 2M ammonia in EtOH) to yield the desired compound (167). MH+ (454).

Example 138

Synthesis of 1-[1-(2-Methoxy-phenyl)-cyclobutyl]-2-[3-(4-trifluoromethyl-phenoxymethyl)-piperidin-1-yl]-ethanol

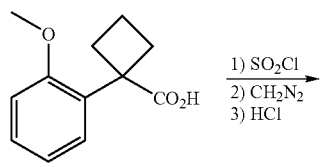

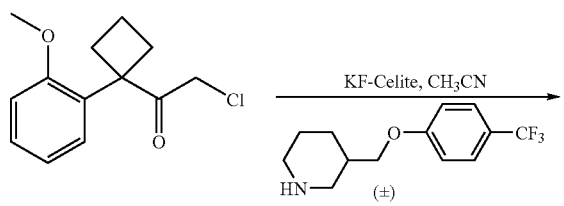

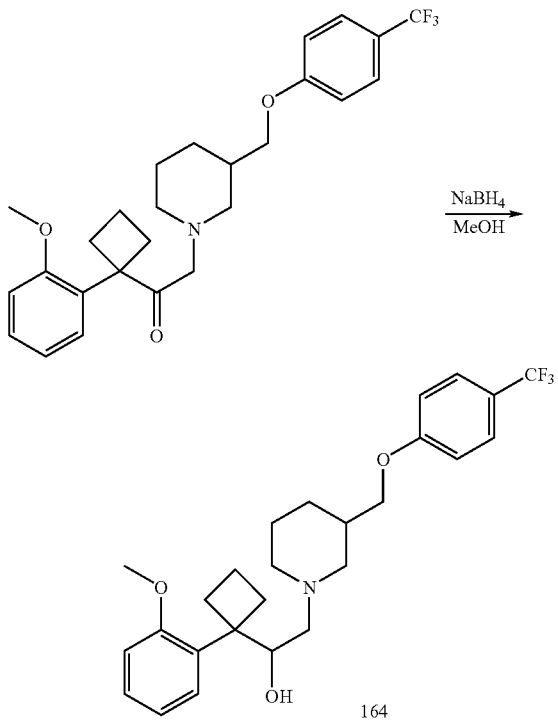

The starting acid 1-(2-methoxy-phenyl)-cyclobutanecarboxylic acid has been described (S. L. Mnhzhoyan et al. *Pharm. Chem., Eng. Translation,* 1980, 14 (2), 114–118). A mixture of this acid (145 mg, 0.70 mmol) and thionyl chloride (2 mL) was heated at reflux for 3 hr. The reaction mixture was concentrated in vacuo, diluted with THF (2 mL), reconcentrated, and residual solvent was removed by vaccuum. The material was dissolved in 2 mL THF, cooled to 0° C., and treated with excess diazomethane in ether (generated from 0.5 g 1-methyl-3-nitro-1-nitrosoguanidine in 3 mL ether and 0.34 g NaOH in 3 mL of water). The solution was stirred overnight at 0 C, and then HCl (1 mL of a 4M solution in dioxane) was added and the mixture was kept at that temperature for 1 hr. The solution was concentrated in vacuo and purified on silica gel (9:1 ethyl acetate/hexane) to give 2-chloro-1-[1-(2-methoxy-phenyl)-cyclobutyl]-ethanone as a colorless oil (92 mg, 55%). Data for this chloroketone: MS 239 (M+1); $^1$H NMR (300 MHz, $CDCl_3$): δ 6.85–7.4 (m, 4H), 3.89 and 3.86 (singlets, total 5 H), 2.0–2.9 (m, 6H).

2-Chloro-1-[1-(2-methoxy-phenyl)-cyclobutyl]-ethanone (55 mg) in 2 mL acetonitrile was treated with freshly flamed-dried KF on Celite (200 mg) and 3-(4-trifluoromethyl-phenoxymethyl)-piperidine (66 mg, 1.1 equiv). The mixture was stirred overnight, diluted with THF (5 mL), filtered, concentrated in vacuo and purified on silica gel to give the desired 1-[1-(2-methoxy-phenyl)-cyclobutyl]-2-[3-(4-trifluoromethyl-phenoxymethyl)-piperidin-1-yl]-ethanone (32 mg, 30%). Data for this amino ketone: MS 462 (M+1); $^1$H NMR (300 MHz, $CDCl_3$) partial: δ 6.8–7.6 (m, 8H), 3.85–3.95 (m, 2H, methylene adjacent to aryl ether), 3.09 (s, 2H, methylene adjacent to keto and amine moieties).

1-[1-(2-Methoxy-phenyl)-cylobutyl]-2-[3-(4-trifluoromethyl-phenoxymethyl)-piperidin-1-yl]-ethanone (15 mg) was dissolved in 2 mL of dry methanol and solid sodium borohydride (10 equiv.) was added in portions. Water (5 mL) was added and the mixture was extracted with ether and the ether extracts were concentrated in vacuo and purified on silica gel to give the desired 1-[1-(2-methoxy-phenyl)-cyclobutyl]-2-[3-(4-trifluoromethyl-phenoxymethyl)-piperidin-1-yl]-ethanol (9 mg, 60%). Data for this mixture of diastereomeric amino alcohols: MS 464 (M+1); $^1$H NMR (300 MHz, CDCl$_3$) partial: δ 6.8–7.6 (m, 8H), 3.85–3.95 (m, 2H, methylene adjacent to aryl ether), the δ 3.09 singlet for the starting material was absent.

Example 139

Synthesis of 1-(1-benzo[1,3]dioxol-5-yl-cyclobutyl)-2-[3-(4-trifluoromethyl-phenoxymethyl)-piperidin-1-yl]-ethanol

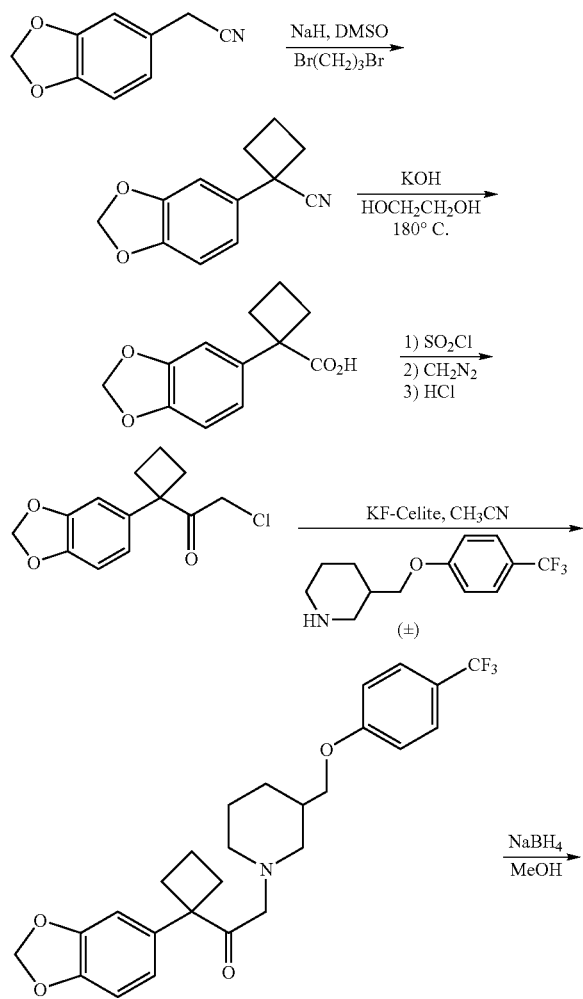

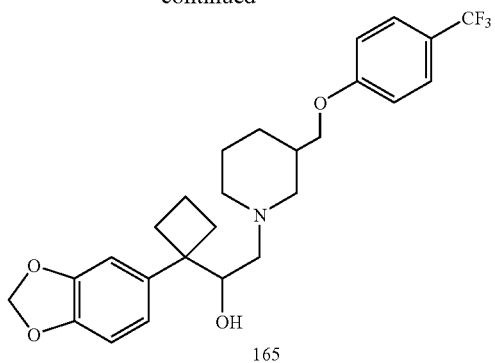

165

A mixture of benzo[1,3]dioxol-5-yl-acetonitrile (1.60 g, 9.94 mmol) and the dibromide (1.11 mL, 1.1 equiv.) in 10 mL of DMSO was added to a mixture of NaH (1 g 60% suspension, 2.5 equiv.) in 30 mL of DMSO at room temperature. After 24 hours the reaction was quenched by addition of 50 mL of pH 7.0 buffer solution, the mixture was extracted with ether, and the ether extracts were concentrated in vacuo and purified on silica gel (85:15 hexane:ethyl acetate) to give the desired 1-benzo[1,3]dioxol-5-yl-cyclobutanecarbonitrile (1.41 g, 71%). Data for this nitrile: MS 202 (M+1); $^1$H NMR (300 MHz, CDCl$_3$): δ 6.8–6.9 (m, 3H), 5.98 (s, 2H), 2.0–2.85 (m, 6H); $^{13}$C NMR (75 MHz, CDCl$_3$): δ 148.5, 147.5, 134.0, 124.7, 119.2, 106.5, 101.6, 40.2, 35.0, 17.2.

1-Benzo[1,3]dioxol-5-yl-cyclobutanecarbonitrile (1.2 g) was slurried in ethylene glycol (10 mL) in a pressure tube and a large excess of KOH (1 g) was added. The tube was sealed and heated at 180° C. for 24 hours, cooled, poured into 100 mL of water, acidified with 1N HCl, extracted with ether, and the ether extracts were concentrated in vacuo and chromatographed on silica gel with an ethyl acetate:hexane:acetic acid mixture to give the desired 1-benzo[1,3]dioxol-5-yl-cyclobutanecarboxylic acid (850 mg, 65%). Data for this acid: MS 220 (M); $^1$H NMR (300 MHz, CDCl$_3$): δ 11.4–11.8 (br. s, 1H), 2.78–6.85 (m, 3H), 5.95 (s, 2H) 2.75–2.85 (m, 2H), 2.40–2.55 (m, 2H), 1.8–2.2 (m, 2H); $^{13}$C NMR (75 MHz, CDCl$_3$): δ 182.9, 147.9, 146.7, 137.2, 119.8, 108.2, 107.5, 101.3, 52.2, 32.6, 16.7.

1-Benzo[1,3]dioxol-5-yl-cyclobutanecarboxylic acid was converted to the corresponding chloroketone following the same procedure used for the conversion of 1-(2-Methoxyphenyl)-cyclobutanecarboxylic acid to give 2-Chloro-1-[1-(2-methoxy-phenyl)-cyclobutyl]-ethanone. 300 mg of 1-benzo[1,3]dioxol-5-yl-cyclobutanecarboxylic acid thus provided 285 mg (83%) of 1-(1-Benzo[1,3]dioxol-5-yl-cyclobutyl)-2-chloro-ethanone. Data for this chloride: $^1$H NMR (300 MHz, CDCl$_3$): δ 6.7–6.85 (m, 3H), 5.98 (s, 2H), 4.03 (s, 2H), 2.75–2.85 (m, 2H), 2.35–2.45 (m, 2H), 1.85–2.0 (m, 2H); $^{13}$C NMR (75 MHz, CDCl$_3$): δ 201.9, 148.6, 147.1, 135.8, 119.8, 108.9, 107.0, 101.6, 57.7, 45.4, 31.2, 16.2.

1-(1-Benzo[1,3]dioxol-5-yl-cyclobutyl)-2-chloro-ethanone was used for the alkylation of 3-(4-Trifluoromethyl-phenoxymethyl)-piperidine by the same method used for the alkylation of 2-Chloro-1-[1-(2-methoxy-phenyl)-cyclobutyl]-ethanone with this amine. 100 mg of 1-(1-Benzo[1,3] dioxol-5-yl-cyclobutyl)-2-chloro-ethanone was used to prepare 85 mg of 1-(1-benzo[1,3]dioxol-5-yl-cyclobutyl)-2-[3-(4-trifluoromethyl-phenoxymethyl)-piperidin-1-yl]-ethanone (45%) by the KF-Celite method described in Example 138. Data for this amino ketone: MS 476(M+1); $^1$H NMR (300 MHz, CDCl$_3$) partial: δ 6.7–7.7 (m, 7H), 6.0 (s, 2H), 3.85–3.95 (m, 2H, methylene adjacent to aryl ether), 3.1 (s, 2H, methylene adjacent to keto and amine moieties).

1-(1-Benzo[1,3]dioxol-5-yl-cyclobutyl)-2-[3-(4-trifluoromethyl-phenoxymethyl)-piperidin-1-yl]-ethanone (15 mg) was dissolved in 2 mL of dry methanol and solid sodium borohydride (10 equiv.) was added in portions. Water (5 mL) was added and the mixture was extracted with ether and the ether extracts were concentrated in vacuo and purified on silica gel to give the desired 1-(1-benzo[1,3]dioxol-5-yl-cyclobutyl)-2-[3-(4-trifluoromethyl-phenoxymethyl)-piperidin-1-yl]-ethanol (10 mg, 66%). Data for this mixture of diastereomeric amino alcohols: MS 478 (M+1); $^1$H NMR (300 MHz, CDCl$_3$) partial: δ 6.7–7.8 (m, 7H), 3.85–3.95 (m, 2H, methylene adjacent to aryl ether), the δ 3.1 singlet for the starting material was absent.

Example 140

Synthesis of 2-[3-(4-Trifluoromethyl-phenoxymethyl)-piperidin-1-yl]-1-[1-(4-trifluoromethyl-phenyl)-cyclobutyl]-ethanol

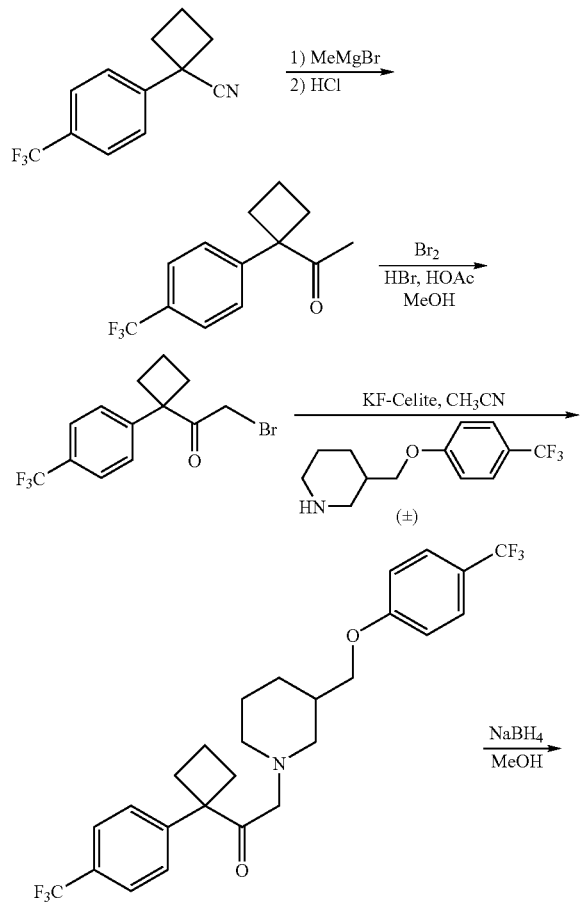

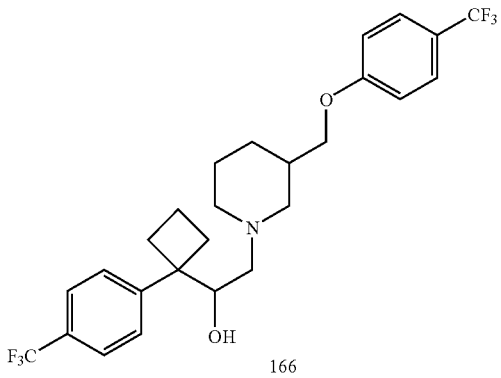

166

The starting nitrile, 1-(4-Trifluoromethyl-phenyl)-cyclobutanecarbonitrile, has been described (Parke Davis & Co., U.S. Pat. No. 3,536,656; 1970 and *Chemical Abstracts* 1970, 73, 109539). To the carbonitrile (2 g) in 5 mL of toluene in a pressure tube was added 10 mL of 3M MeMgBr ether solution (3 equiv.). The tube was sealed and the reaction mixture was heated at 95° C. for 24 hr, cooled to room temperature, poured into 50 mL of water, acidified with 25 mL of 5 M HCl, and this solution was heated at 70° C. for 2 h, cooled, and extracted with ether. The extracts were dried, filtered, concentrated, and purified on silica gel to give pure 1-[1-(4-trifluoromethyl-phenyl)-cyclobutyl]-ethanone (1.9 g, 88%). Data for this ketone: MS 242 (M); $^1$H NMR (300 MHz, CDCl$_3$) δ 7.6 (d, 8.0 Hz, 2H), 7.4 (d, 8.0 Hz, 2H), 2.75–2.85 (m, 2H), 2.35–2.5 (m, 2H), 1.8–2.0 (3H s and 2H m overlapping); $^{13}$C NMR (75 MHz, CDCl$_3$): δ 207.7, 147.5, 129.5, 126.9, 126.1, 125.9 (CF$_3$), 59.5, 30.9, 24.6, 16.1.

1-[1-(4-Trifluoromethyl-phenyl)-cyclobutyl]-ethanone (1.06 g) in methanol (8 mL) was cooled to 0° C. Acetic acid containing 30% HBr (0.35 mL) was added, and then precisely 1 molar equivalent of bromine was added dropwise. The reaction mixture was maintained at 0° C. overnight, poured into 20 mL of water, and extracted with ether. The extracts were dried, filtered, concentrated, and purified on silica gel to give pure 2-bromo-1-[1-(4-trifluoromethyl-phenyl)-cyclobutyl]-ethanone (1.12 g, 80%). Data for this bromoketone: MS 321 (M); $^1$H NMR (300 MHz, CDCl$_3$) δ 7.82 (d, 8 Hz, 2H), 7.39 (d, 8 Hz, 2H), 3.82 (s, 2H), 2.80–2.95 (m, 2H), 2.45–2.60 (m, 2H), 1.90–2.10 (m, 2H).

2-Bromo-1-[1-(4-trifluoromethyl-phenyl)-cyclobutyl]-ethanone was used for the alkylation of 3-(4-Trifluoromethyl-phenoxymethyl)-piperidine by the same method used for the alkylation of 2-Chloro-1-[1-(2-methoxy-phenyl)-cyclobutyl]-ethanone with this amine. 100 mg of 2-Bromo-1-[1-(4-trifluoromethyl-phenyl)-cyclobutyl]-ethanone was converted to 96 mg of 2-[3-(4-trifluoromethyl-phenoxymethyl)-piperidin-1-yl]-1-[1-(4-trifluoromethyl-phenyl)-cyclobutyl]-ethanone (62%) by the KF-Celite method described in Example 138. Data for this amino ketone: MS 500(M+1); $^1$H NMR (300 MHz, CDCl$_3$): δ 7.61 (d, 8.3 Hz, 2H), 7.52 (d, 8.7 Hz, 2H), 7.38 (d, 8.3 Hz, 2H), 6.91 (d, 8.7 Hz, 2H), 3.75–3.85 (m, 2H, methylene adjacent to aryl ether), 3.06 (s, 2H), 1.0–2.9 (various overlapping multiplets totaling 15 H); $^{13}$C NMR (75 MHz, CDCl$_3$): δ 207.0, 161.7, 147.3, 128.6, 127.8, 127.11, 127.06, 126.99, 125.93, 125.88, 114.6, 71.2, 63.2, 58.3, 57.2, 54.2, 36.2, 31.2, 31.1, 27.0, 24.8, 16.5.

2-[3-(4-Trifluoromethyl-phenoxymethyl)-piperidin-1-yl]-1-[1-(4-trifluoromethyl-phenyl)-cyclobutyl]-ethanone (30 mg) was dissolved in 3 mL of dry methanol and solid sodium borohydride (10 equiv.) was added in portions. Water (10 mL) was added and the mixture was extracted with ether and the ether extracts were concentrated in vacuo and purified on silica gel to give the desired 2-[3-(4-Trifluoromethyl-phenoxymethyl)-piperidin-1-yl]-1-[1-(4-trifluoromethyl-phenyl)-cyclobutyl]-ethanol (21 mg, 67%). Data for this mixture of diastereomeric amino alcohols: MS 502 (M+1); $^1$H NMR (300 MHz, CDCl$_3$): δ 7.5–7.6 (m, 4H), 7.29–7.35 (m, 2H), 6.89–6.96 (overlapping doublets, total 2 H), 3.8–4.0 (m, 4H, 1 of which is exchanged upon exposure to D$_2$O), 1.1–3.1 9 (various overlapping multiplets totaling 17 H); $^{13}$C NMR (75 MHz, CDCl$_3$): δ 207 peak in starting ketone is absent. Most peaks are doubled (adjacent equal intensity peaks) due to diastereoisomerism: δ 161.7, 151.0, 128.6 & 128.5, 128.0 & 127.8, 127.15 & 127.10, 126.45, 124.91 & 124.87, 123.30, 122.86, 114.63, 71.2 & 71.1, 59.7 & 59.5, 58.99 & 58.97, 55.96, 49.31 & 49.28, 36.8 & 36.6, 31.0, 29.5 & 29.4, 27.33 & 27.26, 25.24 & 25.03, 16.42.

Example 141

Spontaneous Locomotor Activity in Rats

The effect of 124 and 126 on spontaneous locomotor activity in rats was determined according to the procedures outlined by Silverman et al. (Motor Activity. In "Animal behavior in the laboratory", Chapman and Hall eds, London, p. 79–92, 1978) and Boissier et al. (*Arch. Int. Pharmacodyn.* 1965, 158, 212.)

Test items and test item vehicles were administered to male Sprague-Dawley rats (n=10) as a single i.p. dose (vehicle A=10% hydroxypropyl-β-cyclodextrin in water; vehicle B=4:1 5% aqueous dextrose:PEG 400). Twenty, 60 and 120 minutes following administration, rats were placed in a plastic box 30×30 cm in a room with low light intensity (maximum 50 lux). Locomotor activity was determined during 20 minute periods using video image analyzers. Images recorded with video cameras were digitalized and displacements of the center of gravity of the digital image spot were tracked and analyzed. When the speed of displacement of the center of gravity of the spot was below 4.26 cm/sec, the movement was considered as inactivity. When this speed was between 4.26 and 6.75 cm/sec, the movement was considered as a small movement. When this speed was above 6.75 cm/sec, the movement was considered as a large movement. The number of occurrences, distance and duration of fast and slow movements, number of occurrences and duration of periods of inactivity and number of rears were measured.

Results

Compounds 126 and 124, when dosed at 5 and 10 mg/kg, exhibit a significant increase in locomotor activity compared to control animals.

|  | Vehicle A | Vehicle B | 126 (5 mg/kg in Vehicle A) | 126 (10 mg/kg in Vehicle A) | 124 (5 mg/kg in Vehicle B) | 124 (10 mg/kg in Vehicle B) | Methyl-phenidate, (10 mg/kg in Vehicle B) |
|---|---|---|---|---|---|---|---|
| Large Movement Occurrences | 20 min: 303.7 ± 28.0 60 min: 104.9 ± 11.7 120 min: 65.1 ± 8.9 180 min: 40.6 ± 17.1 | 20 min: 317.4 ± 15.5 60 min: 99.4 ± 19.7 120 min: 43.4 ± 7.9 180 min: 22.8 ± 9.4 | 20 min: 287.0 ± 34.4 60 min: 204.4 ± 36.3 120 min: 293.8 ± 68.9 180 min: 270.5 ± 73.8 | 20 min: 364.7 ± 52.7 60 min: 644.5 ± 127.3 120 min: 752.7 ± 129.4 | 20 min: 228.7 ± 22.5 60 min: 74.3 ± 14.8 120 min: 168.5 ± 61.5 180 min: 212.5 ± 65.1 | 20 min: 391.5 ± 63.3 60 min: 427.6 ± 95.8 120 min: 603.5 ± 97.4 | 20 min: 974.3 ± 125.5 60 min: 423.9 ± 75.9 120 min: 191.8 ± 37.1 |
| Small Movement Occurrences | 20 min: 767.3 ± 46.7 60 min: 357.9 ± 47.3 120 min: 256.3 ± 42.9 180 min: 114.4 ± 38.6 | 20 min: 697.2 ± 36.8 60 min: 307.8 ± 56.4 120 min: 140.3 ± 22.3 180 min: 103.2 ± 42.0 | 20 min: 711.6 ± 65.7 60 min: 563.5 ± 85.0 120 min: 717.4 ± 138.6 180 min: 651.4 ± 141.2 | 20 min: 904.3 ± 110.8 60 min: 1218.7 ± 178.9 120 min: 1358.1 ± 137.1 | 20 min: 589.2 ± 50.4 60 min: 232.8 ± 33.6 120 min: 443.1 ± 100.6 180 min: 484.5 ± 114.1 | 20 min: 919.6 ± 96.4 60 min: 965.2 ± 153.9 120 min: 1201.4 ± 160.9 | 20 min: 1537.0 ± 97.3 60 min: 992.0 ± 126.7 120 min: 555.0 ± 87.0 |

Example 142

Rat Behavioral Assay

The objective of this study was to assess the antidepressant effects of test compounds 124, 125, 126, and 127 in the behavioral despair assay in rats using a modification of a method described by Porsolt R. D., Anton G., Blavet N., Jalfre M., *Behavioural despair in rats: a new model sensitive to antidepressant treatment,* Eur. J. Pharmacol., 1978, 47, 379–391. The animals were preconditioned in a pretest session, where the rats were individually forced to swim inside a vertical plexiglass cylinder containing water maintained at 19–20° C. After 15 minutes in the water, they were allowed to dry for 15 minutes in a heated enclosure. Twenty four hours later, the compounds were administered intraperitoneal to the animals. One hour after administration of the test compound, animals were put back into the cylinder containing water. The total duration of immobility was measured during the last 4 minutes of a 6 minute test.

| Compound | Dose (mg/kg) | % variation |
|---|---|---|
| 126 | 10 | 99 |
|  | 2.5 | 45 |
| 127 | 10 | 67 |
|  | 2.5 | 25 |
| 124 | 10 | 91 |
|  | 2.5 | 6 |

-continued

| Compound | Dose (mg/kg) | % variation |
|---|---|---|
| 125 | 10 | 55 |
| Nomifensine | 3 | 78 |

The results are expressed as the percentage of variation of the total duration of immobility calculated from the mean value of the vehicle-treated group (% variation=[(immobility duration of vehicle−immobility duration of test compound)/(immobility duration of vehicle)]×100%). Only compounds which exhibit a statistically significant variation >30% are considered effective in this in vivo model.

Results

Based on the aforementioned criterion for effectiveness, all four compounds are effective at a dose of 10 mg/kg; compound 126 is also effective at 2.5 mg/kg.

Example 143

Rat Behavioral Assay

The objective of this study was to assess the antidepressant effects of test compounds 124, 125, 126, and 127 in the behavioral despair assay in rats according to the methods described by Porsolt R. D., Anton G., Blavet N., Jalfre M., *Behavioural despair in rats: a new model sensitive to antidepressant treatment*, Eur. J. Pharmacol., 1978, 47, 379–391. The animals were preconditioned in a pretest session, where the rats were individually forced to swim inside a vertical plexiglass cylinder containing water maintained at 19–20° C. After 15 minutes in the water, they were allowed to dry for 15 minutes in a heated enclosure. Twenty four hours later, they were replaced in the cylinder and the total duration of immobility was measured during a 5 minute test (test session). The test compounds and vehicle were administered as a series of 3 intraperitoneal injections 24 h, 5 h and 1 h before the 5 minute test on the second day.

| Compound | Dose (mg/kg) | % variation |
|---|---|---|
| 124 | 2.5 | 59 |
|  | 2.0 | 71 |
|  | 1.0 | 29 |
| 125 | 2.5 | 12 |
| 126 | 1.0 | 58 |
| 126 | 2.5 | 76 |
|  | 0.75 | 47 |
|  | 0.25 | 9 |
| 127 | 1.0 | 14 |
| 127 | 3.0 | 64 |
|  | 2.5 | 39 |
|  | 2.0 | 39 |
| Imipramine | 30 | 55 |

The results are expressed as the percentage of variation of the total duration of immobility calculated from the mean value of the vehicle-treated group (% variation=[(immobility duration of vehicle−immobility duration of test compound)/(immobility duration of vehicle)]×100%). Only compounds which exhibit a statistically significant variation >30% are considered effective in this in vivo model.

Results

Based on the aforementioned criterion for effectiveness, compounds 124, 126, and 127 were effective at a dose of 2.5 mg/kg; compound 126 was also effective at a dose of 1.0 mg/kg.

Example 144

Determination of the Absolute Stereochemistry of Compound 124

The absolute stereochemistry of 124 was determined to be (3S,1'S), by both asymmetric synthesis and X-Ray crystallography. The method of enantiospecific preparation of 124 is depicted in Schemes 1 and 2. The stereocenter at the 3-position of the piperidine was set as the S-isomer according to the literature precedent (See Reference 2). The second stereocenter for the carbinol position was predicted to be the S-isomer by stereoselective reduction of the ketone to give S-epoxide (See Reference 1). Coupling of the 3S-piperidine with the S-epoxide afforded 124. The 1'-stereocenter was confirmed as the S-isomer by its relationship to the 3-position stereocenter through X-ray crystallography (See FIG. 1). The measured optical rotation for 124 was $[\alpha]_D=-263.8°$ (c=1.5; CHCl$_3$; 589 nm, 21° C.).

Scheme 1
Synthesis of R and S 2-[1-(4-Chloro-phenyl)-cyclobutyl]-oxirane

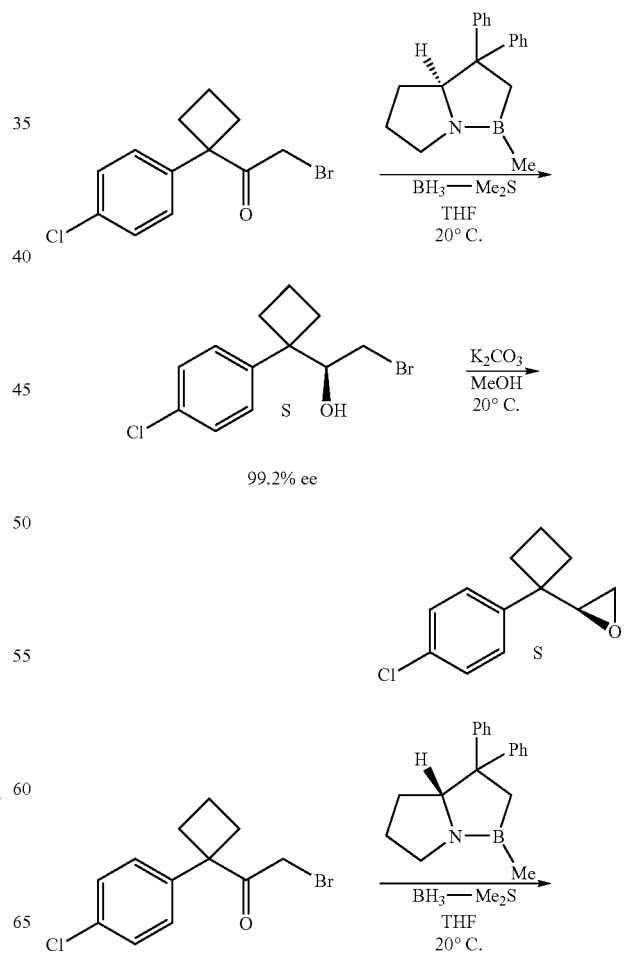

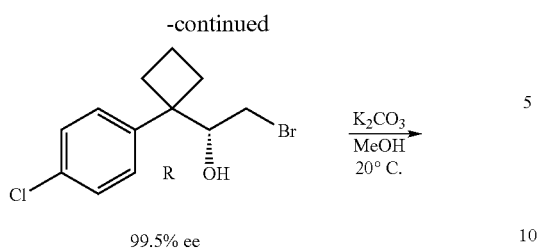
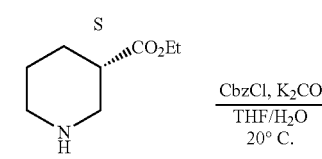
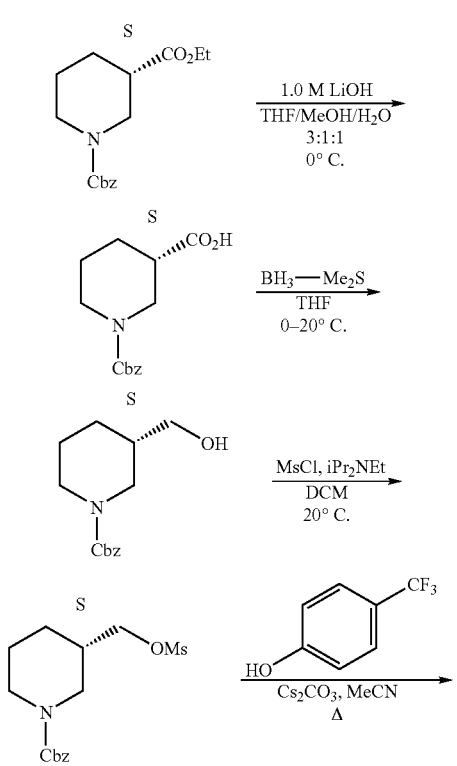
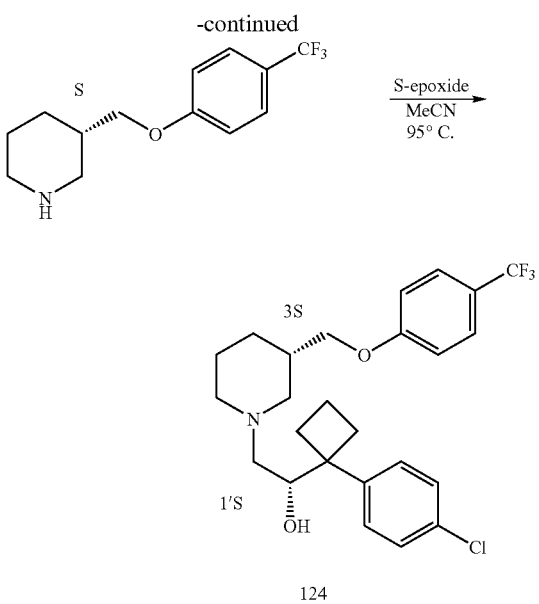
The (3S, 1'R) diastereomer, 125, was prepared by coupling the R-epoxide with the S-piperdine (See Scheme 3). This compound had a unique $^1$H-NMR and $^{13}$C-NMR compared to 124 as expected for a diastereomer. This compound had a measured optical rotation of $[\alpha]_D = -1545.6°$ (c=2.26; CHCl$_3$; 589 nm, 21° C.).
Scheme 3
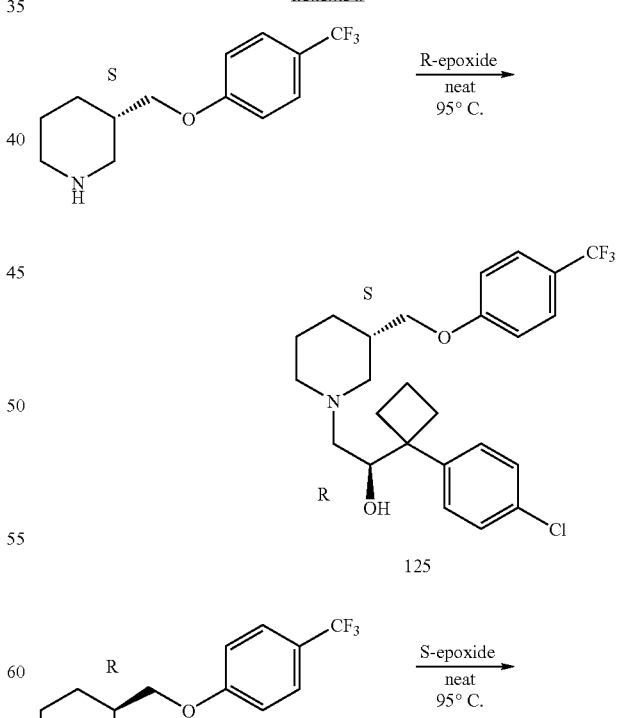

Example 145

Synthesis of (R)-1-[1-(4-Methoxy-phenyl)-cyclobutylmethyl]-3-(4-trifluoromethoxy-phenoxymethyl)-piperidine

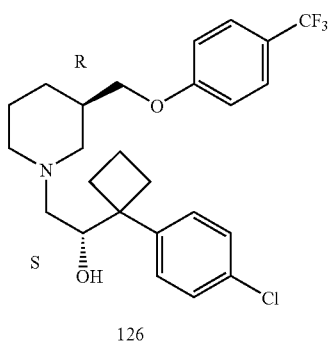

126

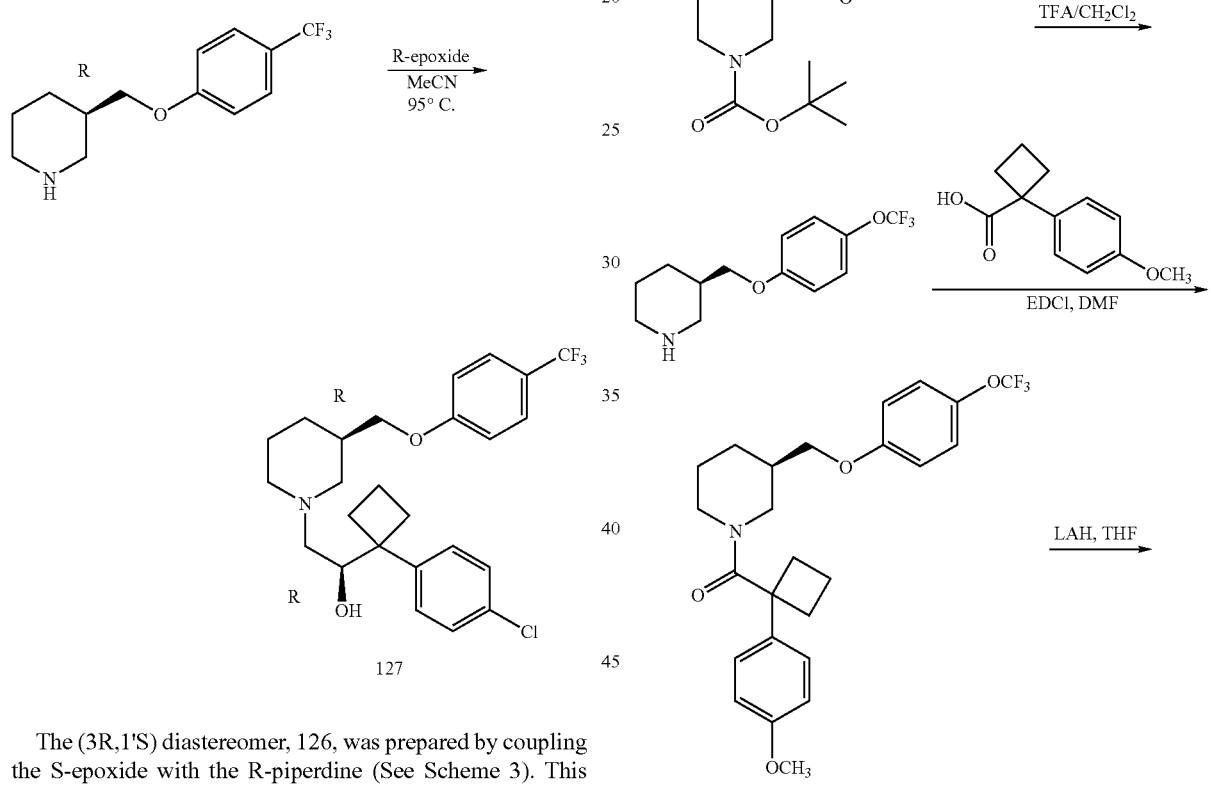

127

The (3R,1'S) diastereomer, 126, was prepared by coupling the S-epoxide with the R-piperdine (See Scheme 3). This compound had identical $^1$H-NMR and $^{13}$C-NMR to its enantiomer, 125. This compound had a measured optical rotation of $[\alpha]_D=+1479.1°$ (c=1.13; CHCl$_3$; 589 nm, 21° C.).

The (3R,1'R) diastereomer, 127, was prepared by coupling the R-epoxide with the R-piperdine (See Scheme 3). This compound had identical $^1$H-NMR and $^{13}$C-NMR to its enantiomer, 124. This compound had a measured optical rotation of $[\alpha]_D=+258.7°$ (c=1.50; CHCl$_3$; 589 nm, 21° C.).

References Cited in Example 144
1) (a) Corey, E. J.; Bakshi, R. K.; Shibata, S. *J. Am. Chem. Soc.* 1987, 109, 5551. (b) Corey, E. J.; Bakshi, R. K.; Shibata, S.; Chen, C.-P.; Singh, V. K. *J. Am. Chem. Soc.,* 1987, 109, 7925. (c) Corey, E. J.; Shibata, S.; Bakshi, R. K. *J. Org. Chem.,* 1988, 53, 2861.
2) Marnus, P.; Thurston, L. S. *J. Org. Chem.* 1991, 56, 1166.

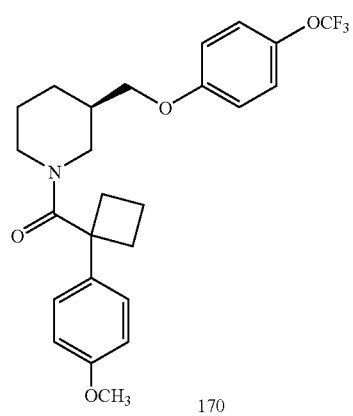

170

Preparation of (R)-[3-(4-trifluoromethoxy-phenoxymethyl)-piperidine-1-carboxylic acid tert-butyl ester]

To a solution of (R)-3-Methanesulfonyloxymethyl-piperidine-1-carboxylic acid tert-butyl ester (3.522 g, 12 mmol) in CH₃CN (100 mL) at room temperature was added 4-(trifluoromethoxy)phenol (1.555 mL, 12 mmol) and Cs₂CO₃ (7.820 g, 24 mmol). The mixture was heated at reflux for 20 hours. After cooling to room temperature, the mixture was filtered and concentrated in vacuo. The residue was dissolved in 250 mL EtOAc, and washed with water (125 mL), saturated Na₂CO₃ (125 mL), and water (125 mL), The organic layer was dried over Na₂SO₄, filtered and concentrated in vacuo. The residue was purified by flash column chromatography using a gradient of 0 to 25% EtOAc in hexane to provide the phenyl ether (3.40 g, 81%). ¹H NMR (300 MHz, CDCl₃): δ 7.14 (d, J=9.0 Hz, 2H), 6.88 (d, J=9.0 Hz, 2H), 3.76–3.91 (m, 4H), 2.92 (br s, 2H), 1.99–2.05 (m, 1H), 1.87–1.92 (m, 1H), 1.67–1.74 (m, 1H), 1.46 (s, 9H), 1.27–1.40 (m, 2H). ¹³C NMR (CDCl₃): δ 157.7, 155.2, 142.9, 122.7, 120.0, 115.4, 79.7, 70.6, 47.1, 44.4, 36.0, 28.6, 27.5, 24.5.

Preparation of (R)-[3-(4-Trifluoromethoxy-phenoxymethyl)-piperidine]

A solution of the phenyl ether (3.40 g, 9.60 mmol) in CH₂Cl₂ (30 mL) at 0° C. was treated with TFA (30 mL). The reaction mixture was allowed to warm up to 25° C., and stirred for 1 hour. The solvent was removed Na₂SO₄. The residue was dissolved in CH₂Cl₂ (50 mL), washed with saturated NaHCO₃ (50 mL) and brine (50 mL). The organic layer was dried over Na₂SO₄, filtered and concentrated in vacuo to yield the secondary amine (2.31 g, 88%). LRMS m/z 276 (M⁺, $C_{13}H_{16}F_3NO_2^+$, requires 276).

Preparation of (R)-[1-(Methoxy-phenyl cyclobutyl]-[3-(4-trifluoromethoxy-phenoxymethyl0-piperidin-1-yl]-methanone To a solution of the secondary amine (1.0 g, 3.63 mmol), 1-(4-methoxy-phenyl)-cyclobutanecarboxylic acid (0.824 g, 4.0 mmol) and HOBt (0.612 g, 4.0 mmol) in DMF (8.0 mL) was added 1-[3-(dimethylamino)propyl]-3-ethylcarbodiimide methiodide (1.19 g, 4.0 mmol). The mixture was stirred at room temperature for 20 hours. Then, the reaction mixture was poured into water (30 mL), extracted with EtOAc (3×30 mL). The organic layer was washed with saturated NaHCO₃ (30 mL), brine (30 mL), and brine (30 mL), dried over Na₂SO₄, and concentrated in vacuo. The residue was purified by flash column chromatography using a gradient of 0 to 25% EtOAc/hexane to provide the corresponding amide (1.40 g, 83%). ¹H NMR (CDCl₃): δ 7.33 (d, J=8.7 Hz, 2H), 7.15 (d, J=8.7 Hz, 2H), 6.76–6.91 (m, 4H), 4.50 (br s, 1H), 3.80 (s, 3H), 3.28–3.65 (m, 3H), 2.30–2.94 (m, 6H), 1.73–2.06 (m, 4H), 1.25–1.45 (m, 3H). ¹³C NMR (CD Cl₃): d 174.6, 158.3, 157.5, 142.9, 135.9, 126.4, 122.7, 120.0, 115.4, 115.2, 114.3, 70.5, 55.4, 52.0, 49.0, 46.3, 45.6, 43.2, 36.0, 33.1, 32.4, 27.4, 24.6, 24.0, 15.6.

Preparation of (R)-1-[1-(4-Methoxy-phenyl)-cyclobutylmethyl]-3-(4-trifluoromethoxy-phenoxymethyl)-piperidine To a solution of the amide (0.70 g, 1.51 mmol) in THF (20 mL) was added LiAlH₄ (0.058 g, 1.51 mmol) at −70° C.

After addition, the reaction mixture was heated at reflux for 3 hours. Then, the mixture was cooled to 0° C. , and quenched with 2 N NaOH (0.3 mL) and water (0.3 mL). The mixture was filtered and concentrated in vacuo. The residue was purified by flash column chromatography, eluting with CH₂Cl₂/MeOH to provide free amine 170 (0.58 g, 86%, >99.9% ee). ¹H NMR (300 MHz, CDCl₃): δ 7.12–7.19 (m, 4H), 6.89 (d, J=2.6 Hz, 2H), 6.85 (d, J=2.6 Hz, 2H), 3.82 (s, 3H), 3.65–3.78 (m, 2H), 2.63 (AB quartet, J=13.5 Hz, 2 H), 1.11–2.54 (m, 15H). ¹³C NMR (CDCl₃): δ 158.0, 157.5, 142.7, 142.2, 127.3, 122.6, 120.0, 115.4, 113.3, 71.3, 69.4, 59.1, 56.6, 55.4, 47.0, 36.3, 32.0, 31.9, 27.0, 24.9, 16.3. LRMS m/z 450 (M⁺, $C_{25}H_{30}F_3NO_3^+$, requires 450).

Example 146

Synthesis of (S)-1-[1-(4-Methoxy-phenyl)-cyclobutylmethyl]-3-(4-trifluoromethoxy-phenoxymethyl)-piperidine

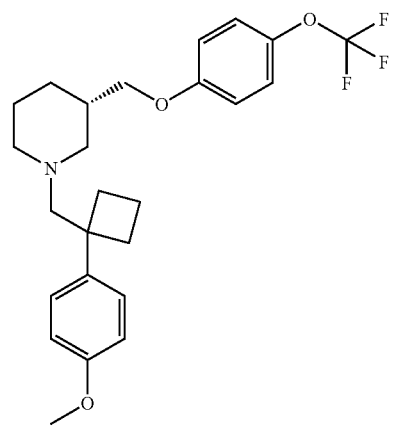

171

Compound 171 was prepared using the procedure outlined in Example 145, starting with the (S)-3-methanesulfonyloxymethyl-piperidine-1-carboxylic acid tert-butyl ester. The chiral purity of 171 was determined to be 98.4% ee using chiral HPLC analysis.

Example 147

Synthesis of [2-{3-[1-(4-Chloro-phenyl)-cyclobutylmethyl]-cyclohexyl}-2-(4-trifluoromethyl-phenoxy)-ethyl]-dimethyl-amine

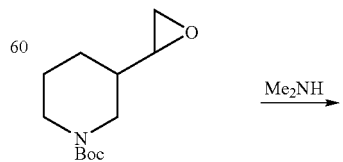

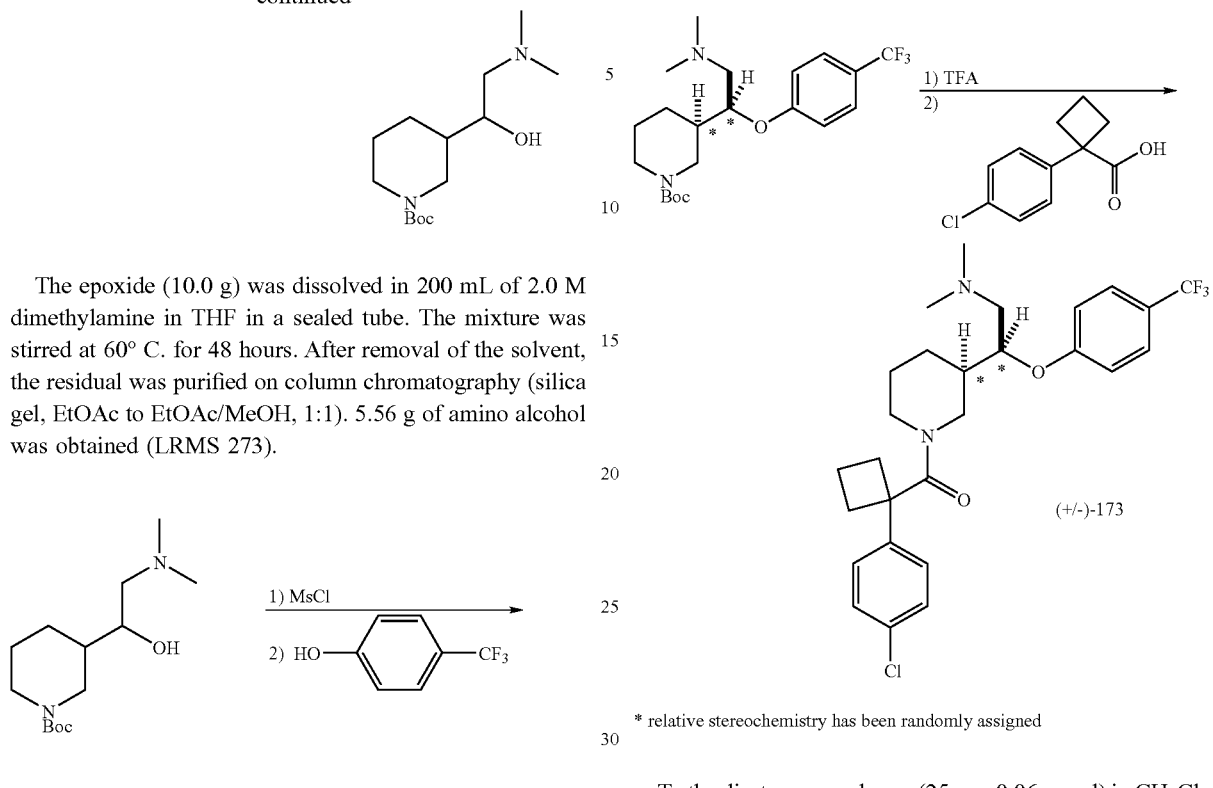

The epoxide (10.0 g) was dissolved in 200 mL of 2.0 M dimethylamine in THF in a sealed tube. The mixture was stirred at 60° C. for 48 hours. After removal of the solvent, the residual was purified on column chromatography (silica gel, EtOAc to EtOAc/MeOH, 1:1). 5.56 g of amino alcohol was obtained (LRMS 273).

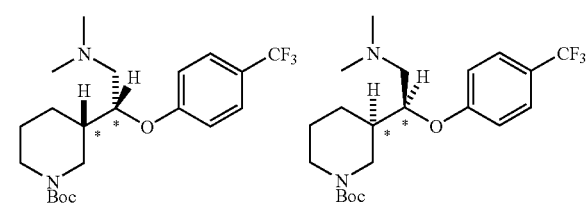

* relative stereochemistry has been randomly assigned

The amino alcohol (8.95 g, 32.9 mmol) was dissolved in 80 mL of $CH_2Cl_2$ and cooled down at 0° C. Then N,N-diisopropylethylamine (11.46 mL, 2 eq.) and methanesulfonyl chloride (3.06 mL, 1.2 eq.) were added. The reaction mixture was stirred at r.t. for 6 hours. To the mixture was added 20 mL of water and the aqueous layer was extracted with EtOAc (3×100 mL). The organic layer was washed with brine and dried over $Na_2SO_4$. After filtration and evaporation, the crude residual (10.5 g) was dissolved in 90 mL of $CH_3CN$. To the solution the potassuim cabonate (20.7 g, 5 eq.) and α,α,α-trifluoro-p-cresol (9.72 g, 2 eq.) were added and the mixture was stirred at 60° C. overnight. The mixture was quenched with water (50 mL), extracted with EtOAc (2×60 mL). The combined organic phase was washed with brine (2×50 mL) and dried over $Na_2SO_4$. After filtration and removal of the solvent, silica gel flash column chromatography gave the diastereomeric phenyl ethers.

* relative stereochemistry has been randomly assigned

To the diastereomer shown (25 mg, 0.06 mmol) in $CH_2Cl_2$ (1.0 mL), trifluoroacetic acid (1.0 mL) was added at 0° C. After completion of addition the reaction mixture continued stirring at r.t. for 20 minutes. The solvent was removed and the residual was dried in vacuo for 2 hours. The resulting oil was dissolved in 1.0 mL of DMF. To this solution 1-(4-chlorophenyl)-1-cyclobutanecarboxylic acid (15.2 mg, 1.2 eq.), 1-[3-(dimethylamino)propyl]-3-ethylcarbodiimide methiodine (21.4, 1.2 eq.) and HOBt were added. The mixture was stirred at r.t. overnight. The reaction was quenched with 20 mL of EtOAc and 5 mL of 10% aqueous NaOH. The organic layer was washed with 5 mL of brine and dried over $Na_2SO_4$. The preparative TLC (silica gel, EtOAc/Hexane, 2:1) gave (+/−)-173 (27 mg, yield 89%). LRMS 509.

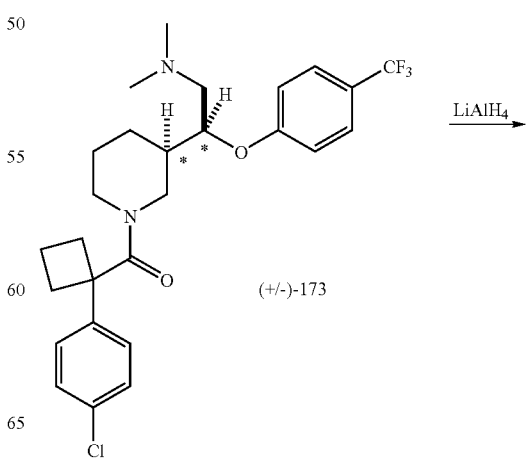

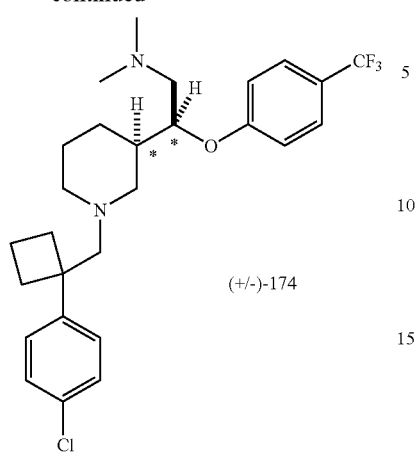

(+/−)-174

* relative stereochemistry has been randomly assigned

To a solution of (+/−)-173 (25 mg, 0.05 mmol) in 3 mL of dry THF was added LiAlH$_4$ (4 mg) at r.t. The mixture was refluxed for 2 hour. The reaction mixture was quenched with 5 mL of water and extracted with EtOAc (3×10 mL). The combined organic layer was washed with brine (2×5 mL) and dried over Na$_2$SO$_4$. The preparative TLC (silica gel, EtOAc) gave (+/−)-174 (13 mg, yield 51%). LRMS 495.

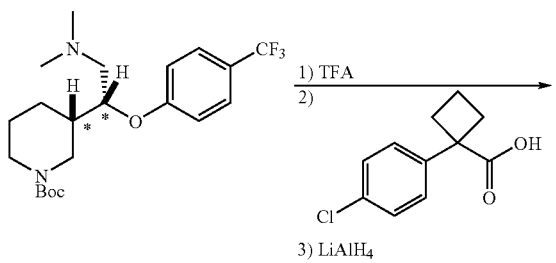

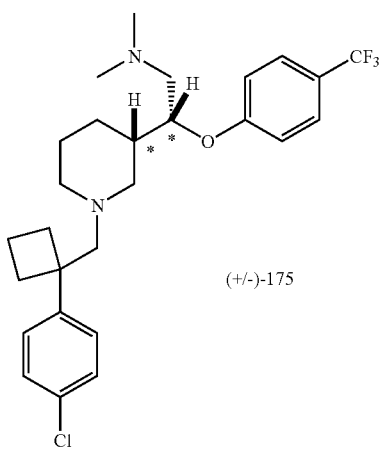

(+/−)-175

* relative stereochemistry has been randomly assigned

Employing the same procedures, compound the diastereomer shown (25 mg) was converted into compound (+/−)-175 (10 mg, LRMS 495).

Example 148

Synthesis of 1-(2,3-Dihydro-benzo[1,4]dioxin-2-ylmethyl)-3-(4-trifluoromethyl-phenoxymethyl)-piperidine

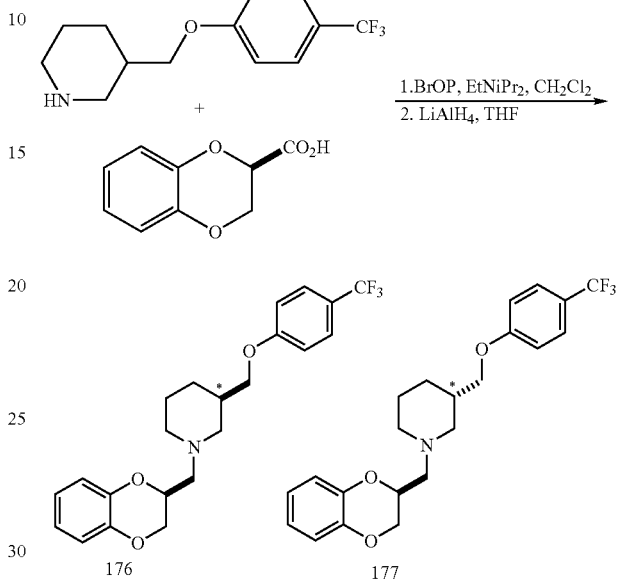

176    177

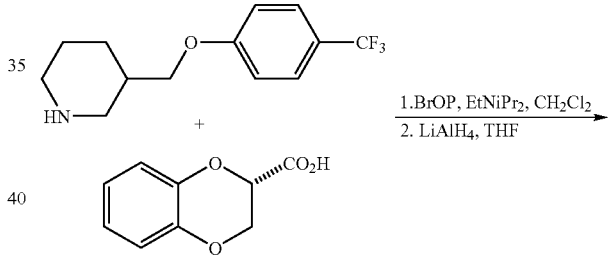

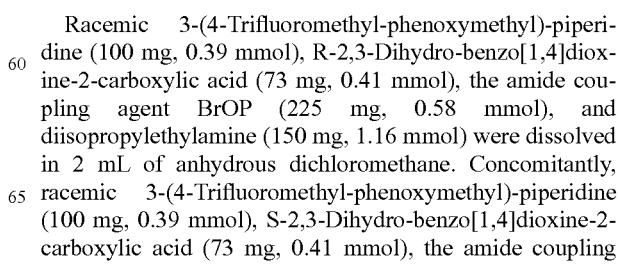

178    179

* stereochemistry has been randomly assigned

Racemic 3-(4-Trifluoromethyl-phenoxymethyl)-piperidine (100 mg, 0.39 mmol), R-2,3-Dihydro-benzo[1,4]dioxine-2-carboxylic acid (73 mg, 0.41 mmol), the amide coupling agent BrOP (225 mg, 0.58 mmol), and diisopropylethylamine (150 mg, 1.16 mmol) were dissolved in 2 mL of anhydrous dichloromethane. Concomitantly, racemic 3-(4-Trifluoromethyl-phenoxymethyl)-piperidine (100 mg, 0.39 mmol), S-2,3-Dihydro-benzo[1,4]dioxine-2-carboxylic acid (73 mg, 0.41 mmol), the amide coupling agent BrOP (225 mg, 0.58 mmol), and diisopropylethylamine (150 mg, 1.16 mmol) were dissolved in 2 mL of anhydrous dichloromethane. Each mixture was kept at room temperature overnight, diluted with 10 mL of water, and 10 mL of ether. Extractive workup gave in each case, after concentration of the organic layers in vacuo and chromatography on silica gel using a EtOAc-hexane gradient column, the desired amide intermediate in 75–88% yield.

Each intermediate amide mixture was dissolved in 5 mL of THF at 0° C. and excess lithium aluminum hydride (100 mg, ca. 7 equivalents) was added. The solutions were heated to reflux for 5 minutes, cooled to 0° C., and quenched by dropwise addition of 0.5 mL 1M NaOH. Additional THF (10 mL) was added to each, and the suspensions were stirred at room temperature for 30 minutes and then filtered though a plug of sodium sulfate. The solutions thus obtained were concentrated in vacuo and the residues were purified by preparative HPLC using a Chiralpak AD™ column from Chiral Technologies, Inc., eluting with an 99:1 mixture of hexane and isopropyl alcohol containing ca. 0.1% diethylamine. Each mixture of diastereomers was separated in this fashion, and the pairs of amines were obtained in 50–65% total yield from each corresponding amide mixture (176, 177, 178, and 179). Data for each diastereomer: MS 408 ($M^++1$). $^1H$ and $^{13}C$ (DEPT) NMR data for each isomer was consistent with the assigned structure. Particularly diagnostic in distinguishing the diastereomers by NMR was the observance of a pair of doublets in the $^1H$ spectrum that appear at δ=3.09 ppm (J=10 Hz) and δ=2.80 ppm (J=10 Hz) for one diastereomer and δ=2.98 ppm (J=7 Hz) and δ=2.91 ppm (J=7 Hz) for the other diastereomer.

Example 149

Synthesis of 1-(4-Chloro-phenoxy)-3-[3-(4-trifluoromethyl-phenoxymethyl)-piperidin-1-yl]-propan-2-ol

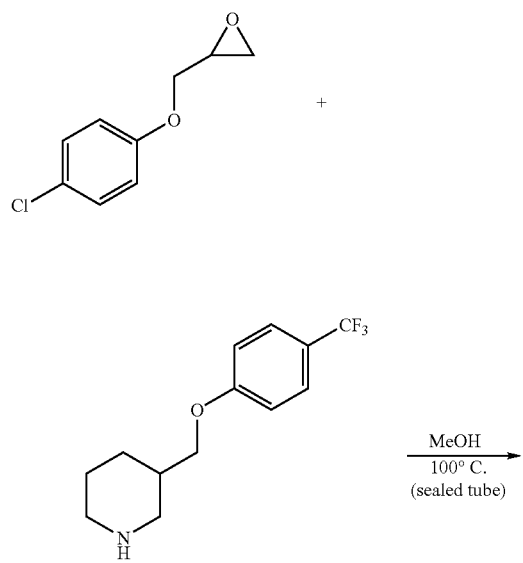

2-(4-Chloro-phenoxymethyl)-oxirane (50 mg) and of 3-(4-Trifluoromethyl-phenoxymethyl)-piperidine (70 mg, 1.0 equivalent) in 4 mL of methanol were heated in a sealed tube at 100° C. for 16 hours, cooled to room temperature, transferred to a round-bottomed flask, and concentrated in vacuo. The crude residue was purified by flash chromatography on silica gel using as eluent a gradient of ethyl acetate in hexane containing 1% ammonium hydroxide. 95 mg of 1-(4-Chloro-phenoxy)-3-[3-(4-trifluoromethyl-phenoxymethyl)-piperidin-1-yl]-propan-2-ol was obtained (79%). Data for this mixture of amino alcohol diastereomers: MS 444 ($M^++1$).

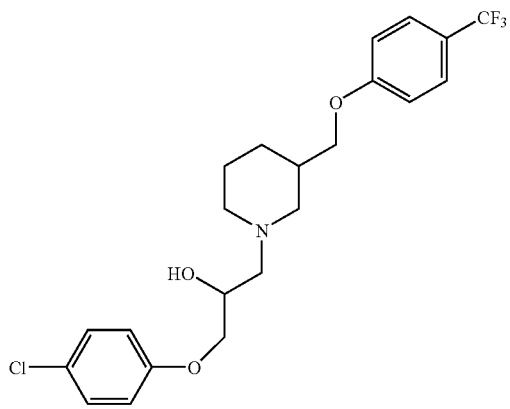

Example 150

Synthesis of 3-{2-[3-(4-Trifluoromethyl-phenoxymethyl)-piperidin-1-yl]-ethyl}-1H-indole

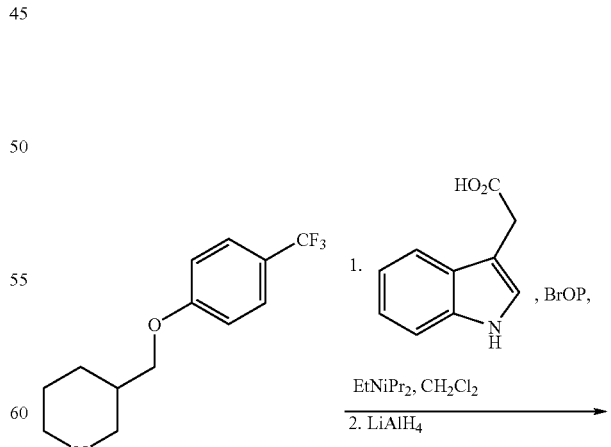

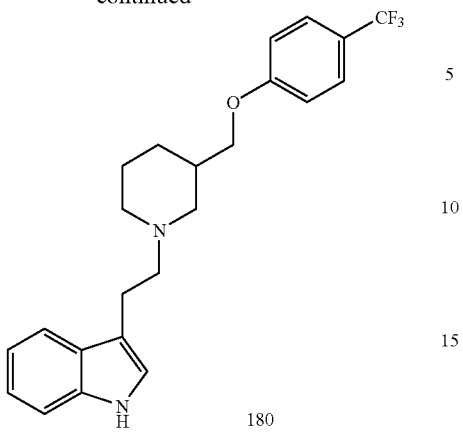

180

3-(4-Trifluoromethyl-phenoxymethyl)-piperidine (50 mg, 0.19 mmol), (1H-Indol-3-yl)-acetic acid (73 mg, 0.21 mmol), the amide coupling agent BrOP (123 mg, 0.32 mmol), and diisopropylethylamine (75 mg, 0.58 mmol) were dissolved in 2 mL of anhydrous dichloromethane. The mixture was kept at room temperature overnight, diluted with 10 mL of water, and 10 mL of ether. Extractive workup gave in each case, after concentration of the organic layers in vacuo and chromatography on silica gel using a EtOAc-hexane gradient column, the desired amide intermediate (71 mg, 90%). This amide was dissolved in 5 mL of THF at 0° C. and excess lithium aluminum hydride (50 mg, ca. 8 equivalents) was added. The solution was heated to reflux for 5 minutes, cooled to 0° C., and quenched by dropwise addition of 0.5 mL 1M NaOH. Additional THF (10 mL) was added, and the suspension was stirred at room temperature for 30 minutes and then filtered though a plug of sodium sulfate. The solution thus obtained was concentrated in vacuo and the residue was purified by flash chromatography on silica gel using as eluent a gradient of ethyl acetate in hexane containing 1% ammonium hydroxide. 53 mg of 3-{2-[3-(4-Trifluoromethyl-phenoxymethyl)-piperidin-1-yl]-ethyl}-1H-indole, 180, was obtained (77%). Data for this compound: MS 403 (M++1).

Example 151

Synthesis of 1-(2-Biphenyl-4-yl-ethyl)-3-(4-trifluoromethyl-phenoxymethyl)-piperidine

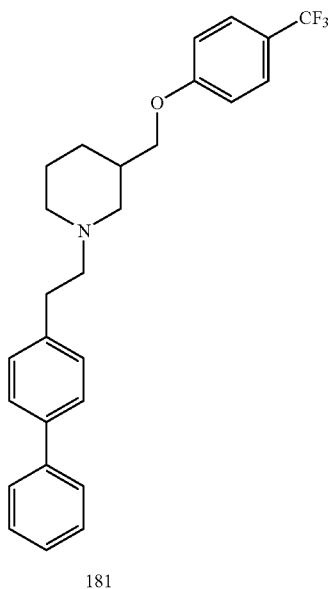

181

Following exactly the same two step procedure used in the previous example for the preparation of 3-{2-[3-(4-Trifluoromethyl-phenoxymethyl)-piperidin-1-yl]-ethyl}-1H-indole but using biphenyl-4-yl-acetic acid in place of (1H-Indol-3-yl)-acetic acid, 1-(2-Biphenyl-4-yl-ethyl)-3-(4-trifluoromethyl-phenoxymethyl)-piperidine was obtained in 54% overall yield from 0.19 mmol of 3-(4-Trifluoromethyl-phenoxymethyl)-piperidine, 181. Data for this compound: MS 440 (M++1).

Example 152

Synthesis of (S)-[2-{1-[1-(4-Chloro-phenyl)-cyclobutylmethyl]-piperidin-3-yl}-1-phenyl-ethanol]

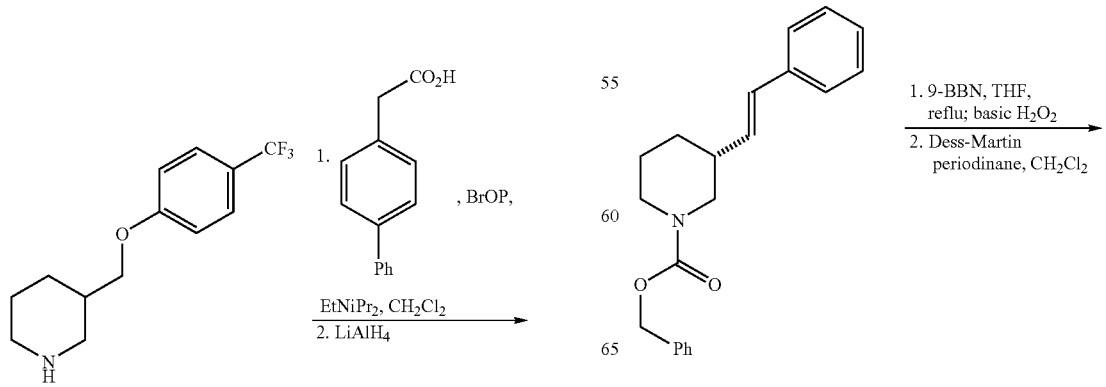

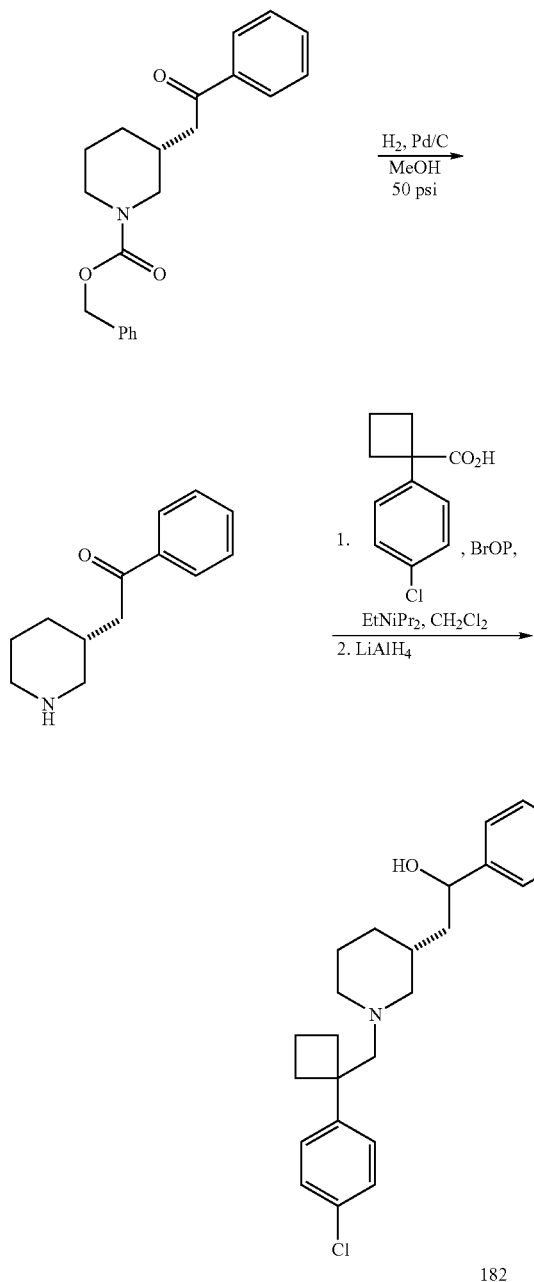

Preparation of (S)-[3-(2-Oxo-2-phenyl-ethyl)-piperidine-1-carboxylic acid benzyl ester]

To a solution of (S)-3-styryl-piperidine-1-carboxylic acid benzyl ester (411 mg, 1.28 mmol, in 5 mL of THF) was added 3.86 mL of a 0.5 M THF solution of 9-borabicyclononane. The solution was brought to reflux and then cooled to room temperature after 3 hours. 2 mL of 30% hydrogen peroxide solution and 2 mL of 3M NaOH were added dropwise. The solution was stirred for 30 minutes, diluted with water (20 mL) and ether (30 mL). Extractive workup gave, after concentration of the organic layers in vacuo and chromatography on silica gel using as eluent an EtOAc-hexane gradient, the desired alcohol intermediate (69 mg, 85%; MS 340=M$^+$+1). This alcohol (350 mg, 1.03 mmol) was dissolved in 5 mL of methylene chloride and treated with 1.1 equivalents of the Dess-Martin periodinane. After 2 hours at room temperature, 1 mL of isopropanol was added, and then after 5 minutes 5 mL of 1M NaOH was added. After 20 minutes, to the mixture was added 30 mL of ether and 30 mL of water. Extractive workup gave, after concentration of the organic layers in vacuo and chromatography on silica gel using as eluent an EtOAc-hexane gradient, the desired ketone intermediate (S)-3-(2-Oxo-2-phenyl-ethyl)-piperidine-1-carboxylic acid benzyl ester (337 mg, 97%; MS 338=M$^+$+1).

Preparation of (S)-[1-phenyl-2-piperidin-3-yl-ethanone]

(S)-[3-(2-Oxo-2-phenyl-ethyl)-piperidine-1-carboxylic acid benzyl ester] (266 mg, 0.79 mmol) was dissolved in 2 mL of methanol in a small vessel for pressurized hydrogenation. 200 mg of 5% palladium on carbon was added. The vessel was charged with 50 psi of hydrogen and shaken for two hours. The vessel was evacuated, filtered, and the residue was concentrated in vacuo to yield 155 mg of the desired product (S)-[1-Phenyl-2-piperidin-3-yl-ethanone] (97%; MS 204=M$^+$+1).

Preparation of (S)-[2-{1-[1-(4-Chloro-phenyl)-cyclobutylmethyl]-piperidin-3-yl}-1-phenyl-ethanol]

(S)-[1-Phenyl-2-piperidin-3-yl-ethanone] (142 mg, 0.70 mmol) and 1-(4-Chloro-phenyl)-cyclobutanecarboxylic acid (148 mg, 0.70 mmol) were dissolved in 5 mL of methylene chloride and treated with the amide coupling agent BrOP (1.05 mmol), and diisopropylethylamine (2.1 mmol). The mixture was kept at room temperature overnight, diluted with 20 mL of water, and 50 mL of ether. Extractive workup gave, after concentration of the organic layers in vacuo and chromatography on silica gel using a EtOAc-hexane gradient column, the desired amide intermediate 2-{1-[1-(4-Chloro-phenyl)-cyclobutanecarbonyl]-piperidin-3-yl}-1-phenyl-ethanone (254 mg, 92%). This amide was dissolved in 10 mL of THF at 0° C. and excess lithium aluminum hydride (245 mg) was added. The solution was heated to reflux for 5 minutes, cooled to 0° C., and quenched by dropwise addition of 1.5 mL 1M NaOH. Additional THF (10 mL) was added, and the suspension was stirred at room temperature for 30 minutes and then filtered though a plug of sodium sulfate. The solution thus obtained was concentrated in vacuo and the residue was purified by flash chromatography on silica gel using as eluent a gradient of ethyl acetate in hexane containing 1% ammonium hydroxide. 205 mg of (S)-[2-{1-[1-(4-Chloro-phenyl)-cyclobutylmethyl]-piperidin-3-yl}-1-phenyl-ethanol], 182, was obtained (83%). $^1$H and $^{13}$C NMR data was consistent with the assigned structure. Data for this compound as a mixture of diastereomers: MS 384 (M$^+$+1).

Example 153

Synthesis of (S)-[2-{1-[1-(4-Chloro-phenyl)-cyclobutylmethyl]-piperidin-3-yl}-1-phenyl-ethanone]

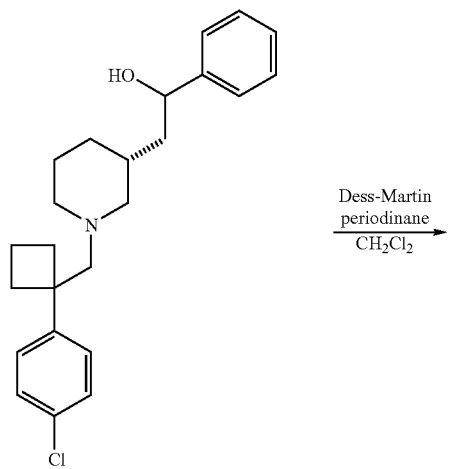

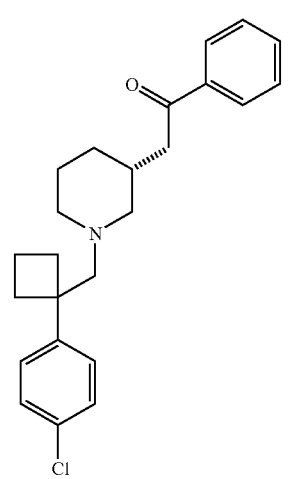

183

(S)-[2-{1-[1-(4-Chloro-phenyl)-cyclobutylmethyl]-piperidin-3-yl}-1-phenyl-ethanol] (29 mg, 0.075 mmol) was dissolved in 2 mL of methylene chloride and treated with 1.1 equivalents of the Dess-Martin periodinane. After 2 hours at room temperature, 0.5 mL of isopropanol was added, and then after 5 minutes 1 mL of 1M NaOH was added. After 20 minutes, to the mixture was added 20 mL of ether and 20 mL of water. Extractive workup gave, after concentration of the organic layers in vacuo and chromatography on silica gel using as eluent an EtOAc-hexane gradient with 1% ammonium hydroxide, the desired product (S)-[2-{1-[1-(4-Chloro-phenyl)-cyclobutylmethyl]-piperidin-3-yl}-1-phenyl-ethanone], 183, (15 mg, 53%). Data for this ketone: MS 382 ($M^+$+1).

Example 154

Synthesis of (S)-[1-[1-(4-Chloro-phenyl)-cyclobutylmethyl]-3-(2-methoxy-2-phenyl-ethyl)-piperidine]

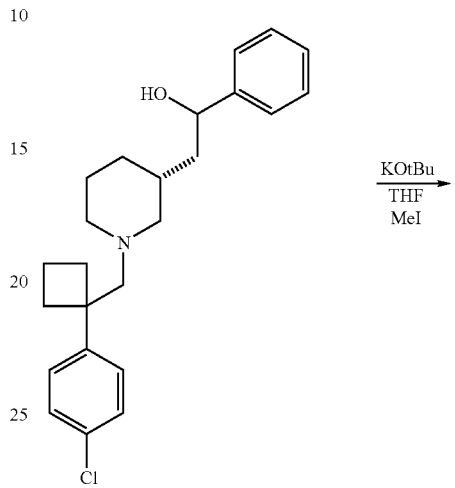

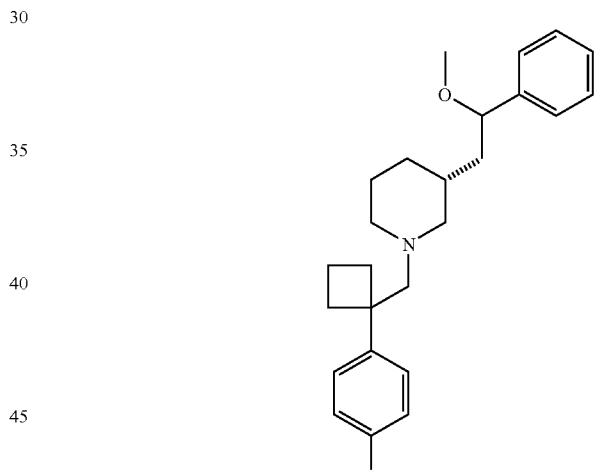

184

(S)-[2-{1-[1-(4-Chloro-phenyl)-cyclobutylmethyl]-piperidin-3-yl}-1-phenyl-ethanol] (38 mg, 0.100 mmol) was dissolved in 1 mL of THF and cooled to 0° C. Potassium tert-butoxide was added (112 mg, 1.0 mmol) followed by methyl iodide in large excess (ca. 0.5 mL). After 30 minutes at 0° C., water (5 mL) and ether (5 mL) were added. Extractive workup gave, after concentration of the organic layers in vacuo and chromatography on silica gel using as eluent an EtOAc-hexane gradient with 1% ammonium hydroxide, the desired product 1-[1-(4-Chloro-phenyl)-cyclobutylmethyl]-3-(2-methoxy-2-phenyl-ethyl)-piperidine, 184, (28 mg, 70%). Data for this compound: MS 398 ($M^+$+1).

Example 155

Synthesis of (S)-[1-{1-[1-(4-Chloro-phenyl)-cyclobutylmethyl]-piperidin-3-yl}-2-phenyl-propan-2-ol]

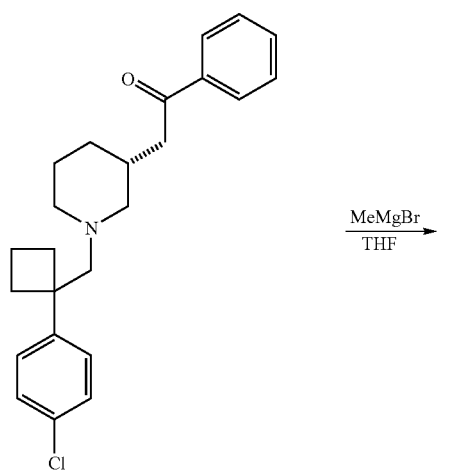

185

(S)-[2-{1-[1-(4-Chloro-phenyl)-cyclobutylmethyl]-piperidin-3-yl}-1-phenyl-ethanone] (10 mg, 0.027 mmol) was dissolved in 1 mL of anhydrous THF and cooled to 0° C. Methyl magnesium bromide solution (0.27 mL of a 1M solution in THF, 0.27 mmol) was added via syringe. After 30 minutes the reaction was quenched by adding 0.5 mL of 1M NaHSO$_4$ solution. Water (4 mL) and ether (10 mL) were added. Extractive workup gave, after concentration of the organic layers in vacuo and chromatography on silica gel using as eluent an EtOAc-hexane gradient with 1% ammonium hydroxide, the desired product (S)-[1-{1-[1-(4-Chloro-phenyl)-cyclobutylmethyl]-piperidin-3-yl}-2-phenyl-propan-2-ol], 185, (8 mg, 75%). Data for this compound: MS 398 (M$^+$+1).

Example 156

Synthesis of (S)-1-[1-(4-Chloro-phenyl)-cyclobutyl-methyl]-3-(2-phenyl-propyl)-piperidine

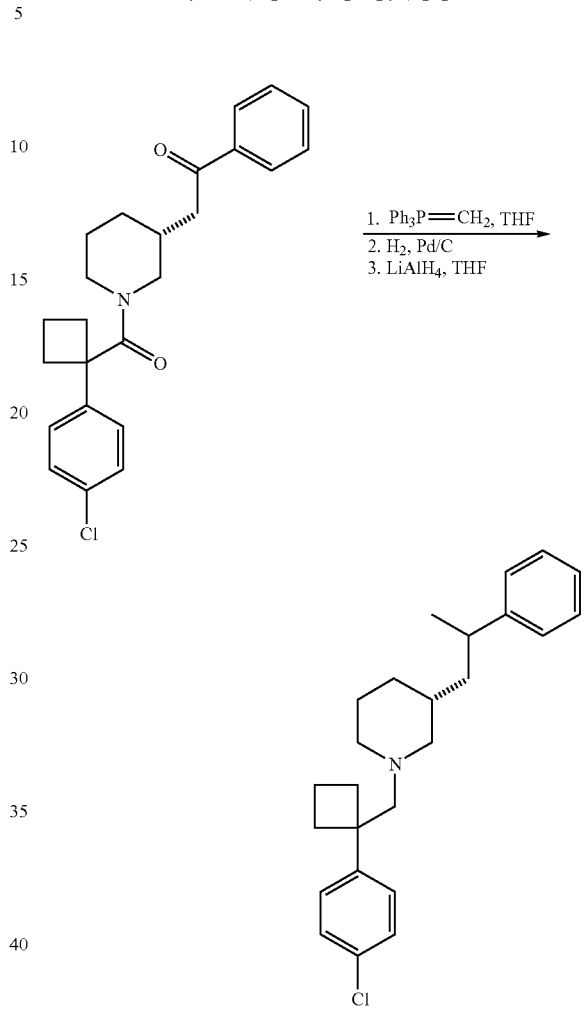

186

(S)-2-{1-[1-(4-Chloro-phenyl)-cyclobutanecarbonyl]-piperidin-3-yl}-1-phenyl-ethanone (12.7 mg, 0.032 mmol) in 1 mL of THF was treated with 5 equivalents of methylene Wittig reagent at room temperature. The crude mixture was concentrated in vacuo, dissolved in a minimal amount of methylene chloride, and then this product mixture purified by flash column chromatography on silica gel using a gradient elution with an EtOAc-hexane mixture. The desired olefin was obtained (10.4 mg, 82%) and was immediately dissolved in 1 mL of methanol in a small vessel for pressurized hydrogenation. 20 mg of 10% palladium on carbon was added. The vessel was charged with 50 psi of hydrogen and shaken for 6 hours. The vessel was evacuated, filtered, and the residue was concentrated in vacuo to yield 10.3 mg of the desired product (99%). This unpurified product was dissolved in 1 mL of THF at 0° C. and excess lithium aluminum hydride (0.30 mL of a 1M solution in ether, ca. 10 equiv.) was added. The solution was heated to reflux for 5 minutes, cooled to 0° C., and quenched by dropwise addition of 0.5 mL 1M NaOH. Additional THF (2 mL) was added, and the suspension was stirred at room temperature for 30 minutes and then filtered though a plug of sodium sulfate.

The solution thus obtained was concentrated in vacuo and the residue was purified by flash chromatography on silica gel using as eluent a gradient of ethyl acetate in hexane containing 1% ammonium hydroxide. (S)-1-[1-(4-Chloro-phenyl)-cyclobutylmethyl]-3-(2-phenyl-propyl)-piperidine, 186, was obtained (7.2 mg, 72%). Data for this compound: MS 382 (M$^+$+1).

Example 157

Synthesis of 1-(4-Chloro-phenyl)-4-[3-(4-trifluoromethyl-phenoxymethyl)-piperidin-1-ylmethyl]-cyclohexanol

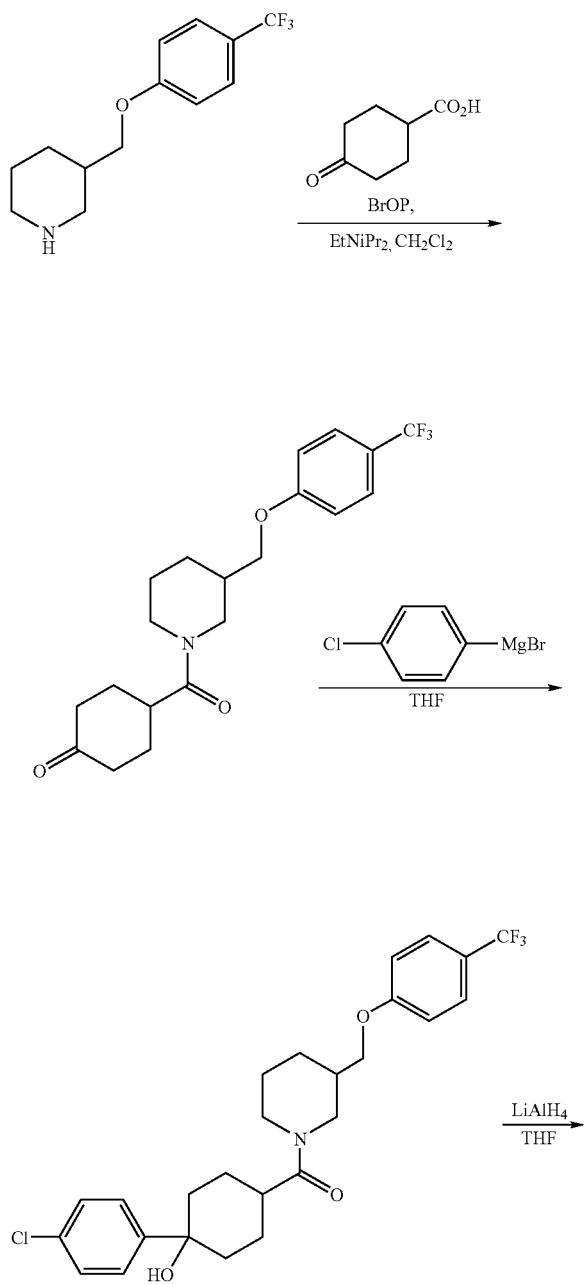

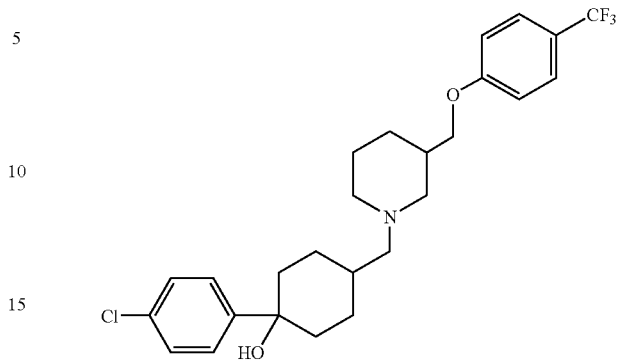

187

3-(4-Trifluoromethyl-phenoxymethyl)-piperidine (122 mg, 0.47 mmol), 4-Oxo-cyclohexanecarboxylic acid (67 mg, 0.47 mmol) the amide coupling agent BrOP (274 mg, 0.71 mmol), and diisopropylethylamine (183 mg, 1.41 mmol) were dissolved in 2 mL of anhydrous dichloromethane. The mixture was kept at room temperature overnight, diluted with 10 mL of water, and 10 mL of ether. Extractive workup gave, after concentration of the organic layers in vacuo and chromatography on silica gel using a EtOAc-hexane gradient column, the desired amide intermediate, 4-[3-(4-Trifluoromethyl-phenoxymethyl)-piperidine-1-carbonyl]-cyclohexanone (136 mg, 75%; MS 384=M$^+$+1).

A portion of this ketone (105 mg, 0.27 mmol) amide mixture was dissolved in 2 mL of THF at 0° C. and p-Cl-phenyl magnesium bromide (0.68 mL of a 1M solution, 2.5 equivalents) was added via syringe. After 30 minutes, 2 mL of 1M NaHSO$_4$ solution was added, followed by 15 mL of water and 15 mL of ether. Extractive workup gave, after concentration of the organic layers in vacuo and chromatography on silica gel using a EtOAc-hexane gradient column, the desired Grignard adduct [4-(4-Chloro-phenyl)-4-hydroxy-cyclohexyl]-[3-(4-trifluoromethyl-phenoxymethyl)-piperidin-1-yl]-methanone (88 mg, 65%; MS 478=M+1 minus water). A portion of this material (41 mg, 0.083 mmol) was dissolved in 2 mL of THF and excess lithium aluminum hydride (31 mg, ca. 10 equivalents) was added. The solution was heated to reflux for 5 minutes, cooled to 0° C., and quenched by dropwise addition of 1 mL 1M NaOH. Additional THF (10 mL) was added, and the suspension was stirred at room temperature for 30 minutes and then filtered though a plug of sodium sulfate. The solution thus obtained was concentrated in vacuo and the residue was purified by flash chromatography on silica gel using as eluent a gradient of ethyl acetate in hexane containing 1% ammonium hydroxide. 1-(4-Chloro-phenyl)-4-[3-(4-trifluoromethyl-phenoxymethyl)-piperidin-1-ylmethyl]-cyclohexanol (187) was obtained (28 mg, 70%). MS 482 (M$^+$+1), 464 (M$^+$+1 minus water).

Example 158

Synthesis of 4-[3-(4-Trifluoromethyl-phenoxymethyl)-piperidin-1-ylmethyl]-cyclohexanol

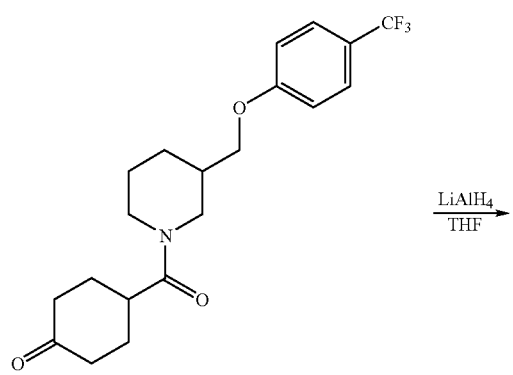

188

4-[3-(4-Trifluoromethyl-phenoxymethyl)-piperidine-1-carbonyl]-cyclohexanone (27 mg, 0.070 mmol) was dissolved in 1 mL of THF and excess lithium aluminum hydride (27 mg, ca. 10 equivalents) was added. The solution was heated to reflux for 5 minutes, cooled to 0° C., and quenched by dropwise addition of 0.5 mL 1M NaOH. Additional THF (10 mL) was added, and the suspension was stirred at room temperature for 30 minutes and then filtered though a plug of sodium sulfate. The solution thus obtained was concentrated in vacuo and the residue was purified by flash chromatography on silica gel using as eluent a gradient of ethyl acetate in hexane containing 1% ammonium hydroxide. 4-[3-(4-Trifluoromethyl-phenoxymethyl)-piperidin-1-ylmethyl]-cyclohexanol, 188, (16 mg, 61%) was obtained. Data for this compound: MS 372 (M$^+$+1).

Example 159

Synthesis of 3-(3,5-Bis-trifluoromethyl-benzyloxy)-1-[1-(4-chloro-phenyl)-cyclobutylmethyl]-piperidine

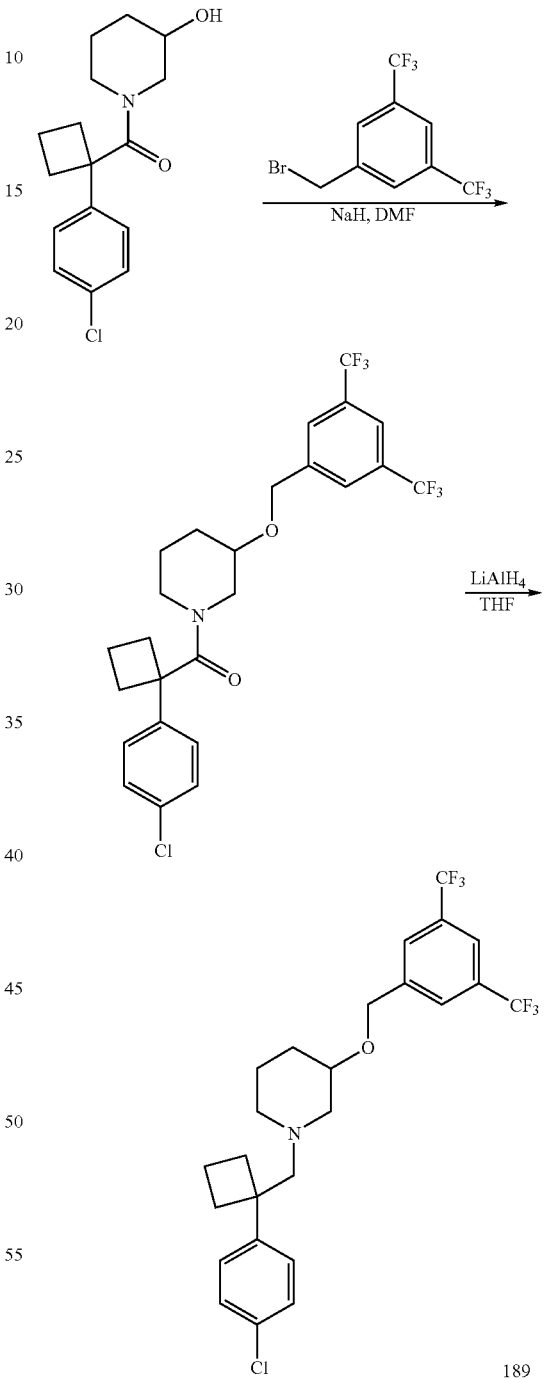

189

Following the procedure described in Example 72, 1-Bromomethyl-3,5-bis-trifluoromethyl-benzene was used to alkylate 56 mg (0.19 mmol) of [1-(4-Chloro-phenyl)-cyclobutyl]-(3-hydroxy-piperidin-1-yl)-methanone, forming the ether adduct [3-(3,5-Bis-trifluoromethyl-benzyloxy)-piperidin-1-yl]-[1-(4-chloro-phenyl)-cyclobutyl]-methanone (39 mg, 39%). A portion of this compound (22 mg, 0.043 mmol) was dissolved in 1 mL of THF and excess lithium aluminum hydride (16 mg, ca. 10 equivalents) was added. The solution was heated to reflux for 5 minutes, cooled to 0° C., and quenched by dropwise addition of 0.5 mL 1M NaOH. Additional THF (10 mL) was added, the suspension was stirred at room temperature for 30 minutes, and then was filtered though a plug of sodium sulfate. The solution thus obtained was concentrated in vacuo and the residue was purified by flash chromatography on silica gel using as eluent a gradient of ethyl acetate in hexane containing 1% ammonium hydroxide. 3-(3,5-Bis-trifluoromethyl-benzyloxy)-1-[1-(4-chloro-phenyl)-cyclobutylmethyl]-piperidine, 189, was obtained (12 mg, 56%). Data for this compound: MS 506 (M$^+$+1).

Example 160

Synthesis of 2-Cyclohexyl-2-hydroxy-2-phenyl-1-[3-(4-trifluoromethyl-phenoxymethyl)-piperidin-1-yl]-ethanone

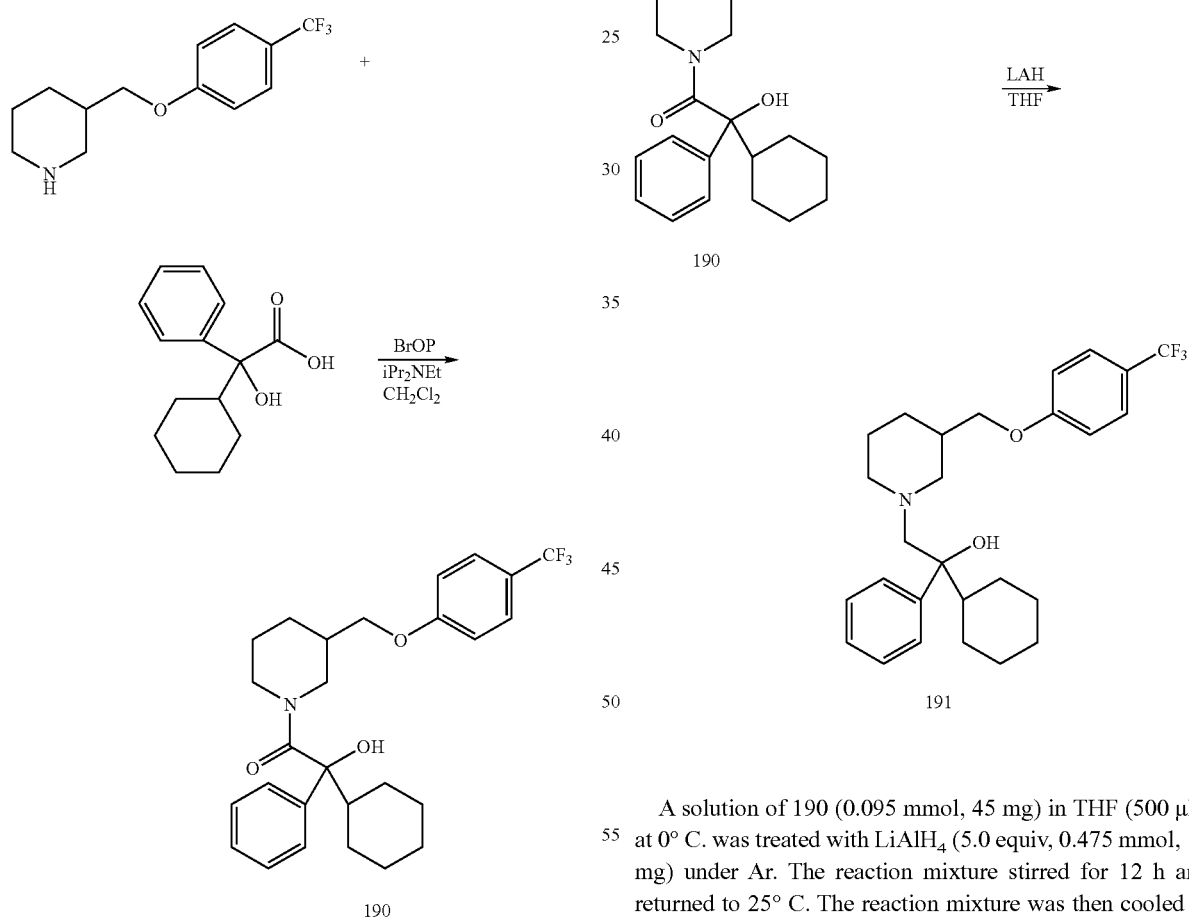

A solution of 3-(4-trifluoromethyl-phenoxymethyl)-piperidine (0.220 minol, 57 mg) and cyclohexyl-hydroxy-phenyl-acetic acid (1.2 equiv, 0.264 mmol, 62 mg) in CH$_2$Cl$_2$ (1 mL) was treated with BrOP (1.5 equiv, 0.330 mmol, 314 mg) and iPr$_2$NEt (3.0 equiv, 0.660 mmol, 115 μL) at 0° C. The reaction mixture stirred for 12 h while warming to rt. The reaction mixture was quenched with 10% HCl (10 mL) and then extracted with EtOAc (2×15 mL). The combined organics were washed with NaHCO$_3$(sat) and dried with NaCl$_{(sat)}$ and Na$_2$SO$_{4(s)}$. The solvents were removed in vacuo and chromatography (PTLC, SiO$_2$, 20 cm×20 cm, 1 mm, 5:1 hexane-ethyl acetate) provided 190 (45 mg, 105 mg theoretical, 43%) as a colorless oil: R$_f$ 0.45 (SiO$_2$, 5:1 hexane-ethyl acetate); LRMS m/z 476 (M$^+$+1, C$_{27}$H$_{32}$F$_3$NO$_3$ requires 476).

Example 161

Synthesis of 1-Cyclohexyl-1-phenyl-2-[3-(4-trifluoromethyl-phenoxymethyl)-piperidin-1-yl]-ethanol A solution of 190 (0.095 mmol, 45 mg) in THF (500 μL) at 0° C. was treated with LiAlH$_4$ (5.0 equiv, 0.475 mmol, 18 mg) under Ar. The reaction mixture stirred for 12 h and returned to 25° C. The reaction mixture was then cooled to 0° C., quenched with 10% aqueous NaOH and extracted with 3×EtOAc (25 mL). The organics were dried with NaCl$_{(sat)}$ and Na$_2$SO$_{4(s)}$. The reaction mixture was purified by chromatography (PTLC, SiO$_2$, 20 cm×20 cm, 1 mm, 4:1 hexane-ethyl acetate) which provided 191 (34 mg, 44 mg theoretical, 77%) as a colorless oil: R$_f$ 0.38 (SiO$_2$, 4:1 hexane-ethyl acetate); LRMS m/z 462 (M$^+$+1, C$_{27}$H$_{34}$F$_3$NO$_2$ requires 462).

Example 162

Synthesis of 1-[1-(4-Chloro-phenyl)-cyclobutyl]-2-{3-[2-(4-trifluoromethyl-phenyl)-ethyl]-piperidin-1-yl}-ethanol; separation of all diastereomers

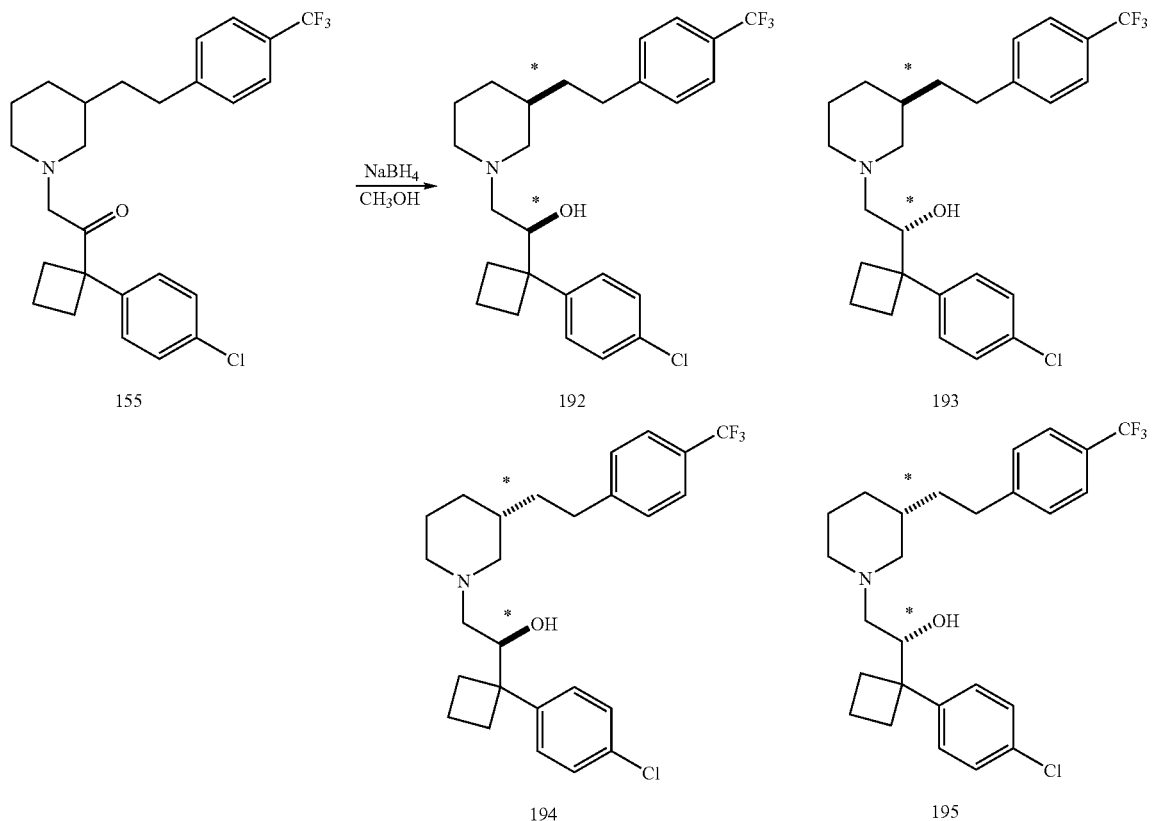

*absolute stereochemistry has been randomly assigned

A solution of 155 (0.293 mmol, 136 mg) in CH$_3$OH (2 mL) was treated with NaBH$_4$ (3.0 equiv, 0.879 mmol, 33 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with NaCl$_{(sat)}$ and Na$_2$SO$_{4(s)}$. The solvents were removed in vacuo and chromatography (Isco Combi-Flash, 35 g cartridge, 2:1 hexane-ethyl acetate) provided a mixture of diastereomers (192, 193, 194, and 195) (120 mg, 137 mg theoretical, 88%) as a colorless oil: R$_f$ 0.35 (SiO$_2$, 2:1 hexane-ethyl acetate); LRMS m/z 467 (M$^+$+1, C$_{26}$H$_{31}$ClF$_3$NO requires 467). The four diastereomers were separated on a Chiralpak AD column by utilizing the following procedure. The mixture was dissolved in 90:10 hexane (0.1% diethylamine) and isopropanol at a concentration of 90 mg/mL. 192 (first peak) and 193 (fourth peak) were separated by using a 99% hexane(0.1% diethylamine) and 1% isopropanol solvent system. The middle peak was collected and concentrated in vacuo and then separated using 95% hexane(0.1% diethylamine) and 5% isopropanol to provide 194 (second peak) and 195 (third peak).

Example 163

Synthesis of 1-[2-(4-Chloro-phenyl)-2-methoxy-ethyl]-3-(R)-phenethyl-piperidine

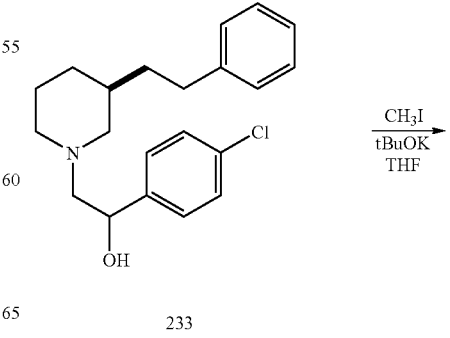

-continued

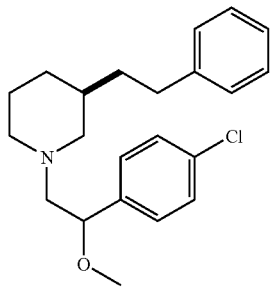

196

A solution of 233 (0.378 mmol, 130 mg) in THF (1 mL) and CH₃I (1 mL) was treated with tBuOK (5.0 equiv, 1.89 mmol, 212 mg) at 25° C. The reaction mixture stirred for 10 min. The reaction mixture was quenched with pH 7 phosphate buffer (10 mL) and extracted with EtOAc (2×10 mL). The combined organics were dried with NaCl$_{(sat)}$ and Na$_2$SO$_{4(s)}$. The solvents were removed in vacuo and the residue was purified by chromatography (PTLC, SiO$_2$, 20 cm×20 cm, 1 mm, 3:1 hexane-acetone) which provided 196 (100 mg, 135 mg theoretical, 74%) as a colorless oil: R$_f$ 0.48 (SiO$_2$, 3:1 hexane-acetone); LRMS m/z 359 (M$^+$+1, C$_{22}$H$_{28}$ClNO requires 359).

Example 164

Synthesis of 2-(4-Chloro-phenyl)-1-(3(R)-phenethyl-piperidin-1-yl)-propan-2-ol

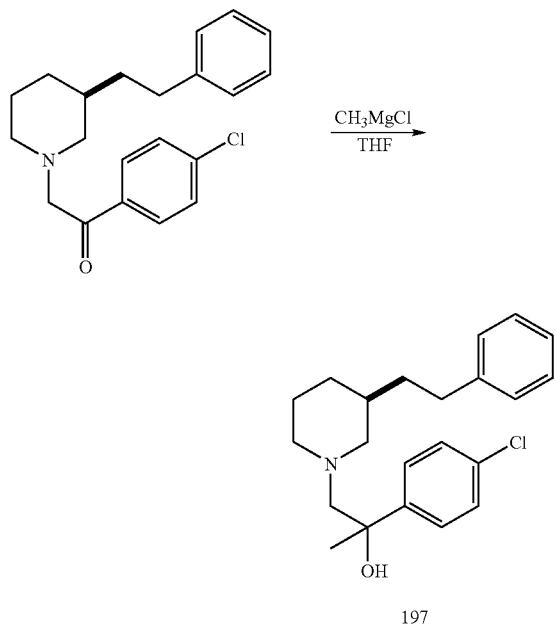

197

A solution of piperidine-ketone (0.693 mmol, 237 mg) in THF (1 mL) was added to a solution of CH₃MgCl (3.0 M in THF) (5.0 equiv, 3.47 mmol, 1.16 mL) in THF (1 mL) at 0° C. The reaction mixture stirred for 1 h. The reaction mixture was quenched with 10% NaOH (10 mL) and extracted with EtOAc (2×10 mL). The combined organics were dried with NaCl$_{(sat)}$ and Na$_2$SO$_{4(s)}$. The solvents were removed in vacuo and the residue was purified by chromatography (PTLC, SiO$_2$, 20 cm×20 cm, 1 mm, 3:1 hexane-acetone) which provided 197 (220 mg, 248 mg theoretical, 89%) as a colorless oil: R$_f$ 0.44 (SiO$_2$, 3:1 hexane-acetone); LRMS m/z 359 (M$^+$+1, C$_{22}$H$_{28}$ClNO requires 359).

Example 165

Synthesis of 3-[2-(4-Trifluoromethoxy-phenyl)-vinyl]-piperidine-1-carboxylic acid benzyl ester

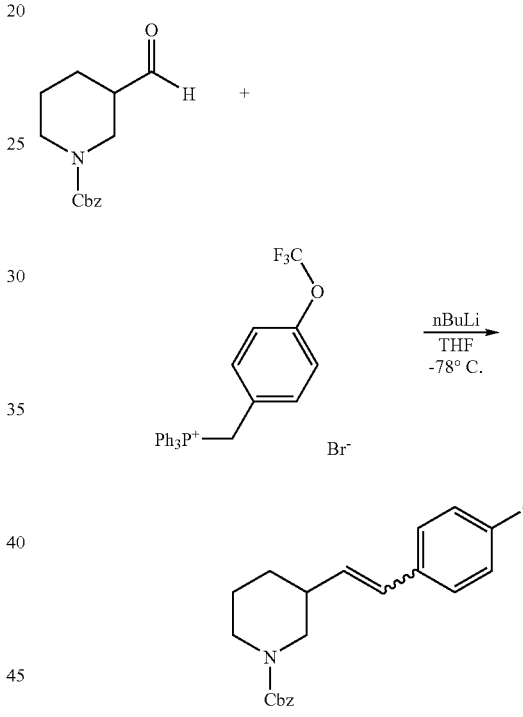

198

A solution of the Wittig salt (1.5 equiv, 12.02 mmol, 6.22 g) in THF (40 mL) was treated with nBuLi (1.5 equiv, 2.5M, 12.02 mmol, 4.8 mL) at −78 OC. The solution was warmed to 0° C. for 30 min and then cooled again to −78° C. A solution of piperidine-3-carbaldehyde (8.01 mmol, 1.98 g) in THF (10 mL) was added to the above reaction mixture at −78° C. The reaction stirred for 12 h. The reaction mixture was quenched with 10% HCl (20 mL) and then extracted with EtOAc (2×50 mL). The combined organics were dried with NaCl$_{(sat)}$ and Na$_2$SO$_{4(s)}$. The solvents were removed in vacuo and chromatography (Isco Combi-Flash, 110 g cartridge, 19:1 hexane-ethyl acetate) provided 198 (1.79 g, 3.25 g theoretical, 55%) as a colorless oil: R$_f$ 0.42 (SiO$_2$, 6:1 hexane-EtOAc); LRMS m/z 406 (M$^+$+1, C$_{22}$H$_{22}$F$_3$NO$_3$ requires 406).

Example 166

Synthesis of 3-[2-(4-Trifluoromethoxy-phenyl)-ethyl]-piperidine

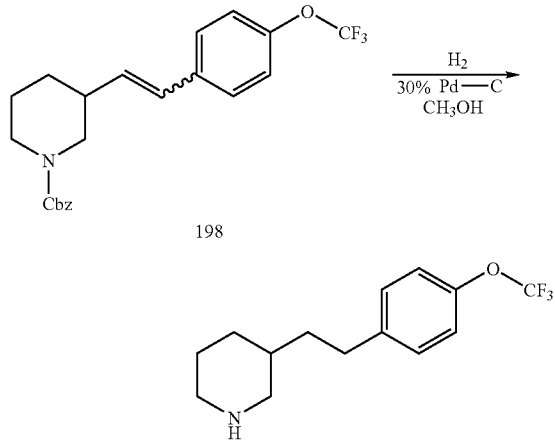

A solution of 198 (4.42 mmol, 1.79 g) in CH$_3$OH (60 mL) was treated 30% Pd—C (500 mg) and H$_2$ (Parr Hydrogenator, starting 65 psi). The reaction was shaken for 4 h. The reaction mixture was filtered through celite, and the solvents were removed in vacuo to provide 199 (1.21 g, 1.21 g theoretical, quantitative) as a colorless oil: LRMS m/z 274 (M$^+$+1, C$_{14}$H$_{18}$F$_3$NO requires 274).

Example 167

Synthesis of 1-(4-Chloro-phenyl)-2-{3-[2-(4-trifluoromethoxy-phenyl)-ethyl]-piperidin-1-yl}-ethanone

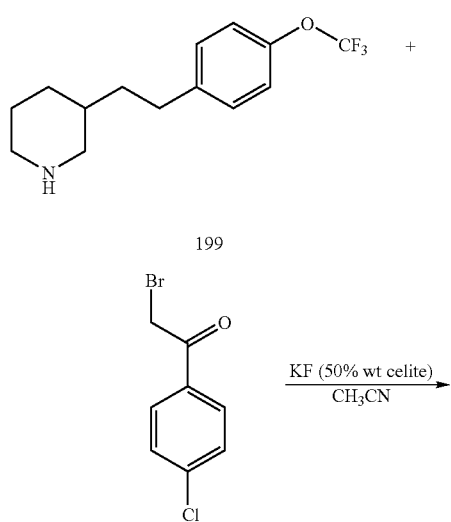

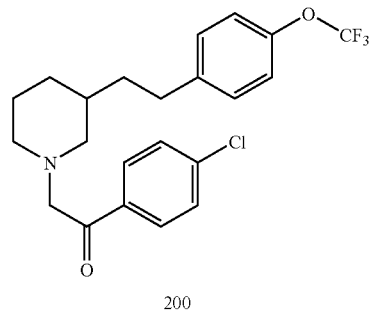

A solution of 199 (3.66 mmol, 1.00 g), 2-bromo-4'-chloroacetophenone (1.0 equiv, 3.66 mmol, 855 mg) and KF (50% wt on celite) (8.0 equiv, 29.28 mol, 1.70 g) in CH$_3$CN (12 mL) was stirred for 12 h at 25° C. The reaction mixture was filtered, and the solvents were removed in vacuo. Chromatography (Isco Combi-Flash, 35 g cartridge, 6:1 hexane-acetone) provided 200 (400 mg, 1.57 g theoretical, 25%) as a colorless oil: R$_f$ 0.49 (SiO$_2$, 6:1 hexane-acetone); LRMS m/z 429 (M$^+$+1, C$_{22}$H$_{23}$ClF$_3$NO$_2$ requires 429).

Example 168

Synthesis of 1-(4-Chloro-phenyl)-2-{3-[2-(4-trifluoromethoxy-phenyl)-ethyl]-piperidin 1-yl}-ethanol

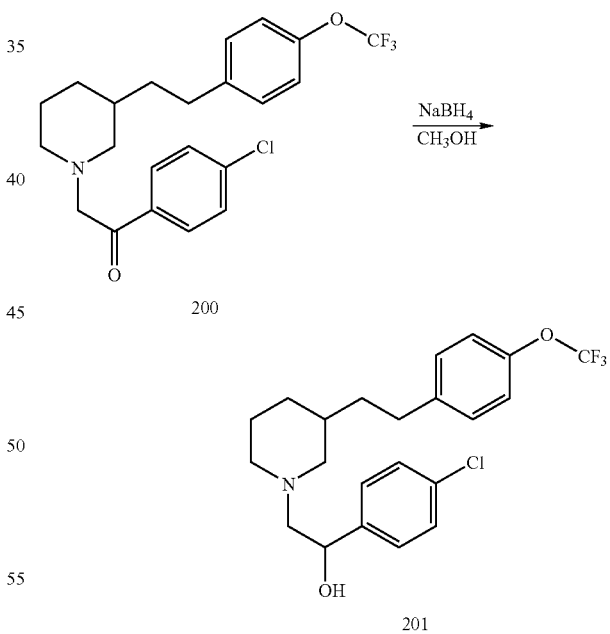

A solution of 200 (0.829 mmol, 353 mg) in CH$_3$OH (4 mL) was treated with NaBH$_4$ (1.5 equiv, 1.24 mmol, 47 mg) at 0° C. The reaction mixture was allowed to warm to rt and stirred for 12 h. The reaction mixture was quenched with pH 7 phosphate buffer (5 mL) and extracted with EtOAc (2×10 mL). The combined organics were dried with NaCl$_{(sat)}$ and Na$_2$SO$_{4(s)}$. The solvents were removed in vacuo and chromatography (Isco Combi-Flash, 35 g cartridge, 2:3 hexaneethyl acetate) provided 201 (200 mg, 355 mg theoretical, 56%) as a colorless oil: $R_f$ 0.36 (SiO$_2$, 2:3 hexane:ethyl acetate); LRMS m/z 429 (M$^+$+1, $C_{22}H_{25}ClF_3NO_2$ requires 429).

Example 169

Synthesis of 1-(4-Trifluoromethoxy-phenyl)-cyclobutanecarbonitrile

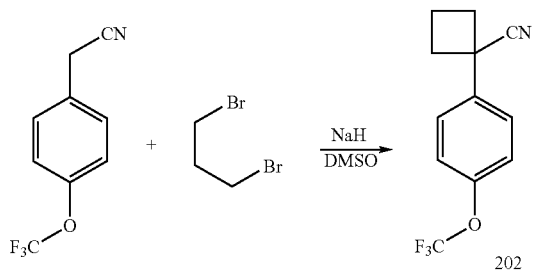

A solution of (4-trifluoromethoxy)-acetophenyl nitrile (9.94 mmol, 2.00 g), dibromopropane (1.1 equiv, 10.93 mmol, 1.1 mL) and NaH (60% wt in mineral oil) (2.5 equiv, 24.85 mol, 1.00 g) in DMSO (35 mL) was stirred for 12 h. The reaction mixture was quenched with pH 7 phosphate buffer (50 mL) and extracted with EtOAc (2×50 mL). The combined organics were dried with NaCl$_{(sat)}$ and Na$_2$SO$_{4(s)}$. The solvents were removed in vacuo and chromatography (Isco Combi-Flash, 110 g cartridge, 6.5:1 hexane-ethyl acetate) provided 202 (1.77 g, 2.42 g theoretical, 73%) as a colorless oil.

Example 170

Synthesis of 1-[1-(4-Trifluoromethoxy-phenyl)-cyclobutyl]-ethanone

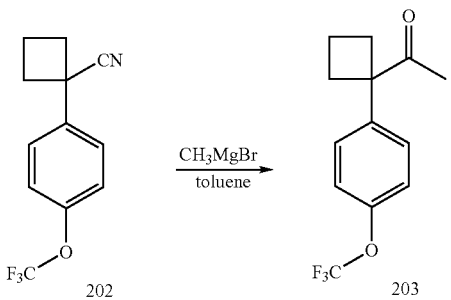

A solution of 202 (4.11 mmol, 1.00 g) in toluene (5 mL) was treated with CH$_3$MgBr (3.0 M in ether) (3.0 equiv, 12.33 mol, 4.2 mL). The reaction was stirred for 12 h at 95° C. The reaction mixture was quenched with 6 M HCl and stirred for 1 h at 95° C. The reaction mixture was extracted with EtOAc (2×50 mL). The combined organics were dried with NaCl$_{(sat)}$ and Na$_2$SO$_{4(s)}$. The solvents were removed in vacuo and chromatography (Isco Combi-Flash, 110 g cartridge, 30:1 hexane-ethyl acetate) provided 203 (0.939 g, 1.06 g theoretical, 89%) as a colorless oil.

Example 171

Synthesis of 2-Bromo-1-[1-(4-trifluoromethoxyphenyl)-cyclobutyl]-ethanone

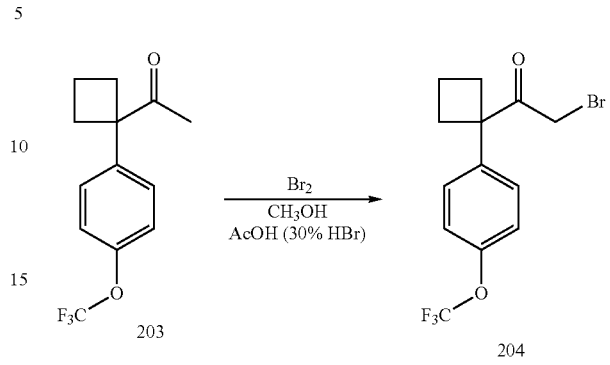

A solution of 203 (1.94 mmol, 500 mg) in CH$_3$OH (5 mL) was cooled to 0° C. and treated with AcOH (30% HBr) (50 μL). Br$_2$ (1.94 mmol, 100 μL) was then added slowly at 0° C. The reaction mixture was stirred for 12 h at 5° C. The reaction mixture was quenched with H$_2$O (40 mL) and extracted with EtOAc (2×50 mL). The combined organics were dried with NaCl$_{(sat)}$ and Na$_2$SO$_{4(s)}$. The solvents were removed in vacuo to give 204 (500 mg, 654 mg theoretical, 76%) as a colorless oil.

Example 172

Synthesis of 1-[1-(4-Trifluoromethoxy-phenyl)-cyclobutyl]-2-[3-(4-trifluoromethyl-phenoxymethyl)-piperidin-1-yl]-ethanone

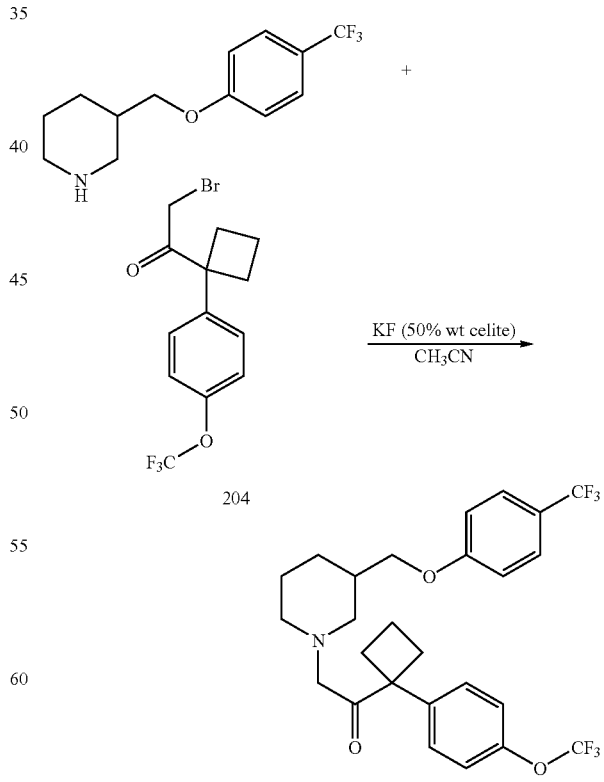

A solution of 3-(4-trifluoromethyl-phenoxymethyl)-piperidine (0.359 mmol, 93 mg), 204 (1.0 equiv, 0.430 mmol, 145 mg) and KF (50% wt on celite) (7.0 equiv, 2.51 mol, 292 mg) in $CH_3CN$ (2 mL) was stirred for 12 h at 25° C. The reaction mixture was filtered, and the solvents were removed in vacuo. Chromatography (Isco Combi-Flash, 10 g cartridge, 2:1 hexane-ethyl acetate) provided 205 (126 mg, 185 mg theoretical, 68%) as a colorless oil: $R_f$ 0.34 ($SiO_2$, 2:1 hexane-ethyl acetate); LRMS m/z 516 ($M^+$+1, $C_{26}H_{27}F_6NO_3$ requires 516).

Example 173

Synthesis of 1-[1-(4-Trifluoromethoxy-phenyl)-cyclobutyl]-2-[3-(4-trifluoromethyl-phenoxymethyl)-piperidin-1-yl]-ethanol

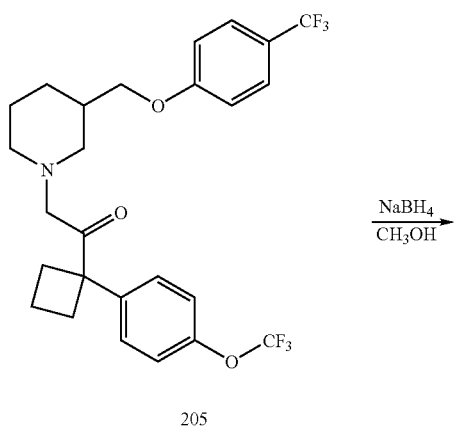

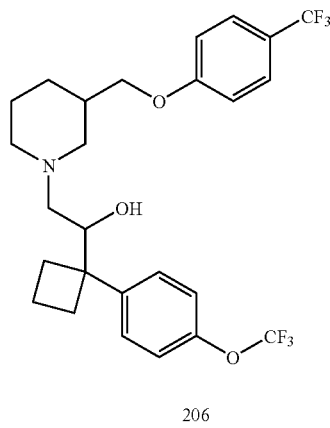

A solution of 205 (0.244 mmol, 126 mg) in $CH_3OH$ (1 mL) was treated with $NaBH_4$ (1.5 equiv, 0.366 mmol, 14 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with $NaCl_{(sat)}$ and $Na_2SO_{4(s)}$. The solvents were removed in vacuo and chromatography (Isco Combi-Flash, 35 g cartridge, 2:1 hexane-ethyl acetate) provided 206 (107 mg, 126 mg theoretical, 85%) as a colorless oil: $R_f$ 0.33 ($SiO_2$, 2:1 hexane-ethyl acetate); LRMS m/z 518 ($M^+$+1, $C_{26}H_{29}F_6NO_3$ requires 518).

Example 174

Synthesis of 3-(4-Trifluoromethoxy-phenoxymethyl)-piperidine-1-carboxylic acid benzyl ester

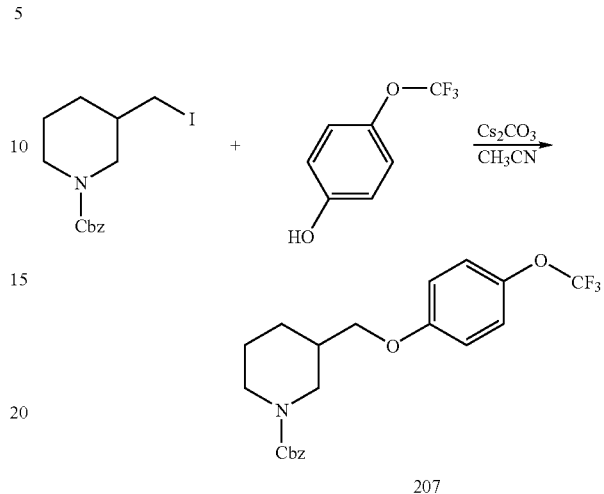

A solution of 3-iodomethylpiperidine-1-carboxylic acid benzyl ester (2.78 mmol, 1.00 g), 4-trifluoromethoxy-phenol (1.1 equiv, 3.06 mmol, 545 mg) and $Cs_2CO_3$ (3.0 equiv, 3.06 mmol, 2.72 g) in $CH_3CN$ (10 mL) was heated to 65° C. The solution was stirred for 12 h. The reaction mixture was quenched with $H_2O$ (20 mL) and then extracted with EtOAc (2×50 mL). The combined organics were dried with NaCl $_{(sat)}$ and $Na_2SO_{4(s)}$. The solvents were removed in vacuo and chromatography (Isco Combi-Flash, 110 g cartridge, 6:1 hexane-ethyl acetate) provided 207 (277 mg, 1.14 g theoretical, 24%) as a colorless oil: $R_f$ 0.32 ($SiO_2$, 6:1 hexane-ethyl acetate); LRMS m/z 410 ($M^+$+1, $C_{21}H_{22}F_3NO_4$ requires 410).

Example 175

Synthesis of 3-(4-Trifluoromethoxy-phenoxymethyl)-piperidine

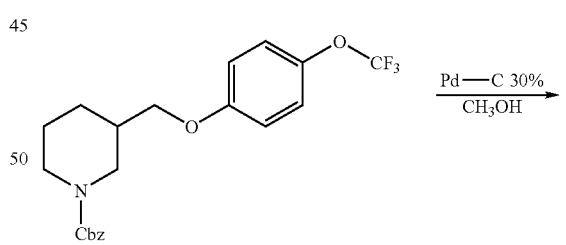

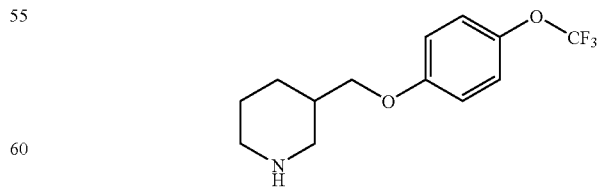

A solution of 207 (0.677 mmol, 277 mg) and Pd—C 30% (50 mg) in $CH_3OH$ (5 mL) at 25° C. were added to a Paar hydrogenator low pressure reaction vessel. The mixture was reacted at 65 psi with vigorous shaking until hydrogen uptake subsided (2 h). The catalyst was filtered through a pad of celite. The filtrate was concentrated in vacuo which provided 208 (125 mg, 186 mg theoretical, 67%) as colorless oil: LRMS m/z 276 (M+, $C_{13}H_{16}F_3NO_2$ requires 276).

Example 176

Synthesis of 1-[1-(4-Chloro-phenyl)-cyclobutyl]-2-[3-(4-trifluoromethyl-phenoxymethyl)-piperidin-1-yl]-ethanone

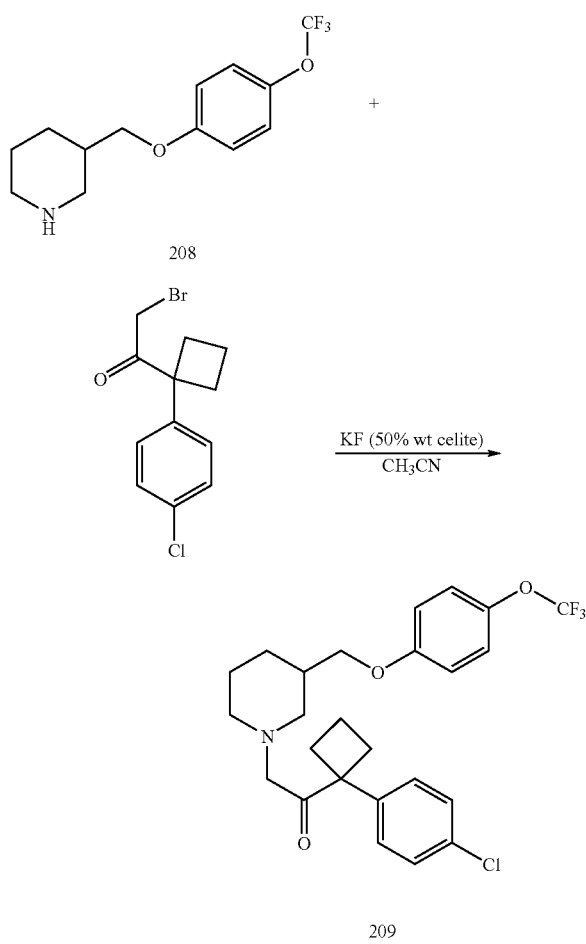

Example 177

Synthesis of 1-[1-(4-Chloro-phenyl)-cyclobutyl]-2-[3-(4-trifluoromethoxy-phenoxymethyl)-piperidin-1-yl]-ethanol

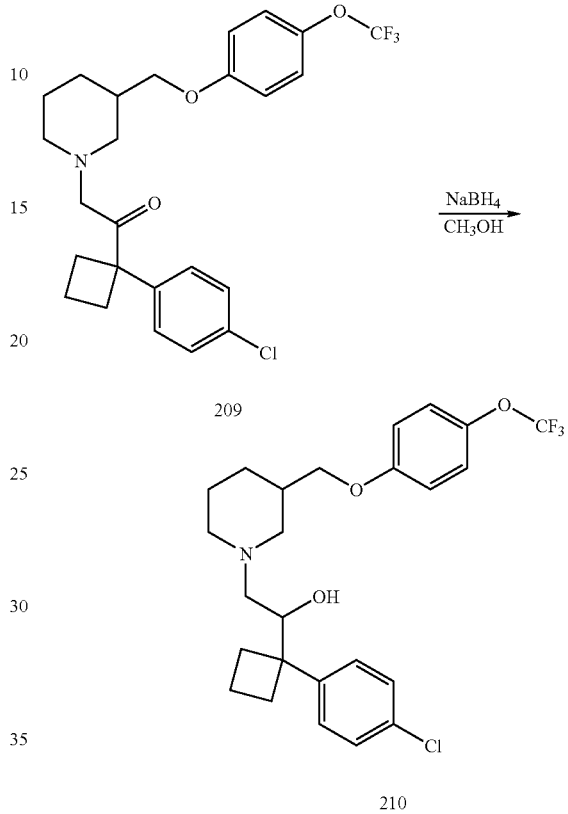

A solution of 209 (0.203 mmol, 98 mg) in $CH_3OH$ (1 mL) was treated with $NaBH_4$ (1.5 equiv, 0.305 mmol, 12 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with $NaCl_{(sat)}$ and $Na_2SO_{4(s)}$. The solvents were removed in vacuo and chromatography (Isco Combi-Flash, 10 g cartridge, 2:1 hexane-ethyl acetate) provided 210 (93 mg, 98 mg theoretical, 95%) as a colorless oil: $R_f$ 0.42 ($SiO_2$, 2:1 hexaneethyl acetate); LRMS m/z 485 (M++1, $C_{25}H_{29}ClF_3NO_3$ requires 485).

Example 178

Synthesis of 2-[3-(4-Trifluoromethoxy-phenoxymethyl)-piperidin-1-yl]-1-[1-(4-trifluoromethoxy-phenyl)-cyclobutyl]-ethanone

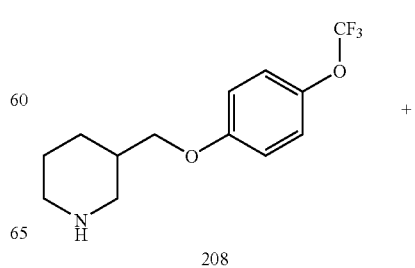

A solution of 208 (0.301 mmol, 83 mg), 2-bromo-1-[1-(4-chloro-phenyl)-cyclobutyl]-ethanone (1.4 equiv, 0.417 mmol, 120 mg) and KF (50% wt on celite) (7.0 equiv, 2.11 mol, 245 mg) in $CH_3CN$ (2 mL) was stirred for 12 h at 25° C. The reaction mixture was filtered, and the solvents were removed in vacuo. Chromatography (Isco Combi-Flash, 10 g cartridge, 2:1 hexane-ethyl acetate) provided 209 (98 mg, 145 mg theoretical, 68%) as a colorless oil: $R_f$ 0.46 ($SiO_2$, 2:1 hexane-ethyl acetate); LRMS m/z 483 (M++1, $C_{25}H_{27}ClF_3NO_3$ requires 483).

-continued

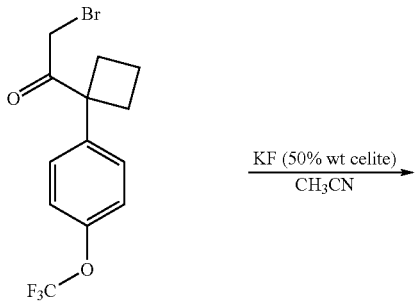

204

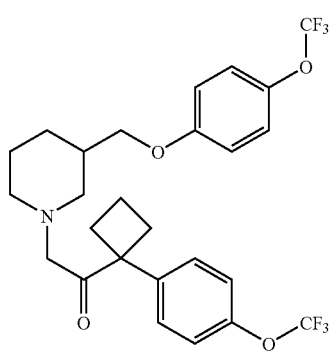

211

A solution of 208 (0.236 mmol, 65 mg), 204 (1.4 equiv, 0.323 mmol, 109 mg) and KF (50% wt on celite) (7.0 equiv, 1.65 mol, 192 mg) in CH$_3$CN (2 mL) was stirred for 12 h at 25° C. The reaction mixture was filtered, and the solvents were removed in vacuo. Chromatography (Isco Combi-Flash, 10 g cartridge, 2:1 hexane-ethyl acetate) provided 211 (101 mg, 125 mg theoretical, 81%) as a colorless oil: R$_f$ 0.52 (SiO$_2$, 2:1 hexane-ethyl acetate); LRMS m/z 532 (M$^+$+1, C$_{26}$H$_{27}$F$_6$NO$_4$ requires 532).

Example 179

Synthesis of 2-[3-(4-Trifluoromethoxy-phenoxymethyl)-piperidin-1-yl]-1-[1-(4-trifluoromethoxy-phenyl)-cyclobutyl]-ethanol

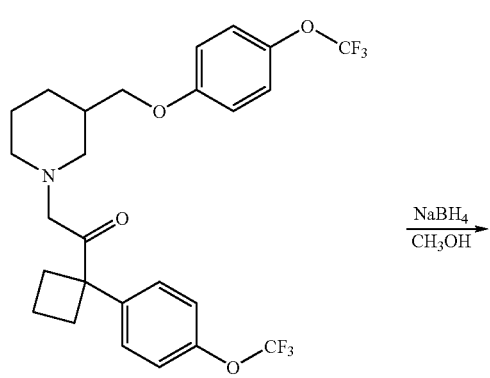

211

-continued

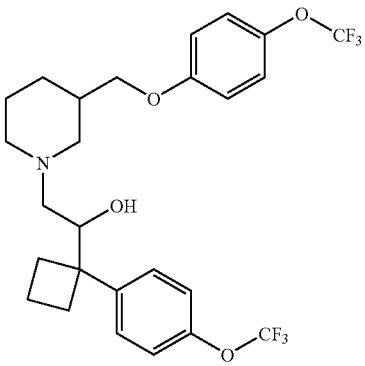

212

A solution of 211 (0.190 mmol, 101 mg) in CH$_3$OH (1 mL) was treated with NaBH$_4$ (1.5 equiv, 0.285 mmol, 11 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with NaCl$_{(sat)}$ and Na$_2$SO$_{4(s)}$. The solvents were removed in vacuo and chromatography (Isco Combi-Flash, 10 g cartridge, 2:1 hexane-ethyl acetate) provided 212 (101 mg, 101 mg theoretical, 99%) as a colorless oil: R$_f$ 0.49 (SiO$_2$, 2:1 hexane-ethyl acetate); LRMS m/z 535 (M$^+$+1, C$_{26}$H$_{29}$F$_6$NO$_4$ requires 535).

Example 180

Synthesis of [1-(4-Chloro-phenyl)-2-(3 (R)-phenethyl-piperidin-1-yl)-ethyl]-methyl-amine

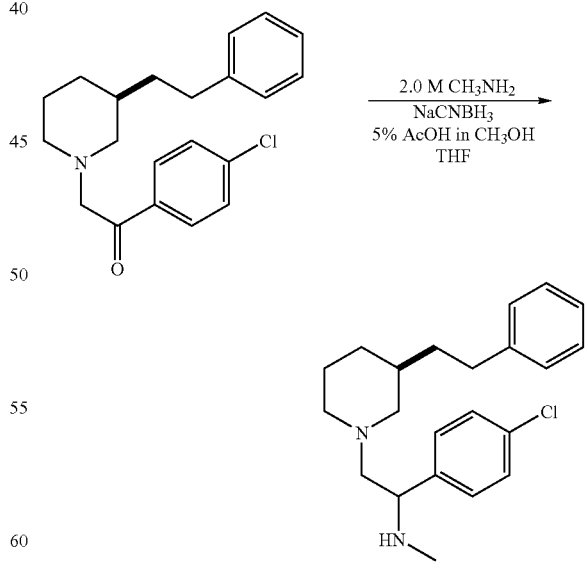

213

A solution of piperidine-phenyl ketone (0.493 mmol, 168 mg), CH$_3$NH$_2$ (2.0 M in THF) (4.0 equiv, 1.97 mmol, 1 mL), NaCNBH$_3$ (4.0 equiv, 1.97 mmol, 123 mg) in 5% AcOH in CH₃OH (2 mL) was stirred at 40° C. for 12 h. The reaction mixture was quenched with 10% NaOH (10 mL) and extracted with EtOAc (2×10 mL). The combined organics were dried with NaCl$_{(sat)}$ and Na₂SO$_{4(s)}$. The solvents were removed in vacuo and the residue was purified by chromatography (PTLC, SiO₂, 20 cm×20 cm, 1 mm, 9:1 CH₂Cl₂—CH₃OH) which provided 213 (28 mg, 175 mg theoretical, 16%) as a colorless oil: R$_f$ 0.35 (SiO₂, 9:1 CH₂Cl₂—CH₃OH); LRMS m/z 358 (M⁺+1, C₂₂H₂₉ClN₂ requires 358).

Example 181

Synthesis of N-1-Carbobenzyloxy[3-S-(2'-anilino)carboxy]piperidine

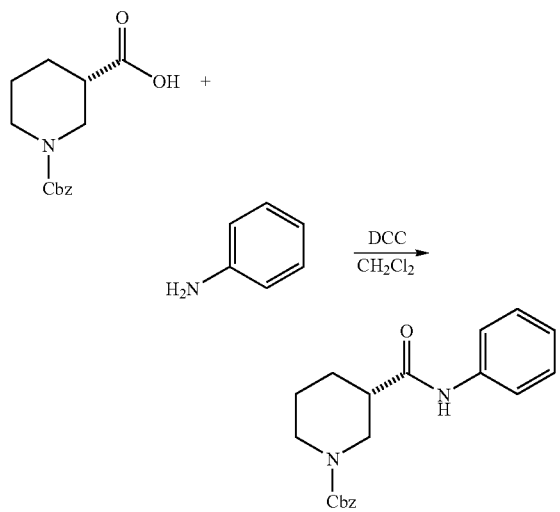

A solution of S-Cbz-nipecotic acid (3.80 mmol, 1.00 g) and aniline (1.1 equiv, 4.18 mmol, 381 µL) in CH₂Cl₂ (10 mL) at 0° C. was treated with DCC (1.5 equiv, 5.70 mmol, 1.18 g) under Ar. The reaction mixture was allowed to warm to 25° C. and stirred for 12 h. The reaction mixture was then filtered to remove the urea and the solvents were removed in vacuo. Chromatography (Isco Combi-Flash, 110 g cartridge, 3:1 hexane-ethyl acetate) provided the desired product (1.29 g, 1.29 g theoretical, 99%) as a white foam: R$_f$ 0.45 (SiO₂, 1:1 hexane-ethyl acetate): LRMS m/z 338 (M⁺+1, C₂₀H₂₂N₂O₃ requires 338).

Example 182

Synthesis of Piperidine-3-S-carboxilic acid phenylamide

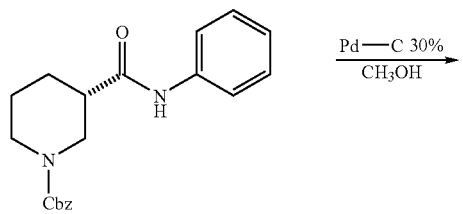

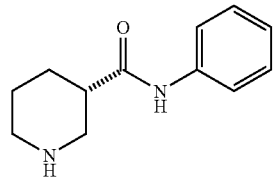

A solution of 3-(S)-Phenylcarbamoyl-piperidine-1-carboxylic acid benzyl ester (1.80 mol, 608 mg) and Pd—C 30% (100 mg) in CH₃OH (10 mL) at 25° C. were added to a Paar hydrogenator low pressure reaction vessel. The mixture was reacted at 55 psi with vigorous shaking until hydrogen uptake subsided (2 h). The catalyst was filtered through a pad of celite. The filtrate was concentrated in vacuo which provided piperidine-3-carboxylic acid phenylamide (367 mg, 367 mg theoretical, 99%) as a white foam: LRMS m/z 205 (M⁺+1, C₁₂H₁₆N₂O requires 205).

Example 183

Synthesis of 1-[1-(4-Chloro-phenyl)-cyclobutanecarbonyl]-piperidine-3-S-carboxylic acid phenylamide

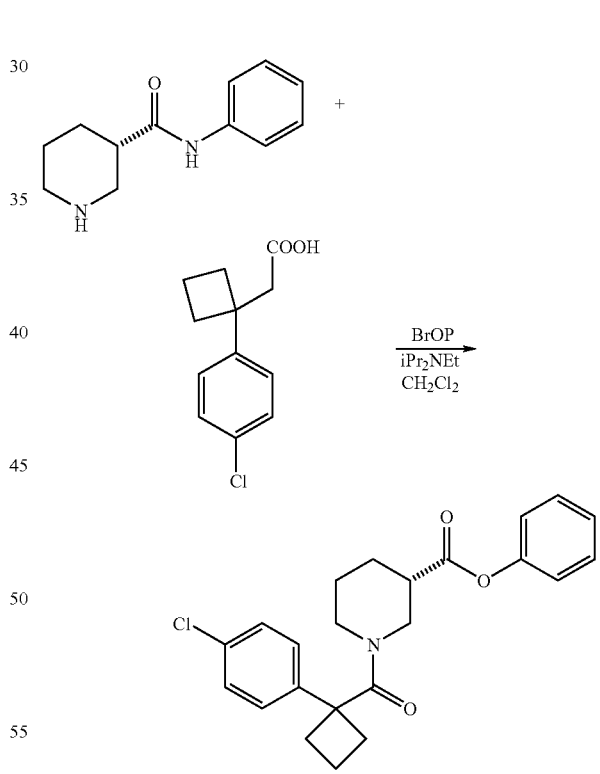

214

A solution of the piperidine-3-carboxylic acid phenylamide (1.80 mmol, 367 mg), 1-(4-Chlorophenyl)-1-cyclobutane carboxylic acid (1.2 equiv, 2.16 mmol, 455 mg) and iPr₂NEt (3.0 equiv, 5.40 mmol, 0.941 mL) in CH₂Cl₂ (5 mL) was treated with BroP (1.5 equiv, 2.70 mmol, 2.07 g) under Ar at 0° C. After warming to 25° C. and stirring for 12 h, the reaction mixture was quenched with 10% aqueous HCl and extracted with 3×EtOAc (25 mL). The organic layer was then washed with NaHCO$_{3(sat)}$ and dried with NaCl$_{(sat)}$ and MgSO$_{4(s)}$. Chromatography (Isco Combi-Flash, 35 g cartridge, 3:2 hexane-ethyl acetate) provided 214 (632 mg, 714 mg theoretical, 89%) as a white foam: R$_f$ 0.17 (SiO$_2$, 2:1 hexane-ethyl acetate); LRMS m/z 397 (M$^+$+1, C$_{23}$H$_{25}$ClN$_2$O$_2$ requires 397).

Example 184

Synthesis of {1-[1-(4-Chloro-phenyl)-cyclobutylmethyl]-piperidin-3-S-ylmethyl}-phenyl-amine

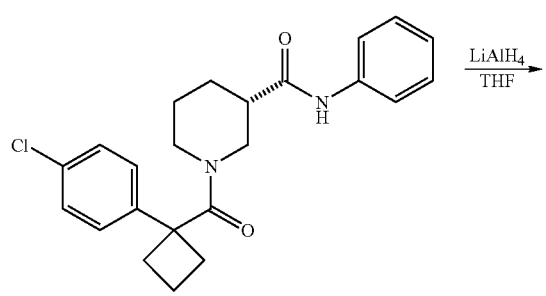

214

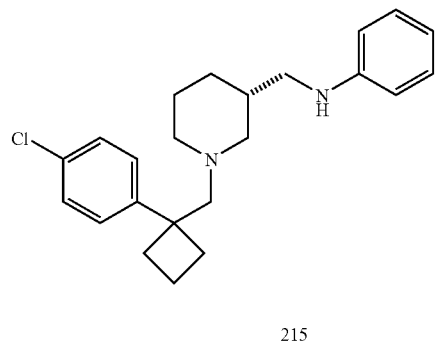

215

A solution of 214 (0.504 mmol, 200 mg) in THF (2 mL) at 0° C. was treated with LiAlH$_4$ (3.0 equiv, 1.51 mmol, 57 mg) under Ar. The reaction mixture stirred for 12 h and returned to 25° C. The reaction mixture was then cooled to 0° C., quenched with 10% aqueous NaOH and extracted with 3×EtOAc (25 mL). The organics were dried with NaCl$_{(sat)}$ and Na$_2$SO$_{4(s)}$. The reaction mixture was purified by chromatography (Isco Combi-Flash, 10 g cartridge, 8:2 hexane-ethyl acetate) which provided 215 (88 mg, 186 mg theoretical, 47%) as a colorless oil: R$_f$ 0.61 (SiO$_2$, 2:1 hexane-ethyl acetate); LRMS m/z 369 (M$^+$+1, C$_{23}$H$_{29}$ClN$_2$ requires 369).

Example 185

Synthesis of {1-[1-(4-Chloro-phenyl)-cyclobutylmethyl]-piperidin-3-S-ylmethyl}-methyl-phenyl-amine

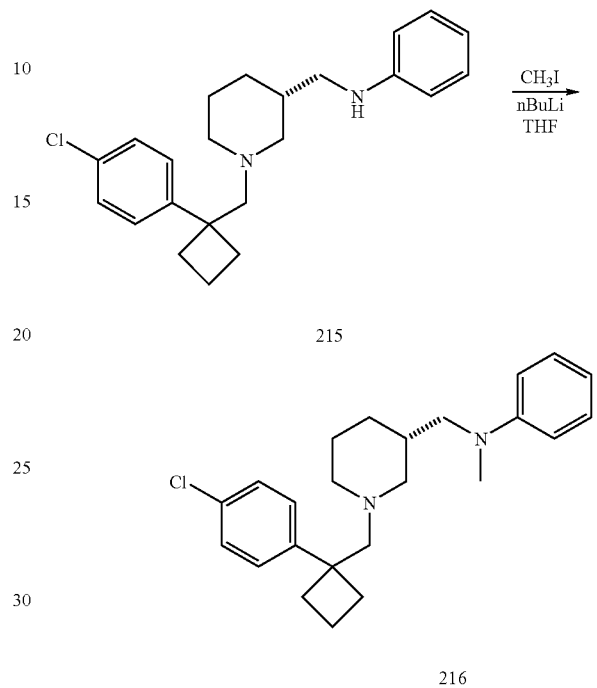

215

216

A solution of the 215 (0.238 mmol, 88 mg) in THF (1 mL) at −78° C. was treated with 1.6 M nBuLi (1.5 equiv, 0.358 mmol, 224 µL) under Ar. The reaction mixture was warmed to 0° C. for 30 min and then cooled again to −78° C. CH$_3$I (1.5 equiv, 0.358 mmol, 22 µL) was then added and the reaction mixture stirred at 0° C. for 5 min. The reaction was quenched with NaHCO$_{3(sat)}$ and extracted with EtOAc. The combined organics were dried with NaCl$_{(sat)}$ and Na$_2$SO$_{4(s)}$. The solvents were removed in vacuo and chromatography (PTLC, SiO$_2$, 20 cm×20 cm, 1 mm, 6:1 hexanes-ethyl acetate) provided 216 (30 mg, 91 mg theoretical, 33%) as a yellow oil: R$_f$ 0.38 (SiO$_2$, 3:1 hexanes-EtOAc); LRMS m/z 384 (M$^+$+1, C$_{24}$H$_{31}$ClN$_2$ requires 384).

Example 186

Synthesis of 1-(4-Chloro-phenyl)-2-methyl-3-[3-(4-trifluoromethyl-phenoxymethyl)-piperidin-1-yl]-propan-1-one

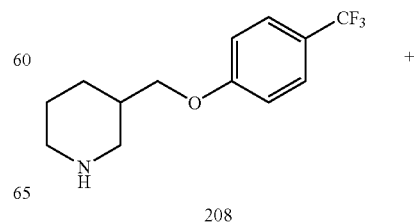

208

-continued

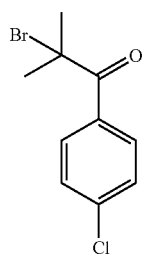

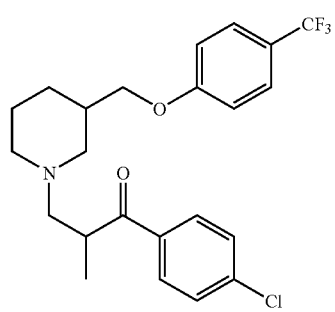

217

A solution of 208 (0.579 mmol, 150 mg), 2-bromo-1-(4-chloro-phenyl)-2-methyl-propan-1-one (1.2 equiv, 0.695 mmol, 182 mg) and KF (50% wt on celite) (7.0 equiv, 4.05 mol, 471 mg) in CH$_3$CN (2 mL) was stirred for 12 h at 25° C. The reaction mixture was filtered, and the solvents were removed in vacuo. Chromatography (Isco Combi-Flash, 10 g cartridge, 3:1 hexane-ethyl acetate) provided 217 (35 mg, 255 mg theoretical, 14%) as a colorless oil: R$_f$ 0.31 (SiO$_2$, 3:1 hexane-ethyl acetate); LRMS m/z 441 (M$^+$+1, C$_{23}$H$_{25}$ClF$_3$NO$_2$ requires 441).

Example 187

Synthesis of 1-(4-Chloro-phenyl)-2-methyl-3-[3-(4-trifluoromethyl-phenoxymethyl)-piperidin-1-yl]-propan-1-ol

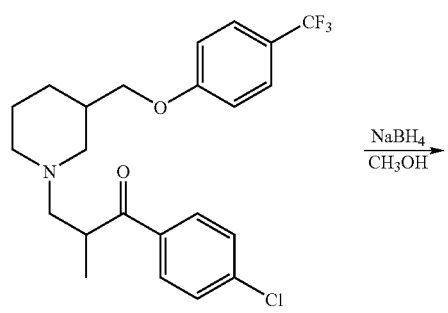

217

-continued

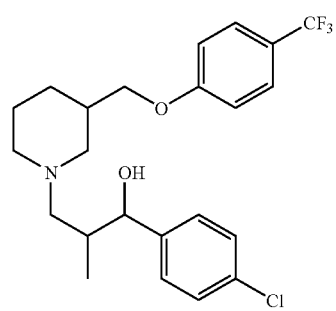

218

A solution of 217 (0.068 mmol, 30 mg) in CH$_3$OH (1 mL) was treated with NaBH$_4$ (4.0 equiv, 0.264 mmol, 10 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with NaCl$_{(sat)}$ and Na$_2$SO$_{4(s)}$. The solvents were removed in vacuo and chromatography (PTLC, SiO$_2$, 20 cm×20 cm, 1 mm, 1:1 hexanes-ethyl acetate) provided 218 (93 mg, 98 mg theoretical, 95%) as a colorless oil: R$_f$ 0.38 (SiO$_2$, 1:1 hexane-ethyl acetate); LRMS m/z 443 (M$^+$+1, C$_{23}$H$_{27}$ClF$_3$NO$_2$ requires 443).

Example 188

Synthesis of 2-(5-Methoxy-1H-indol-3-yl)-1-[3-(4-trifluoromethyl-phenoxymethyl)-piperidin-1-yl]-ethanone

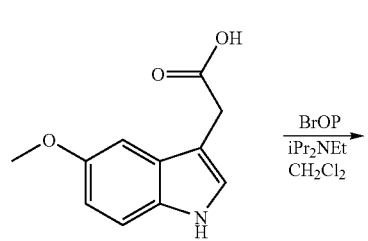

208

-continued

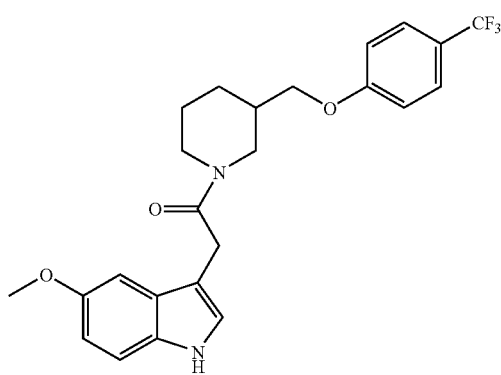

219

A solution of 208 (1.93 mmol, 500 mg) and (5-methoxy-1H-indol-3-yl)-acetic acid (1.2 equiv, 2.32 mmol, 476 mg) in CH$_2$Cl$_2$ (5 mL) was treated with BrOP (1.5 equiv, 2.90 mmol, 1.13 g) and iPr$_2$NEt (3.0 equiv, 5.79 mmol, 1.00 mL) at 0° C. The reaction mixture stirred for 12 h while warming to rt. The reaction mixture was quenched with 10% HCl (10 mL) and then extracted with EtOAc (2×15 mL). The combined organics were washed with NaHCO$_3$(sat) and dried with NaCl$_{(sat)}$ and Na$_2$SO$_{4(s)}$. The solvents were removed in vacuo and chromatography (Isco Combi-Flash, 110 g cartridge, 3:1 hexane-ethyl acetate) provided 219 (617 mg, 862 mg theoretical, 72%) as a colorless oil: R$_f$ 0.33 (SiO$_2$, 3:1 hexane-ethyl acetate); LRMS m/z 447 (M$^+$+1, C$_{24}$H$_{25}$F$_3$N$_2$O$_3$ requires 447).

Example 189

Synthesis of 5-Methoxy-3-{2-[3-(4-trifluoromethyl-phenoxymethyl)-piperidin-1-yl]-ethyl}-1H-indole

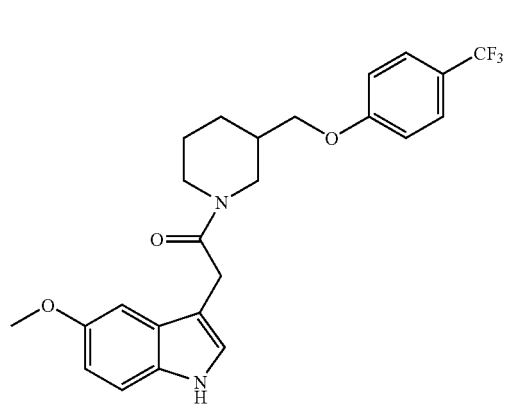

219

-continued

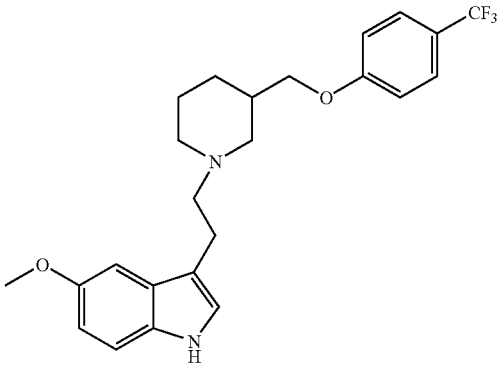

220

A solution of 219 (0.343 mmol, 153 mg) in THF (2 mL) at 0° C. was treated with LiAlH$_4$ (3.0 equiv, 1.028 mmol, 39 mg) under Ar. The reaction mixture stirred for 12 h and returned to 25° C. The reaction mixture was then cooled to 0° C., quenched with 10% aqueous NaOH and extracted with 3×EtOAc (25 mL). The organics were dried with NaCl$_{(sat)}$ and Na$_2$SO$_{4(s)}$. The reaction mixture was purified by chromatography (Isco Combi-Flash, 10 g cartridge, 9:1 CH$_2$Cl$_2$—CH$_3$OH) which provided 220 (128 mg, 148 mg theoretical, 86%) as a colorless oil: R$_f$ 0.16 (SiO$_2$, 9:1 CH$_2$Cl$_2$—CH$_3$OH); LRMS m/z 433 (M$^+$+1, C$_{24}$H$_{27}$F$_3$N$_2$O$_2$ requires 433).

Example 190

Synthesis of 1-(5-Chloro-1H-indol-3-yl)-2-[3-(4-trifluoromethyl-phenoxymethyl)-piperidin-1-yl]-ethanone

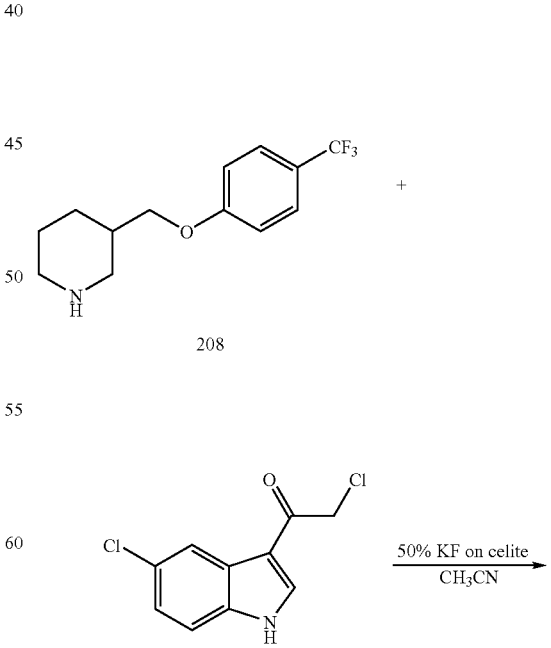

-continued

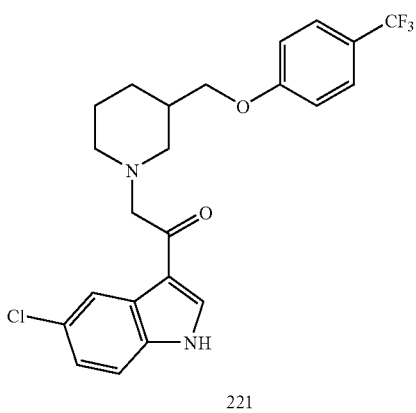

221

A solution of 208 (0.197 mmol, 51 mg), 2-chloro-1-(5-chloro-1H-indol-3-yl)-ethanone (1.0 equiv, 0.197 mmol, 45 mg) and KF (50% wt on celite) (7.0 equiv, 1.38 mol, 160 mg) in CH$_3$CN (2 mL) was stirred for 12 h at 25° C. The reaction mixture was filtered, and the solvents were removed in vacuo. Chromatography (Isco Combi-Flash, 10 g cartridge, 3:1 hexane-ethyl acetate) provided 221 (53 mg, 89 mg theoretical, 60%) as a colorless oil: R$_f$ 0.34 (SiO$_2$, 3:1 hexane-ethyl acetate); LRMS m/z 451 (M$^+$+1, C$_{23}$H$_{22}$F$_3$N$_2$O$_2$ requires 451).

Example 191

Synthesis of 1-(5-Chloro-1H-indol-3-yl)-2-[3-(4-trifluoromethyl-phenoxymethyl)-piperidin-1-yl]-ethanol -continued

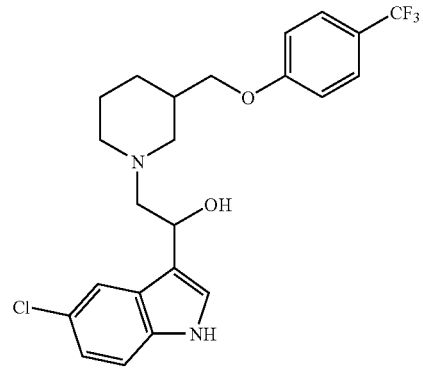

222

A solution of 221 (0.118 mmol, 53 mg) in CH$_3$OH (1 mL) was treated with NaBH$_4$ (3.0 equiv, 0.354 mmol, 13 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with NaCl$_{(sat)}$ and Na$_2$SO$_{4(s)}$. The solvents were removed in vacuo and chromatography (Isco Combi-Flash, 10 g cartridge, 2:1 hexane-ethyl acetate) provided 222 (23 mg, 53 mg theoretical, 43%) as a colorless oil: R$_f$ 0.33 (SiO$_2$, 2:1 hexane-ethyl acetate); LRMS m/z 454 (M$^+$+1, C$_{23}$H$_{24}$F$_3$N$_2$O$_2$ requires 454).

Example 192

Synthesis of 1-[1-(2-Trifluoromethoxy-phenyl)-cyclobutyl]-2-[3-(4-trifluoromethyl-phenoxy-R-methyl)-piperidin-1-yl]-ethanone

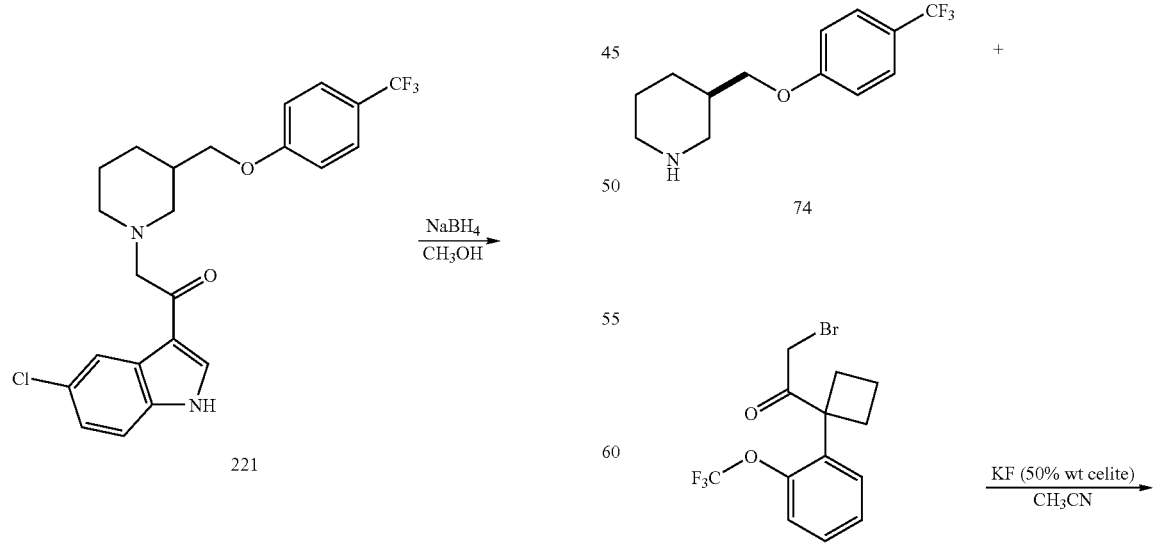

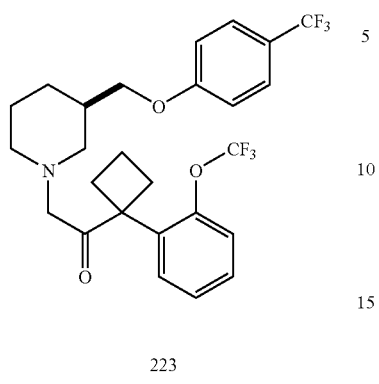

223

A solution of 74 (0.683 mmol, 177 mg), 2-bromo-1-[1-(2-trifluoromethoxy-phenyl0-cyclobutyl]-ethanone (1.0 equiv, 0.683 mmol, 200 mg) and KF (50% wt on celite) (7.0 equiv, 4.78 mol, 560 mg) in CH$_3$CN (4 mL) was stirred for 12 h at 25° C. The reaction mixture was filtered, and the solvents were removed in vacuo. Chromatography (Isco Combi-Flash, 25 g cartridge, 3:1 hexane-ethyl acetate) provided 223 (193 mg, 352 mg theoretical, 55%) as a colorless oil: R$_f$ 0.55 (SiO$_2$, 2:1 hexane-ethyl acetate); LRMS m/z 516 (M$^+$+1, C$_{26}$H$_{27}$F$_6$NO$_3$ requires 516).

Example 193

Synthesis of 1-[1-(2-Trifluoromethoxy-phenyl)-cyclobutyl]-2-[3-(4-trifluoromethyl-phenoxymethyl)-piperidin-1-yl]-ethanol; Preparation of diastereomers

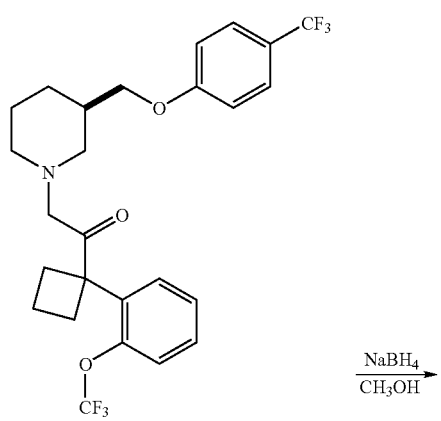

223

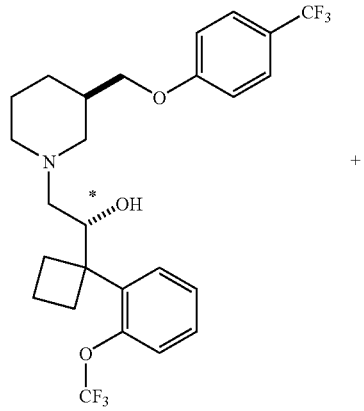

224

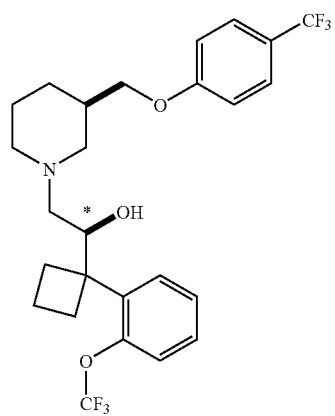

225

*absolute stereochemistry has been randomly assigned

A solution of 223 (0.374 mmol, 193 mg) in CH$_3$OH (1 mL) was treated with NaBH$_4$ (3.0 equiv, 1.12 mmol, 42 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with NaCl$_{(sat)}$ and Na$_2$SO$_{4(s)}$. The solvents were removed in vacuo and chromatography (Isco Combi-Flash, 10 g cartridge, 2:1 hexane-ethyl acetate) provided 224 and 225 (174 mg, 194 mg theoretical, 90%) as a colorless oil: R$_f$ 0.48 (SiO$_2$, 2:1 hexane-ethyl acetate); LRMS m/z 518 (M$^+$+1, C$_{26}$H$_{29}$F$_6$NO$_3$ requires 518). The two diastereomers were then separated on a Chiracel OD column: 224 and 225 were dissolved in hexane at a concentration of 85 mg/mL; and the compounds were separated by using a 99.5% hexane and 0.5% isopropanol solvent system providing 224 (first peak) and 225 (second peak).

Example 194

Synthesis of 1-[1-(2-Trifluoromethoxy-phenyl)-cyclobutyl]-2-[3-(4-trifluoromethyl-phenoxy-3S-methyl)-piperidin-1-yl]-ethanone

Example 195

Synthesis of 1-[1-(2-Trifluoromethoxy-phenyl)-cyclobutyl]-2-[3-(4-trifluoromethyl-phenoxymethyl)-piperidin-1-yl]-ethanol

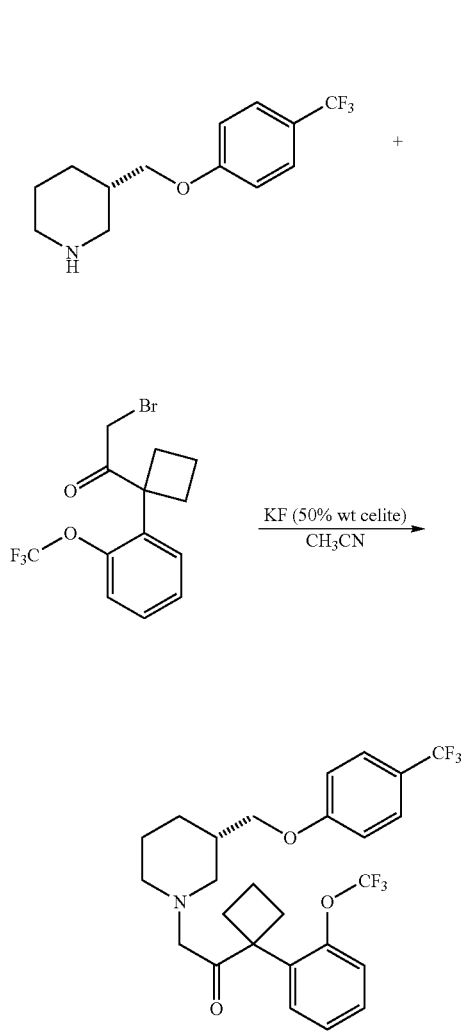

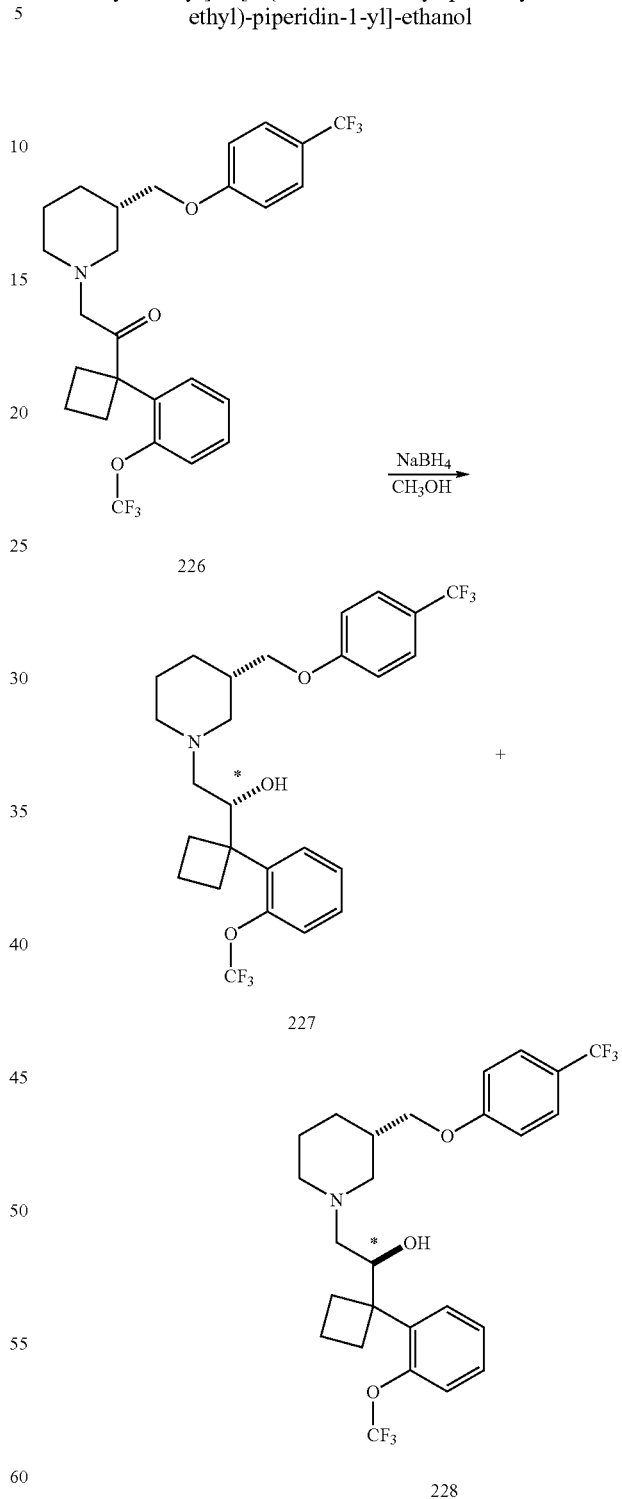

*absolute stereochemistry has been randomly assigned

A solution of 3(S)-(4-trifluoromethyl-phenoxymethyl)-piperidine (0.683 mmol, 177 mg), 2-bromo-1-[1-(2-trifluoromethoxy-phenyl0-cyclobutyl]-ethanone (1.0 equiv, 0.683 mmol, 200 mg) and KF (50% wt on celite) (7.0 equiv, 4.78 mol, 556 mg) in $CH_3CN$ (4 mL) was stirred for 12 h at 25° C. The reaction mixture was filtered, and the solvents were removed in vacuo. Chromatography (Isco Combi-Flash, 25 g cartridge, 3:1 hexane-ethyl acetate) provided 226 (160 mg, 352 mg theoretical, 45%) as a colorless oil: $R_f$ 0.55 ($SiO_2$, 2:1 hexane-ethyl acetate); LRMS m/z 516 ($M^+$+1, $C_{26}H_{27}F_6NO_3$ requires 516).

A solution of 226 (0.374 mmol, 193 mg) in $CH_3OH$ (1 mL) was treated with $NaBH_4$ (3.0 equiv, 1.12 mmol, 42 mg) at 0° C. The reaction mixture was allowed to warm to rt and stirred for 12 h. The reaction mixture was quenched with pH 7 phosphate buffer (10 mL) and extracted with EtOAc (2×10 mL). The combined organics were dried with $NaCl_{(sat)}$ and $Na_2SO_{4(s)}$. The solvents were removed in vacuo and chromatography (Isco Combi-Flash, 10 g cartridge, 2:1 hexane-ethyl acetate) provided 227 and 228 (140 mg, 160 mg theoretical, 88%) as a colorless oil: $R_f$ 0.48 ($SiO_2$, 2:1 hexane-ethyl acetate); LRMS m/z 518 ($M^++1$, $C_{26}H_{29}F_6NO_3$ requires 518). The two diastereomers were separated on a Chiracel OD column: 227 and 228 were dissolved in hexane at a concentration of 70 mg/mL; and the compounds were separated by using a 99.5% hexane and 0.5% isopropanol solvent system providing 227 (first peak) and 228 (second peak).

Example 196

Synthesis of (3-Azidomethyl-piperidin-1-yl)-[1-(4-chloro-phenyl)-cyclobutyl]-methanone

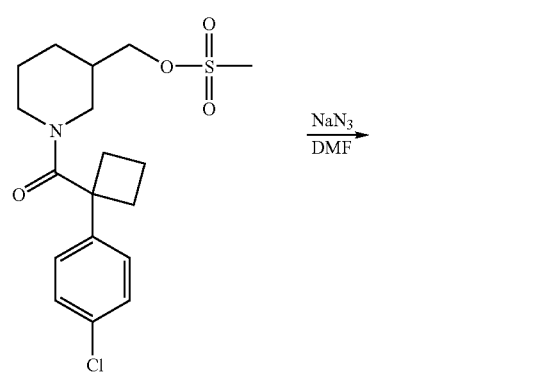

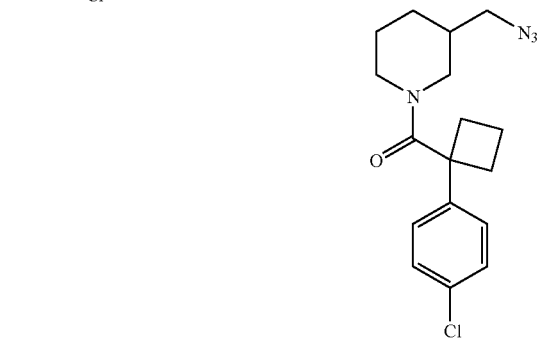

A solution of methanesulfonic acid 1-[1-(4-chloro-phenyl)-cyclobutanecarbonyl]-piperidin-3-ylmethyl ester (2.46 mmol, 950 mg) and $NaN_3$ (10 equiv, 24.6 mmol, 1.60 g) in DMF (10 mL) was heated at 70° C. for 48 h. The reaction mixture was quenched with $H_2O$ (50 mL) and then extracted with EtOAc (2×50 mL). The combined organics were dried with $NaCl_{(sat)}$ and $Na_2SO_{4(s)}$. The solvents were removed in vacuo and chromatography (Isco Combi-Flash, 110 g cartridge, 2:1 hexane-ethyl acetate) provided 229 (725 mg, 819 mg theoretical, 89%) as a pale yellow oil: $R_f$ 0.68 ($SiO_2$, 1:1 hexane-ethyl acetate); LRMS m/z 333 ($M^++1$, $C_{17}H_{23}ClN_4O$ requires 333).

Example 197

Synthesis of C-{1-[1-(4-Chloro-phenyl)-cyclobutyl-methyl]-piperidin-3-yl}-methylamine

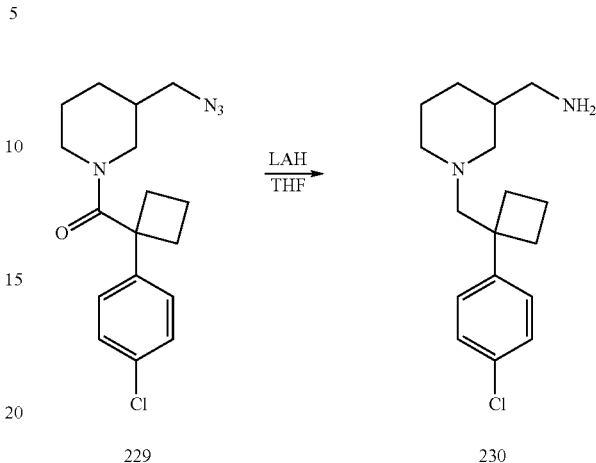

A solution of 229 (0.225 mmol, 75 mg) in THF (1 mL) at 0° C. was treated with $LiAlH_4$ (3.0 equiv, 0.676 mmol, 26 mg) under Ar. The reaction mixture stirred at 60° C. for 12 h. The reaction mixture was then cooled to 0° C., quenched with 10% aqueous NaOH and extracted with 2×EtOAc (15 mL). The organics were dried with $NaCl_{(sat)}$ and $Na_2SO_{4(s)}$. The solvents were removed to provide 230 (57 mg, 66 mg theoretical, 86%) as a colorless oil: LRMS m/z 293 ($M^++1$, $C_{17}H_{25}ClN_2$ requires 293).

Example 198

Synthesis of 2-[3-(benzo[1,3]dioxol-5-yloxymethyl)-piperidin-1-yl]-1-[1-(2-methoxy-phenyl)-cyclobutyl]-ethanol

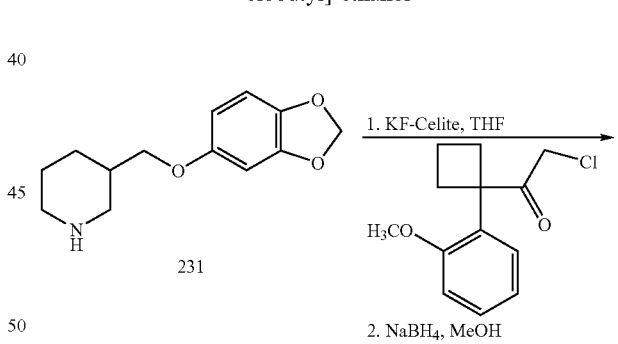

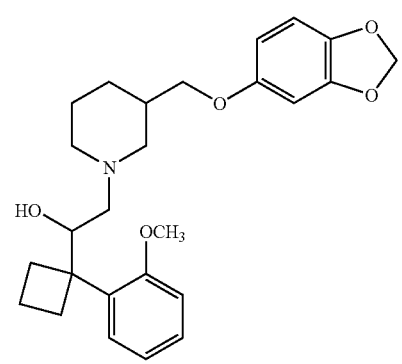

2-[3-(Benzo[1,3]dioxol-5-yloxymethyl)-piperidin-1-yl]-1-[1-(2-methoxy-phenyl)-cyclobutyl]-ethanone (ketone not shown) was prepared according to the procedures outlined in Example 138, using 231 (150 mg, 0.638 mmol), KF-Celite (50% weight on Celite; 520 mg, 0.638 mmol), and 2-chloro-1-[1-(2-methoxy-phenyl)-cyclobutyl]-ethanone (152 mg, 0.638 mmol) in acetonitrile (4 mL); yield: 71 mg; MS+ (437).

2-[3-(Benzo[1,3]dioxol-5-yloxymethyl)-piperidin-1-yl]-1-[1-(2-methoxy-phenyl)-cyclobutyl]-ethanol (232) was prepared according to the procedures outlined in Example 138, using sodium borohydride (17 mg, 0.453 mmol), and 2-[3-(benzo[1,3]dioxol-5-yloxymethyl)-piperidin-1-yl]-1-[1-(2-methoxy-phenyl)-cyclobutyl]-ethanone (100 mg, 0.227 mmol) in MeOH (1.6 mL); MS+ (440).

Example 199

Synthesis of the Individual Stereoisomers of 1-[1-(2-Methoxy-phenyl)-cyclobutyl]-2-[3-(4-trifluoromethyl-phenoxymethyl)-piperidin-1-yl]-ethanol Preparation of chiral epoxides

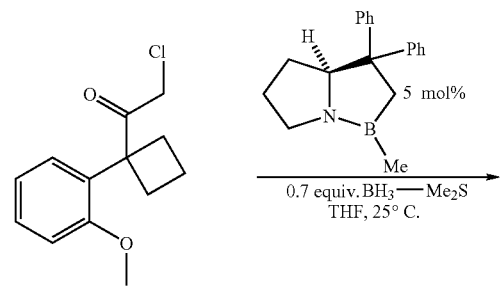

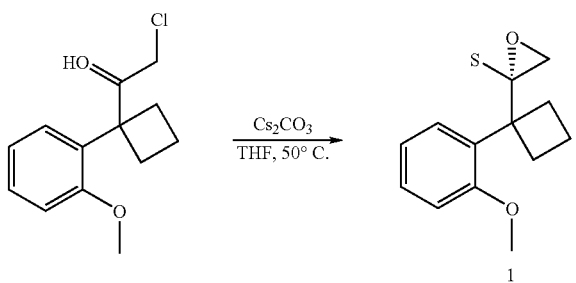

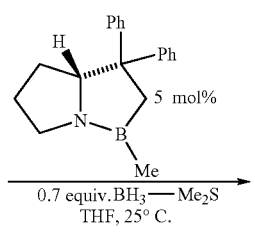

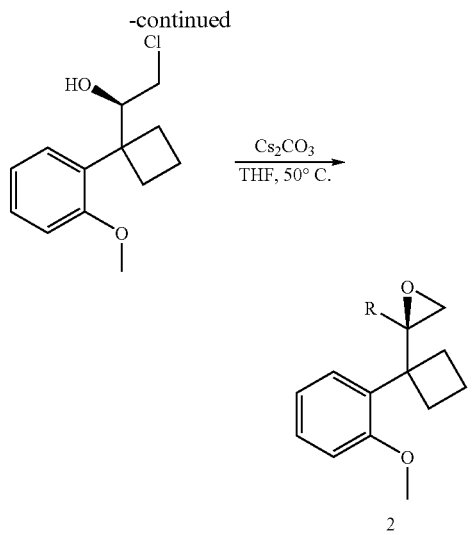

Following the same procedures used for the asymmetric reduction of 2-Bromo-1-[1-(4-chloro-phenyl)-cyclobutyl]-ethanone (See Example 127), 500 mg samples of 2-Chloro-1-[1-(2-methoxy-phenyl)-cyclobutyl]-ethanone were reduced to the enantiomerically enriched alcohols with borane-methyl sulfide in the presence of S-2-methyl CBS-oxazaborolidine or R-2-methyl CBS-oxazaborolidine. Each isomer of 2-Chloro-1-[1-(2-methoxy-phenyl)-cyclobutyl]-ethanol was obtained in approximately 70% yield and ca. 90% e.e. based on chiral HPLC analysis. 240 mg of each chloroalcohol was converted to the corresponding epoxide using 1.1 equivalents of cesium carbonate in 5 mL of THF at 50° C. for 3 hours. Dilution with 20 mL of water, addition of 30 mL ether, and extractive workup gave in each instance, after concentration of the organic layers in vacuo and chromatography on silica gel, each of the desired epoxides (176 mg and 184 mg, 86% and 90% yield).

Preparation of individual stereoisomers

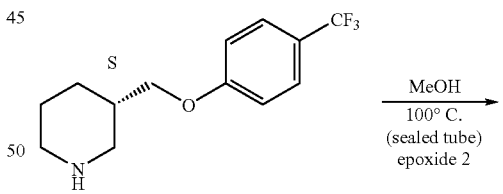

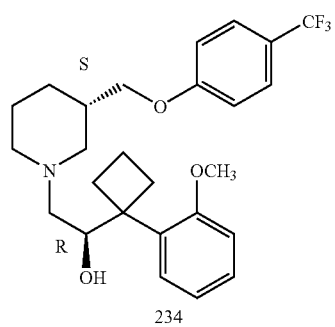

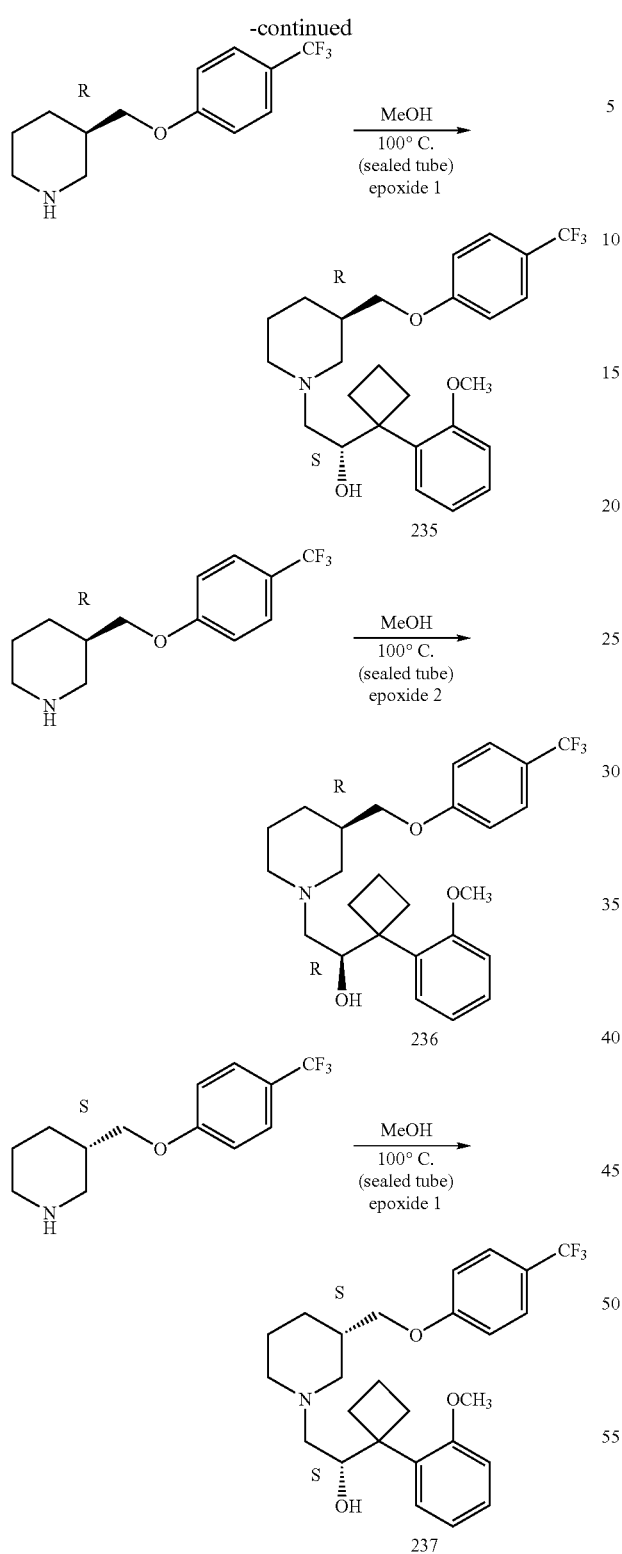

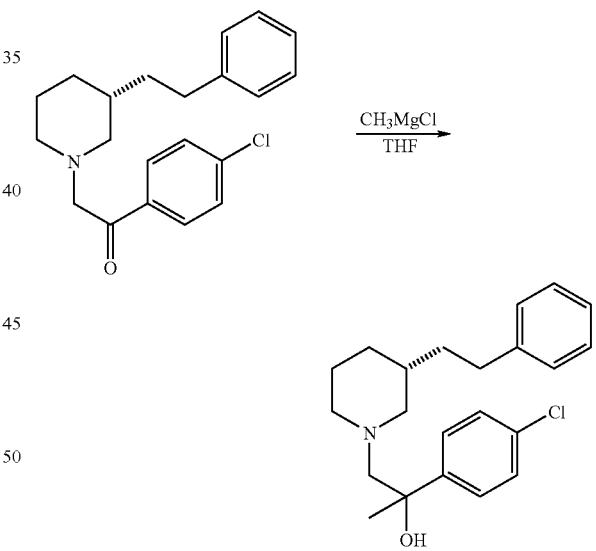

50 mg of R-2-[1-(2-Methoxy-phenyl)-cyclobutyl]-oxirane and 63 mg of R-3-(4-Trifluoromethyl-phenoxymethyl)-piperidine in 4 mL of methanol were heated in a sealed tube at 100° C. for 16 hours, cooled to room temperature, transferred to a round-bottomed flask, and concentrated in vacuo. The crude residue was purified by prepara-tive HPLC using a Chiralpak AD™ column from Chiral Technologies, Inc., eluting with a 98:2 mixture of hexane and isopropyl alcohol containing ca. 0.1% diethylamine. 43 mg of the R,R' isomer of 1-[1-(2-Methoxy-phenyl)-cyclobutyl]-2-[3-(4-trifluoromethyl-phenoxymethyl)-piperidin-1-yl]-ethanol (236) was obtained (38%).

In the same fashion, 50 mg of R-2-[1-(2-Methoxy-phenyl)-cyclobutyl]-oxirane and 63 mg of S-3-(4-Trifluoromethyl-phenoxymethyl)-piperidine gave the S,R' isomer of 1-[1-(2-Methoxy-phenyl)-cyclobutyl]-2-[3-(4-trifluoromethyl-phenoxymethyl)-piperidin-1-yl]-ethanol (234) (35%), 50 mg of S-2-[1-(2-Methoxy-phenyl)-cyclobutyl]-oxirane and 63 mg of R-3-(4-Trifluoromethyl-phenoxymethyl)-piperidine gave the R,S' isomer of 1-[1-(2-Methoxy-phenyl)-cyclobutyl]-2-[3-(4-trifluoromethyl-phenoxymethyl)-piperidin-1-yl]-ethanol (235) (40%), and 50 mg of S-2-[1-(2-Methoxy-phenyl)-cyclobutyl]-oxirane and 63 mg of S-3-(4-Trifluoromethyl-phenoxymethyl)-piperidine gave the S,S' isomer of 1-[1-(2-Methoxy-phenyl)-cyclobutyl]-2-[3-(4-trifluoromethyl-phenoxymethyl)-piperidin-1-yl]-ethanol (237) (41%). $^1$H and $^{13}$C (DEPT) NMR data for each isomer was consistent with the assigned structure. Data for each diastereomer: MS 464 (M$^+$+1).

Example 200

Synthesis of 2-(4-Chloro-phenyl)-1-(3(S)-phenethyl-piperidin-1-yl)-propan-2-ol

A solution of (S)-piperidine-ketone (0.292 mmol, 100 mg) in THF (1 mL) was added to a solution of CH$_3$MgCl (1.0 M in THF) (1.5 equiv, 0.44 mmol, 0.44 mL) in THF (1 mL) at 0° C. The reaction mixture stirred for 1 h. The reaction mixture was quenched with 10% NaOH (10 mL) and extracted with EtOAc (2×10 mL). The combined organics were dried with NaCl$_{(sat)}$ and Na$_2$SO$_{4(s)}$. The solvents were removed in vacuo and the residue was purified by chromatography (PTLC, SiO$_2$, 20 cm×20 cm, 1 mm, 3:1 hexane-acetone) which provided desired product (40 mg, 38%) as a colorless oil: R$_f$ 0.44 (SiO$_2$, 3:1 hexane-acetone); LRMS m/z 359 (M$^+$+1, C$_{22}$H$_{28}$ClNO requires 359).

Example 201

Synthesis of R-3-Hydroxymethyl-pyrrolidine-1-carboxylic acid benzyl ester

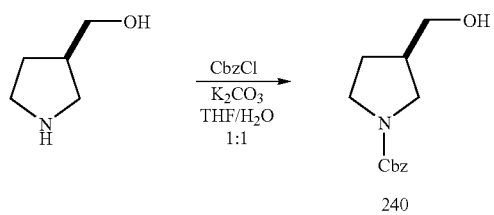

240

A solution of (−)-2-pyrrolidinemethanol (20 mmol, 2.0 g), CbzCl (2.0 equiv, 40 mmol, 6 mL) and $K_2CO_3$ (1.5 equiv, 30 mmol, 4.1 g) in $THF/H_2O$ (1:1) (66 mL) at 0° C. was allowed to warm to 25° C. and stirred for 12 h. Ethyl acetate (100 mL) was added and the layers were separated. The organic layer was washed with 10% aqueous HCl and then washed with $NaHCO_{3(sat)}$ and dried with $NaCl_{(sat)}$ and $Na_2SO_{4(s)}$. The solvents were removed in vacuo and chromatography (Isco Combi-Flash, 110 g cartridge, 1:1 Hexane-EtOAc) provided 240 (3.74 g, 4.71 g theoretical, 79%) as a colorless oil: LRMS m/z 236 (M$^+$+1, $C_{13}H_{17}NO_3$, requires 236).

Example 202

Synthesis of S-3-Hydroxymethyl-pyrrolidine-1-carboxylic acid benzyl ester

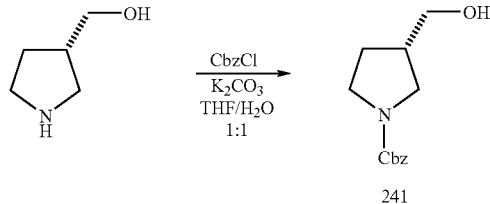

241

A solution of (−)-2-pyrrolidinemethanol (20 mmol, 2.0 g), CbzCl (2.0 equiv, 40 mmol, 6 mL) and $K_2CO_3$ (1.5 equiv, 30 mmol, 4.1 g) in $THF/H_2O$ (1:1) (66 mL) at 0° C. was allowed to warm to 25° C. and stirred for 12 h. Ethyl acetate (100 mL) was added and the layers were separated. The organic layer was washed with 10% aqueous HCl and then washed with $NaHCO_{3(sat)}$ and dried with $NaCl_{(sat)}$ and $Na_2SO_{4(s)}$. The solvents were removed in vacuo and chromatography (Isco Combi-Flash, 110 g cartridge, 1:1 Hexane-EtOAc) provided 241 (4.38 g, 4.71 g theoretical, 93%) as a colorless oil: LRMS m/z 236 (M$^+$+1, $C_{13}H_{17}NO_3$, requires 236).

Example 203

Synthesis of R-3-Methanesulfonyloxymethyl-pyrrolidine-1-carboxylic acid benzyl ester

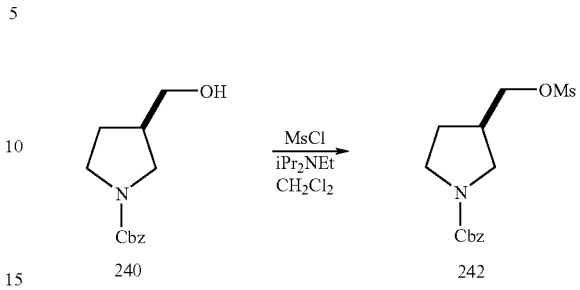

240 242

A solution of 240 (4.2 mmol, 1.0 g), MsCl (1.5 equiv, 6.4 mmol, 0.5 mL) and $iPr_2NEt$ (1.5 equiv, 6.4 mmol, 1.1 mL) in $CH_2Cl_2$ (14 mL) at 0° C. was allowed to warm to 25° C. and stirred for 12 h. The reaction mixture was quenched with 10% HCl (20 mL) and then extracted with EtOAc (2×50 mL). The combined organics were dried with $NaCl_{(sat)}$ and $Na_2SO_{4(s)}$. The solvents were removed in vacuo and chromatography (Isco Combi-Flash, 110 g cartridge, 1:1 Hexane-EtOAc) provided 242 as a colorless oil: LRMS m/z 314 (M$^+$+1, $C_{14}H_{19}NO_5S$, requires 314).

Example 204

Synthesis of S-3-Methanesulfonyloxymethyl-pyrrolidine-1-carboxylic acid benzyl ester

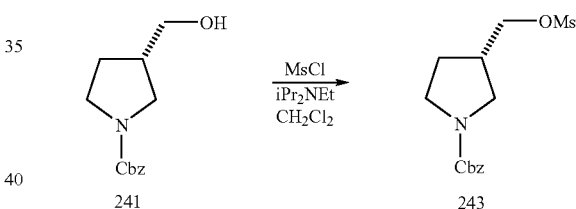

241 243

A solution of 241 (4.2 mmol, 1.0 g), MsCl (1.5 equiv, 6.4 mmol, 0.5 mL) and $iPr_2NEt$ (1.5 equiv, 6.4 mmol, 1.1 mL) in $CH_2Cl_2$ (14 mL) at 0° C. was allowed to warm to 25° C. and stirred for 12 h. The reaction mixture was quenched with 10% HCl (20 mL) and then extracted with EtOAc (2×50 mL). The combined organics were dried with $NaCl_{(sat)}$ and $Na_2SO_{4(s)}$. The solvents were removed in vacuo and chromatography (Isco Combi-Flash, 110 g cartridge, 1:1 Hexane-EtOAc) provided 243 as a colorless oil: LRMS m/z 314 (M$^+$+1, $C_{14}H_{19}NO_5S$, requires 314).

Example 205

Synthesis of R-3-(4-Trifluoromethyl-phenoxymethyl)-pyrrolidine-1-carboxylic acid benzyl ester

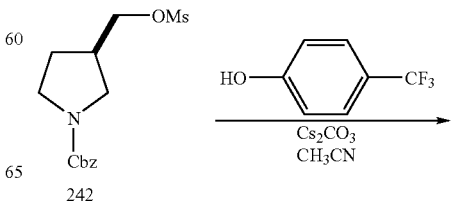

242

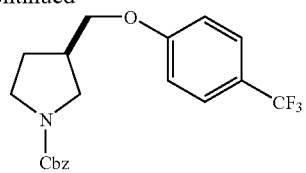

244

A solution of 242 (3.8 mmol, 1.2 g), α,α,α-trifluoro-p-cresol (1.5 equiv, 5.7 mmol, 0.9 g) and Cs$_2$CO$_3$ (2.0 equiv, 7.6 mmol, 2.5 g) in CH$_3$CN (13 mL) was heated to 90° C. and stirred for 12 h. Ethyl acetate (100 mL) and H$_2$O (100 mL) were added and the layers were separated. The organic layer was dried with NaCl$_{(sat)}$ and Na$_2$SO$_{4(s)}$. The solvents were removed in vacuo and chromatography (Isco Combi-Flash, 110 g cartridge, 9:1 Hexane-EtOAc) provided 244 (0.762 g, 1.44 g theoretical, 53%) as a colorless oil: LRMS m/z 380 (M$^+$+1, C$_{20}$H$_{20}$F$_3$NO$_3$, requires 380).

Example 206

Synthesis of S-3-(4-Trifluoromethyl-phenoxymethyl)-pyrrolidine-1-carboxylic acid benzyl ester

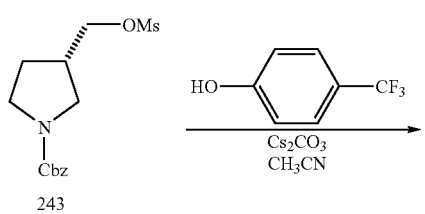

243

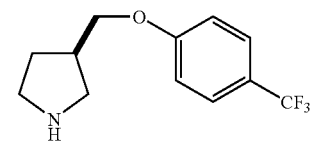

245

A solution of 243 (3.8 mmol, 1.2 g), α,α,α-trifluoro-p-cresol (1.5 equiv, 5.7 mmol, 0.9 g) and Cs$_2$CO$_3$ (2.0 equiv, 7.6 mmol, 2.5 g) in CH$_3$CN (13 mL) was heated to 90° C. and stirred for 12 h. Ethyl acetate (100 mL) and H$_2$O (100 mL) were added and the layers were separated. The organic layer was dried with NaCl$_{(sat)}$ and Na$_2$SO$_{4(s)}$. The solvents were removed in vacuo and chromatography (Isco Combi-Flash, 110 g cartridge, 9:1 Hexane-EtOAc) provided 245 (0.421 g, 1.44 g theoretical, 29%) as a colorless oil: LRMS m/z 380 (M$^+$+1, C$_{20}$H$_{20}$F$_3$NO$_3$, requires 380).

Example 207

Synthesis of R-3-(4-Trifluoromethyl-phenoxymethyl)-pyrrolidine

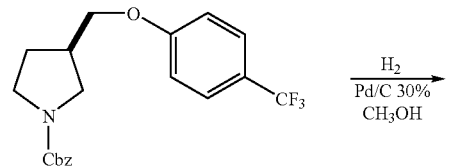

246

A solution of 244 (1.3 mmol, 486 mg) in CH$_3$OH (13 mL) was treated 30% Pd—C (81 mg) and H$_2$ (Hydrogen balloon). The reaction was stirred for 5 h. The reaction mixture was filtered through celite, and the solvents were removed in vacuo to provide 246 (319 mg, 319 mg theoretical, quantitative) as a colorless oil: LRMS m/z 246 (M$^+$+1, C$_{12}$H$_{14}$F$_3$NO, requires 246).

Example 208

Synthesis of S-3-(4-Trifluoromethyl-phenoxymethyl)-pyrrolidine

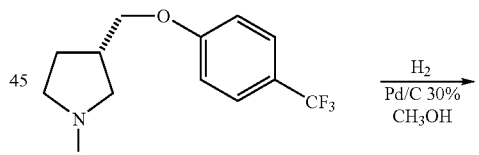

245

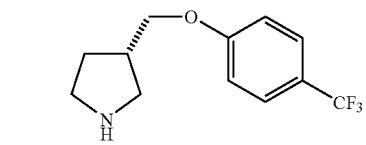

247

A solution of 245 (1.1 mmol, 421 mg) in CH$_3$OH (11 mL) was treated 30% Pd—C (70 mg) and H$_2$ (Hydrogen balloon). The reaction was stirred for 5 h. The reaction mixture was filtered through celite, and the solvents were removed in vacuo to provide 247 (270 mg, 270 mg theoretical, quantitative) as a colorless oil: LRMS m/z 246 (M$^+$+1, C$_{12}$H$_{14}$F$_3$NO, requires 246).

Example 209

Synthesis of R-[3-(4-Trifluoromethyl-phenoxymethyl)-pyrrolidin-1-yl]-[1-(4-trifluoromethyl-phenyl)-cyclobutyl]-methanone

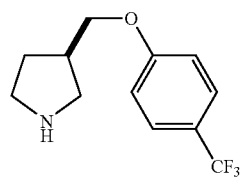

246

+

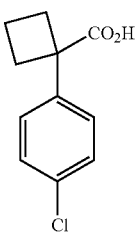

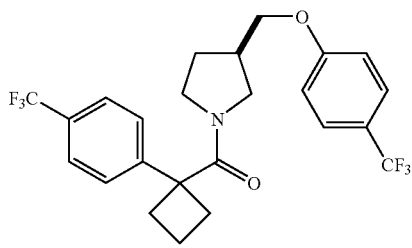

248

A solution of the 246 (1.3 mmol, 310 mg), 1-(4-Chlorophenyl)-1-cyclobutane carboxylic acid (1.5 equiv, 1.9 mmol, 400 mg) and iPr$_2$NEt (3.0 equiv, 4.0 mmol, 0.7 mL) in CH$_2$Cl$_2$ (5 mL) was treated with PyBroP (1.5 equiv, 1.9 mmol, 890 mg) under Ar at 0° C. After warming to 25° C. and stirring for 12 h, the reaction mixture was quenched with 10% aqueous HCl and extracted with 3×EtOAc (25 mL). The organic layer was then washed with NaHCO$_{3(sat)}$ and dried with NaCl$_{(sat)}$ and Na$_2$SO$_{4(s)}$. The solvents were removed in vacuo and chromatography (Isco Combi-Flash, 110 g cartridge, 3:1 Hexane-EtOAc) provided 248 (406 mg, 569 mg theoretical, 71%) as a colorless oil: LRMS m/z 439 (M$^+$+1, C$_{23}$H$_{23}$ClF$_3$NO$_2$, requires 439).

Example 210

Synthesis of S-[3-(4-Trifluoromethyl-phenoxymethyl)-pyrrolidin-1-yl]-[1-(4-trifluoromethyl-phenyl)-cyclobutyl]-methanone

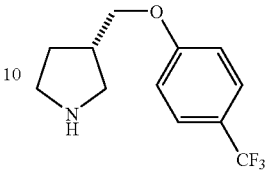

+

247

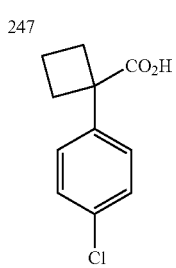

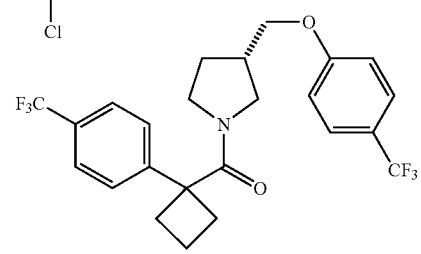

249

A solution of the 247 (1.1 mmol, 280 mg), 1-(4-Chlorophenyl)-1-cyclobutane carboxylic acid (1.5 equiv, 1.7 mmol, 358 mg) and iPr$_2$NEt (3.0 equiv, 3.4 mmol, 0.6 mL) in CH$_2$Cl$_2$ (4 mL) was treated with PyBroP (1.5 equiv, 1.7 mmol, 792 mg) under Ar at 0° C. After warming to 25° C. and stirring for 12 h, the reaction mixture was quenched with 10% aqueous HCl and extracted with 3×EtOAc (25 mL). The organic layer was then washed with NaHCO$_{3(sat)}$ and dried with NaCl$_{(sat)}$ and Na$_2$SO$_{4(s)}$. The solvents were removed in vacuo and chromatography (Isco Combi-Flash, 110 g cartridge, 3:1 Hexane-EtOAc) provided 249 (230 mg, 482 mg theoretical, 48%) as a colorless oil: LRMS m/z 439 (M$^+$+1, C$_{23}$H$_{23}$ClF$_3$NO$_2$, requires 439).

Example 211

Synthesis of R-3-(4-Trifluoromethyl-phenoxymethyl)-1-[1-(4-trifluoromethyl-phenyl)-cyclobutylmethyl]-pyrrolidine

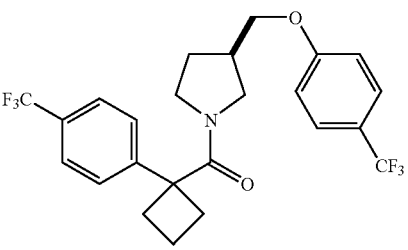

248

-continued

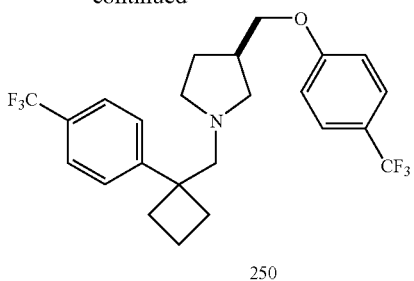

250

A solution of 248 (0.23 mmol, 100 mg) in THF (1 mL) at 25° C. was treated with LiAlH₄ (3.0 equiv, 0.69 mmol, 26 mg) under Ar. The reaction mixture stirred for 12 h at 60° C. The reaction mixture was then cooled to 0° C., quenched with 10% aqueous NaOH and extracted with 3×EtOAc (25 mL). The organics were dried with NaCl$_{(sat)}$ and Na$_2$SO$_{4(s)}$. The solvents were removed in vacuo and chromatography (Isco Combi-Flash, 25 g cartridge, 3:1 Hexane-EtOAc) provided 250 (65 mg, 97 mg theoretical, 67%) as a colorless oil: LRMS m/z 425 (M⁺+1, C$_{23}$H$_{25}$ClF$_3$NO, requires 425).

Example 212

Synthesis of S-3-(4-Trifluoromethyl-phenoxymethyl)-1-[1-(4-trifluoromethyl-phenyl)-cyclobutylmethyl]-pyrrolidine

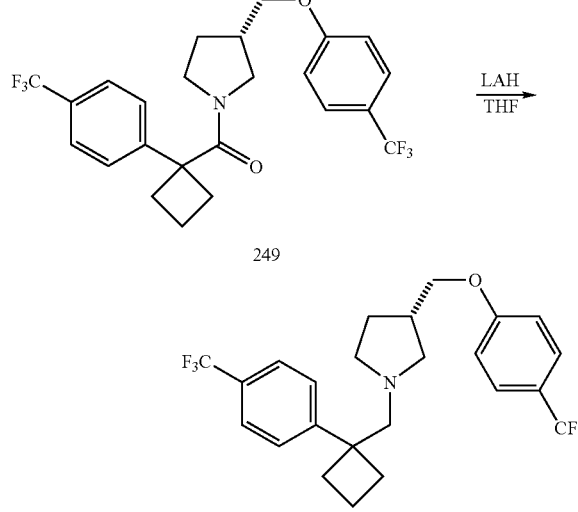

A solution of 249 (0.23 mmol, 100 mg) in THF (1 mL) at 25° C. was treated with LiAlH₄ (3.0 equiv, 0.69 mmol, 26 mg) under Ar. The reaction mixture stirred for 12 h at 60° C. The reaction mixture was then cooled to 0° C., quenched with 10% aqueous NaOH and extracted with 3×EtOAc (25 mL). The organics were dried with NaCl$_{(sat)}$ and Na$_2$SO$_{4(s)}$. The solvents were removed in vacuo and chromatography (Isco Combi-Flash, 25 g cartridge, 3:1 Hexane-EtOAc) provided 251 (73 mg, 97 mg theoretical, 75%) as a colorless oil: LRMS m/z 425 (M⁺+1, C$_{23}$H$_{25}$ClF$_3$NO, requires 425).

Example 213

Synthesis of 1-[1-(4-Chloro-phenyl)-cyclobutyl]-2-(3-S-phenethyl-piperidin-1-yl)-S-ethanol

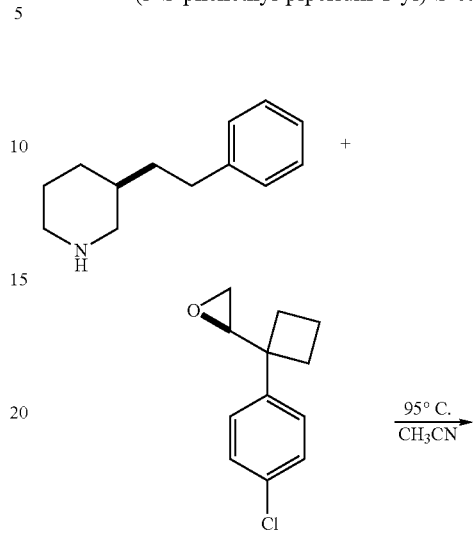

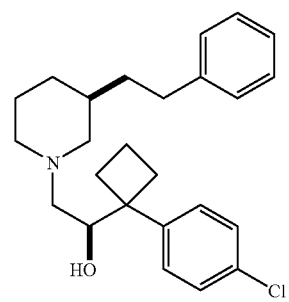

252

A solution of the amine (1.2 equiv, 1.58 mmol, 300 mg) and the epoxide (1.32 mmol, 275 mg) in CH$_3$CN (2 mL) was stirred for 12 h at 95° C. The reaction mixture was quenched with H$_2$O and extracted with 3×EtOAc (25 mL). The organics were dried with NaCl$_{(sat)}$ and Na$_2$SO$_{4(s)}$. The solvents were removed in vacuo and chromatography (Isco Combi-Flash, 10 g cartridge, 1:1 Hexane-EtOAc) provided 252 (439 mg, 525 mg theoretical, 84%) as a colorless oil: R$_f$ 0.42 (SiO$_2$, 1:1 hexane-ethyl acetate); LRMS m/z 399 (M⁺+1, C$_{25}$H$_{32}$ClNO, requires 399).

Example 214

Synthesis of 1-[1-(4-Chloro-phenyl)-cyclobutyl]-2-(3-R-phenethyl-piperidin-1-yl)-R-ethanol

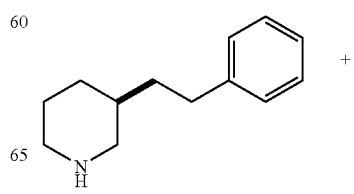

-continued

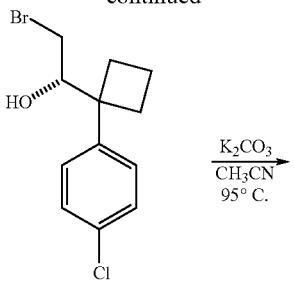

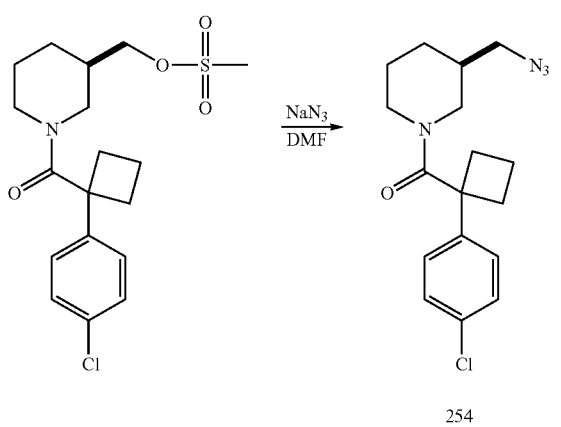

253

A solution of (R)-3-phenethyl piperidine (1.0 equiv, 2.14 mmol, 405 mg), alcohol (2.14 mmol, 619 mg) and K$_2$CO$_3$ (1.5 equiv, 3.21 mmol, 444 mg), in CH$_3$CN (2 mL) was stirred for 12 h at 95° C. in a sealed pressure tube. The reaction mixture was quenched with H$_2$O and extracted with 3×EtOAc (25 mL). The organics were dried with NaCl$_{(sat)}$ and Na$_2$SO$_{4(s)}$. The solvents were removed in vacuo and chromatography (Isco Combi-Flash, 25 g cartridge, Hexane-EtOAc (45%)) provided 253 (852 mg, 760 mg theoretical, 89%) as a colorless oil: R$_f$ 0.38 (SiO$_2$, hexane-ethyl acetate (45%)); LRMS m/z 399 (M$^+$+1, C$_{25}$H$_{32}$ClNO, requires 399).

Example 215

Synthesis of R-(3-Azidomethyl-piperidin-1-yl)-[1-(4-chloro-phenyl)-cyclobutyl]-methanone

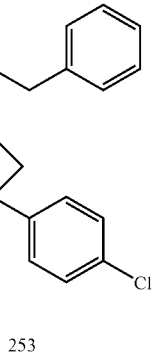

254

A solution of the mesylate (2.29 mmol, 884 mg) and NaN$_3$ (10 equiv, 22.9 mmol, 1.49 g) in DMF (10 mL) was heated at 70° C. for 48 h. The reaction mixture was quenched with H$_2$O (50 mL) and then extracted with EtOAc (2×50 mL). The combined organics were dried with NaCl$_{(sat)}$ and Na$_2$SO$_{4(s)}$. The solvents were removed in vacuo which provided 254 (762 mg, 650 mg theoretical, 85%) as a pale yellow oil: R$_f$ 0.68 (SiO$_2$, 1:1 hexane-ethyl acetate); LRMS m/z 333 (M$^+$+1, C$_{17}$H$_{23}$ClN$_4$O requires 333).

Example 216

Synthesis of C-{1-[1-(4-Chloro-phenyl)-cyclobutyl-methyl]-piperidin-3-R-yl}-methylamine

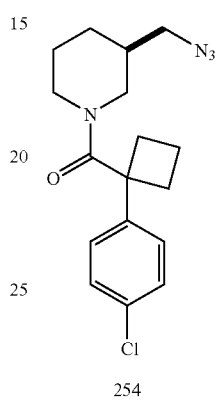 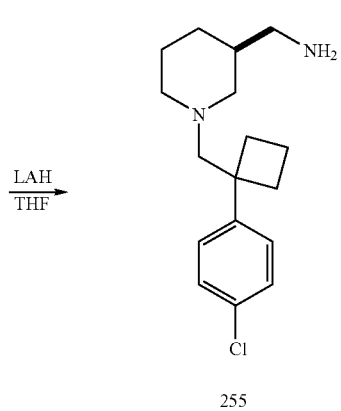

254                                             255

A solution of 254 (0.451 mmol, 150 mg) in THF (2 mL) at 0° C. was treated with LiAlH$_4$ (3.0 equiv, 1.35 mmol, 51 mg) under Ar. The reaction mixture stirred for 12 h and returned to 60° C. The reaction mixture was then cooled to 0° C., quenched with 10% aqueous NaOH and extracted with 2×EtOAc (25 mL). The organics were dried with NaCl$_{(sat)}$ and Na$_2$SO$_{4(s)}$. The solvents were removed to provide 255 as a colorless oil: LRMS m/z 293 (M$^+$+1, C$_{17}$H$_{25}$ClN$_2$ requires 293).

Example 217

Synthesis of 3-Iodomethyl-piperidine-1-carboxylic acid benzyl ester

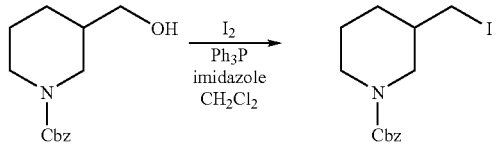

A solution of triphenyl phosphine (1.5 equiv, 30 mmol, 7.87 g) and imidazole (1.5 equiv, 30 mmol, 2.05 g) in CH$_2$Cl$_2$ (50 mL) at 0° C. was treated with I$_2$ (1.5 equiv, 30 mmol, 7.61 g). After 5 min, the alcohol (20 mmol, 5.00 g) in CH$_2$Cl$_2$ (10 mL) was added at 0° C. The reaction stirred for 1 h at 25. The reaction mixture was quenched with 10% aqueous HCl and extracted with 3×EtOAc (75 mL). The organics were washed with H$_2$O then dried with NaCl$_{(sat)}$ and Na$_2$SO$_{4(s)}$. The solvents were removed in vacuo and chromatography (Isco Combi-Flash, 110 g cartridge, 7:1 Hexane-EtOAc) provided the desired compound (5.90 g, 7.18 g theoretical, 82%) as a colorless oil: LRMS m/z 360 (M$^+$+1, C$_{14}$H$_{18}$ClNO$_2$, requires 360).

Example 218

Synthesis of 2-[3-(4-Trifluoromethyl-phenoxymethyl)-piperidine-1-carbonyl]-morpholine-4-carboxylic acid tert-butyl ester

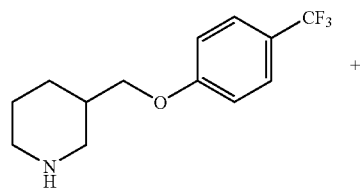

A solution of the amine (1.93 mmol, 500 mg), morpholine-2,4-dicarboxylic acid 4-tert-butyl ester (1.1 equiv, 2.12 mmol, 490 mg) and iPr₂NEt (3.0 equiv, 5.79 mmol, 1.00 mL) in CH₂Cl₂ (10 mL) was treated with BroP (1.5 equiv, 2.90 mmol, 1.13 g) under Ar at 0° C. After warming to 25° C. and stirring for 12 h, the reaction mixture was quenched with 10% aqueous HCl and extracted with 3×EtOAc (25 mL). The organic layer was then washed with NaHCO$_{3(sat)}$ and dried with NaCl$_{(sat)}$ and Na₂SO$_{4(s)}$. The solvents were removed in vacuo and chromatography (Isco Combi-Flash, 110 g cartridge, 1:1 Hexane-EtOAc) provided the desired compound (632 mg, 912 mg theoretical, 69%) as a colorless oil: LRMS m/z 474 (M⁺+1, C₂₃H₃₁F₃N₂O₅, requires 474).

Example 219

Synthesis of morpholin-2-yl-[3-(4-trifluoromethyl-phenoxymethyl)-piperidin-1-yl]-methanone

A solution of the amide (1.93 mmol, 500 mg) in CH₂Cl₂ (0.5 mL) was treated with TFA (0.5 mL) under Ar at 0° C. After stirring for 1 h, the solvents were removed in vacuo, and the residue was dissolved in EtOAc (25 mL). The organic layer was then washed with NaHCO$_{3(sat)}$ and dried with NaCl$_{(sat)}$ and Na₂SO$_{4(s)}$. The solvents were removed in vacuo which provided 256 (74 mg, 74 mg theoretical, quantitative) as a colorless oil: LRMS m/z 373 (M⁺+1, C₁₈H₂₃F₃N₂O₃, requires 373).

Example 220

Synthesis of 2-[3-(4-Trifluoromethyl-phenoxymethyl)-piperidin-1-ylmethyl]-morpholine-4-carboxylic acid benzyl ester

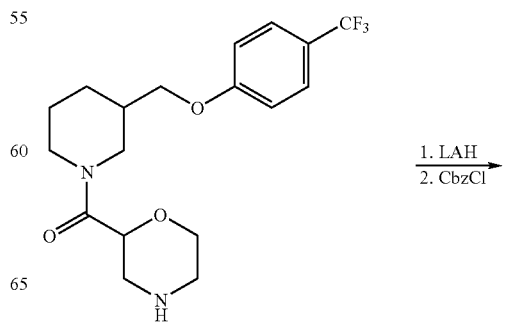

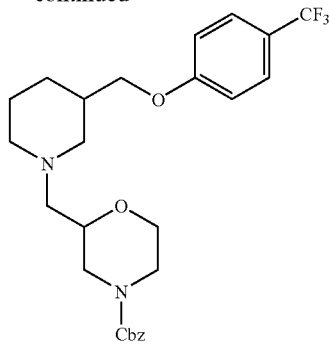

A solution of the amide (0.849 mmol, 316 mg) in THF (2 mL) at 0° C. was treated with LiAlH₄ (3.0 equiv, 2.55 mmol, 97 mg) under Ar. The reaction mixture stirred for 12 h and returned to 60° C. The reaction mixture was then cooled to 0° C., quenched with 10% aqueous NaOH and extracted with 2×EtOAc (25 mL). The organics were dried with $NaCl_{(sat)}$ and $Na_2SO_{4(s)}$. After removing the solvents, the residue was dissolved in THF/H₂O (3 mL) and treated with K₂CO₃ (3.0 equiv, 2.55 mmol, 352 mg) and CbzCl (1.5 equiv, 1.27 mmol, 182 μL). The reaction mixture was quenched with H₂O and extracted with 3×EtOAc (10 mL). The organics were dried with $NaCl_{(sat)}$ and $Na_2SO_{4(s)}$. The solvents were removed in vacuo and chromatography (Isco Combi-Flash, 25 g cartridge, CH₂Cl₂—CH₃OH (10%)) provided the desired compound (166 mg, 418 mg theoretical, 40%) as a colorless oil: LRMS m/z 494 (M⁺+1, $C_{26}H_{31}F_3N_2O_4$, requires 494).

Example 221

Synthesis of 2-[3-(4-Trifluoromethyl-phenoxymethyl)-piperidin-1-ylmethyl]-morpholine

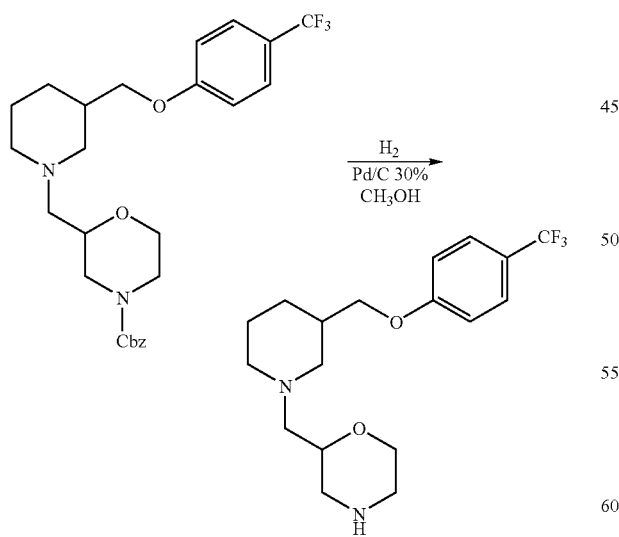

A solution of the amine (0.337 mmol, 166 mg) in CH₃OH (2 mL) was treated 30% Pd—C (50 mg) and H₂ (Hydrogen balloon). The reaction was stirred for 5 h. The reaction mixture was filtered through celite, and the solvents were removed in vacuo to provide 257 (114 mg, 121 mg theoretical, 94%) as a colorless oil: LRMS m/z 359 (M⁺+1, $C_{18}H_{25}F_3N_2O_2$, requires 359).

Example 222

Synthesis of 4-(4-Chloro-phenyl)-2-[3-(4-trifluoromethyl-phenoxymethyl)-piperidin-1-ylmethyl]-morpholine

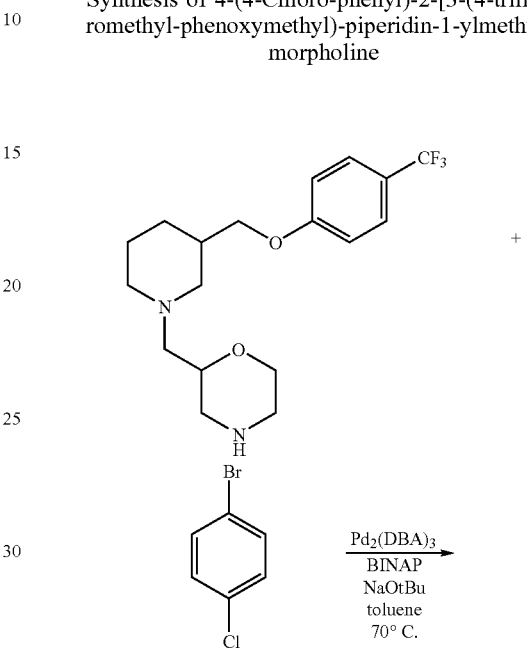

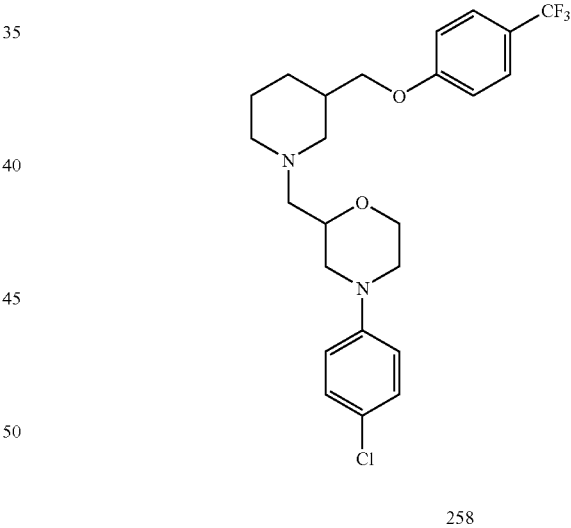

258

A solution of the amine (0.318 mmol, 114 mg), 1-bromo-4-chloro-benzene (1.0 equiv, 0.318 mmol, 61 mg), BINAP (4.0 mol %, 0.0127 mmol, 8 mg) and NaOtBu (1.4 equiv, 0.445 mmol, 43 mg) in toluene (0.5 mL) was treated with $Pd_2(DBA)_3$ (2.0 mol %, 0.00636 mmol, 6 mg) under Ar at 0° C. The reaction was heated to 70° C. for 12 h. The reaction mixture was quenched with pH 7 buffer solution and extracted with 3×EtOAc (10 mL). The organic layer was then dried with $NaCl_{(sat)}$ and $Na_2SO_{4(s)}$. The solvents were removed in vacuo and chromatography (Isco Combi-Flash, 10 g cartridge, 1:1 Hexane-EtOAc) provided 258 (100 mg, 149 mg theoretical, 67%) as a colorless oil: $R_f$ 0.37 (SiO₂, 1:1 hexane-ethyl acetate); LRMS m/z 470 (M$^+$+1, C$_{24}$H$_{28}$ClF$_3$N$_2$O$_2$, requires 470).

Example 223

Spontaneous Locomotor Activity in Rats

The effect of 124 and 126 on spontaneous locomotor activity in rats was determined according to the procedures outlined by Silverman et al. (Motor Activity. In "Animal behavior in the laboratory", Chapman and Hall eds, London, p. 79–92, 1978) and Boissier et al. (*Arch. Int. Pharmacodyn.* 1965, 158, 212.)

Test items and test item vehicles were administered to male Sprague-Dawley rats (n=10) as a single i.p. dose. One, three, five, eight and twenty four hours following administration, rats were placed in a plastic box 30×30 cm in a room with low light intensity (maximum 50 lux). Locomotor activity was determined during 20 minute periods using video image analyzers. Images recorded with video cameras were digitalized and displacements of the center of gravity of the digital image spot were tracked and analyzed. When the speed of displacement of the center of gravity of the spot was below 4.26 cm/sec, the movement was considered as inactivity. When this speed was between 4.26 and 6.75 cm/sec, the movement was considered as a small movement. When this speed was above 6.75 cm/sec, the movement was considered as a large movement. The number of occurrences, distance and duration of fast and slow movements, number of occurrences and duration of periods of inactivity and number of rears were measured.

Compounds 124 and 126, when dosed at 10 mg/kg, showed a significant increase in locomotor activity compared to control animals at all times tested.

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:
1. A compound represented by C:

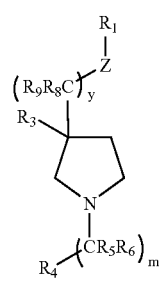

wherein
Z represents C(R$_3$)$_2$, C(O), O, NR, NC(O)OR, S, SO, or SO$_2$;
m is 1, 2, 3, 4 or 5;
p is 0, 1, 2, or 3;

|  | Vehicle A | Vehicle B | 126 10 mg/kg (Dosed in Vehicle A) | 124 10 mg/kg (Dosed in Vehicle B) | Methylphenidate, 10 mg/kg (Dosed in Vehicle B) |
|---|---|---|---|---|---|
| Large Movement Occurrences | 1 hour: 294 ± 47 | 1 hour: 236 ± 50 | 1 hour: 774 ± 110 | 1 hour: 655 ± 83 | 1 hour: 958 ± 118 |
|  | 3 hours: 108 ± 25 | 3 hours: 139 ± 32 | 3 hours: 956 ± 93 | 3 hours: 751 ± 122 | 3 hours: 504 ± 114 |
|  | 5 hours: 114 ± 56 | 5 hours: 68 ± 26 | 5 hours: 866 ± 117 | 5 hours: 616 ± 82 | 5 hours: 196 ± 62 |
|  | 8 hours: 64 ± 26 | 8 hours: 89 ± 18 | 8 hours: 746 ± 95 | 8 hours: 455 ± 69 | 8 hours: 71 ± 20 |
|  | 24 hours: 215 ± 38 | 24 hours: 124 ± 30 | 24 hours: 1012 ± 81 | 24 hours: 440 ± 55 | 24 hours: 335 ± 68 |
| Small Movement Occurrences | 1 hour: 815 ± 86 | 1 hour: 661 ± 96 | 1 hour: 1357 ± 125 | 1 hour: 1258 ± 83 | 1 hour: 1595 ± 83 |
|  | 3 hours: 488 ± 77 | 3 hours: 564 ± 77 | 3 hours: 1610 ± 73 | 3 hours: 1386 ± 96 | 3 hours: 1072 ± 122 |
|  | 5 hours: 461 ± 108 | 5 hours: 329 ± 99 | 5 hours: 1575 ± 90 | 5 hours: 1277 ± 100 | 5 hours: 612 ± 108 |
|  | 8 hours: 309 ± 80 | 8 hours: 441 ± 59 | 8 hours: 1489 ± 111 | 8 hours: 1042 ± 109 | 8 hours: 358 ± 65 |
|  | 24 hours: 642 ± 82 | 24 hours: 486 ± 71 | 24 hours: 1544 ± 75 | 24 hours: 934 ± 87 | 24 hours: 790 ± 81 | y is 0, 1 or 2;

R represents alkyl, cycloalkyl, aryl, or aralkyl;

$R_1$ represents alkyl, aryl, or aralkyl;

R and $R_1$ may be connected through a covalent bond;

$R_2$ represents independently for each occurrence H, alkyl, fluoroalkyl, aryl, or cycloalkyl;

$R_3$ represents independently for each occurrence H, alkyl, aryl, $OR_2$, $OC(O)R_2$, $CH_2OR_2$, or $CO_2R_2$;

$R_4$ represents independently for each occurrence H, alkyl, cycloalkyl, aryl, alkenyl, or OR;

$R_5$ and $R_6$ are selected independently for each occurrence from the group consisting of H, alkyl, $(CH_2)_pY$, aryl, F, $OR_2$, and $OC(O)R_2$; or an instance of $CR_5R_6$ taken together is C(O);

$R_8$ and $R_9$ are selected independently for each occurrence from the group consisting of H, alkyl, $(CH_2)_pY$, aryl, F, $OR_2$, and $OC(O)R_2$; or an instance of $CR_8R_9$ taken together is C(O);

Y represents independently for each occurrence $OR_2$, $N(R_2)_2$, $SR_2$, $S(O)R_2$, $S(O)_2R_2$, or $P(O)(OR_2)_2$;

any two instances of $R_2$ may be connected through a covalent bond;

a covalent bond may connect $R_4$ and an instance of $R_5$ or $R_6$;

any two instances of $R_5$ and $R_6$ may be connected through a covalent bond;

any two geminal or vicinal instances of $R_8$ and $R_9$ may be connected through a covalent bond; and the stereochemical configuration at any stereocenter of a compound represented by C is R or S, or a mixture of these configurations.

2. The compound of claim 1, wherein Z is O or NR.

3. The compound of claim 1, wherein m is 3.

4. The compound of claim 1, wherein y is 1.

5. The compound of claim 1, wherein $R_1$ represents aryl.

6. The compound of claim 1, wherein $R_3$ represents independently for each occurrence H or alkyl.

7. The compound of claim 1, wherein $R_4$ represents cycloalkyl, or aryl.

8. The compound of claim 1, wherein $R_5$ and $R_6$ are selected independently for each occurrence from the group consisting of H, alkyl, $OR_2$, aryl, and F.

9. The compound of claim 1, wherein $R_8$ and $R_9$ are selected independently for each occurrence from the group consisting of H, alkyl, $OR_2$, aryl, and F.

10. The compound of claim 1, wherein Z is O or NR; and m is 3.

11. The compound of claim 1, wherein Z is O or NR; and y is 1.

12. The compound of claim 1, wherein Z is O or NR; m is 3; and y is 1.

13. The compound of claim 1, wherein Z is O or NR; m is 3; y is 1; and $R_1$ is aryl.

14. The compound of claim 1, wherein Z is O or NR; m is 3; y is 1; $R_1$ is aryl; and $R_3$ is H or alkyl.

15. The compound of claim 1, wherein Z is O or NR; m is 3; y is 1; $R_1$ is aryl; $R_3$ is H or alkyl; and $R_4$ is cycloalkyl, or aryl.

16. The compound of claim 1, wherein Z is O or NR; m is 3; y is 1; $R_1$ is aryl; $R_3$ is H or alkyl; $R_4$ is cycloalkyl, or aryl; and $R_5$ and $R_6$ are selected independently for each occurrence from the group consisting of H, alkyl, $OR_2$, aryl, and F.

17. The compound of claim 1, wherein Z is O or NR; m is 3; y is 1; $R_1$ is aryl; $R_3$ is H or alkyl; $R_4$ is cycloalkyl, or aryl; $R_5$ and $R_6$ are selected independently for each occurrence from the group consisting of H, alkyl, $OR_2$, aryl, and F; and $R_8$ and $R_9$ are selected independently for each occurrence from the group consisting of H, alkyl, $OR_2$, aryl, and F.

* * * * *